(12) United States Patent
Koehler et al.

(10) Patent No.: US 10,051,861 B2
(45) Date of Patent: Aug. 21, 2018

(54) N-ARYLAMIDINE-SUBSTITUTED TRIFLUOROETHYL SULFIDE DERIVATIVES AS ACARICIDES AND INSECTICIDES

(71) Applicants: BAYER CROPSCIENCE AG, Monheim (DE); BAYER INTELLECTUAL PROPERTY GMBH, Monheim (DE)

(72) Inventors: Adeline Koehler, Langenfeld (DE); Bernd Alig, Koenigswinter (DE); Angela Becker, Duesseldorf (DE); Arnd Voerste, Cologne (DE); Ulrich Goergens, Ratingen (DE); Reiner Fischer, Monheim (DE); Wahed Ahmed Moradi, Monheim (DE); Silvia Cerezo-Galvez, Langenfeld (DE); Julia Johanna Hahn, Duesseldorf (DE); Kerstin Ilg, Cologne (DE); Hans-Georg Schwarz, Dorsten (DE); Takuya Gomibuchi, Ibaraki (JP); Masahito Ito, Ibaraki (JP); Daiei Yamazaki, Yamaguchi (JP); Katsuhiko Shibuya, Tochigi (JP); Eiichi Shimojo, Osaka (JP)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 15/349,297

(22) Filed: Nov. 11, 2016

(65) Prior Publication Data

US 2017/0057914 A1 Mar. 2, 2017

Related U.S. Application Data

(62) Division of application No. 14/366,715, filed as application No. PCT/EP2012/075269 on Dec. 12, 2012, now Pat. No. 9,642,363.

(30) Foreign Application Priority Data

Dec. 21, 2011 (EP) .................................... 11194855

(51) Int. Cl.
*C07D 207/22* (2006.01)
*C07D 207/34* (2006.01)
(Continued)

(52) U.S. Cl.
CPC ............ *A01N 41/10* (2013.01); *A01N 41/12* (2013.01); *A01N 43/08* (2013.01); *A01N 43/10* (2013.01); *A01N 43/36* (2013.01); *A01N 43/40* (2013.01); *A01N 43/60* (2013.01); *A01N 43/84* (2013.01); *A01N 43/86* (2013.01); *C07C 315/02* (2013.01); *C07C 317/34* (2013.01); *C07C 317/40* (2013.01); *C07C 319/14* (2013.01); *C07C 319/20* (2013.01); *C07C 323/36* (2013.01); *C07C 323/41* (2013.01); *C07C 323/44* (2013.01); *C07C 323/45* (2013.01); *C07C 335/16* (2013.01); *C07D 207/22* (2013.01); *C07D 207/34* (2013.01); *C07D 211/38* (2013.01); *C07D 211/72* (2013.01); *C07D 211/98* (2013.01); *C07D 213/61* (2013.01); *C07D 213/78* (2013.01); *C07D 239/28* (2013.01); *C07D 241/24* (2013.01);
(Continued)

(58) Field of Classification Search
CPC .. C07D 207/22; C07D 207/34; C07D 211/38; C07D 211/72; C07D 211/98; C07D 213/61; C07D 213/78; C07D 239/28; C07D 241/24; C07D 263/28; C07D 277/16; C07D 277/18; C07D 277/38; C07D 277/54; C07D 279/06; C07D 285/08; C07D 295/125; C07D 295/13; C07D 305/08; C07D 307/24; C07D 307/68; C07D 331/04; C07D 333/38; C07D 333/48; C07D 401/06
See application file for complete search history.

(56) References Cited

FOREIGN PATENT DOCUMENTS

DE     112450 A5     4/1975
EP     1006102 A2     6/2000
(Continued)

OTHER PUBLICATIONS

International Search Report received in PCT/EP2012/075269, dated Mar. 22, 2013.

*Primary Examiner* — Rebecca L Anderson
(74) *Attorney, Agent, or Firm* — McBee Moore Woodward & Vanik IP, LLC

(57) ABSTRACT

The present invention relates to novel N-arylamide-substituted trifluoroethyl sulfide derivatives of the formula (I)

(I)

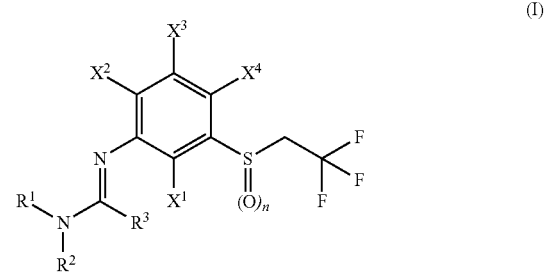

in which $X^1$, $X^2$, $X^3$, $X^4$, $R^1$, $R^2$, $R^3$, n have the meanings given in the description—to their use as acaricides and insecticides for controlling animal pests and to processes and intermediates for their preparation.

17 Claims, No Drawings

(51) Int. Cl.

| | | |
|---|---|---|
| *C07D 211/38* | (2006.01) | |
| *C07D 211/72* | (2006.01) | |
| *C07D 211/98* | (2006.01) | |
| *C07D 239/28* | (2006.01) | |
| *C07D 241/24* | (2006.01) | |
| *C07D 263/28* | (2006.01) | |
| *C07D 277/16* | (2006.01) | |
| *C07D 277/18* | (2006.01) | |
| *C07D 277/38* | (2006.01) | |
| *C07D 277/54* | (2006.01) | |
| *C07D 279/06* | (2006.01) | |
| *C07D 285/08* | (2006.01) | |
| *C07D 295/125* | (2006.01) | |
| *C07D 295/13* | (2006.01) | |
| *C07D 305/08* | (2006.01) | |
| *C07D 307/24* | (2006.01) | |
| *C07D 307/68* | (2006.01) | |
| *C07D 331/04* | (2006.01) | |
| *C07D 333/38* | (2006.01) | |
| *C07D 333/48* | (2006.01) | |
| *C07D 401/06* | (2006.01) | |
| *A01N 41/10* | (2006.01) | |
| *A01N 41/12* | (2006.01) | |
| *A01N 43/40* | (2006.01) | |
| *C07C 323/36* | (2006.01) | |
| *C07C 323/44* | (2006.01) | |
| *C07D 213/78* | (2006.01) | |
| *C07C 317/40* | (2006.01) | |
| *C07C 323/41* | (2006.01) | |
| *C07C 335/16* | (2006.01) | |
| *C07D 213/61* | (2006.01) | |
| *A01N 43/08* | (2006.01) | |
| *A01N 43/10* | (2006.01) | |
| *A01N 43/36* | (2006.01) | |
| *A01N 43/60* | (2006.01) | |
| *A01N 43/84* | (2006.01) | |
| *A01N 43/86* | (2006.01) | |
| *C07C 315/02* | (2006.01) | |
| *C07C 317/34* | (2006.01) | |
| *C07C 319/20* | (2006.01) | |
| *C07C 323/45* | (2006.01) | |
| *C07C 319/14* | (2006.01) | |

(52) U.S. Cl.
CPC ......... *C07D 263/28* (2013.01); *C07D 277/16* (2013.01); *C07D 277/18* (2013.01); *C07D 277/38* (2013.01); *C07D 277/54* (2013.01); *C07D 279/06* (2013.01); *C07D 285/08* (2013.01); *C07D 295/125* (2013.01); *C07D 295/13* (2013.01); *C07D 305/08* (2013.01); *C07D 307/24* (2013.01); *C07D 307/68* (2013.01); *C07D 331/04* (2013.01); *C07D 333/38* (2013.01); *C07D 333/48* (2013.01); *C07D 401/06* (2013.01); *C07C 2601/02* (2017.05); *C07C 2601/04* (2017.05); *C07C 2601/08* (2017.05); *C07C 2601/14* (2017.05)

(56) References Cited

FOREIGN PATENT DOCUMENTS

| | | |
|---|---|---|
| EP | 1380568 A2 | 1/2004 |
| EP | 1803712 A1 | 4/2007 |
| JP | S-6023371 A | 2/1985 |
| JP | 2005298438 A | 10/2005 |
| JP | 2007-308392 | 11/2007 |
| JP | 2008064739 A | 3/2008 |
| JP | 2011042611 A | 3/2011 |
| WO | 2005021488 A1 | 3/2005 |
| WO | 2006/043635 A1 | 4/2006 |
| WO | 2006065479 A2 | 6/2006 |
| WO | 2007131680 A1 | 11/2007 |
| WO | 2012088438 A1 | 6/2012 |
| WO | 2013174947 A1 | 11/2013 |
| WO | 2013184755 A2 | 12/2013 |

N-ARYLAMIDINE-SUBSTITUTED TRIFLUOROETHYL SULFIDE DERIVATIVES AS ACARICIDES AND INSECTICIDES

CROSS REFERENCE TO RELATED APPLICATIONS

This application is a divisional application of U.S. application Ser. No. 14/366,715 (filed Jun. 19, 2014), which is a § 371 National Stage Application of PCT/EP2012/075269 (filed Dec. 12, 2012), which claims priority to EP 11194855.0 (filed Dec. 21, 2011), the contents of each of which are incorporated herein by reference.

BACKGROUND

Field of the Invention

The present invention relates to novel N-arylamidine-substituted trifluoroethyl sulfide derivatives, to their use as acaricides and insecticides for controlling animal pests and to processes and intermediates for their preparation.

Description of Related Art

Various substituted N-arylamidines and their insecticidal and acaricidal action have already been described in the literature in WO 2007/131680.

On application, the active compounds already known from the publications mentioned above have disadvantages, be it that they may have no or else only insufficient insecticidal and/or acaricidal activity against animal pests, in particular at relatively low application rates.

SUMMARY

Accordingly, it is an object of the present invention to provide corresponding N-arylamidine-substituted trifluoroethyl sulfide derivatives which can be employed as insecticides and/or acaricides with satisfactory insecticidal and/or acaricidal activity against animal pests, in particular at relatively low application rates, with high selectivity and improved compatibility in crops of useful plants.

The present invention now provides novel compounds of the formula (I)

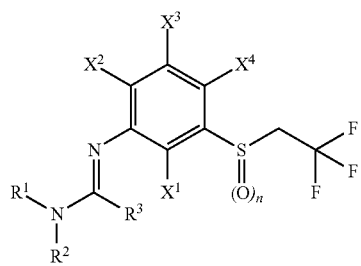

(I)

in which n represents the number 0, 1 or 2, $X^1$, $X^2$, $X^3$, $X^4$ independently of one another represent hydrogen, halogen, hydroxy, amino, OCN, SCN, $SF_5$, trialkylsilyl, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, hydroxycarbonylalkoxy, alkoxycarbonylalkoxy, alkoxyalkoxy, alkylhydroxyimino, alkoxyimino, alkylalkoxyimino, haloalkylalkoxyimino, alkylthio, haloalkylthio, alkoxyalkylthio, alkylthioalkyl, alkylsulfinyl, haloalkylsulfinyl, alkoxyalkylsulfinyl, alkylsulfinylalkyl, alkylsulfonyl, haloalkylsulfonyl, alkoxyalkylsulfonyl, alkylsulfonylalkyl, alkylsulfonyloxy, alkylcarbonyl, haloalkylcarbonyl, carboxyl, alkylcarbonyloxy, alkoxycarbonyl, haloalkoxycarbonyl, alkoxycarbonylalkyl, aminocarbonyl, alkylaminocarbonyl, dialkylaminocarbonyl, alkenylaminocarbonyl, dialkenylaminocarbonyl, cycloalkylaminocarbonyl, alkylsulfonylamino, aminosulfonyl, alkylaminosulfonyl, dialkylaminosulfonyl, alkylsulfoximino, aminothiocarbonyl, alkylaminothiocarbonyl, dialkylaminothiocarbonyl, or represent optionally substituted phenylalkyl, phenoxy, phenylalkyloxy, phenoxyalkyl, phenylthio, phenylthioalkyl, phenylsulfinyl, phenylsulfonyl, hetarylalkyl, hetaryloxy, hetarylalkyloxy, hetarylthio, hetarylsulfinyl, hetarylsulfonyl, or represent optionally substituted saturated or unsaturated cycloalkylalkyl, cycloalkyloxy, cycloalkylalkoxy, cycloalkylthio, cycloalkylalkylthio, cycloalkylsulfinyl, cycloalkylalkylsulfinyl, cycloalkylsulfonyl, cycloalkylalkylsulfonyl, or represent $NR^4R^5$, where $R^4$ and $R^5$ independently of one another represent hydrogen, cyano, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl, alkoxycarbonyl, or $R^4$ and $R^5$ together with the nitrogen atom to which they are attached may form an optionally substituted saturated or unsaturated five- to eight-membered ring which is optionally interrupted by heteroatoms from the group consisting of O, S and N, or represent a 3- to 6-membered saturated, partially saturated or aromatic ring which may optionally contain one to three heteroatoms from the group consisting of O, S and N and which is optionally mono- or polysubstituted by identical or different substituents from the group consisting of halogen, cyano, nitro, hydroxy, amino, carboxy, alkyl, haloalkyl, alkenyl, haloalkenyl, alkynyl, alkoxy, haloalkoxy, alkylthio, alkylsulfinyl, alkylsulfonyl, alkylsulfonyloxy, haloalkylthio, haloalkylsulfinyl, haloalkylsulfonyl, alkylamino, dialkylamino, alkylcarbonylamino, alkoxycarbonyl, alkylcarbonyl, alkylcarbonyloxy, aminocarbonyl, alkylaminocarbonyl, dialkylaminocarbonyl, aminothiocarbonyl, alkylaminothiocarbonyl, dialkylaminothiocarbonyl, cycloalkylamino, alkylsulfonylamino, aminosulfonyl, alkylaminosulfonyl and dialkylaminosulfonyl, or by optionally substituted cycloalkyl, cycloalkoxy, cycloalkylalkyl or cycloalkylalkoxy which are optionally interrupted by heteroatoms from the group consisting of O, S and N, or $X^2$ and $X^3$ or $X^3$ and $X^4$, form, together with the carbon atoms to which they are attached, a 5- or 6-membered ring which is optionally substituted and optionally interrupted by heteroatoms from the group consisting of O, S, N and CO, $R^3$ represents hydrogen, $(C_2$-$C_8)$-alkyl, cyano, haloalkyl, alkoxyalkyl, cyanoalkyl, alkylthioalkyl, alkenyl, haloalkenyl, alkynyl, haloalkynyl, or represents a 3- to 6-membered saturated, partially saturated or aromatic ring which may optionally contain one to three heteroatoms from the group consisting of O, S and N and which is optionally mono- or polysubstituted by identical or different substituents from the group consisting of halogen, cyano, nitro, hydroxy, amino, carboxy, alkyl, haloalkyl, alkenyl, haloalkenyl, alkynyl, alkoxy, haloalkoxy, alkylthio, alkylsulfinyl, alkylsulfonyl, alkylsulfonyloxy, haloalkylthio, haloalkylsulfinyl, haloalkylsulfonyl, alkylamino, dialkylamino, alkylcabonylamino, alkoxycarbonyl, alkylcarbonyl, alkylcarbonyloxy, aminocarbonyl, alkylaminocarbonyl, dialkylaminocarbonyl, aminothiocarbonyl, alkylaminothiocarbonyl, dialkylaminothiocarbonyl, cycloalkylamino, alkylsulfonylamino, aminosulfonyl, alkylaminosulfonyl and dialkylaminosulfonyl, or by optionally substituted cycloalkyl, cycloalkoxy, cycloalkylalkyl or cycloalkylalkoxy which are optionally interrupted by heteroatoms from the group consisting of O, S and N, $R^1$ and $R^2$ independently of one another represent hydrogen, cyano, alkyl, haloalkyl, alkoxy, cyanoalkyl, hydroxyalkyl, alkoxyalkyl, alkylthioalkyl, alkenyl, haloalkenyl, cyanoalkenyl, alkynyl, haloalkynyl, cyanoalkynyl, represent optionally substituted alkylcarbonyl, alkoxycarbonyl, arylcarbonyl, hetarylcarbonyl, aryloxycarbonyl, hetaryloxycarbonyl, alkylsulfinyl, haloalkylsulfinyl, arylsulfinyl, arylalkylsulfinyl, hetarylsulfinyl, hetarylalkylsulfinyl, alkylsulfonyl, haloalkylsulfonyl, arylsulfonyl, arylalkylsulfonyl, hetarylsulfonyl, hetarylalkylsulfonyl, or represent a 3- to 6-membered saturated, partially saturated or aromatic ring which may optionally contain one to three heteroatoms from the group consisting of O, S and N, which may optionally be interrupted once or twice by C=O, SO or $SO_2$ and which is optionally mono- or polysubstituted by identical or different substituents from the group consisting of halogen, cyano, nitro, hydroxy, amino, carboxy, alkyl, haloalkyl, alkenyl, haloalkenyl, alkynyl, alkoxy, haloalkoxy, alkylthio, alkylsulfinyl, alkylsulfonyl, alkylsulfonyloxy, haloalkylthio, haloalkylsulfinyl, haloalkylsulfonyl, alkylamino, dialkylamino, alkylcarbonylamino, alkoxycarbonyl, alkylcarbonyl, alkylcarbonyloxy, aminocarbonyl, alkylaminocarbonyl, dialkylaminocarbonyl, aminothiocarbonyl, alkylaminothiocarbonyl, dialkylaminothiocarbonyl, cycloalkylamino, alkylsulfonylamino, aminosulfonyl, alkylaminosulfonyl and dialkylaminosulfonyl, or by optionally substituted cycloalkyl, cycloalkoxy, cycloalkylalkyl or cycloalkylalkoxy which are optionally interrupted by heteroatoms from the group consisting of O, S and N, or represent $—(CH_2)_m—R^6$, $—O—(CH_2)_m—R^6$, $—(CH_2)_m—O—R^6$, where $R^6$ represents a 3- to 6-membered saturated, partially saturated or aromatic ring which may optionally contain one to three heteroatoms from the group consisting of O, S and N, which may optionally be interrupted once or twice by C=O and which is optionally mono- or polysubstituted by identical or different substituents from the group consisting of halogen, cyano, nitro, hydroxy, amino, carboxy, alkyl, haloalkyl, alkenyl, haloalkenyl, alkynyl, alkoxy, haloalkoxy, alkylthio, alkylsulfinyl, alkylsulfonyl, alkylsulfonyloxy, haloalkylthio, haloalkylsulfinyl, haloalkylsulfonyl, alkylamino, dialkylamino, alkylcarbonylamino, alkoxycarbonyl, alkylcarbonyl, alkylcarbonyloxy, aminocarbonyl, alkylaminocarbonyl, dialkylaminocarbonyl, aminothiocarbonyl, alkylaminothiocarbonyl, dialkylaminothiocarbonyl, cycloalkylamino, alkylsulfonylamino, aminosulfonyl, alkylaminosulfonyl and dialkylaminosulfonyl, or by optionally substituted cycloalkyl, cycloalkoxy, cycloalkylalkyl or cycloalkylalkoxy which are optionally interrupted by heteroatoms from the group consisting of O, S and N, where m represents the number 1, 2, 3 or 4, or $R^1$ and $R^2$ may also form, together with the nitrogen atom to which they are attached, a saturated or unsaturated and optionally substituted 4- to 8-membered ring which may optionally contain one or more further heteroatoms from the group consisting of sulfur, oxygen (where oxygen atoms must not be directly adjacent to one another) and nitrogen and/or optionally at least one carbonyl group, or $R^1$ and $R^3$ may also form, together with the atoms to which they are attached, a saturated or unsaturated and optionally substituted 4- to 8-membered ring which may contain one or more further heteroatoms from the group consisting of sulfur, oxygen (where oxygen atoms must not be directly adjacent to one another) and nitrogen and/or optionally at least one carbonyl group, If appropriate, the compounds of the formula (I) may be present in various polymorphic forms or as mixtures of different polymorphic forms. Both the pure polymorphs and the polymorph mixtures are provided by the invention and can be used according to the invention.

The compounds of the formula (I) optionally comprise diastereomers or enantiomers and also rotamers, tautomers and salts of the compounds of the formula (I).

DETAILED DESCRIPTION OF A PREFERRED EMBODIMENT

The compounds of the formula (I) include in particular E/Z diastereomers such as, for example,

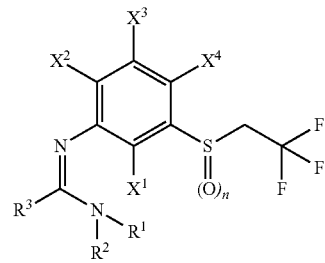

A general definition of the compounds according to the invention is provided by the formula (I). Preferred substituents or ranges of the radicals given under the formulae shown above and below are defined, where n preferably represents the number 0, 1 or 2, $X^1$, $X^2$, $X^3$, $X^4$ independently of one another preferably represent hydrogen, halogen, hydroxy, amino, OCN, SCN, $SF_5$, tri-$(C_1$-$C_6)$-alkylsilyl, $(C_1$-$C_6)$-alkyl, $(C_1$-$C_6)$-haloalkyl, $(C_1$-$C_6)$-cyanoalkyl, $(C_1$-$C_6)$-hydroxyalkyl, hydroxycarbonyl-$(C_1$-$C_4)$-alkoxy, $(C_1$-$C_6)$-alkoxycarbonyl-$(C_1$-$C_4)$-alkyl, $(C_1$-$C_6)$-alkoxy-$(C_1$-$C_6)$-alkyl, $(C_2$-$C_6)$-alkenyl, $(C_2$-$C_6)$-haloalkenyl, $(C_2$-$C_6)$-cyanoalkenyl, $(C_2$-$C_6)$-alkynyl, $(C_2$-$C_6)$-haloalkynyl, $(C_2$-$C_6)$-cyanoalkynyl, $(C_1$-$C_6)$-alkoxy, $(C_1$-$C_6)$-haloalkoxy, $(C_1$-$C_6)$-cyanoalkoxy, $(C_1$-$C_7)$-alkoxycarbonyl-$(C_1$-$C_6)$-alkoxy, $(C_1$-$C_6)$-alkoxy-$(C_1$-$C_6)$-alkoxy, $(C_1$-$C_7)$-alkylhydroxyimino, $(C_1$-$C_7)$-alkoxyimino, $(C_1$-$C_6)$-alkyl-$(C_1$-$C_7)$-alkoxyimino, $(C_1$-$C_6)$-haloalkyl-$(C_1$-$C_7)$-alkoxyimino, $(C_1$-$C_6)$-haloalkylthio, $(C_1$-$C_6)$-alkoxy-$(C_1$-$C_6)$-alkylthio, $(C_1$-$C_6)$-alkylthio-$(C_1$-$C_6)$-alkyl, $(C_1$-$C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_7)$-alkylcarbonyl, $(C_1-C_7)$-haloalkylcarbonyl, carboxyl, $(C_1-C_7)$-alkylcarbonyloxy, $(C_1-C_7)$-alkoxycarbonyl, $(C_1-C_7)$-haloalkoxycarbonyl, $(C_1-C_7)$-alkoxycarbonyl-$(C_1-C_6)$-alkyl, aminocarbonyl, $(C_1-C_7)$-alkylaminocarbonyl, di-$(C_1-C_7)$-alkylaminocarbonyl, $(C_1-C_7)$-alkenylaminocarbonyl, di-$(C_1-C_7)$-alkenylaminocarbonyl, $(C_3-C_8)$-cycloalkylaminocarbonyl, $(C_1-C_6)$-alkylsulfonylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, or represent phenyl-$(C_1-C_6)$-alkyl, phenoxy, phenyl-$(C_1-C_4)$-alkyloxy, phenoxy-$(C_1-C_4)$-alkyl, phenylthio, phenylthio-$(C_1-C_4)$-alkyl, phenylsulfinyl, phenylsulfonyl, hetaryl-$(C_1-C_6)$-alkyl, hetaryloxy, hetaryl-$(C_1-C_4)$-alkyloxy, hetarylthio, hetarylsulfinyl, hetarylsulfonyl, optionally saturated or unsaturated $(C_3-C_8)$-cycloalkyl-$(C_1-C_6)$-alkyl, $(C_3-C_8)$-cycloalkyloxy, $(C_3-C_8)$-cycloalkyl-$(C_1-C_6)$-alkoxy, $(C_3-C_8)$-cycloalkylthio, $(C_3-C_8)$-cycloalkyl-$(C_1-C_6)$-alkylthio, $(C_3-C_8)$-cycloalkylsulfinyl, $(C_3-C_8)$-cycloalkyl-$(C_1-C_6)$-alkylsulfinyl, $(C_3-C_8)$-cycloalkylsulfonyl, $(C_3-C_8)$-cycloalkyl-$(C_1-C_6)$-alkylsulfonyl, substituted by optionally saturated or unsaturated $(C_3-C_8)$-cycloalkyl, $(C_3-C_8)$-cycloalkoxy, $(C_3-C_8)$-cycloalkyl-$(C_1-C_6)$-alkyl or $(C_3-C_8)$-cycloalkyl-$(C_1-C_6)$-alkoxy optionally substituted by identical or different substituents from the group consisting of halogen, cyano, nitro, hydroxy, amino, carboxy, $(C_1-C_6)$-alkyl, $(C_1-C_6)$-haloalkyl, $(C_2-C_8)$-alkenyl, $(C_2-C_8)$-haloalkenyl, $(C_2-C_6)$-alkynyl, $(C_1-C_6)$-alkoxy, $(C_1-C_6)$-haloalkoxy, $(C_1-C_6)$-alkylthio, $(C_1-C_6)$-alkylsulfinyl, $(C_1-C_6)$-alkylsulfonyl, $(C_1-C_6)$-alkylsulfonyloxy, $(C_1-C_6)$-haloalkylthio, $(C_1-C_6)$-haloalkylsulfinyl, $(C_1-C_6)$-haloalkylsulfonyl, $(C_1-C_6)$-alkylamino, di-$(C_1-C_6)$-alkylamino, $(C_1-C_7)$-alkylcarbonylamino, $(C_1-C_7)$-alkoxycarbonyl, $(C_1-C_7)$-alkylcarbonyl, $(C_1-C_7)$-alkylcarbonyloxy, aminocarbonyl, $(C_1-C_6)$-alkylaminocarbonyl, di-$(C_1-C_6)$-alkylaminocarbonyl, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylsulfonylamino, aminosulfonyl, $(C_1-C_6)$-alkylaminosulfonyl and di-$(C_1-C_6)$-alkylaminosulfonyl and optionally interrupted by one or two heteroatoms from the group consisting of O, S and N, or represent $NR^4R^5$, where $R^4$ and $R^5$ independently of one another represent hydrogen, cyano, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-alkyl-$(C_1-C_6)$-thioalkyl, $(C_2-C_8)$-alkenyl, $(C_2-C_8)$-haloalkenyl, $(C_2-C_8)$-cyanoalkenyl, $(C_2-C_8)$-alkynyl, $(C_2-C_8)$-haloalkynyl, $(C_2-C_8)$-cyanoalkynyl, acyl, $(C_1-C_7)$-alkoxycarbonyl, or $R^4$ and $R^5$ together with the nitrogen atom to which they are attached may form a saturated or unsaturated five- to seven-membered ring which is optionally substituted by identical or different substituents from the group consisting of halogen, cyano, hydroxy, amino, $(C_1-C_6)$-alkyl, $(C_1-C_6)$-haloalkyl, $(C_1-C_6)$-alkoxy, $(C_1-C_6)$-haloalkoxy or by $(C_3-C_8)$-cycloalkyl or $(C_3-C_8)$-cycloalkyl-$(C_1-C_6)$-alkyl optionally substituted by identical or different substituents from the group consisting of halogen, cyano, $(C_1-C_6)$-alkyl, $(C_1-C_6)$-alkoxy, $(C_1-C_6)$-haloalkyl and optionally interrupted by heteroatoms from the group consisting of O, S and N and is optionally interrupted by heteroatoms from the group consisting of O, S and N, or represent $(C_3-C_8)$-cycloalkyl, $(C_3-C_8)$-cycloalkoxy, $(C_3-C_8)$-cycloalkylthio, $(C_3-C_8)$-cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl which is optionally mono- or polysubstituted by identical or different substituents from the group consisting of halogen, cyano, nitro, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-alkylsulfinyl, $(C_1-C_6)$-alkylsulfonyl, $(C_1-C_6)$-alkylsulfonyloxy, $(C_1-C_6)$-haloalkylthio, $(C_1-C_6)$-haloalkylsulfinyl, $(C_1-C_6)$-haloalkylsulfonyl, or by $(C_3-C_8)$-cycloalkyl, $(C_3-C_8)$-cycloalkoxy, $(C_3-C_8)$-cycloalkyl-$(C_1-C_6)$-alkyl or $(C_3-C_8)$-cycloalkyl-$(C_1-C_6)$-alkoxy, optionally substituted by halogen, cyano, $(C_1-C_6)$-alkyl, $(C_1-C_6)$-alkoxy, $(C_1-C_6)$-haloalkyl and optionally interrupted by heteroatoms from the group consisting of O, S and N, or $X^2$ and $X^3$ or $X^3$ and $X^4$ may form the following 5- or 6-membered rings which are optionally substituted by identical or different substituents from the group consisting of halogen, cyano, $(C_1-C_6)$-alkyl, $(C_3-C_8)$-cycloalkyl, $(C_1-C_6)$-haloalkyl, $(C_3-C_8)$-halocycloalkyl, $(C_1-C_6)$-alkoxy, $(C_1-C_6)$-haloalkoxy, or $X^2$ and $X^3$ or $X^3$ and $X^4$ may form the following fused rings which are optionally mono- or polysubstituted by identical or different substituents, where the substituents independently of one another may be selected from the group consisting of hydrogen, halogen, cyano, $(C_1-C_6)$-alkyl, $(C_3-C_8)$-cycloalkyl, $(C_1-C_6)$-haloalkyl, $(C_3-C_8)$-halocycloalkyl, $(C_1-C_6)$-alkoxy, $(C_1-C_6)$-haloalkoxy, $(C_1-C_6)$-alkoxy-$(C_1-C_6)$-alkyl, $(C_1-C_6)$-alkylthio, $(C_1-C_6)$-alkylsulfonyl, amino, $(C_1-C_6)$-alkylamino, di-$(C_1-C_6)$-alkylamino and $(C_3-C_8)$-cycloalkylamino,

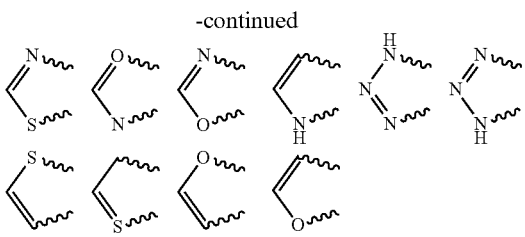

R³ preferably represents hydrogen, (C₂-C₆)-alkyl, cyano, (C₁-C₆)-haloalkyl, (C₁-C₆)-alkoxy-(C₁-C₆)-alkyl, (C₁-C₆)-cyanoalkyl, (C₁-C₆)-alkylthio-(C₁-C₆)-alkyl, (C₂-C₆)-alkenyl, (C₂-C₆)-haloalkenyl, (C₂-C₆)-alkynyl, (C₂-C₆)-haloalkynyl, or represents a 3- to 6-membered saturated, partially saturated or aromatic ring which may optionally contain one to three heteroatoms from the group consisting of O, S and N and which is optionally mono- or polysubstituted by identical or different substituents from the group consisting of halogen, cyano, nitro, hydroxy, amino, carboxy, (C₁-C₆)-alkyl, (C₁-C₆)-haloalkyl, (C₂-C₆)-alkenyl, (C₂-C₆)-haloalkenyl, (C₂-C₆)-alkynyl, (C₁-C₆)-alkoxy, (C₁-C₆)-haloalkoxy, (C₁-C₆)-alkylthio, (C₁-C₆)-alkylsulfinyl, (C₁-C₆)-alkylsulfonyl, (C₁-C₆)-alkylsulfonyloxy, (C₁-C₆)-haloalkylthio, (C₁-C₆)-haloalkylsulfinyl, (C₁-C₆)-haloalkylsulfonyl, (C₁-C₆)-alkylamino, di-(C₁-C₆)-alkylamino, (C₁-C₇)-alkylcarbonylamino, (C₁-C₇)-alkoxycarbonyl, (C₁-C₇)-alkylcarbonyl, (C₁-C₇)-alkylcarbonyloxy, aminocarbonyl, (C₁-C₇)-arylaminocarbonyl, di-(C₁-C₆)alkyl-aminocarbonyl, aminothiocarbonyl, (C₁-C₆)-alkylaminothiocarbonyl, di-(C₁-C₆)-alkylaminothiocarbonyl, (C₃-C₆)-cycloalkylamino, (C₁-C₆)-alkylsulfonylamino, aminosulfonyl, (C₁-C₆)-alkylaminosulfonyl and di-(C₁-C₆)-alkylaminosulfonyl, or substituted by (C₃-C₈)-cycloalkyl, (C₃-C₈)-cycloalkoxy, (C₃-C₈)-cycloalkyl-(C₁-C₆)-alkyl or (C₃-C₈)-cycloalkyl-(C₁-C₆)-alkoxy optionally substituted by identical or different substituents from the group consisting of halogen, cyano, nitro, hydroxy, amino, carboxy, (C₁-C₆)-alkyl, (C₁-C₆)-haloalkyl, (C₁-C₆)-alkoxy, (C₁-C₆)-haloalkoxy and optionally interrupted by heteroatoms from the group consisting of O, S and N, R¹ and R² independently of one another preferably represent hydrogen, cyano, (C₁-C₆)-alkyl, (C₁-C₆)-haloalkyl, (C₁-C₆)-alkoxy, (C₁-C₆)-cyanoalkyl, (C₁-C₆)-hydroxyalkyl, (C₁-C₆)-alkoxy-(C₁-C₆)-alkyl, (C₁-C₆)-alkylthio-(C₁-C₆)-alkyl, (C₂-C₆)-alkenyl, (C₂-C₆)-haloalkenyl, (C₂-C₆)-cyanoalkenyl, (C₂-C₆)-alkynyl, (C₂-C₆)-haloalkynyl, (C₂-C₆)-cyanoalkynyl, represent (C₁-C₆)-alkylcarbonyl, (C₁-C₇)-alkoxycarbonyl, arylcarbonyl, hetarylcarbonyl, aryloxycarbonyl, hetaryloxycarbonyl, (C₁-C₆)-alkylsulfinyl, (C₁-C₆)-haloalkylsulfinyl, arylsulfinyl, aryl-(C₁-C₆)-alkylsulfinyl, hetarylsulfinyl, hetaryl-(C₁-C₆)-alkylsulfinyl, (C₁-C₆)-alkylsulfonyl, (C₁-C₆)-haloalkylsulfonyl, arylsulfonyl, aryl-(C₁-C₆)-alkylsulfonyl, hetarylsulfonyl, hetaryl-(C₁-C₆)-alkylsulfonyl optionally substituted by identical or different substituents from the group consisting of halogen, cyano, nitro, hydroxy, amino, carboxy, (C₁-C₆)-alkyl, (C₁-C₆)-haloalkyl, (C₂-C₈)-alkenyl, (C₂-C₈)-haloalkenyl, (C₂-C₈)-alkynyl, (C₁-C₆)-alkoxy, (C₁-C₆)-haloalkoxy, (C₁-C₆)-alkylthio, (C₁-C₆)-alkylsulfinyl, (C₁-C₆)-alkylsulfonyl, (C₁-C₆)-alkylamino, di-(C₁-C₆)-alkylamino, or represent a 3- to 6-membered saturated, partially saturated or aromatic ring which may optionally contain one to three heteroatoms from the group consisting of O, S and N, which may optionally be interrupted one or twice by C=O, SO or SO₂ and which is optionally mono- or polysubstituted by identical or different substituents from the group consisting of halogen, cyano, nitro, hydroxy, amino, carboxy, (C₁-C₆)-alkyl, (C₁-C₆)-haloalkyl, (C₂-C₆)-alkenyl, (C₂-C₆)-haloalkenyl, (C₂-C₆)-alkynyl, (C₁-C₆)-alkoxy, (C₁-C₆)-haloalkoxy, (C₁-C₆)-alkylthio, (C₁-C₆)-alkylsulfinyl, (C₁-C₆)-alkylsulfonyl, (C₁-C₆)-alkylsulfonyloxy, (C₁-C₆)-haloalkylthio, (C₁-C₆)-haloalkylsulfinyl, (C₁-C₆)-haloalkylsulfonyl, (C₁-C₆)-alkylamino, di-(C₁-C₆)-alkylamino, (C₁-C₇)-alkylcarbonylamino, (C₁-C₇)-alkoxycarbonyl, (C₁-C₇)-alkylcarbonyl, (C₁-C₇)-alkylcarbonyloxy, aminocarbonyl, (C₁-C₇)-arylaminocarbonyl, di-(C₁-C₇)-alkylaminocarbonyl, aminothiocarbonyl, (C₁-C₇)-alkylaminothiocarbonyl, di-(C₁-C₇)-alkylaminothiocarbonyl, (C₃-C₈)-cycloalkylamino, (C₁-C₆)-alkylsulfonylamino, aminosulfonyl, (C₁-C₆)-alkylaminosulfonyl and di-(C₁-C₆)-alkylaminosulfonyl, or by (C₃-C₈)-cycloalkyl, (C₃-C₈)-cycloalkoxy, (C₃-C₈)-cycloalkyl-(C₁-C₆)-alkyl or (C₃-C₈)-cycloalkyl-(C₁-C₆)-alkoxy optionally interrupted by heteroatoms from the group consisting of O, S and N, or represent —(CH₂)ₘ—R⁶, —O—(CH₂)ₘ—R⁶, —(CH₂)ₘ—O—R⁶, where R⁶ represents a 3- to 6-membered saturated, partially saturated or aromatic ring which may optionally contain one to three heteroatoms from the group consisting of O, S and N, which may optionally be interrupted once or twice by C=O and which is optionally mono- or polysubstituted by identical or different substituents from the group consisting of halogen, cyano, nitro, hydroxy, amino, carboxy, (C₁-C₆)-alkyl, (C₁-C₆)-haloalkyl, (C₂-C₆)-alkenyl, (C₂-C₆)-haloalkenyl, (C₂-C₆)-alkynyl, (C₁-C₆)-alkoxy, (C₁-C₆)-haloalkoxy, (C₁-C₆)-alkylthio, (C₁-C₆)-alkylsulfinyl, (C₁-C₆)-alkylsulfonyl, (C₁-C₆)-alkylsulfonyloxy, (C₁-C₆)-haloalkylthio, (C₁-C₆)-haloalkylsulfinyl, (C₁-C₆)-haloalkylsulfonyl, (C₁-C₆)-alkylamino, di-(C₁-C₆)alkylamino, (C₁-C₇)-alkylcabonylamino, (C₁-C₇)-alkoxycarbonyl, (C₁-C₇)-alkylcarbonyl, (C₁-C₇)-alkylcarbonyloxy, aminocarbonyl, (C₁-C₇)-alkylaminocarbonyl, di-(C₁-C₇)-alkylaminocarbonyl, aminothiocarbonyl, (C₁-C₇)-alkylaminothiocarbonyl, di-(C₁-C₇)alkylaminothiocarbonyl, (C₃-C₈)-cycloalkylamino, (C₁-C₆)-alkylsulfonylamino, aminosulfonyl, (C₁-C₆)-alkylaminosulfonyl or di-(C₁-C₆)-alkylaminosulfonyl, or by identical or different substituents from the group consisting of (C₃-C₈)-cycloalkyl, (C₃-C₈)-cycloalkoxy, (C₃-C₈)-cycloalkyl-(C₁-C₆)-alkyl and (C₃-C₈)-cycloalkyl-(C₁-C₆)-alkoxy optionally substituted by halogen, cyano, nitro, hydroxy, amino, carboxy, (C₁-C₆)-alkyl, (C₁-C₆)-haloalkyl, (C₂-C₈)-alkenyl, (C₂-C₈)-haloalkenyl, (C₂-C₈)-alkynyl, (C₁-C₆)-alkoxy, (C₁-C₆)-haloalkoxy, (C₁-C₆)-alkylthio, (C₁-C₆)-alkylsulfinyl, (C₁-C₆)-alkylsulfonyl, (C₁-C₆)-alkylsulfonyloxy, (C₁-C₆)-haloalkylthio, (C₁-C₆)-haloalkylsulfinyl, (C₁-C₆)-haloalkylsulfonyl, (C₁-C₆)-alkylamino, di-(C₁-C₆)-alkylamino, (C₁-C₇)-alkylcabonylamino, (C₁-C₇)-alkoxycarbonyl, (C₁-C₇)-alkylcarbonyl, (C₁-C₇)- alkylcarbonyloxy, aminocarbonyl, $(C_1-C_6)$-alkylaminocarbonyl, di-$(C_1-C_6)$-alkylaminocarbonyl, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylsulfonylamino, aminosulfonyl, $(C_1-C_6)$-alkylaminosulfonyl or di-$(C_1-C_6)$-alkylaminosulfonyl and optionally interrupted by heteroatoms from the group consisting of O, S and N, where m represents the number 1, 2 or 3, or $R^1$ and $R^2$ together with the atoms to which they are attached may form a saturated or unsaturated 4- to 8-membered ring which is optionally mono- or polysubstituted by $(C_1-C_4)$-alkyl, $(C_1-C_4)$-alkoxy, halogen, $(C_1-C_4)$-haloalkyl and which may optionally contain one or two further heteroatoms from the group consisting of sulfur, oxygen and nitrogen (where oxygen atoms must not be directly adjacent to one another) and/or at least one carbonyl group, $R^1$ and $R^3$ together with the atoms to which they are attached may form a 4- to 8-membered saturated or unsaturated ring which is optionally mono- or polysubstituted by identical or different substituents from the group consisting of $(C_1-C_4)$-alkyl, $(C_1-C_4)$-alkoxy, halogen, $(C_1-C_4)$-haloalkyl, cyano, $(C_3-C_6)$-cycloalkyl, $(C_3-C_6)$-halocycloalkyl, $(C_3-C_6)$-cyanocycloalkyl, $(C_1-C_2)$-alkyl-$(C_3-C_6)$-cycloalkyl $(C_2-C_4)$-alkanediyl, $(C_2-C_4)$-alkenediyl, butanedienyl (where alkanediyl, alkenediyl and butanedienyl may optionally be substituted by $(C_1-C_4)$-alkyl, $(C_1-C_4)$-alkoxy, halogen, $(C_1-C_4)$-haloalkyl and/or may optionally be interrupted by at least one oxygen or/and nitrogen atom) and which may optionally contain one or two further heteroatoms from the group consisting of sulfur, oxygen and nitrogen (where oxygen atoms must not be directly adjacent to one another) and/or at least one carbonyl group, A general definition of the compounds according to the invention is provided by the formula (I). Particularly preferred substituents or ranges of the radicals given under the formulae shown above and below are defined, where n particularly preferably represents the number 0 or 1, $X^1$, $X^2$, $X^3$, $X^4$ independently of one another particularly preferably represent hydrogen, fluorine, chlorine, bromine, iodine, $(C_1-C_4)$-alkyl, $(C_1-C_4)$-haloalkyl, $(C_2-C_4)$-alkenyl, $(C_2-C_4)$-alkynyl, $(C_1-C_4)$-alkoxy, $(C_1-C_4)$-haloalkoxy, aminothiocarbonyl, or represent phenyl-$(C_1-C_4)$-alkyl, phenoxy, hetaryl-$(C_1-C_4)$-alkyl, hetaryloxy, optionally saturated or unsaturated $(C_3-C_6)$-cycloalkyl-$(C_1-C_4)$-alkyl, $(C_3-C_6)$-cycloalkyloxy, $(C_3-C_6)$-cycloalkyl-$(C_1-C_4)$-alkoxy, optionally mono- or disubstituted by identical or different substituents from the group consisting of fluorine, chlorine, bromine, cyano, nitro, $(C_1-C_4)$-alkyl, $(C_1-C_4)$-haloalkyl, $(C_1-C_4)$-alkoxy, $(C_1-C_4)$-haloalkoxy or by optionally saturated or unsaturated $(C_3-C_6)$-cycloalkyl which is optionally interrupted by a heteroatom from the group consisting of O, S and N, or represent $(C_3-C_6)$-cycloalkyl, phenyl, pyridyl, pyrimidyl, pyridazinyl, pyrazinyl, triazinyl, thiazolyl, thiadiazolyl, oxazolyl, oxadiazolyl, pyrazolyl, triazolyl or tetrazolyl which is optionally mono- or disubstituted by identical or different substituents from the group consisting of fluorine, chlorine, bromine, cyano, nitro, $(C_1-C_4)$-alkyl, $(C_1-C_4)$-haloalkyl, $(C_1-C_4)$-alkoxy, $(C_1-C_4)$-haloalkoxy, $(C_3-C_6)$-cycloalkyl, or $X^2$ and $X^3$ or $X^3$ and $X^4$ may form the following 5- or 6-membered ring which are optionally mono- to tetrasubstituted by fluorine or $(C_1-C_4)$-alkyl,

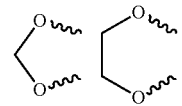

or $X^2$ and $X^3$ or $X^3$ and $X^4$ may form the fused rings below which are optionally monosubstituted or two by identical or different substituents, where the substituents independently of one another may be selected from the group consisting of hydrogen, fluorine, chlorine, bromine, cyano, $(C_1-C_4)$-alkyl, $(C_3-C_6)$-cycloalkyl, $(C_1-C_4)$-haloalkyl, $(C_1-C_4)$-alkoxy, $(C_1-C_4)$-haloalkoxy,

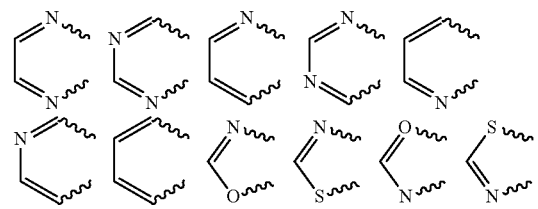

$R^3$ particularly preferably represents hydrogen, $(C_2-C_4)$-alkyl, cyano, $(C_1-C_4)$-haloalkyl, $(C_1-C_4)$-alkoxy-$(C_1-C_4)$-alkyl, $(C_1-C_4)$-cyanoalkyl, or represents a 3- to 6-membered saturated, partially saturated or aromatic ring which may optionally contain one to two heteroatoms from the group consisting of O, S and N and which is optionally mono- or trisubstituted by identical or different substituents from the group consisting of fluorine, chlorine, bromine, iodine, cyano, nitro, $(C_1-C_4)$-alkyl, $(C_1-C_4)$-haloalkyl, $(C_2-C_4)$-alkenyl, $(C_2-C_4)$-alkynyl, $(C_1-C_4)$-alkoxy, $(C_1-C_4)$-haloalkoxy, or substituted by $(C_3-C_6)$-cycloalkyl, $R^1$ and $R^2$ independently of one another particularly preferably represent hydrogen, cyano, $(C_1-C_4)$-alkyl, $(C_1-C_4)$-haloalkyl, $(C_1-C_4)$-alkoxy, $(C_1-C_4)$-cyanoalkyl, $(C_1-C_4)$-hydroxyalkyl, $(C_1-C_4)$-alkoxy-$(C_1-C_4)$-alkyl, $(C_2-C_4)$-alkenyl, $(C_2-C_4)$-alkynyl, represent $(C_1-C_4)$-alkylcarbonyl, $(C_1-C_5)$-alkoxycarbonyl, arylcarbonyl, thiophenylcarbonyl, pyridylcarbonyl, pyrimidylcarbonyl, thiazolylcarbonyl, pyrazolylcarbonyl, $(C_1-C_4)$-alkylsulfinyl, $(C_1-C_4)$-haloalkylsulfinyl, arylsulfinyl, aryl-$(C_1-C_4)$-alkylsulfinyl, hetarylsulfinyl, hetaryl-$(C_1-C_4)$-alkylsulfinyl, $(C_1-C_4)$-alkylsulfonyl, $(C_1-C_4)$-haloalkylsulfonyl, arylsulfonyl, aryl-$(C_1-C_4)$-alkylsulfonyl, hetarylsulfonyl, hetaryl-$(C_1-C_4)$-alkylsulfonyl optionally mono- to trisubstituted independently of one another by substituents from the group consisting of fluorine, chlorine, bromine, cyano, nitro, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_1-C_4)$-alkoxy, $(C_1-C_4)$-haloalkoxy, $(C_1-C_4)$-alkylthio, $(C_1-C_4)$-alkylsulfinyl, $(C_1-C_4)$-alkylsulfonyl, $(C_1-C_4)$-alkylamino, di-$(C_1-C_4)$-alkylamino, or represent a 3- to 6-membered saturated or aromatic ring which may optionally contain one to two heteroatoms from the group consisting of O, S and N, which may optionally be interrupted once or twice by C=O and which is optionally mono- or trisubstituted by identical or different substituents from the group consisting of fluorine, chlorine, bromine, cyano, nitro, $(C_1-C_4)$-alkyl, $(C_1-C_4)$-haloalkyl, $(C_2-C_4)$-alkenyl, $(C_2-C_4)$-alkynyl, $(C_1-C_4)$-alkoxy, $(C_1-C_4)$-haloalkoxy or $(C_3-C_6)$-cycloalkyl, or represent —$(CH_2)_m$—$R^6$, —$(CH_2)_m$—O—$R^6$, where $R^6$ represents a 3- to 6-membered saturated, partially saturated or aromatic ring which may optionally contain one to two heteroatoms from the group consisting of O, S and N, which may optionally be interrupted once or twice by C=O and which is optionally mono- or trisubstituted by identical or different substituents from the group consisting of fluorine, chlorine, bromine, cyano, nitro, $(C_1-C_4)$-alkyl, $(C_1-C_4)$-haloalkyl, $(C_2-C_4)$-alkenyl, $(C_2-C_4)$-alkynyl, $(C_1-C_4)$-alkoxy, $(C_1-C_4)$-haloalkoxy or $(C_3-C_6)$-cycloalkyl, where m represents the number 1 or 2, or $R^1$ and $R^2$ together with the nitrogen atom to which they are attached may form a saturated or unsaturated 3- to 6-membered ring which is optionally mono- or tetrasubstituted by fluorine, chlorine, $(C_1-C_4)$-alkyl, $(C_1-C_4)$-alkoxy, $(C_1-C_4)$-haloalkyl and which may optionally contain a further heteroatom from the group consisting of sulfur, oxygen and nitrogen and/or at least one carbonyl group, $R^1$ and $R^3$ together with the atoms to which they are attached may form a saturated or unsaturated 5- to 6-membered ring which is optionally mono- or polysubstituted by methyl, ethyl, methoxy, ethoxy, fluorine, chlorine, trifluoromethyl, cyclopropyl, cyano, chlorocyclopropyl, fluorocyclopropyl, cyanocyclopropyl, methylcyclopropyl, $(C_2-C_4)$-alkanediyl, $(C_2-C_4)$-alkenediyl, butanedienyl (where butanedienyl may optionally be mono- or disubstituted by methyl, fluorine, chlorine, bromine, methoxy or trifluoromethyl and/or may optionally be interrupted by at least one oxygen or/and nitrogen atom) and which may optionally contain a further sulfur or oxygen or nitrogen atom and/or a carbonyl group, A general definition of the compounds according to the invention is provided by the formula (I). Very particularly preferred substituents or ranges of the radicals given under the formulae shown above and below are defined, where n very particularly preferably represents the number 0 or 1, $X^1$ and $X^3$ very particularly preferably represent hydrogen, $X^2$ and $X^4$ very particularly preferably independently of one another represent hydrogen, fluorine, chlorine, bromine, methyl, ethyl, trifluoromethyl, difluoromethyl, difluoromethoxy, trifluoromethoxy, $OCH_2CF_3$, especially preferably, $X^2$ and $X^4$ represent the following combinations $X^2/X^4$: F/F, Cl/Cl, F/Cl, Cl/F, Br/Br, Br/Cl, Cl/Br, Br/F, F/Br, methyl/methyl, methyl/F, F/methyl, methyl/Cl, Cl/methyl, methyl/Br, Br/methyl, ethyl/ethyl, ethyl/F, F/ethyl, ethyl/Cl, Cl/ethyl, ethyl/Br, Br/ethyl, $R^3$ very particularly preferably represents hydrogen, ethyl, propyl, cyano, trifluoromethyl, difluoromethyl, dichloromethyl, chloromethyl, trichloromethyl, difluorochloromethyl, dichlorofluoromethyl, (2,2,2)-trifluoroethyl, 2-chloro-(2,2)-difluoroethyl, (2,2)-dichloro-2-fluoroethyl, (2,2,2)-trichloroethyl, pentafluoroethyl, or represents aryl, especially preferably represents phenyl, $R^1$ very particularly preferably represents hydrogen, methyl, ethyl, propyl, butyl, sec-butyl, isopropyl, tert-butyl, (2,2,2)-trifluoroethyl, (2,2)-difluoromethyl, methoxy, ethoxy, methoxymethyl, methoxyethyl, or represents aryl which is optionally mono- or trisubstituted by identical or different substituents from the group consisting of fluorine, chlorine, bromine, cyano, nitro, methyl, ethyl, trifluoromethyl, vinyl, ethynyl, methoxy, ethoxy, difluoromethoxy, trifluoromethoxy, trifluoroethoxy or cyclopropyl, especially phenyl is explicitly mentioned, which may optionally be substituted by the substituents mentioned under very particularly preferred, or represents —$(CH_2)_m$—$R^6$, where $R^6$ represents aryl which is optionally mono-, di- or trisubstituted by identical or different substituents from the group consisting of fluorine, chlorine, bromine, cyano, nitro, methyl, ethyl, trifluoromethyl, vinyl, ethynyl, methoxy, ethoxy, difluoromethoxy, trifluoromethoxy, trifluoroethoxy or cyclopropyl, where m represents the number 1, especially phenyl is explicitly mentioned for $R^6$, which may optionally be substituted by the substituents mentioned under very particularly preferred, $R^2$ very particularly preferably represents hydrogen, methyl or ethyl, or $R^1$ and $R^2$ together with the nitrogen atom to which they are attached may form a saturated or unsaturated 5- to 6-membered ring which may optionally contain an oxygen atom, especially the following rings are explicitly mentioned,

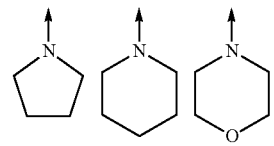

in which the nitrogen atom which is attached to $R^1$ and $R^2$ represents the cycle and the arrow points to the remainder of the molecule, $R^1$ and $R^3$ together with the atoms to which they are attached may form a saturated or unsaturated 5- to 6-membered ring and/or one which is optionally mono- or disubstituted by methyl, ethyl, methoxy, ethoxy, fluorine, chlorine, trifluoromethyl, difluoromethyl, cyano, cyclopropyl, chlorocyclopropyl, fluorocyclopropyl, cyanocyclopropyl, methylcyclopropyl, $(C_3-C_4)$-alkanediyl, $(C_3-C_4)$-alkenediyl, butanedienyl (where butanedienyl may optionally be mono- or disubstituted by methyl, fluorine, chlorine, bromine, methoxy or trifluoromethyl and/or may optionally be interrupted by at least one oxygen or/and nitrogen atom) and which may optionally contain a carbonyl group, especially $R^1$ and $R^3$ together with the atoms to which they are attached represent the following group,

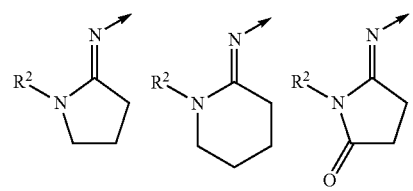

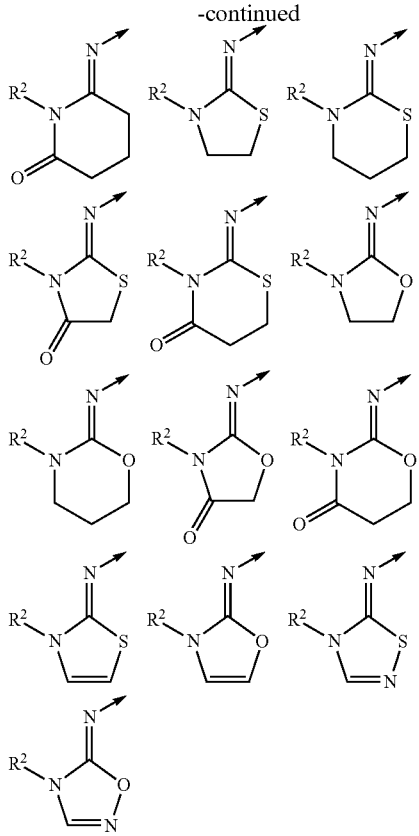

each of which may optionally be mono- or disubstituted by methyl, ethyl, methoxy, ethoxy, fluorine, chlorine, trifluoromethyl, difluoromethyl, cyclopropyl, chlorocyclopropyl, fluorocyclopropyl, cyanocyclopropyl, methylcyclopropyl, where the arrow points to the remainder of the molecule.

A general definition of the compounds according to the invention is provided by the formula (I). Likewise very particularly preferred substituents or ranges of the radicals given under the formulae shown above and below are defined, n very particularly preferably represents the number 0 or 1, $X^1$ and $X^3$ very particularly preferably represent hydrogen, $X^2$ and $X^4$ very particularly preferably independently of one another represent hydrogen, fluorine, chlorine, bromine, methyl, ethyl, trifluoromethyl, difluoromethyl, vinyl, ethynyl, methoxy, ethoxy, difluoromethoxy, trifluoromethoxy, $OCH_2CF_3$, aminothiocarbonyl, or phenylmethyl, phenoxy, pyridylmethyl, pyrimidylmethyl, thiazolylmethyl, pyrazolylmethyl, pyridyloxy, pyrimidyloxy, thiazolyloxy, pyrazolyloxy, cyclopropylmethyl, cyclopropylmethoxy or optionally mono- or disubstituted by identical or different substituents from the group consisting of fluorine, chlorine, bromine, cyano, nitro, methyl, ethyl, trifluoromethyl, difluoromethyl, methoxy, trifloromethoxy, difluoromethoxy or cyclopropyl, or represents $(C_3-C_6)$-cycloalkyl, phenyl, pyridyl, pyrimidyl, pyridazinyl, pyrazinyl, triazinyl, thiazolyl, thiadiazolyl, oxazolyl, oxadiazolyl, pyrazolyl, triazolyl or tetrazolyl which is optionally mono- or disubstituted by identical or different substituents from the group consisting of fluorine, chlorine, bromine, cyano, nitro, methyl, ethyl, trifluoromethyl, difluoromethyl, methoxy, trifluoromethoxy or by cyclopropyl, especially preferably, $X^2$ and $X^4$ represent the following combinations $X^2/X^4$: F/F, Cl/Cl, F/Cl, Cl/F, Br/Br, Br/Cl, Cl/Br, Br/F, F/Br, methyl/methyl, methyl/F, F/methyl, methyl/Cl, Cl/methyl, methyl/Br, Br/methyl, ethyl/ethyl, ethyl/F, F/ethyl, ethyl/Cl, Cl/ethyl, ethyl/Br, Br/ethyl, methoxy/methyl, methyl/methoxy, methyl/H, ethyl/H, chlorine/H, bromine/H, fluorine/H, methoxy/H, H/chlorine, H/fluorine, H/bromine, H/methyl, H/methoxy, H/ethyl $R^3$ very particularly preferably represents hydrogen, ethyl, propyl, cyano, trifluoromethyl, difluoromethyl, dichloromethyl, trichloromethyl, difluorochloromethyl, dichlorofluoromethyl, (2,2,2)-trifluoroethyl, 2-chloro-(2,2)-difluoroethyl, (2,2)-dichloro-2-fluoroethyl, (2,2,2)-trichloroethyl, pentafluoroethyl, methoxymethyl, methoxyethyl, cyanomethyl, allyl, butenyl, or represents a 3- to 6-membered saturated, partially saturated or aromatic ring which may optionally contain one to three heteroatoms from the group consisting of O, S and N and which may optionally be mono- or disubstituted by identical or different substituents from the group consisting of fluorine, chlorine, bromine, cyano, nitro, methyl, ethyl, trifluoromethyl, vinyl, ethynyl, methoxy, ethoxy, difluoromethoxy, trifluoromethoxy, trifluoroethoxy and cyclopropyl, especially the following rings are explicitly mentioned: cyclopropyl, phenyl, pyridyl, pyrimidyl, thiazolyl, pyrazolyl and thienyl which may optionally be substituted by the substituents mentioned under very particularly preferred, $R^1$ very particularly preferably represents cyano, cyanomethyl, methylcarbonyl, ethylcarbonyl, propylcarbonyl, isopropylcarbonyl, methoxycarbonyl, ethoxycarbonyl, represents arylcarbonyl, pyridylcarbonyl, pyrimidylcarbonyl, thiazolylcarbonyl, pyrazolylcarbonyl, methylsulfinyl, trifluoromethylsulfinyl, methylsulfonyl, trifluoromethylsulfonyl optionally mono- or disubstituted independently of one another by fluorine, chlorine, bromine, cyano, nitro, methyl, trifluoromethyl, allyl, butenyl, methoxy, trifluoromethoxy, methylthio, methylsulfinyl, methylsulfonyl, methylamino, dimethylamino, or represents oxetanyl, thietanyl, trimethylenesulfonyl, trimethylenesulfinyl, oxanyl or thianyl which may optionally be mono- or polysubstituted by identical or different substituents from the group consisting of fluorine, chlorine, bromine, cyano, nitro, methyl, ethyl, trifluoromethyl, vinyl, ethynyl, methoxy, ethoxy, difluoromethoxy, trifluoromethoxy, trifluoroethoxy and cyclopropyl, or represents cyclopropyl, cyclobutyl, cyclopentyl, cyclohexyl which are optionally mono- or polysubstituted by identical or different substituents from the group consisting of fluorine, chlorine, bromine, cyano, nitro, methyl, ethyl, trifluoromethyl, vinyl, ethynyl, methoxy, ethoxy, difluoromethoxy, trifluoromethoxy, trifluoroethoxy and cyclopropyl, $R^2$ very particularly preferably represents hydrogen, methyl or ethyl, or R$^1$ and R$^2$ together with the nitrogen atom to which they are attached may form a saturated or unsaturated 3- to 6-membered ring which is optionally mono-, di-, tri- or tetrasubstituted by methyl, ethyl, methoxy, ethoxy, fluorine, chlorine, bromine, trifluoromethyl, difluoromethyl and which contains one or two further heteroatoms from the group consisting of sulfur and nitrogen, or together with the nitrogen atom to which they are attached may form a saturated or unsaturated 4-membered ring which is optionally mono-, di-, tri- or tetrasubstituted by methyl, ethyl, methoxy, ethoxy, fluorine, chlorine, bromine, trifluoromethyl, difluoromethyl and which optionally contains one further heteroatom from the group consisting of oxygen, sulfur and nitrogen, especially the following rings are explicitly mentioned,

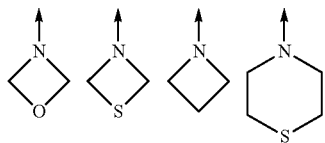

in which the nitrogen atom to which R$^1$ and R$^2$ are attached represent the cycle and the arrow points to the remainder of the molecule, which may optionally be mono- or disubstituted by methyl, ethyl, methoxy, ethoxy, fluorine, chlorine, bromine, trifluoromethyl, difluoromethyl.

A general definition of the compounds according to the invention is provided by the formula (I). Likewise very particularly preferred substituents or ranges of the radicals given under the formulae shown above and below are defined, where n very particularly preferably represents the number 0 or 1, X$^1$ and X$^3$ very particularly preferably represent hydrogen, X$^2$ and X$^4$ very particularly preferably independently of one another represents hydrogen, fluorine, chlorine, bromine, methyl, ethyl, trifluoromethyl, difluoromethyl, vinyl, ethynyl, methoxy, ethoxy, difluoromethoxy, trifluoromethoxy, OCH$_2$CF$_3$, aminothiocarbonyl, or phenylmethyl, phenoxy, pyridylmethyl, pyrimidylmethyl, thiazolylmethyl, pyrazolylmethyl, pyridyloxy, pyrimidyloxy, thiazolyloxy, pyrazolyloxy, cyclopropylmethyl, cyclopropylmethoxy, optionally mono- or disubstituted by identical or different substituents from the group consisting of fluorine, chlorine, bromine, cyano, nitro, methyl, ethyl, trifluoromethyl, difluoromethyl, methoxy, trifloromethoxy, difluoromethoxy or cyclopropyl, or represents (C$_3$-C$_6$)-cycloalkyl, phenyl, pyridyl, pyrimidyl, pyridazinyl, pyrazinyl, triazinyl, thiazolyl, thiadiazolyl, oxazolyl, oxadiazolyl, pyrazolyl, triazolyl or tetrazolyl which is optionally mono- or disubstituted by identical or different substituents from the group consisting of fluorine, chlorine, bromine, cyano, nitro, methyl, ethyl, trifluoromethyl, difluoromethyl, methoxy, trifluoromethoxy or by cyclopropyl, especially preferably, X$^2$ and X$^4$ represent the following combinations X$^2$/X$^4$: F/F, Cl/Cl, F/Cl, Cl/F, Br/Br, Br/Cl, Cl/Br, Br/F, F/Br, methyl/methyl, methyl/F, F/methyl, methyl/Cl, Cl/methyl, methyl/Br, Br/methyl, ethyl/ethyl, ethyl/F, F/ethyl, ethyl/Cl, Cl/ethyl, ethyl/Br, Br/ethyl, methoxy/methyl, methyl/methoxy, methyl/H, ethyl/H, chlorine/H, bromine/H, fluorine/H, methoxy/H, H/chlorine, H/fluorine, H/bromine, H/methyl, H/methoxy, H/ethyl R$^3$ very particularly preferably represents methoxymethyl, methoxyethyl, cyanomethyl, allyl, butenyl, oxolanyl, pentandienyl, butadienyl, or represents cyclopropyl, cyclobutyl, cyclopentyl, cyclohexyl, pyridyl, pyrimidyl, pyrazinyl, pyridazinyl, pyrrolyl, furanyl, thiazolyl, pyrazolyl or thienyl which may optionally be mono- or polysubstituted by identical or different substituents from the group consisting of fluorine, chlorine, bromine, cyano, nitro, methyl, ethyl, trifluoromethyl, vinyl, ethynyl, methoxy, ethoxy, difluoromethoxy, trifluoromethoxy, trifluoroethoxy and cyclopropyl, or represents aryl, in particular phenyl, which is mono- or polysubstituted by identical or different substituents from the group consisting of fluorine, chlorine, bromine, cyano, nitro, methyl, ethyl, trifluoromethyl, vinyl, ethynyl, methoxy, ethoxy, difluoromethoxy, trifluoromethoxy, trifluoroethoxy and cyclopropyl, R$^1$ and R$^2$ very particularly preferably independently of one another represent hydrogen, cyano, methyl, ethyl, propyl, butyl, sec-butyl, isopropyl, tert-butyl, (2,2,2)-trifluoroethyl, (2,2)-difluoromethyl, methoxy, ethoxy, cyanomethyl, methoxymethyl, methoxyethyl, allyl, butenyl, propynyl, methylcarbonyl, ethylcarbonyl, propylcarbonyl, isopropylcarbonyl, methoxycarbonyl, ethoxycarbonyl, represent arylcarbonyl, pyridylcarbonyl, pyrimidylcarbonyl, thiazolylcarbonyl, pyrazolylcarbonyl, methylsulfinyl, trifluoromethylsulfinyl, methylsulfonyl, trifluoromethylsulfonyl optionally mono- or disubstituted independently of one another by fluorine, chlorine, bromine, cyano, nitro, methyl, trifluoromethyl, allyl, butenyl, methoxy, trifluoromethoxy, methylthio, methylsulfinyl, methylsulfonyl, methylamino, dimethylamino, or represent a 3- to 6-membered saturated or aromatic ring which may optionally contain one to two heteroatoms from the group consisting of O, S and N, which may optionally be interrupted once, twice or three times by C═O and which may optionally be mono- or trisubstituted by identical or different substituents from the group consisting of fluorine, chlorine, bromine, cyano, nitro, methyl, ethyl, trifluoromethyl, vinyl, ethynyl, methoxy, ethoxy, difluoromethoxy, trifluoromethoxy, trifluoroethoxy and cyclopropyl, especially the following rings are explicitly mentioned: cyclopropyl, cyclobutyl, cyclopentyl, cyclohexyl, oxetane, phenyl, thienyl and pyridyl which may optionally be substituted by the substituents mentioned under very particularly preferred, or represent —(CH$_2$)$_m$—R$^6$, where R$^6$ represents a 3- to 6-membered saturated, partially saturated or aromatic ring which may optionally contain one to two heteroatoms from the group consisting of O, S and N, may optionally be interrupted once or twice by C═O and which may optionally be mono-, di- or trisubstituted by identical or different substituents from the group consisting of fluorine, chlorine, bromine, cyano, nitro, methyl, ethyl, trifluoromethyl, vinyl, ethynyl, methoxy, ethoxy, difluoromethoxy, trifluoromethoxy, trifluoroethoxy and cyclopropyl, where m represents the number 1, especially the following $R^6$ are explicitly mentioned: cyclopropyl, phenyl and pyridyl which may optionally be substituted by the substituents mentioned under very particularly preferred, or $R^1$ and $R^2$ together with the nitrogen atom to which they are attached may form a saturated or unsaturated 3- to 6-membered ring which is optionally mono-, di-, tri- or tetrasubstituted by methyl, ethyl, methoxy, ethoxy, fluorine, chlorine, bromine, trifluoromethyl, difluoromethyl, which may optionally contain one or two further heteroatoms from the group consisting of sulfur, oxygen and nitrogen (where oxygen atoms must not be directly adjacent to one another) and/or at least one CH2 group is replaced by a carbonyl group, especially the following rings are explicitly mentioned:

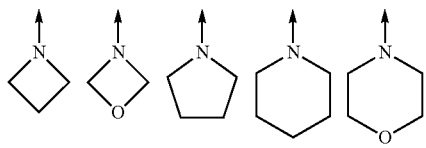

in which the nitrogen atom to which $R^1$ and $R^2$ are attached represent the cycle and the arrow points to the remainder of the molecule, which may optionally be mono- or disubstituted by methyl, ethyl, methoxy, ethoxy, fluorine, chlorine, bromine, trifluoromethyl, difluoromethyl.

A general definition of the compounds according to the invention is provided by the formula (I). Likewise very particularly preferred substituents or ranges of the radicals given under the formulae shown above and below are defined, n very particularly preferably represents the number 0 or 1, $X^1$ and $X^3$ very particularly preferably represent hydrogen, $X^2$ and $X^4$ very particularly preferably represent the following combinations $X^2/X^4$: vinyl/H, H/vinyl, ethynyl/H, H/ethynyl, methoxy/H, H/methoxy, ethoxy/H, H/ethoxy, aminothiocarbonyl/H, H/aminothiocarbonyl, vinyl/methyl, methyl/vinyl, ethynyl/methyl, methyl/ethynyl, methoxy/methyl, methyl/methoxy, ethoxy/methyl, methyl/ethoxy, aminothiocarbonyl/methyl, methyl/aminothiocarbonyl, vinyl/F, F/vinyl, ethynyl/F, F/ethynyl, methoxy/F, F/methoxy, ethoxy/F, F/ethoxy, aminothiocarbonyl/F, F/aminothiocarbonyl, vinyl/Cl, Cl/vinyl, ethynyl/Cl, Cl/ethynyl, methoxy/Cl, Cl/methoxy, ethoxy/Cl, Cl/ethoxy, aminothiocarbonyl/Cl, Cl/aminothiocarbonyl, or phenylmethyl, phenoxy, pyridylmethyl, pyrimidylmethyl, thiazolylmethyl, pyrazolylmethyl, pyridyloxy, pyrimidyloxy, thiazolyloxy, pyrazolyloxy, cyclopropylmethyl, cyclopropylmethoxy optionally mono- or disubstituted by identical or different substituents from the group consisting of fluorine, chlorine, bromine, cyano, nitro, methyl, ethyl, trifluoromethyl, difluoromethyl, methoxy, trifloromethoxy, difluoromethoxy or cyclopropyl, or represents $(C_3-C_6)$-cycloalkyl, phenyl, pyridyl, pyrimidyl, pyridazinyl, pyrazinyl, triazinyl, thiazolyl, thiadiazolyl, oxazolyl, oxadiazolyl, pyrazolyl, triazolyl or tetrazolyl which is optionally mono- or disubstituted by identical or different substituents from the group consisting of fluorine, chlorine, bromine, cyano, nitro, methyl, ethyl, trifluoromethyl, difluoromethyl, methoxy, trifluoromethoxy or by cyclopropyl, $R^3$ very particularly preferably represents hydrogen, ethyl, propyl, cyano, trifluoromethyl, difluoromethyl, dichloromethyl, trichloromethyl, difluorochloromethyl, dichlorofluoromethyl, (2,2,2)-trifluoroethyl, 2-chloro-(2,2)-difluoroethyl, (2,2)-dichloro-2-fluoroethyl, (2,2,2)-trichloroethyl, pentafluoroethyl, methoxymethyl, methoxyethyl, cyanomethyl, allyl, butenyl, or represents a 3- to 6-membered saturated, partially saturated or aromatic ring which may optionally contain one to three heteroatoms from the group consisting of O, S and N and which may optionally be mono- or disubstituted by identical or different substituents from the group consisting of fluorine, chlorine, bromine, cyano, nitro, methyl, ethyl, trifluoromethyl, vinyl, ethynyl, methoxy, ethoxy, difluoromethoxy, trifluoromethoxy, trifluoroethoxy and cyclopropyl especially the following rings are explicitly mentioned: cyclopropyl, phenyl, pyridyl, pyrimidyl, thiazolyl, pyrazolyl and thienyl which may optionally be substituted by the substituents mentioned under very particularly preferred, $R^1$ and $R^2$ very particularly preferably independently of one another represent hydrogen, cyano, methyl, ethyl, propyl, butyl, sec-butyl, isopropyl, tert-butyl, (2,2,2)-trifluoroethyl, (2,2)-difluoromethyl, methoxy, ethoxy, cyanomethyl, methoxymethyl, methoxyethyl, allyl, butenyl, propynyl, methylcarbonyl, ethylcarbonyl, propylcarbonyl, isopropylcarbonyl, methoxycarbonyl, ethoxycarbonyl, represent arylcarbonyl, pyridylcarbonyl, pyrimidylcarbonyl, thiazolylcarbonyl, pyrazolylcarbonyl, methylsulfinyl, trifluoromethylsulfinyl, methylsulfonyl, trifluoromethylsulfonyl optionally mono- or disubstituted independently of one another by fluorine, chlorine, bromine, cyano, nitro, methyl, trifluoromethyl, allyl, butenyl, methoxy, trifluoromethoxy, methylthio, methylsulfinyl, methylsulfonyl, methylamino, dimethylamino, or represent a 3- to 6-membered saturated or aromatic ring which may optionally contain one to two heteroatoms from the group consisting of O, S and N, which may optionally be interrupted once, twice or three times by C=O and which may optionally be mono- or trisubstituted by identical or different substituents from the group consisting of fluorine, chlorine, bromine, cyano, nitro, methyl, ethyl, trifluoromethyl, vinyl, ethynyl, methoxy, ethoxy, difluoromethoxy, trifluoromethoxy, trifluoroethoxy and cyclopropyl, especially the following rings are explicitly mentioned: cyclopropyl, cyclobutyl, cyclopentyl, cyclohexyl, oxetane, phenyl, thienyl and pyridyl which may optionally be substituted by the substituents mentioned under very particularly preferred, or represent $-(CH_2)_m-R^6$, where $R^6$ represents a 3- to 6-membered saturated, partially saturated or aromatic ring which may optionally contain one to two heteroatoms from the group consisting of O, S and N, may optionally be interrupted once or twice by C=O and which may optionally be mono-, di- or trisubstituted by identical or different substituents from the group consisting of fluorine, chlorine, bromine, cyano, nitro, methyl, ethyl, trifluoromethyl, vinyl, ethynyl, methoxy, ethoxy, difluoromethoxy, trifluoromethoxy, trifluoroethoxy and cyclopropyl, where m represents the number 1, especially the following $R^6$ are explicitly mentioned: cyclopropyl, phenyl and pyridyl which may optionally be substituted by the substituents mentioned under very particularly preferred, or $R^1$ and $R^2$ together with the nitrogen atom to which they are attached may form a saturated or unsaturated 3- to 6-membered ring which is optionally mono-, di-, tri- or tetrasubstituted by methyl, ethyl, methoxy, ethoxy, fluorine, chlorine, bromine, trifluoromethyl, difluoromethyl, which may optionally contain one or two further heteroatoms from the group consisting of sulfur, oxygen and nitrogen (where oxygen atoms must not be directly adjacent to one another) and/or at least one CH2 group is replaced by a carbonyl group, especially the following rings are explicitly mentioned,

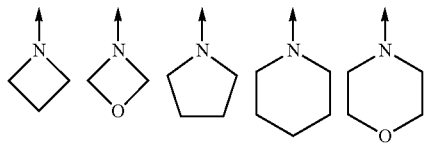

in which the nitrogen atom to which $R^1$ and $R^2$ are attached represent the cycle and the arrow points to the remainder of the molecule, which may optionally be mono- or disubstituted by methyl, ethyl, methoxy, ethoxy, fluorine, chlorine, bromine, trifluoromethyl, difluoromethyl, $R^1$ and $R^3$ together with the atoms to which they are attached may form a saturated or unsaturated 5- to 6-membered ring and/or one which is optionally mono- or disubstituted by methyl, ethyl, methoxy, ethoxy, fluorine, chlorine, trifluoromethyl, difluoromethyl, cyano, cyclopropyl, chlorocyclopropyl, fluorocyclopropyl, cyanocyclopropyl, methylcyclopropyl, ($C_3$-$C_4$)-alkanediyl, ($C_3$-$C_4$)-alkenediyl, butanedienyl (where butanedienyl may optionally be mono- or disubstituted by methyl, fluorine, chlorine, bromine, methoxy or trifluoromethyl and/or may optionally be interrupted by at least one oxygen or/and nitrogen atom) and which may optionally contain a further sulfur or oxygen or nitrogen atom and/or a carbonyl group, especially $R^1$ and $R^3$ together with the atoms to which they are attached represent the following group,

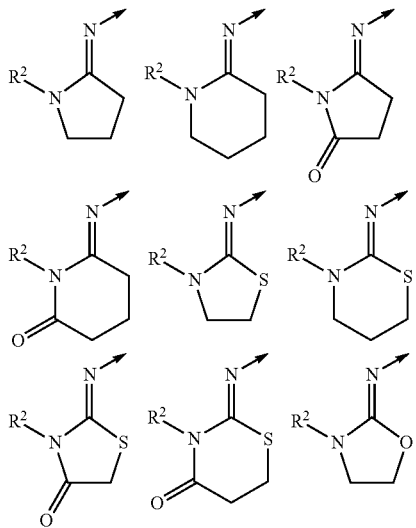

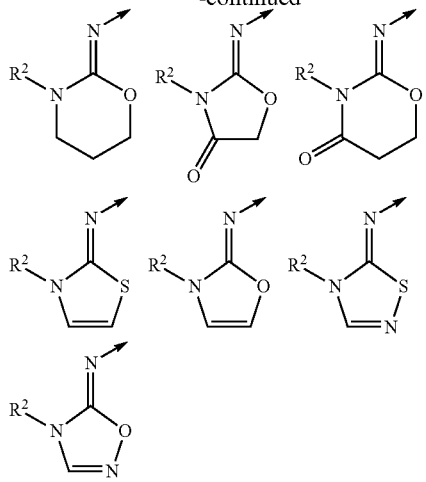

each of which may optionally be mono- or disubstituted by methyl, ethyl, methoxy, ethoxy, fluorine, chlorine, trifluoromethyl, difluoromethyl, cyclopropyl, chlorocyclopropyl, fluorocyclopropyl, cyanocyclopropyl, methylcyclopropyl, where the arrow points to the remainder of the molecule.

A general definition of the compounds according to the invention is provided by the formula (I). Likewise very particularly preferred substituents or ranges of the radicals given under the formulae shown above and below are defined, n very particularly preferably represents the number 0 or 1, $X^1$ and $X^3$ very particularly preferably represent hydrogen, $X^2$ and $X^4$ very particularly preferably independently of one another represents hydrogen, fluorine, chlorine, bromine, methyl, ethyl, trifluoromethyl, difluoromethyl, vinyl, ethynyl, methoxy, ethoxy, difluoromethoxy, trifluoromethoxy, $OCH_2CF_3$, aminothiocarbonyl, or phenylmethyl, phenoxy, pyridylmethyl, pyrimidylmethyl, thiazolylmethyl, pyrazolylmethyl, pyridyloxy, pyrimidyloxy, thiazolyloxy, pyrazolyloxy, cyclopropylmethyl, cyclopropylmethoxy optionally mono- or disubstituted by identical or different substituents from the group consisting of fluorine, chlorine, bromine, cyano, nitro, methyl, ethyl, trifluoromethyl, difluoromethyl, methoxy, trifloromethoxy, difluoromethoxy or cyclopropyl, or represents ($C_3$-$C_6$)-cycloalkyl, phenyl, pyridyl, pyrimidyl, pyridazinyl, pyrazinyl, triazinyl, thiazolyl, thiadiazolyl, oxazolyl, oxadiazolyl, pyrazolyl, triazolyl or tetrazolyl which is optionally mono- or disubstituted by identical or different substituents from the group consisting of fluorine, chlorine, bromine, cyano, nitro, methyl, ethyl, trifluoromethyl, difluoromethyl, methoxy, trifluoromethoxy or by cyclopropyl, especially preferably, $X^2$ and $X^4$ represent the following combinations $X^2/X^4$: F/F, Cl/Cl, F/Cl, Cl/F, Br/Br, Br/Cl, Cl/Br, Br/F, F/Br, methyl/methyl, methyl/F, F/methyl, methyl/Cl, Cl/methyl, methyl/Br, Br/methyl, ethyl/ethyl, ethyl/F, F/ethyl, ethyl/Cl, Cl/ethyl, ethyl/Br, Br/ethyl, methoxy/methyl, methyl/methoxy, methyl/H, ethyl/H, chlorine/H, bromine/H, fluorine/H, methoxy/H, H/chlorine, H/fluorine, H/bromine, H/methyl, H/methoxy, H/ethyl $R^1$ and $R^3$ together with the atoms to which they are attached may form a saturated or unsaturated 5- to 6-membered ring and/or one which is optionally mono- or disubstituted by methyl, ethyl, methoxy, ethoxy, fluorine, chlorine, trifluoromethyl, difluoromethyl, cyano, cyclopropyl, chlorocyclopropyl, fluorocyclopropyl, cyanocyclopropyl, methylcyclopropyl, ($C_3$-$C_4$)-alkanediyl, ($C_3$-$C_4$)-alkenediyl, butanedienyl (where butanedienyl may optionally be mono- or disubstituted by methyl, fluorine, chlorine, bromine, methoxy or trifluoromethyl and/or may optionally be interrupted by at least one oxygen or/and nitrogen atom) and which may optionally contain a further sulfur or oxygen or nitrogen atom and/or a carbonyl group, especially $R^1$ and $R^3$ together with the atoms to which they are attached represent the following group,

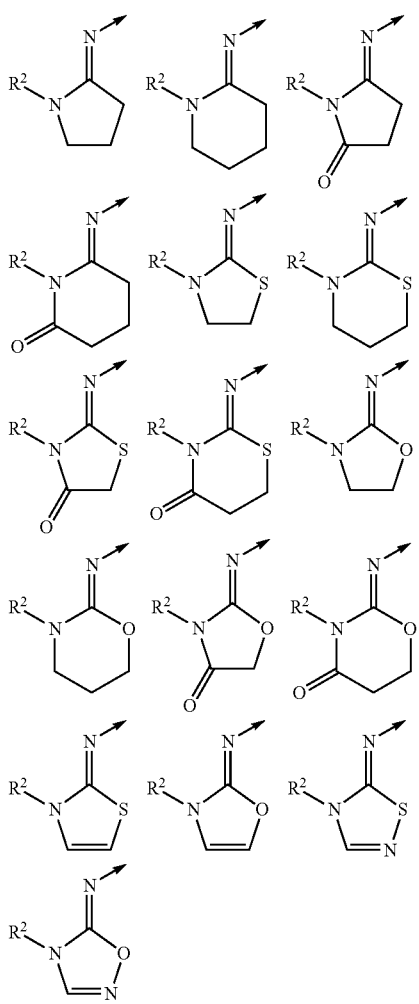

each of which may optionally be mono- or disubstituted by methyl, ethyl, methoxy, ethoxy, fluorine, chlorine, trifluoromethyl, difluoromethyl, cyclopropyl, chlorocyclopropyl, fluorocyclopropyl, cyanocyclopropyl, methylcyclopropyl, where the arrow points to the remainder of the molecule.

$R^2$ very particularly preferably represents cyano, (2,2,2)-trifluoroethyl, (2,2)-difluoromethyl, 2-chloro-(2,2)-difluoroethyl, (2,2)-dichloro-2-fluoroethyl, (2,2,2)-trichloroethyl, pentafluoroethyl, 2-chlorotetrafluoroethyl, allyl, butenyl, propynyl, methylsulfinyl, trifluoromethylsulfinyl, methylsulfonyl, trifluoromethylsulfonyl, or represent a 3- to 6-membered saturated or aromatic ring which may optionally contain one to two heteroatoms from the group consisting of O, S and N, which may optionally be interrupted once, twice or three times by C=O and which may optionally be mono- or trisubstituted by identical or different substituents from the group consisting of fluorine, chlorine, bromine, cyano, nitro, methyl, ethyl, trifluoromethyl, vinyl, ethynyl, methoxy, ethoxy, difluoromethoxy, trifluoromethoxy, trifluoroethoxy and cyclopropyl, especially the following rings are explicitly mentioned: cyclopropyl, cyclobutyl, cyclopentyl, cyclohexyl, oxetane, phenyl, thienyl and pyridyl which may optionally be substituted by the substituents mentioned under very particularly preferred, or represent —$(CH_2)_m$—$R^6$, where $R^6$ represents a 3- to 6-membered saturated, partially saturated or aromatic ring which may optionally contain one to two heteroatoms from the group consisting of O, S and N, may optionally be interrupted once or twice by C=O and which may optionally be mono-, di- or trisubstituted by identical or different substituents from the group consisting of fluorine, chlorine, bromine, cyano, nitro, methyl, ethyl, trifluoromethyl, vinyl, ethynyl, methoxy, ethoxy, difluoromethoxy, trifluoromethoxy, trifluoroethoxy and cyclopropyl, where m represents the number 1, especially the following $R^6$ are explicitly mentioned: cyclopropyl, cyclobutyl, cyclopentyl, cyclohexyl, phenyl and pyridyl which may optionally be substituted by the substituents mentioned under very particularly preferred.

The abovementioned general or preferred radical definitions or illustrations can be combined with one another as desired, i.e. including combinations between the respective ranges and preferred ranges. They apply both to the end products and, correspondingly, to precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Unless indicated otherwise, optionally substituted radicals may be mono- or polysubstituted, where in the case of polysubstitutions the substituents may be identical or different.

In the radical definitions mentioned as being preferred, halogen represents fluorine, chlorine, bromine and iodine, particularly preferably fluorine, chlorine and bromine and very particularly preferably fluorine and chlorine.

Preparation Processes

The compounds of the general formula (I) can be prepared by the methods described in the application WO 2007/131680. Alternatively to these described methods, the compounds of the formula (I) can also be prepared by process A, process B, process C, process E, process F, process G, process H, process I, process J and process K. Process D provides an alternative to the preparation of the precursors.

A number of general processes for preparing amidines are described in S. Patai and Z. Rappoport, The Chemistry of Amidines and Imidates, Vol. 27, John Wiley & Sons, New York, N.Y., USA, 1991.

Also described in the literature are palladium(II)-catalyzed syntheses of arylamidines with the aid of trifluoroborates, see, for example, J. Sävmarker, Ph.D. thesis University of Uppsala, 2012 or J. Sävmarker, Org. Lett. 14 (2012), 2394-2397.

Process A

The anilides (III) are chlorinated, for example with diphenyl chlorophosphate or phosphorus pentachloride, to give imidoyl chlorides of the formula (II) and reacted with amines to give amidines (Ia).

The thioethers (Ia) are converted into the corresponding sulfoxides (Ib) by reaction with oxidizing agents such as, for example, meta-chloroperbenzoic acid.

The oxidation of compounds of the formula (Ia) to compounds of the formula (Ib) can be performed using an oxidizing agent in a suitable solvent and diluent. Suitable oxidizing agents are, for example, dilute nitric acid, hydrogen peroxide and peroxycarboxylic acids such as meta-chloroperbenzoic acid. Suitable solvents are inert organic solvents, typically acetonitrile and halogenated solvents such as dichloromethane, chloroform or dichloroethane.

A large number of different methods are suitable for generating enantiomerically enriched sulfoxides, as described by A. R. Maguire in ARKIVOC, 2011(i), 1-110 or by WO2011/006646: metal-catalyzed asymmetric oxidations of thioethers, for example with titanium and vanadium

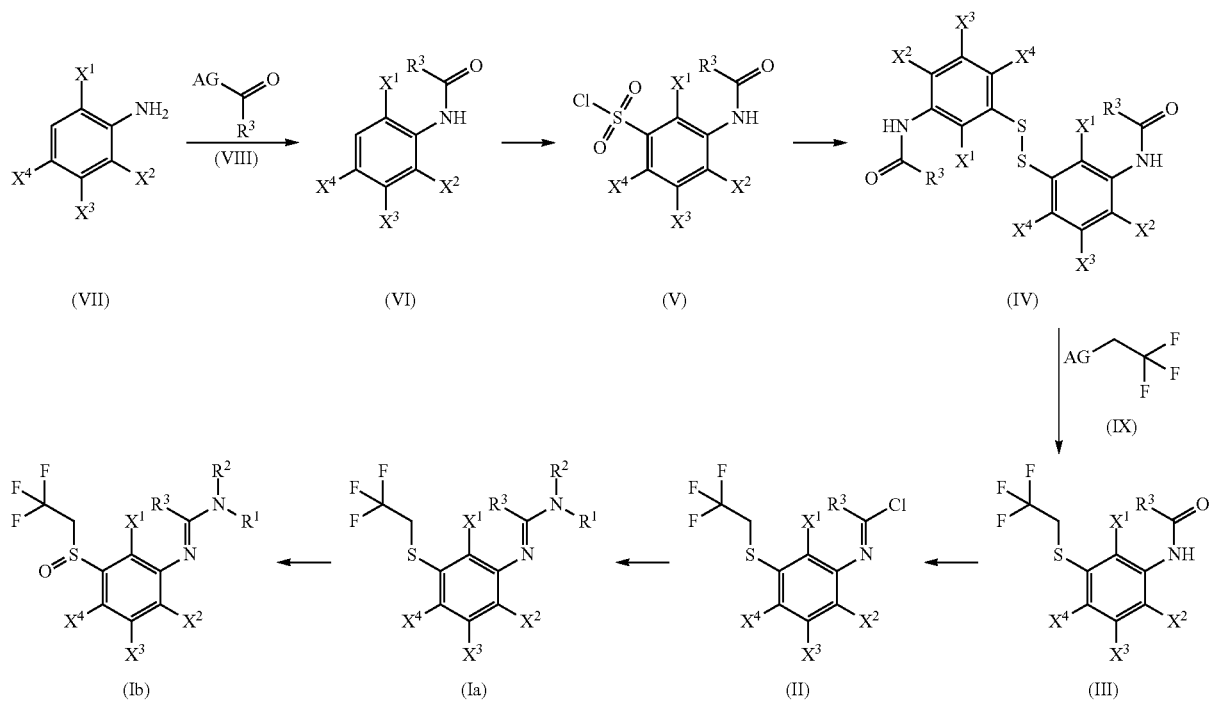

where $X^1$, $X^2$, $X^3$, $X^4$, $R^1$, $R^2$ and $R^3$ have the meanings given above, AG represents a leaving group and PG represents a protective group.

Anilines of the formula (VII) are either commercially available or they can be prepared by known methods. In the presence of acids, acid anhydrides or acid chlorides of the formula (VIII), the anilines (VII) are converted into the corresponding anilides (VI). Chlorosulfonation of the anilides (VI) with chlorosulfonic acid affords the corresponding sulfonyl chlorides (V). Reduction of the sulfonyl chlorides (V) to the disulfides (IV) can be carried out using methods known from the literature such as iron in hydrochloric acid or iodide. Reaction of the disulfides (IV) with trifluoroethyl electrophiles of the formula (XVI) where AG represents a leaving group such as, for example, chlorine, bromine, tosylate, mesylate or triflate affords the sulfides (III).

as the most frequently employed catalyst sources, in the form of Ti(O$^i$Pr$_4$) and VO(acac)$_2$, together with a chiral ligand and an oxidizing agent such as tert-butyl hydroperoxide (TBHP), 2-phenylpropan-2-yl hydroperoxide (CHP) or hydrogen peroxide; non-metal-catalyzed asymmetric oxidations employing chiral oxidizing agents or chiral catalysts; electrochemical or biological asymmetric oxidations and also kinetic resolution of sulfoxides and nucleophilic shift (according to Andersen's method).

The enantiomers can also be obtained from the racemate, for example by separating them on a preparative scale by chiral HPLC.

The compounds of the formulae (II), (III), (IV) and (V) in process A can be prepared in particular under the conditions mentioned in the Preparation Examples.

Alternatively, the thioethers of the formula (III) can be prepared by process B.

Process B

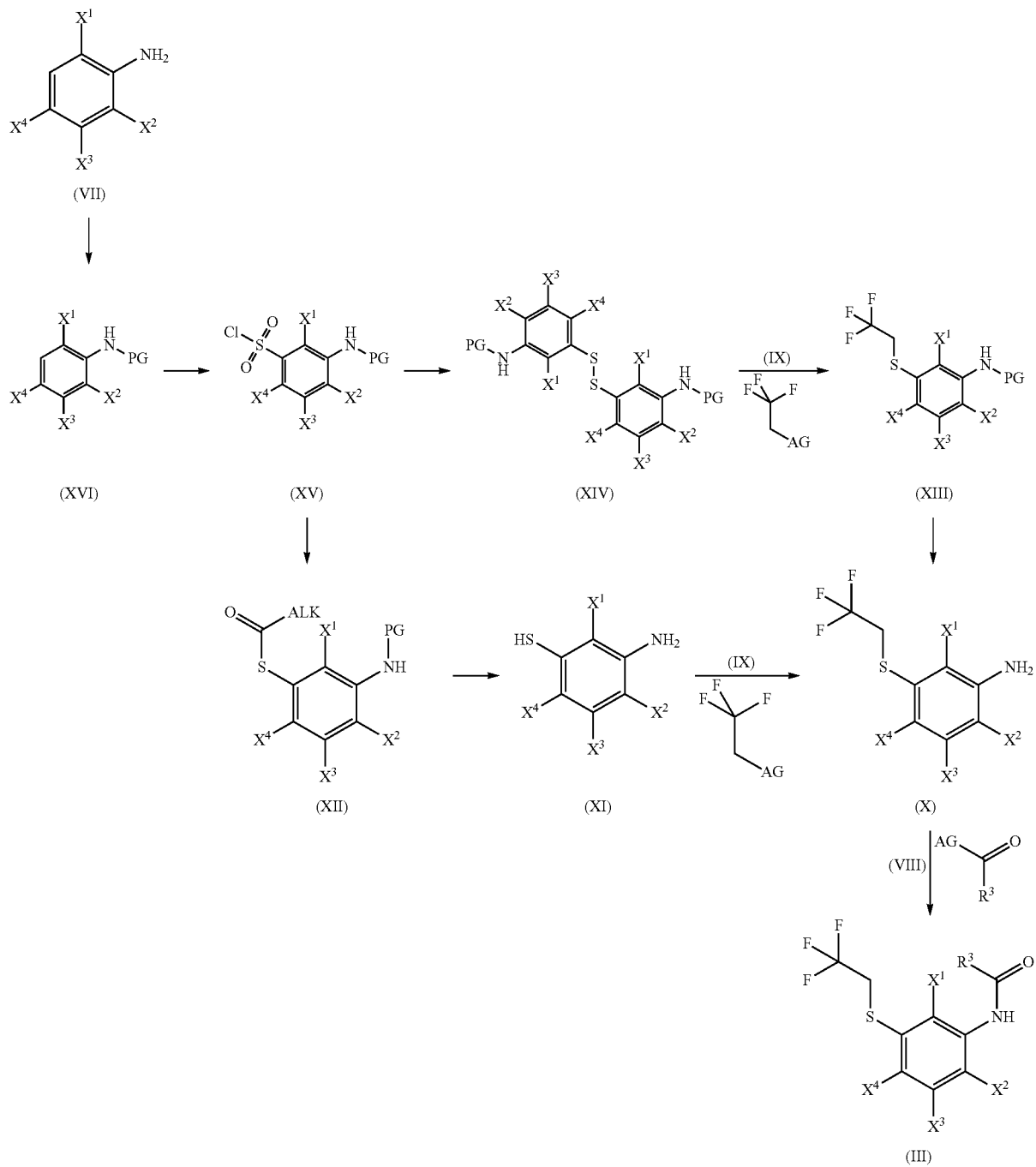

where $X^1$, $X^2$, $X^3$, $X^4$ and $R^3$ have the meanings given above, AG represents a leaving group and PG represents a protective group.

The anilines (VII) can be protected with a suitable protective group known from the literature such as, for example, an acetyl group, to give compounds of the formula (XVI). Chlorosulfonation of the compounds of the formula (XVI) with chlorosulfonic acid affords the corresponding sulfonyl chlorides (XV). Reduction of the sulfonyl chlorides (XV) to the disulfides (XIV) can be carried out using methods known from the literature such as iron in hydrochloric acid or iodide. Reaction of the disulfides (XIV) with trifluoroethyl electrophiles of the formula (IX) where AG represents a leaving group such as, for example, chlorine, bromine, tosylate, mesylate or triflate affords the sulfides (XIII). The protective group is removed by suitable methods known from the literature, giving anilines of the formula (X). The latter are converted in the presence of acids, acid anhydrides or acid chlorides of the formula (VIII) into the corresponding anilides (III).

Instead of the reduction to the disulfide (XIV), it is also possible to reduce with a suitable reducing agent such as, for example, iodine/phosphorus to give the alkyl thioate (XI), which is then deprotected using a suitable method, for example with potassium hydroxide solution, to afford compounds of the formula (X). Reaction of the thiols (XI) with trifluoroethyl electrophiles of the formula (IX) where AG represents a leaving group such as, for example, chlorine, bromine, tosylate, mesylate or triflate affords the sulfides (X). The latter are converted in the presence of acids, acid anhydrides or acid chlorides of the formula (VIII) into the corresponding anilides (III).

The compounds of the formulae (III), (X), (XI), (XII), (XV) and (XVI) in process B can be prepared in particular under the conditions mentioned in the Preparation Examples.

Process C

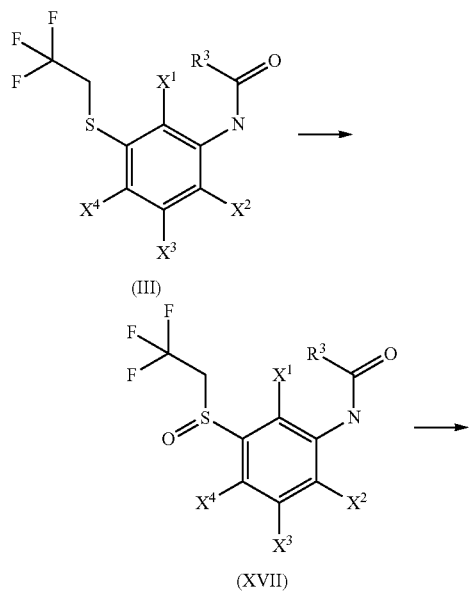

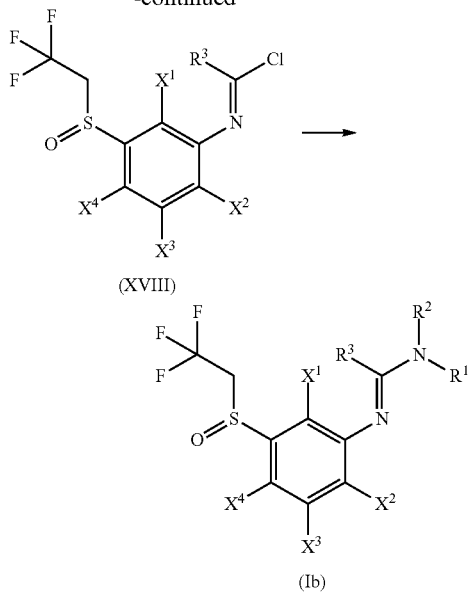

where $X^1$, $X^2$, $X^3$, $X^4$, $R^1$, $R^2$ and $R^3$ have the meanings given above.

Furthermore it has been found that chiral compounds (Ib) are obtained by process C when compounds of the formula (III) are chirally oxidized to sulfoxides of the formula (XVII).

The anilides (XVII) are chlorinated, for example with diphenyl chlorophosphate or phosphorus pentachloride, to give imidoyl chlorides of the formula (XVIII) and reacted with amines to give amidines (Ib).

Some of the compounds of the formula (XVII) in process C are novel, and they can be prepared in particular under the conditions mentioned in the Preparation Examples.

Process D

Alternatively, the thioethers of the formula (X) can be prepared by process D.

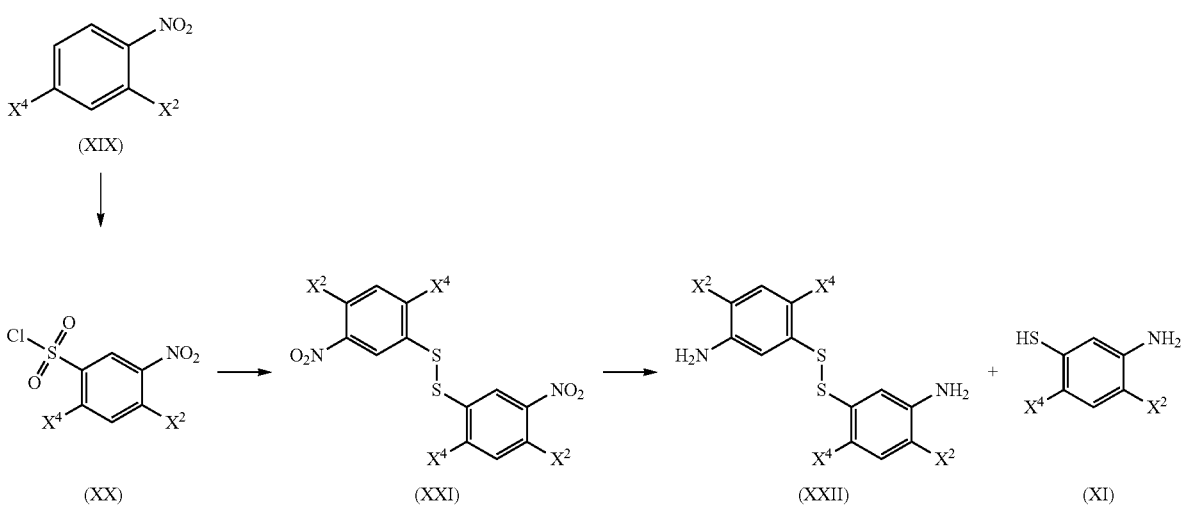

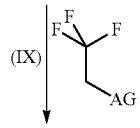

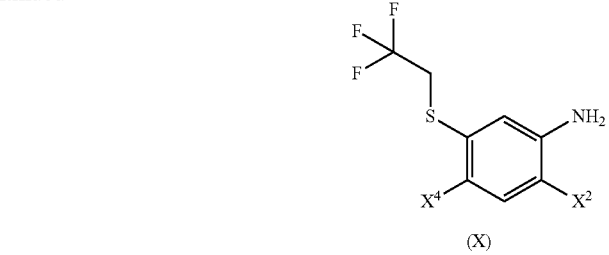

(X)

$X^2$, $X^4$ independently of one another may particularly preferably represent hydrogen, fluorine, chlorine, bromine.

Chlorosulfonation of the nitroaromatics of the formula (XIX) with chlorosulfonic acid affords the corresponding sulfonyl chlorides (XX). Reduction of the sulfonyl chlorides (XX) to the bis(nitroaryl) disulfides (XXI) can be carried out using methods known from the literature, for example iodide. Reduction of the disulfides (XXI) to the disulfanediyldianilines (XXII), some of which are formed as a mixture with the corresponding aminoarylthiols (XI), is possible using reducing agents such as, for example, hydrogen with the aid of heterogeneous catalysts such as, for example, Raney nickel, platinum on activated carbon or palladium on activated carbon. Reaction of the disulfides (XXII) or thiophenols (XI) with trifluoroethyl electrophiles of the formula (IX) where AG represents a leaving group such as, for example, chlorine, bromine, iodine, tosylate, mesylate or triflate affords the 3-[(2,2,2-trifluoroethyl)sulfanyl]anilines of the formula (X).

The compounds of the formulae (X), (XI), (XII), (XX) and (XXI) in process D can be prepared in particular under the conditions mentioned in the Preparation Examples.

Process E

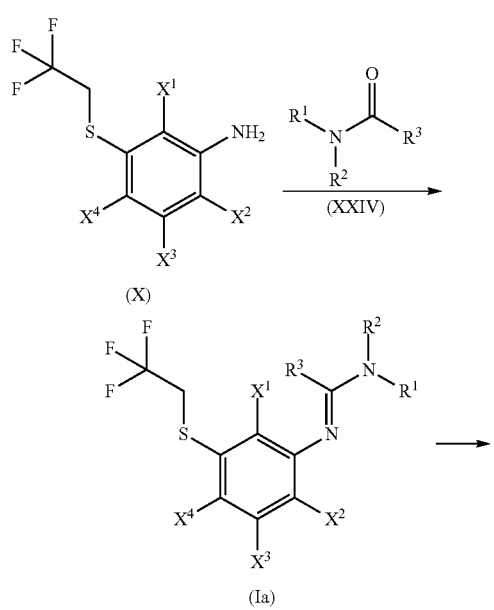

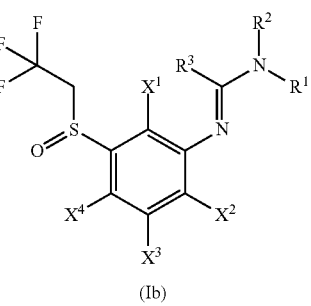

(Ib)

where $X^1$, $X^2$, $X^3$, $X^4$, $R^1$, $R^2$ and $R^3$ have the meanings given above.

Anilines of the formula (X) can be converted into the trifluoroethyl sulfide derivatives of the formula (Ia) by methods known from the literature, for example by reaction with amides of the formula (XXIV) and phosphoryl chloride, if appropriate in the presence of an inert organic solvent.

The sulfoxides (Ib) can be obtained by oxidation of the thioethers (Ia) by methods known from the literature.

Amides of the formula (XXIV) in which $R^3$ represents optionally substituted cyclopropyl and $R^1$ represents hydrogen and $R^2$ represents optionally substituted haloalkyl afford, when reacted with anilines of the formula (X) in the presence of phosphoryl chloride, a mixture of the N-arylamidines according to the invention of the general formulae (Ia-a) and (Ia-b)

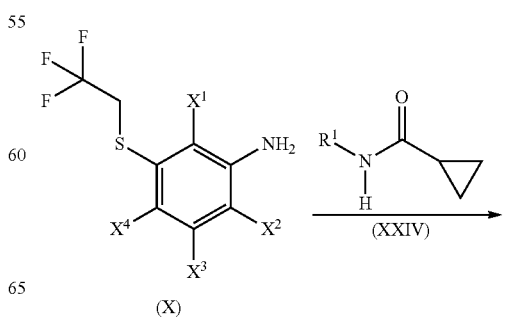

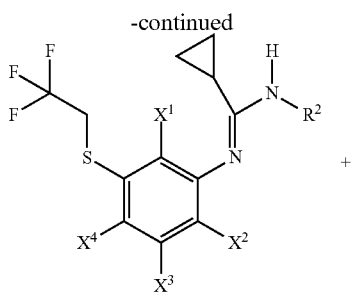

(Ia-a)

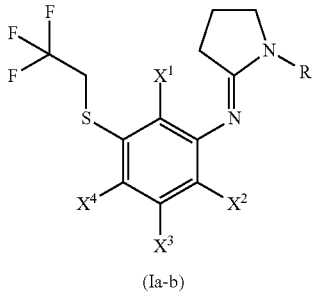

(Ia-b)

where $X^1$, $X^2$, $X^3$, $X^4$ and $R^2$ have the meanings given above.

Oxidation of the thioethers (Ia-a) by methods known from the literature gives sulfoxides of the formula (Ib) where R3 represents optionally substituted cyclopropyl and $R^1$ represents hydrogen and $R^2$ represents optionally substituted haloalkyl.

Oxidation of the thioethers (Ia-b) by methods known from the literature gives sulfoxides of the formula (Ib) where $R^1$ and $R^3$ together form a 5-membered ring and $R^2$ represents optionally substituted haloalkyl.

Amides of the formula (XXIV) are commercially available or can be prepared by generally known processes, for example by reacting acid chlorides with amines, optionally in the presence of bases and optionally in the presence of a solvent, for example analogously to Houben-Weyl VIII, 655.

The compounds of the formulae (X) and (XXIV) in process E can be prepared in particular under the conditions mentioned in the Preparation Examples.

Process F

The 3-substituted 2-arylimino-1,3-thiazolidines (n=0, A=S), 2-arylimino-1,3-thiazinanes (n=1, A=S), 2-arylimino-1,3-oxazolidines (n=0, A=O) and 2-arylimino-1,3-oxazinanes (n=1, A=O) of the general formula (I) can be prepared, for example, by process F

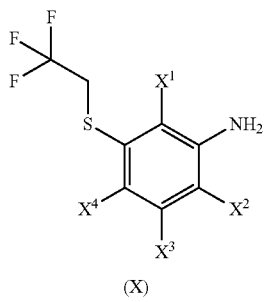

(X)

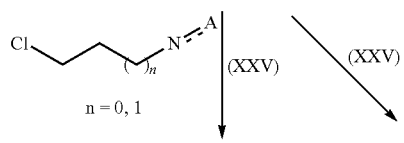

n = 0, 1

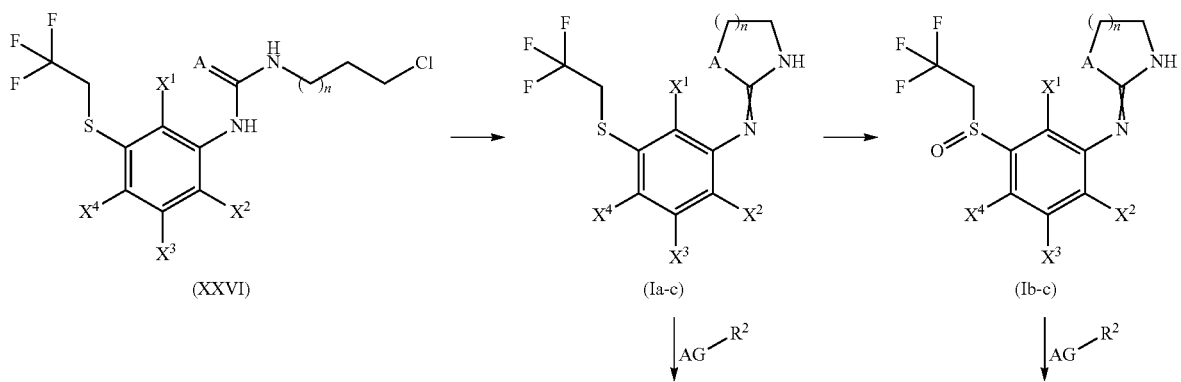

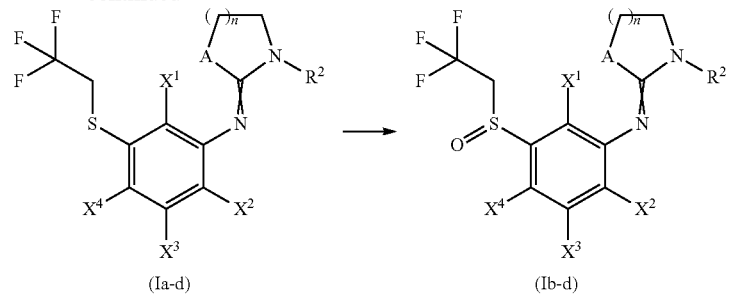

where $X^1$, $X^2$, $X^3$, $X^4$ and $R^2$ have the meanings given above.

Anilines of the formula (X) can be reacted directly by reaction with isocyanates (XXV, A=O) or isothiocyanates (XXV, A=S) to give the cyclic amidines of the formula (Ia-c). In the case of intermediate isolation of the (thio)ureas of the formula (XXVI), these can be converted in the presence of bases into the cyclic amidines of the formula (Ia-c).

In the patent JP2011/042611, (thio)ureas and their sulfoxides are claimed as acaricides. The (thio)ureas of the formula (XXVI) are novel and also form part of the subject matter of the invention.

(alkyl chlorides, alkyl bromides and alkyl iodides), alkyl triflates, alkyl mesylates and dialkyl sulfates.

The sulfoxides of the formula (Ib) can be obtained by oxidation of the thioethers of the formula (Ia) by methods known from the literature.

The compounds of the formulae (X) and (XXVI) in process F can be prepared in particular under the conditions mentioned in the Preparation Examples.

Process G

The 3-substituted 2-arylimino-1,3-oxazoles of the general formula (I) can be prepared, for example, by process G,

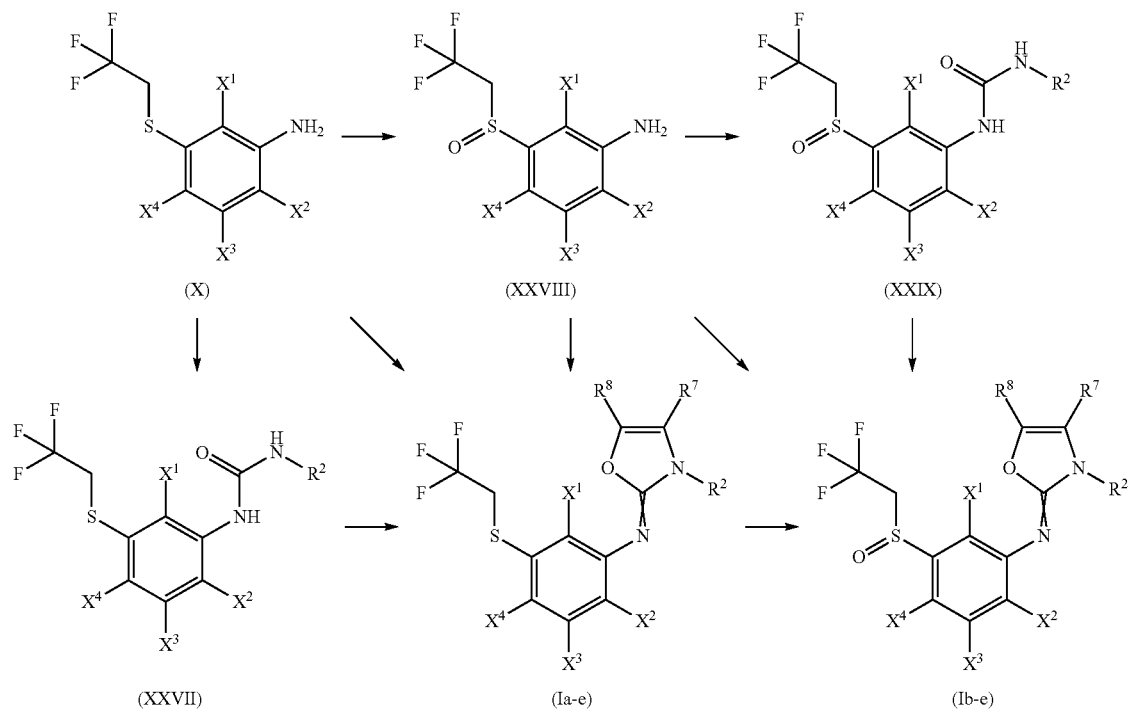

The sulfoxides of the formula (Ib-c) can be obtained by oxidation of the thioethers (Ia-c) by methods known from the literature.

The thioethers (Ia-c) and the sulfoxides (Ib-c) can then be converted by methods known from the literature into the compounds of the general formulae (Ia-d) and (Ib-d), respectively, where $R^2$ may have the meanings given above. Suitable alkylating agents are, for example, alkyl halides where $X^1$, $X^2$, $X^3$, $X^4$ and $R^2$ have the meanings given above.

$R^7$ and $R^8$ are the substituents at the ring formed by $R^1$ and $R^3$ together with the atoms to which they are attached.

Anilines of the formula (XXVIII) can be prepared by oxidation of the anilines of the formula (X), for example with meta-chlorobenzoic acid as oxidizing agent in an inert organic solvent. The anilines of the formula (XXVIII) are novel and also form part of the subject matter of the invention.

Anilines of the formula (X) and (XXVIII) can be converted into the ureas of the formulae (XXVII) and (XXIX), respectively, by methods known from the literature, for example according to JP2011/042611, by treating them with isocyanates, optionally in the presence of a base and optionally in the presence of an organic solvent. Alternatively, these anilines can be converted by generally known methods into their isocyanates, which are then converted with amines into the ureas.

The 3-substituted 2-aryliminooxazoles (Ia-e) and (Ib-e) can be synthesized from ureas (XXVII) and (XXIX), respectively, for example by the method of M. Han in Bull. Korean Chem. Soc. 2012, 33(4), 1371-1374, where initially, using carbon tetrachloride and triphenylphosphine, an N'-substituted N-arylimidoformamide is prepared which is then reacted with an adequate hydroxycarbonyl compound under Ku(I) catalysis in an inert high-boiling solvent to yield selectively the 2-aryliminooxazole.

The sulfoxides (Ib) can be obtained by oxidation of the thioether (Ia) by methods known from the literature.

These 2-aryliminooxazoles (I) can also be synthesized directly from the anilines of the formula (X) or (XXVIII), for example by reaction with 3-alkyl-1,3-oxazolinethiones of the formula (J) or their oxazolium salts, optionally in the presence of a base and optionally in an inert solvent, generally at high temperatures, as described by Gompper in Chem. Ber. 1959, 92, 1928-1932.

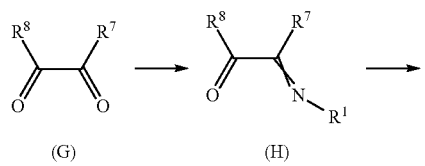

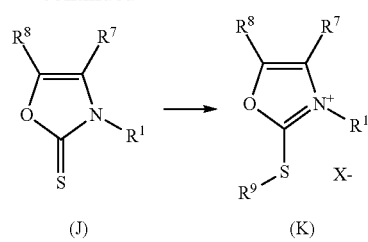

3-Substituted 1,3-oxazolinethiones of the formula (J) can be obtained from commercial sources or be prepared by methods known from the literature, for example from dicarbonyl compounds of the formula (G) via the synthesis intermediates (H), analogously to the procedures of K. N. Mehrotra in Bull. Chem. Soc. Jap. 1985, 58 (8), 2399-2402 for $R^7=R^8=$aryl, using carbon disulfide as sulfur source.

The oxazolium salts of the formula (K) can be prepared by alkylation of the corresponding oxazolinethiones of the formula (J). Suitable alkylating agents are, for example, alkyl halides (alkyl chlorides, alkyl bromides and alkyl iodides), alkyl triflates, alkyl mesylates and dialkyl sulfates. The nature of the anion X in the general formula (K) is determined by this agent and can be, for example, chloride, bromide, iodide, triflate, mesylate or sulfate.

The compounds of the formulae (X) and (XXVIII) in process G can be prepared in particular under the conditions mentioned in the Preparation Examples.

Process H

The 3-substituted 2-aryliminothiadiazoles of the general formula (I) can be prepared, for example, by process H

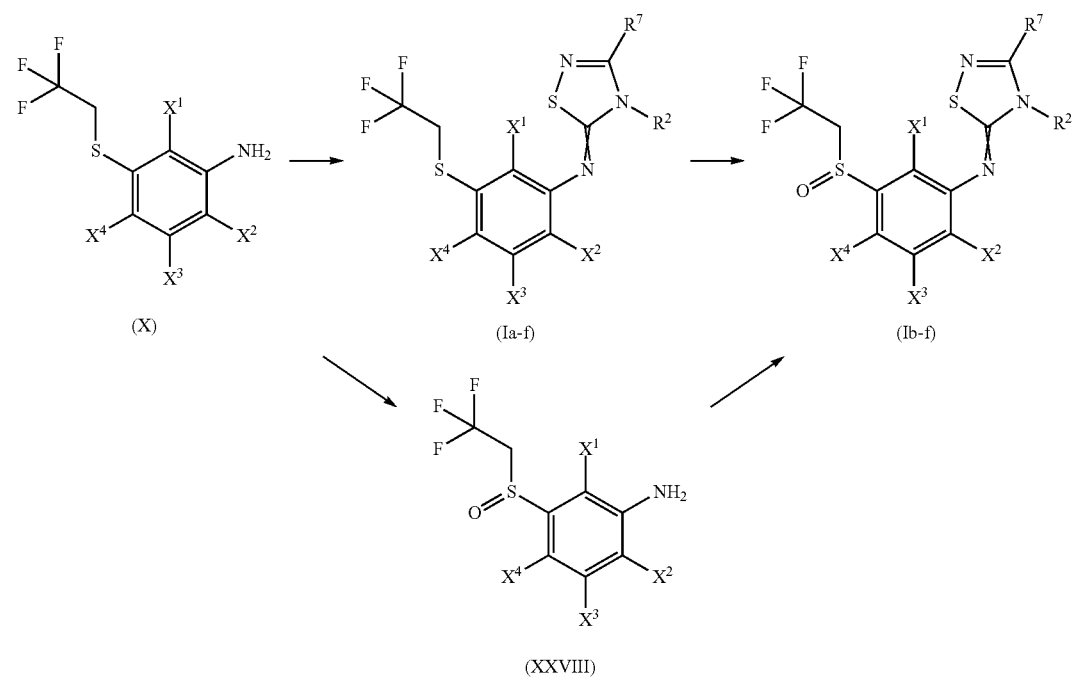

where $X^1$, $X^2$, $X^3$, $X^4$ and $R^2$ have the meanings given above.

$R^7$ is the substituent at the ring formed by $R^1$ and $R^3$ together with the atoms to which they are attached.

Anilines of the general formula (X) or the general formula (XXVIII) can be reacted, for example, with thiadiazolinethiones of the formula (XXX) or with the corresponding thiadiazolium salts of the formula (XXXI) to give the 2-aryliminothiadiazoles of the formula (Ia-f) and (Ib-f), respectively. This succeeds optionally in the presence of a base, optionally in an inert solvent or in an agent that can simultaneously serve as base and solvent, for example pyridine.

The synthesis of the thiadiazolinethiones of the formula (XXX) and their thiadiazolium salts (XXXI) can be carried out, for example, by the following process:

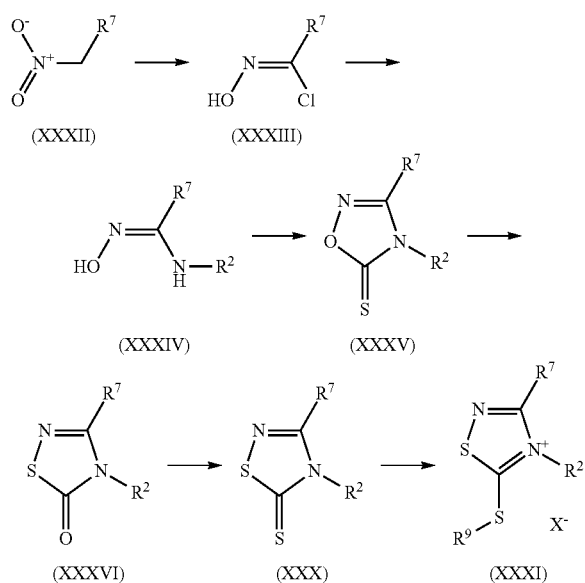

The synthesis of N-substituted amidoximes of the formula (XXXIV) has been described in detail in the literature. They can be, for example, according to J. Org. Chem. 1980, 45 (21), 4198 from the corresponding imidoyl chlorides of the formula (XXXIII) by reaction with the desired amines. Optionally, this takes place in an inert solvent at temperatures from 0° C. to 100° C. with reaction times from 1 h to 36 h. For the preparation of the imidoyl chlorides, it is possible to apply processes known from the literature, for example the reaction of the appropriate nitro compounds of the formula (XXXII) with alkoxylates, optionally in the corresponding alcohol as solvent, followed by addition of a chlorinating agent, for example titanium tetrachloride.

The literature discloses a number of methods for synthesizing oxadiazolinethiones of the formula (XXXV), for example the reaction of 1,2,4-oxadiazolin-5-ones with phosphorus pentasulfide, described by D. Sümengen in J. Chem. Soc. Perkin Trans 1 1983, 4, 687-691. The 1,2,4-oxadiazolin-5-ones required are commercially available or can be obtained from the N-substituted amidoximes (XXXIV) by reaction with a suitable halocarbonyl derivative, as described by H. Argibas in Phosp., Sulf., Silicon and rel. elem. 1998, 134/135, 381-319. Alternatively, the oxadiazolinethiones can be obtained directly from N-substituted amidoximes of the formula (XXXIV), for example by reaction with thiophosgene, as also published by D. Sümengen.

For the synthesis of the thiadiazolinones of the formula (XXXVI) from oxadiazolinethiones of the formula (XXXV), it is possible to employ the method of D. Sümengen in J. Chem. Soc. Perkin Trans 1 1983, 4, 687-691: this is a rearrangement of 3,4-disubstituted 1,2,4-oxadiazoline-5-thiones under copper catalysis in a high-boiling inert solvent at elevated temperature.

Thiadiazolinethiones of the formula (XXX) can be prepared, for example, from thiadiazolinones of the formula (XXXVI) by treatment with suitable sulfurizing agents such as, for example, phosphorus pentasulfide or Lawesson's reagent, optionally in an inert solvent at temperatures of up to 140° C.

The thiadiazolium salts of the formula (XXXI) can be prepared by methods known from the literature by alkylation of the corresponding thiadiazolinethiones of the formula (XXX). Suitable alkylating agents are, for example, alkyl halides (alkyl chlorides, alkyl bromides and alkyl iodides), alkyl triflates, alkyl mesylates and dialkyl sulfates.

The compounds of the formula (XXVIII) in process H can be prepared in particular under the conditions mentioned in the Preparation Examples.

Process I

The 3-substituted 2-arylimino-1-3-oxazolidin-4-ones (A=O, n=0), 2-arylimino-1-3-oxazinan-4-ones (A=O, n=1), 2-arylimino-1,3-thiazolidin-4-ones (A=S, n=0) and 2-arylimino-1,3-thiazinan-4-ones (A=S, n=1) of the general formula (I) can be prepared, for example, by process I

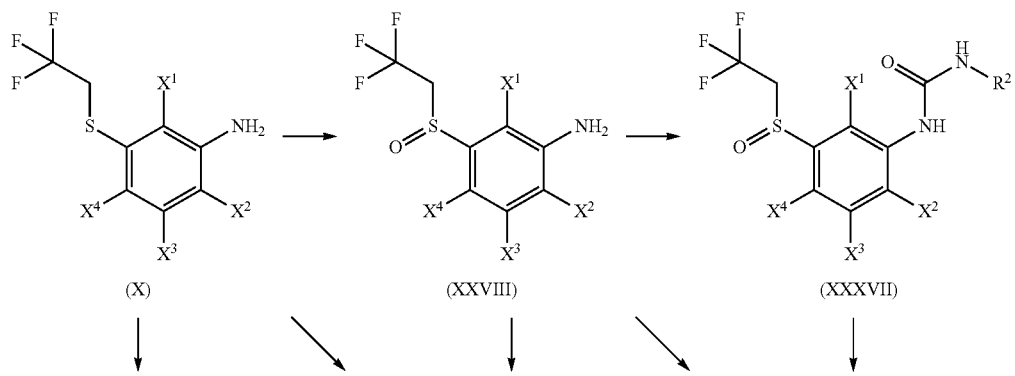

-continued

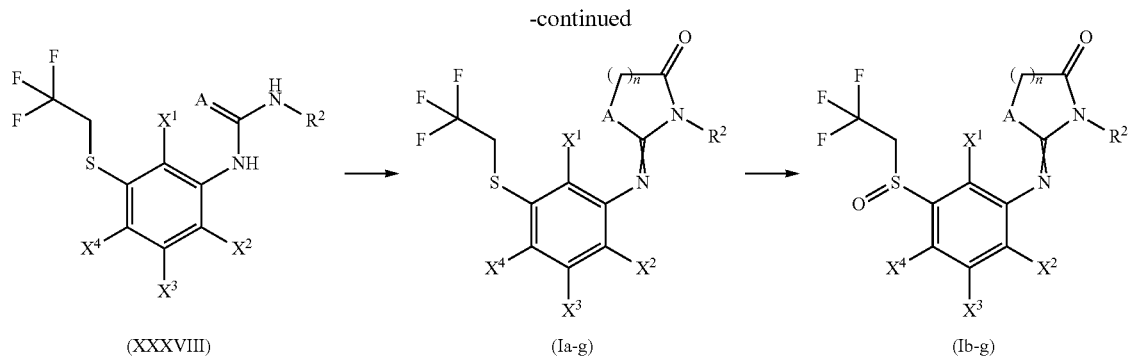

(XXXVIII)  (Ia-g)  (Ib-g)

where $X^1$, $X^2$, $X^3$, $X^4$ and $R^2$ have the meanings given above and n may represent 0 or 1.

Anilines of the formula (X) and (XXVIII) can be converted into the ureas (A=O) and thioureas (S) of the formulae (XXXVIII) and (XXXVII), respectively, by methods known from the literature, for example according to JP2011/042611, by treating them with isocyanates (for A=O) and isothiocyanates (for A=S), optionally in the presence of a base and optionally in the presence of an organic solvent, or by converting them by generally known methods into their isocyanates (A=O) and isothiocyanates (A=S) and reacting these with amines to give the thioureas.

From the ureas (A=O) and thioureas (A=S) of the general formulae (XXXVIII) and (XXXVII), respectively, it is possible to synthesize the 2-arylimino-1,3-oxazolidin-4-ones (A=O) and -thiazolidin-4-ones (A=S) of the general formulae (Ia-g) and (Ib-g), respectively, for example by cycloacylation with an adequate halocarbonyl derivative in an inert solvent, in most cases at temperatures of more than 100° C. Suitable halocarbonyl derivatives are, for example for n=0, chloroacetic acid and its acid chloride, bromoacetic acid and its acid chloride or bromide; for n=1 the literature mentions 3-substituted 2-propenoyl chlorides, as described by C. F. Howell in J. Org. Chem. 1962, 27, 1686 and 1691 for analogous conversions into oxazolidinones and V. N. Britsun in Russ. J. Org. Chem. 2006, 41 (11), 1719-1729 for thiazolidinones.

The compounds of the formulae (XXVIII), (XXXVIII) and (XXXVII) in process I can be prepared in particular under the conditions mentioned in the Preparation Examples.

Process J

The 3-substituted 2-arylimino-1,3-thiazoles of the general formula (I) can be prepared, for example, by process J,

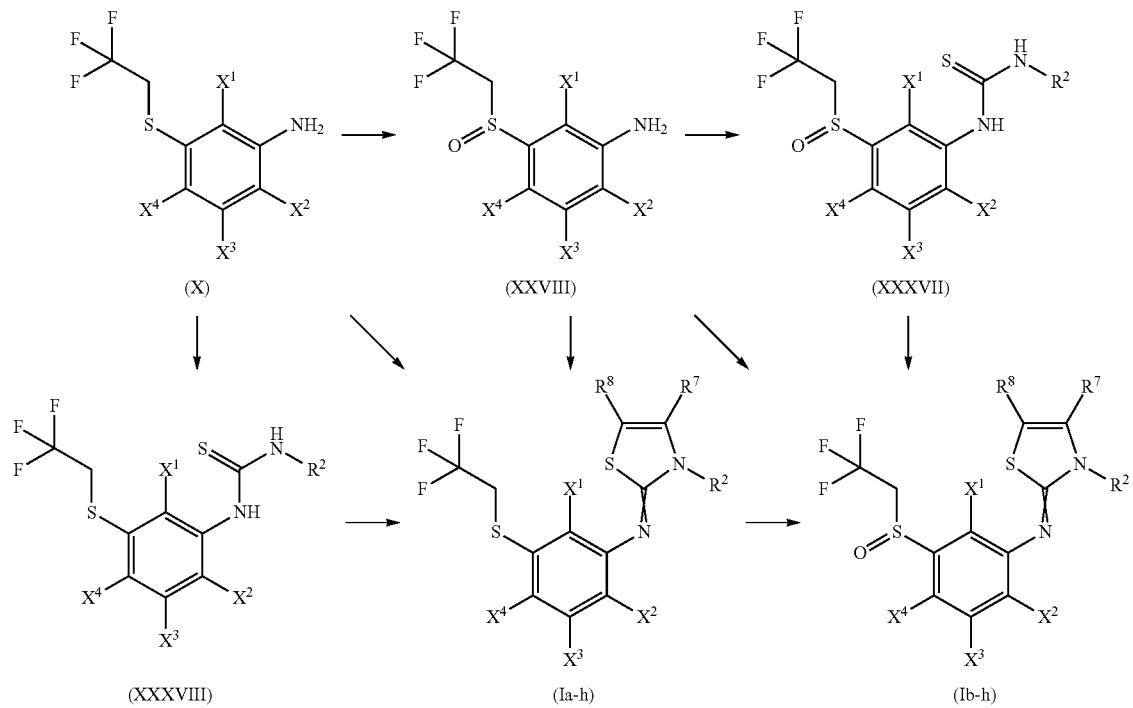

(X)  (XXVIII)  (XXXVII)

(XXXVIII)  (Ia-h)  (Ib-h)

where $X^1$, $X^2$, $X^3$, $X^4$ and $R^2$ have the meanings given above.

$R^7$ and $R^8$ are the substituents at the ring formed by $R^1$ and $R^3$ together with the atoms to which they are attached.

The 3-substituted 2-aryliminothiazoles (Ia-h) and (Ib-h) can be synthesized from the thioureas (XXXVIII) and (XXXVII), respectively, for example by reaction with an adequate halocarbonyl derivative in an inert solvent. This may take place, for example, by cycloacylation with α-haloketo compounds or derivatives thereof, for example with 3-bromo-2-butanone for $R^7$=$R^8$=methyl, as described by A. Yahyazadeh in J. Pharm. Res. 1998, 9, 536-537(S), 2126-2139(M), or with 2-chloro-1,1-diethoxyethane for $R^7$=$R^8$=H as described in the U.S. Pat. No. 4,079,144.

The sulfoxides (Ib) can be obtained by oxidation of the thioether (Ia) by methods known from the literature. Known methods of enantioselective enrichment of the sulfoxides may be employed for this purpose.

These 2-arylimino-1,3-thiazoles (I) can also be synthesized directly from the anilines of the formula (X) or (XXVIII), for example by reaction with 3-alkyl-1,3-thiazolinethiones of the formula (A) or their thiazolium salts, optionally in the presence of a base and optionally in an inert solvent.

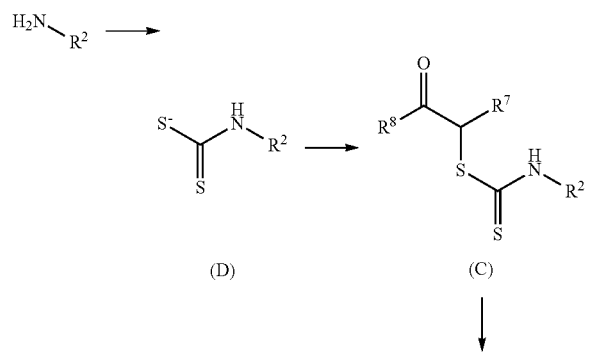

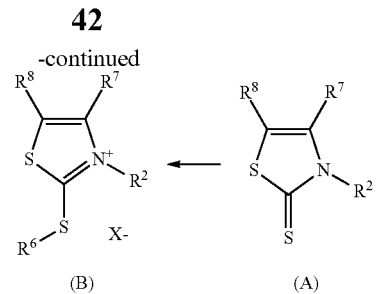

3-Substituted 1,3-thiazolinthiones of the formula (A) can be obtained from commercial sources or be prepared by methods known from the literature as described, for example, by K. Janikowska in Phosp. Sulf. Sil. and rel. elem. 2011, 186(1), 12-20. As in J. Amer. Chem. Soc. 1987, 109 (2), 492-507, amines can be reacted with carbon disulfide to give dithiocarbamates of the formula (D) which then, using an adequate halocarbonyl synthone, afford alkylated compounds of the formula (C). Suitable halocarbonyl compounds are, for example, chloroethanal or 2-chloro-1,1-diethoxyethane for $R^7$=$R^8$=H, chloropropanone for $R^7$=H and $R^8$=methyl, 3-bromo-2-butanone for $R^7$=$R^8$=methyl, 2-bromo-3-pentanone for $R^7$=methyl and $R^8$=ethyl, etc. The compounds of the formula (C) can either cyclize spontaneously to the desired thiazolinethiones (A) or only after dehydration, in most cases under acidic conditions and with heating.

The thiazolinium salts of the formula (B) can be prepared by alkylation of the corresponding thiadiazolinethiones of the formula (B). Suitable alkylating agents are, for example, alkyl halides (alkyl chlorides, alkyl bromides and alkyl iodides), alkyl triflates, alkyl mesylates and dialkyl sulfates.

The compounds of the formulae (XXVIII), (XXXVII) and (XXXVIII) in process J can be prepared in particular under the conditions mentioned in the Preparation Examples.

Process K

The 3-substituted 2-aryliminooxadiazoles of the general formula (I) can be prepared, for example, by process K

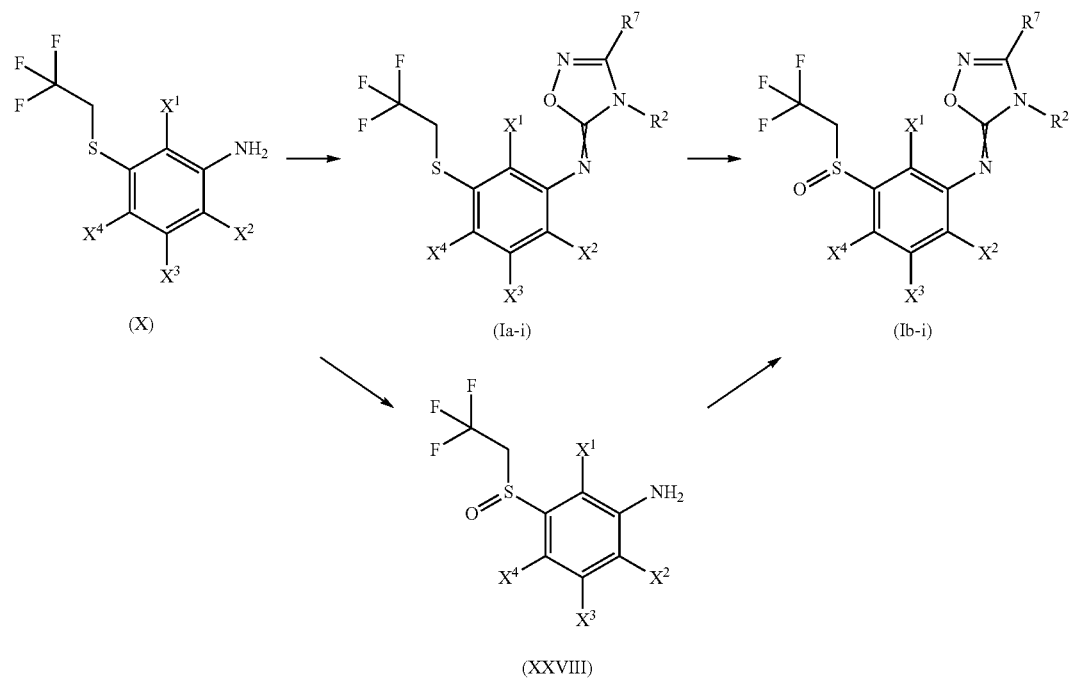

where $X^1$, $X^2$, $X^3$, $X^4$ and $R^2$ have the meanings given above.

$R^7$ is the substituent at the ring formed by $R^1$ and $R^3$ together with the atoms to which they are attached.

Anilines of the general formula (X) or the general formula (XXVIII) can be reacted, for example, with oxadiazolinethiones of the formula (XXXV) or with the corresponding oxadiazolium salts of the formula (XXXIX) to give the 2-aryliminooxadiazoles of the formula (Ia-i) and (Ib-i), respectively. This succeeds optionally in the presence of a base, optionally in an inert solvent or in an agent that can assume both roles, for example pyridine.

The synthesis of the oxadiazolinethiones of the formula (XXXV) and their oxadiazolium salts (XXXIX) can be carried out, for example, by the following process:

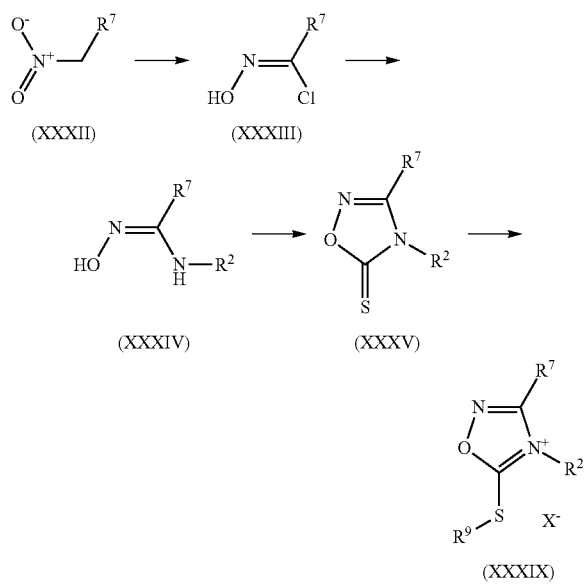

The oxadiazolium salts of the formula (XXXIX) can be prepared by methods known from the literature by alkylation of the corresponding oxadiazolinethiones of the formula (XXXV). Suitable alkylating agents are, for example, alkyl halides (alkyl chlorides, alkyl bromides and alkyl iodides), alkyl triflates, alkyl mesylates and dialkyl sulfates.

The compounds of the formula (XXVIII) in process K can be prepared in particular under the conditions mentioned in the Preparation Examples.

All these processes lead to the compounds of the general formula (I) according to the invention.

The active compounds according to the invention, in combination with good plant tolerance and favorable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can be used with preference as crop protection agents. They are effective against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus mactans*, *Metatetranychus* spp., *Nuphersa* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus carpophagus* and *Scutigera* spp.

From the order of the Coleoptera, for example, *Acalymma vittatum*, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnosterna consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Psylliodes* spp., *Ptinus* spp., *Rhizobius ventralis*, *Rhizopertha dominica*, *Sitophilus* spp., *Sphenophorus* spp., *Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Cochliomyia* spp., *Contarinia* spp., *Cordylobia anthropophaga*, *Culex* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia* spp., *Phorbia* spp., *Prodiplosis* spp., *Psila rosae*, *Rhagoletis* spp., *Stomoxys* spp., *Tabanus* spp., *Tannia* spp., *Tetanops* spp., *Tipula* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti.*

It is also possible to control protozoa, such as *Eimeria.*

From the order of the Heteroptera, for example, *Anasa tristis, Antestiopsis* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., Psallus spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the Hymenoptera, for example, *Athalia* spp., *Diprion* spp., *Hoplocampa* spp., *Lasius* spp., *Monomorium pharaonis, Vespa* spp.

From the order of the Isopoda, for example *Armadillidium vulgare, Oniscus asellus, Porcellio scaber.*

From the order of the Isoptera, for example, *Acromyrmex* spp., *Atta* spp., *Cornitermes cumulans, Microtermes obesi, Odontotermes* spp., *Reticulitermes* spp.

From the order of the Lepidoptera, for example, *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia kuehniella, Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichoplusia* spp., *Tuta absoluta, Virachola* spp.

From the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp. and *Xenopsylla cheopis.*

From the order of the Symphyla, for example, *Scutigerella* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Aphelenchoides* spp., *Bursaphelenchus* spp., *Ditylenchus* spp., *Globodera* spp., *Heterodera* spp., *Longidorus* spp., *Meloid-*

*ogyne* spp., *Pratylenchus* spp., *Radopholus similis*, *Trichodorus* spp., *Tylenchulus semipenetrans*, *Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (*mycoplasma*-like organisms) and RLO (*rickettsia*-like organisms). If appropriate, they can also be used as intermediates or precursors for the synthesis of other active compounds.

The present invention further relates to formulations and use forms prepared therefrom as crop protection compositions and/or pesticides, for example drench, drip and spray liquors, comprising at least one of the active compounds according to the invention. The use forms optionally comprise further crop protection agents and/or pesticides and/or action-improving adjuvants, such as penetrants, e.g. vegetable oils, for example rapeseed oil, sunflower oil, mineral oils, for example paraffin oils, alkyl esters of vegetable fatty acids, for example rapeseed oil methyl ester or soybean oil methyl ester, or alkanol alkoxylates, and/or spreaders, for example alkylsiloxanes, and/or salts, for example organic or inorganic ammonium or phosphonium salts, for example ammonium sulfate or diammonium hydrogenphosphate, and/or retention promoters, for example dioctyl sulfosuccinate or hydroxypropyl guar polymers, and/or humectants, for example glycerol, and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations optionally comprise, in addition to one or more active compounds according to the invention, further agrochemically active compounds.

These are preferably formulations or use forms which comprise auxiliaries, for example extenders, solvents, spontaneity promoters, carriers, emulsifiers, dispersants, antifreezes, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are produced in a known manner, for example by mixing the active ingredients with auxiliaries, for example extenders, solvents and/or solid carriers and/or further auxiliaries, for example surfactants. The formulations are produced either in suitable production plants or else before or during application.

The auxiliaries used may be substances suitable for imparting special properties, such as certain physical, technical and/or biological properties, to the formulation of the active ingredient, or to the use forms prepared from these formulations (for example ready-to-use crop protection compositions such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to employ, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

In principle, it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulfoxide, and also water.

In principle, it is possible to use all suitable carriers. Useful carriers include in particular: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers may also be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam formers, dispersants or wetting agents with ionic or nonionic properties, or mixtures of these surfactants, include salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkyl sulfonates, alkylsulfates, arylsulfonates, protein hydrolyzates, lignosulfite waste liquors and methylcellulose.

The presence of a surfactant is advantageous when one of the active ingredients and/or one of the inert carriers is insoluble in water and when application is effected in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability. Foam formers or antifoams may also be present.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids may also be present as additional auxiliaries in the formulations and the use forms derived therefrom. Further auxiliaries may be mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the active compounds can be combined with any solid or liquid additive customarily used for formulation purposes.

Useful retention promoters include all those substances which reduce the dynamic surface tension, for example dioctyl sulfosuccinate, or increase the viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) application liquor and/or from the spray coating into the cuticle of the plant and thereby increase the mobility of active ingredients in the cuticle. The method described in the literature (Baur et al., 1997, Pesticide Science 51, 131-152) can be used to determine this property. Examples include alcohol alkoxylates such as coconut fatty ethoxylate (10) or isotridecyl ethoxylate (12), fatty acid esters, for example rapeseed oil methyl ester or soybean oil methyl ester, fatty amine alkoxylates, for example tallowamine ethoxylate (15), or ammonium and/or phosphonium salts, for example ammonium sulfate or diammonium hydrogenphosphate.

The formulations contain preferably between 0.00000001% and 98% by weight of active ingredient or more preferably between 0.01% and 95% by weight of active ingredient, more preferably between 0.5% and 90% by weight of active ingredient, based on the weight of the formulation.

The active ingredient content of the use forms (crop protection compositions) prepared from the formulations can vary within wide limits. The active ingredient concentration of the use forms may typically be between 0.00000001% and 95% by weight of active ingredient, preferably between 0.00001% and 1% by weight, based on the weight of the use form. Application is accomplished in a customary manner appropriate for the use forms.

The active compounds according to the invention may be used as such or in formulations thereof, including in a mixture with one or more suitable fungicides, bactericides, acaricides, nematicides, insecticides, microbicides, fertilizers, attractants, phytotonics, sterilants, synergists, safeners, semiochemicals and/or plant growth regulators, in order thus, for example, to broaden the spectrum of action, to prolong the duration of action, to increase the rate of action, to prevent repulsion or prevent evolution of resistance. In addition, plant growth can be improved by those combinations which enhance tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products. In general, by combining the active compounds according to the invention and mixing partners, synergistic effects are obtained, i.e. the efficacy of the mixture in question is greater than the efficacy of the individual components. It is generally possible to use the combinations in premixes, tank mixes or ready mixes, and also in seed applications.

Particularly favorable mixing partners are, for example, the following:

Insecticides/Acaricides/Nematicides

The active compounds identified here by their common name are known and are described, for example, in the pesticide handbook ("The Pesticide Manual" 14th Ed., British Crop Protection Council 2006) or can be found on the Internet (e.g. http://www.alanwood.net/pesticides).

(1) Acetylcholinesterase (AChE) inhibitors such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chloropyrifos, chloropyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion.

(2) GABA-gated chloride channel antagonists such as, for example, cyclodiene organochlorines, for example chlordane and endosulfan; or phenylpyrazoles (fiproles), for example ethiprole and fipronil.

(3) Sodium channel modulators/voltage-dependent sodium channel blockers such as, for example, pyrethroids, for example acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers), esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer), prallethrin, pyrethrine (pyrethrum), resmethrin, silafluofen, tefluthrin, tetramethrin, tetramethrin [(1R) isomers)], tralomethrin and transfluthrin; or DDT; or methoxychlor.

(4) Nicotinergic acetylcholine receptor (nAChR) agonists such as, for example, neonicotinoids, for example acetamiprid, clothianidin, dinotefuran, imidacloprid, nitenpyram, thiacloprid and thiamethoxam; or nicotine.

(5) Nicotinergic acetylcholine receptor (nAChR) allosteric activators such as, for example, spinosyns, for example spinetoram and spinosad.

(6) Chloride channel activators such as, for example, avermectins/milbemycins, for example abamectin, emamectin benzoate, lepimectin and milbemectin.

(7) Juvenile hormone imitators such as, for example, juvenile hormone analogs, for example hydroprene, kinoprene and methoprene; or fenoxycarb; or pyriproxyfen.

(8) Active compounds with unknown or nonspecific mechanisms of action such as, for example, alkyl halides, for example methyl bromide and other alkyl halides; or chloropicrin; or sulfuryl fluoride; or borax; or tartar emetic.

(9) Selective antifeedants, for example pymetrozine; or flonicamid.

(10) Mite growth inhibitors, for example clofentezine, hexythiazox and diflovidazin; or etoxazole.

(11) Microbial disruptors of the insect gut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors such as, for example, diafenthiuron; or organotin compounds, for example azocyclotin, cyhexatin and fenbutatin oxide; or propargite; or tetradifon.

(13) Oxidative phosphorylation decouplers acting by interrupting the H proton gradient such as, for example, chlorfenapyr, DNOC and sulfluramid.

(14) Nicotinergic acetylcholine receptor antagonists such as, for example, bensultap, cartap hydrochloride, thiocyclam, and thiosultap-sodium.

(15) Chitin biosynthesis inhibitors, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, such as, for example, buprofezin.

(17) Molting disruptors, dipteran, such as, for example, cyromazine.

(18) Ecdysone receptor agonists such as, for example, chromafenozide, halofenozide, methoxyfenozide and tebufenozide.

(19) Octopaminergic agonists such as, for example, amitraz.

(20) Complex-III electron transport inhibitors such as, for example, hydramethylnone; or acequinocyl; or fluacrypyrim.

(21) Complex-I electron transport inhibitors, for example METI acaricides, for example fenazaquin, fenpyroximate, pyrimidifen, pyridaben, tebufenpyrad and tolfenpyrad; or rotenone (Derris).

(22) Voltage-dependent sodium channel blockers, for example indoxacarb; or metaflumizone.

(23) Inhibitors of acetyl-CoA carboxylase such as, for example, tetronic and tetramic acid derivatives, for example spirodiclofen, spiromesifen and spirotetramat.

(24) Complex-IV electron transport inhibitors such as, for example, phosphines, for example aluminum phosphide, calcium phosphide, phosphine and zinc phosphide; or cyanide.

(25) Complex-II electron transport inhibitors such as, for example, cyenopyrafen.

(28) Ryanodine receptor effectors such as, for example, diamides, for example chlorantraniliprole and flubendiamide.

Further active compounds with unknown mechanism of action, such as, for example, amidoflumet, azadirachtin, benclothiaz, benzoximate, bifenazate, bromopropylate, chinomethionat, cryolite, cyantraniliprole (Cyazypyr), cyflumetofen, dicofol, diflovidazin, fluensulfone, flufenerim, flufiprole, fluopyram, fufenozide, imidaclothiz, iprodione, meperfluthrin, pyridalyl, pyrifluquinazon, tetramethylfluthrin and iodomethane; and additionally preparations based on *Bacillus firmus* (particularly strain CNCM 1-1582, for example VOTiVO™, BioNem), and the following known active compounds:

3-bromo-N-{2-bromo-4-chloro-6-[(1-cyclopropylethyl) carbamoyl]phenyl}-1-(3-chloropyridin-2-yl)-1H-pyrazole-5-carboxamide (known from WO2005/077934), 4-{[(6-bromopyrid-3-yl)methyl](2-fluoroethyl)amino}furan-2(5H)-one (known from WO2007/115644), 4-{[(6-fluoropyrid-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2(5H)-one (known from WO2007/115644), 4-{[(6-chloropyrid-3-yl)methyl](2-fluoroethyl)amino}furan-2(5H)-one (known from WO2007/115644), flupyradifurone, 4-{[(6-chloro-5-fluoropyrid-3-yl) methyl](methyl)amino}furan-2(5H)-one (known from WO2007/115643), 4-{[(5,6-dichloropyrid-3-yl)methyl](2-fluoroethyl)amino}furan-2(5H)-one (known from WO2007/115646), 4-{[(6-chloro-5-fluoropyrid-3-yl)methyl](cyclopropyl)amino}furan-2(5H)-one (known from WO2007/115643), 4-{[(6-chloropyrid-3-yl)methyl](cyclopropyl) amino}furan-2(5H)-one (known from EP-A-0 539 588), 4-{[(6-chloropyrid-3-yl)methyl](methyl)amino}furan-2 (5H)-one (known from EP-A-0 539 588), {[1-(6-chloropyridin-3-yl)ethyl](methyl)oxido-$\lambda^4$-sulfanylidene}cyanamide (known from WO2007/149134) and diastereomers thereof {[(1R)-1-(6-chloropyridin-3-yl)ethyl](methyl)oxido-$\lambda^4$-sulfanylidene}cyanamide (A) and {[(1S)-1-(6-chloropyridin-3-yl)ethyl](methyl)oxido-$\lambda^4$-sulfanylidene}cyanamide (B) (likewise known from WO2007/149134) and sulfoxaflor and diastereomers thereof [(R)-methyl(oxido){(1R)-1-[6-(trifluoromethyl)pyridin-3-yl]ethyl}-$\lambda^4$-sulfanylidene]cyanamide (A1) and [(S)-methyl(oxido){(1S)-1-[6-(trifluoromethyl)pyridin-3-yl]ethyl}-$\lambda^4$-sulfanylidene]cyanamide (A2), designated as diastereomer group A (known from WO 2010/074747, WO 2010/074751), [(R)-methyl(oxido){(1S)-1-[6-(trifluoromethyl)pyridin-3-yl]ethyl}-λ⁴-sulfanylidene]cyanamide (B1) and [(S)-methyl(oxido){(1R)-1-[6-(trifluoromethyl)pyridin-3-yl]ethyl}-λ⁴-sulfanylidene]cyanamide (B2), designated as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5]dec-3-en-2-one (known from WO2008/067911), 1-{2-fluoro-4-methyl-5-[(2,2,2-trifluoroethyl)sulfinyl]phenyl}-3-(trifluoromethyl)-1H-1,2,4-triazole-5-amine (known from WO2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H, 11H-benzo[f]pyrano[4,3-b]chromen-4-yl]methyl cyclopropanecarboxylate (known from WO2008/066153), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethylbenzenesulfonamide (known from WO2005/035486), 4-(difluoromethoxy)-N-ethyl-N-methyl-1,2-benzothiazol-3-amine 1,1-dioxide (known from WO2007/057407), N-[1-(2,3-dimethylphenyl)-2-(3,5-dimethylphenyl)ethyl]-4,5-dihydro-1,3-thiazole-2-amine (known from WO2008/104503), {1'-[(2E)-3-(4-chlorophenyl)prop-2-en-1-yl]-5-fluorospiro[indol-3,4'-piperidin]-1(2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280), flometoquin, PF1364 (CAS Reg. No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO2010/005692), NNI-0711 (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), 2-{6-[2-(5-fluoropyridin-3-yl)-1,3-thiazol-5-yl]pyridin-2-yl}pyrimidine (known from WO2010/006713), 2-{6-[2-(pyridin-3-yl)-1,3-thiazol-5-yl]pyridin-2-yl}pyrimidine (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO2010/069502), (1E)-N-[(6-chloropyridin-3-yl)methyl]-N'-cyano-N-(2,2-difluoroethyl)ethanimidamide (known from WO2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925) and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO2011/049233).

Fungicides (1) Inhibitors of ergosterol biosynthesis such as, for example, (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifin (65472-88-0), (1.33) nuarimol (63284-71-9), (1.34) oxpoconazole (174212-12-5), (1.35) paclobutrazole (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-

67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafin (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl) cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy] phenyl}imidoformamide and (1.64) 0-[1-(4-methoxyphenyl)-3,3-dimethylbutan-2-yl]1H-imidazole-1-carbothioate (111226-71-2).

(2) Respiration inhibitors (respiratory chain inhibitors) such as, for example, (2.1) bixafen (581809-46-3), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam mixture of the syn-epimeric racemate 1RS,4SR, 9RS and the anti-empimeric racemate 1RS,4SR,9SR (881685-58-1), (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamid (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7), (2.28) 5,8-difluoro-N-[2-(2-fluoro-4-{[4-(trifluoromethyl)pyridin-2-yl]oxy}phenyl)ethyl]quinazoline-4-amine (1210070-84-0) (known from WO2010025451), (2.29) N-[9-(dichloromethylene)-1,2,3,4-tetrahydro-1,4-methanonaphthalen-5-yl]-3-(difluoromethyl)-1-methyl-1H-pyrazole-4-carboxamide, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene-1,2,3,4-tetrahydro-1,4-methanonaphthalen-5-yl]-3-(difluoromethyl)-1-methyl-1H-pyrazole-4-carboxamide.

(3) Respiration inhibitors (respiratory chain inhibitors) acting on complex III of the respiratory chain such as, for example, (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.6) dimoxystrobin (141600-52-4), (3.6) enestroburin (238410-11-2) (known from WO 2004/058723), (3.9) famoxadone (131807-57-3) (known from WO 2004/058723), (3.10) fenamidone (161326-34-7) (known from WO 2004/058723), (3.11) fenoxystrobin (918162-02-4), (3.12) fluoxastrobin (361377-29-9) (known from WO 2004/058723), (3.13) kresoxim-methyl (143390-89-0) (known from WO 2004/058723), (3.14) metominostrobin (133408-50-1) (known from WO 2004/058723), (3.15) orysastrobin (189892-69-1) (known from WO 2004/058723), (3.16) picoxystrobin (117428-22-5) (known from WO 2004/058723), (3.17) pyraclostrobin (175013-18-0) (known from WO 2004/058723), (3.18) pyrametostrobin (915410-70-7) (known from WO 2004/058723), (3.19) pyraoxystrobin (862588-11-2) (known from WO 2004/058723), (3.20) pyribencarb (799247-52-2) (known from WO 2004/058723), (3.21) triclopyricarb (902760-40-1), (3.22) trifloxystrobin (141517-21-7) (known from WO 2004/058723), (3.23) (2E)-2-(2-{[6-(3-chloro-2-methylphenoxy)-5-fluoropyrimidin-4-yl]oxy}phenyl)-2-(methoxyimino)-N-methylethanamide (known from WO 2004/058723), (3.24) (2E)-2-(methoxyimino)-N-methyl-2-(2-{[({(1E)-1-[3-(trifluoromethyl)phenyl]ethylidene}amino)oxy] methyl}phenyl)ethanamide (known from WO 2004/058723), (3.25) (2E)-2-(methoxyimino)-N-methyl-2-{2-[(E)-({1-[3-(trifluoromethyl)phenyl]ethoxy}imino)methyl] phenyl}ethanamide (158169-73-4), (3.26) (2E)-2-{2-[({[(1E)-1-(3-{[(E)-1-fluoro-2-phenylethenyl]oxy}phenyl) ethylidene]amino}oxy)methyl]phenyl}-2-(methoxyimino)-N-methylethanamide (326896-28-0), (3.27) (2E)-2-{2-[({[(2E,3E)-4-(2,6-dichlorophenyl)but-3-en-2-ylidene] amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (119899-14-8), (3.29) 5-methoxy-2-methyl-4-(2-{[({(1E)-1-[3-(trifluoromethyl)phenyl]ethylidene}amino)oxy] methyl}phenyl)-2,4-dihydro-3H-1,2,4-triazol-3-one, (3.30) methyl (2E)-2-{2-[({cyclopropyl[(4-methoxyphenyl)imino] methyl}sulfanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-9), (3.32) 2-{2-[(2,5-dimethylphenoxy)methyl]phenyl}-2-methoxy-N-methylacetamide (173662-97-0) and (3.33) (2R)-2-{2-[(2,5-dimethylphenoxy)methyl]phenyl}-2-methoxy-N-methylacetamide (394657-24-0).

(4) Inhibitors of mitosis and cell division such as, for example, (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolid (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7).

(5) Compounds having multisite activity such as, for example, (5.1) Bordeaux mixture (8011-63-0), (5.2) captafol (2425-06-1), (5.3) captan (133-06-2) (known from WO 02/12172), (5.4) chlorothalonil (1897-45-6), (5.5) copper preparations such as copper hydroxide (20427-59-2), (5.6) copper naphthenate (1338-02-9), (5.7) copper oxide (1317-39-1), (5.8) copper oxychloride (1332-40-7), (5.9) copper sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) zinc metiram (9006-42-2), (5.27) copper-oxine (10380-28-6), (5.28) propamidine (104-32-5), (5.29) propineb (12071-83-9), (5.30) sulfur and sulfur preparations such as, for example, calcium polysulfide (7704-34-9), (5.31) thiram (137-26-8), (5.32) tolylfluanid (731-27-1), (5.33) zineb (12122-67-7) and (5.34) ziram (137-30-4).

(6) Resistance inducers such as, for example, (6.1) acibenzolar-S-methyl (135158-54-2), (6.2) isotianil (224049-04-1), (6.3) probenazole (27605-76-1) and (6.4) tiadinil (223580-51-6).

(7) Inhibitors of amino acid and protein biosynthesis such as, for example, (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and (7.8) 3-(5-fluoro-3,3,4,4-tetramethyl-3,4-dihydroisoquinolin-1-yl)quinoline (861647-32-7) (known from WO2005070917).

(8) ATP production inhibitors such as, for example, (8.1) fentin acetate (900-95-8), (8.2) fentin chloride (639-58-7), (8.3) fentin hydroxide (76-87-9) and (8.4) silthiofam (175217-20-6).

(9) Inhibitors of cell wall synthesis such as, for example, (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of lipid and membrane synthesis such as, for example, (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Melanin biosynthesis inhibitors such as, for example, (11.1) carpropamid (104030-54-8), (11.2) diclocymet (139920-32-4), (11.3) fenoxanil (115852-48-7), (11.4) fthalide (27355-22-2), (11.5) pyroquilon (57369-32-1), (11.6) tricyclazole (41814-78-2) and (11.7) 2,2,2-trifluoroethyl {3-methyl-1-[(4-methylbenzoyl)amino]butan-2-yl}carbamate (851524-22-6) (known from WO2005042474).

(12) Inhibitors of nucleic acid synthesis such as, for example, (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazole (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Signal transduction inhibitors such as, for example, (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Decouplers such as, for example, (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds such as, for example, (15.1) benthiazole (21564-17-0), (15.2) bethoxazine (163269-30-5), (15.3) capsimycin (70694-08-5), (15.4) carvone (99-49-0), (15.5) chinomethionat (2439-01-2), (15.6) pyriofenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulfate (43222-48-6), (15.17) diphenylamine (122-39-4), (15.18) EcoMate, (15.19) fenpyrazamine (473798-59-3), (15.20) flumetover (154025-04-4), (15.21) fluoromid (41205-21-4), (15.22) flusulfamide (106917-52-6), (15.23) flutianil (304900-25-2), (15.24) fosetyl-aluminum (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and its salts (87-86-5), (15.40) phenothrin, (15.41) phosphoric acid and its salts (13598-36-2), (15.42) propamocarb-fosetylate, (15.43) propanosine-sodium (88498-02-6), (15.44) proquinazid (189278-12-4), (15.45) pyrimorph (868390-90-3), (15.45e) (2E)-3-(4-tert-butylphenyl)-3-(2-chloropyridin-4-yl)-1-(morpholin-4-yl)prop-2-en-1-one (1231776-28-5), (15.45z) (2Z)-3-(4-tert-butylphenyl)-3-(2-chloropyridin-4-yl)-1-(morpholin-4-yl)prop-2-en-1-one (1231776-29-6), (15.46) pyrrolnitrin (1018-71-9) (known from EP-A 1 559 320), (15.47) tebufloquin (376645-78-2), (15.48) tecloftalam (76280-91-6), (15.49) tolnifanide (304911-98-6), (15.50) triazoxide (72459-58-6), (15.51) trichlamid (70193-21-4), (15.52) zarilamid (84527-51-5), (15.53) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate (517875-34-2) (known from WO2003035617), (15.54) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-79-6), (15.55) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9), (15.56) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9), (15.57) 1-(4-methoxyphenoxy)-3,3-dimethylbutan-2-yl 1H-imidazole-1-carboxylate (111227-17-9), (15.58) 2,3,5,6-tetrachloro-4-(methylsulfonyl)pyridine (13108-52-6), (15.59) 2,3-dibutyl-6-chlorothieno[2,3-d]pyrimidin-4(3H)-one (221451-58-7), (15.60) 2,6-dimethyl-1H,5H-[1,4]dithiino[2,3-c:5,6-c']dipyrrole-1,3,5,7(2H,6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7), (15.62) 2-[5-methyl-3-(trifluoromethyl)-1H-pyrazol-1-yl]-1-(4-{4-[(5S)-5-phenyl-4,5-dihydro-1,2-oxazol-3-yl]-1,3- thiazol-2-yl}piperidin-1-yl)ethanone (1003316-54-8), (15.63) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5), (15.64) 2-butoxy-6-iodo-3-propyl-4H-chromen-4-one, (15.65) 2-chloro-5-[2-chloro-1-(2,6-difluoro-4-methoxyphenyl)-4-methyl-1H-imidazol-5-yl]pyridine, (15.66) 2-phenylphenol and its salts (90-43-7), (15.67) 3-(4,4,5-trifluoro-3,3-dimethyl-3,4-dihydroisoquinolin-1-yl)quinoline (861647-85-0) (known from WO2005070917), (15.68) 3,4,5-trichloropyridine-2,6-dicarbonitrile (17824-85-0), (15.69) 3-[5-(4-chlorophenyl)-2,3-dimethyl-1,2-oxazolidin-3-yl]pyridine, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiole, (15.73) 5-chloro-N'-phenyl-N'-(prop-2-yn-1-yl)thiophene-2-sulfonohydrazide (134-31-6), (15.74) 5-fluoro-2-[(4-fluorobenzyl)oxy]pyrimidine-4-amine (1174376-11-4) (known from WO2009094442), (15.75) 5-fluoro-2-[(4-methylbenzyl)oxy]pyrimidine-4-amine (1174376-25-0) (known from WO2009094442), (15.76) 5-methyl-6-octyl[1,2,4]triazolo[1,5-a]pyrimidine-7-amine, (15.77) ethyl-(2Z)-3-amino-2-cyano-3-phenylprop-2-enoate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloropyridine-3-carboxamide, (15.82) N-[1-(5-bromo-3-chloropyridin-2-yl)ethyl]-2,4-dichloropyridine-3-carboxamide, (15.83) N-[1-(5-bromo-3-chloropyridin-2-yl)ethyl]-2-fluoro-4-iodopyridine-3-carboxamide, (15.84) N-{(E)-[(cyclopropylmethoxy)imino][6-(difluoromethoxy)-2,3-difluorophenyl]methyl}-2-phenylacetamide (221201-92-9), (15.85) N-{(Z)-[(cyclopropylmethoxy)imino][6-(difluoromethoxy)-2,3-difluorophenyl]methyl}-2-phenylacetamide (221201-92-9), (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6), (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-07-6), (15.89) N-methyl-2-(1-{[5-methyl-3-(trifluoromethyl)-1H-pyrazol-1-yl]acetyl}piperidin-4-yl)-N-[(1 S)-1,2,3,4-tetrahydronaphthalen-1-yl]-1,3-thiazole-4-carboxamide (922514-48-5), (15.90) pentyl-{6-[({[(1-methyl-1H-tetrazol-5-yl)(phenyl)methylidene]amino}oxy)methyl]pyridin-2-yl}carbamate, (15.91) phenazine-1-carboxylic acid, (15.92) quinolin-8-ol (134-31-6), (15.93) quinolin-8-ol sulfate (2:1) (134-31-6) and (15.94) tert-butyl {6-[({[(1-methyl-1H-tetrazol-5-yl)(phenyl)methylene]amino}oxy)methyl]pyridin-2-yl}carbamate.

(16) Further compounds such as, for example, (16.1) 1-methyl-3-(trifluoromethyl)-N-[2'-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazole-4-carboxamide, (16.4) 3-(difluoromethyl)-1-methyl-N-[4'-(trifluoromethyl)biphenyl-2-yl]-1H-pyrazole-4-carboxamide, (16.5) N-(2',5'-difluorobiphenyl-2-yl)-1-methyl-3-(trifluoromethyl)-1H-pyrazole-4-carboxamide, (16.6) 3-(difluoromethyl)-1-methyl-N-[4'-(prop-1-yn-1-yl)biphenyl-2-yl]-1H-pyrazole-4-carboxamide, (16.7) 5-fluoro-1,3-dimethyl-N-[4'-(prop-1-yn-1-yl)biphenyl-2-yl]-1H-pyrazole-4-carboxamide, (16.8) 2-chloro-N-[4'-(prop-1-yn-1-yl)biphenyl-2-yl]pyridine-3-carboxamide, (16.9) 3-(difluoromethyl)-N-[4'-(3,3-dimethylbut-1-yn-1-yl)biphenyl-2-yl]-1-methyl-1H-pyrazole-4-carboxamide, (16.10) N-[4'-(3,3-dimethylbut-1-yn-1-yl)biphenyl-2-yl]-5-fluoro-1,3-dimethyl-1H-pyrazole-4-carboxamide, (16.11) 3-(difluoromethyl)-N-(4'-ethynylbiphenyl-2-yl)-1-methyl-1H-pyrazole-4-carboxamide, (16.12) N-(4'-ethynylbiphenyl-2-yl)-5-fluoro-1,3-dimethyl-1H-pyrazole-4-carboxamide, (16.13) 2-chloro-N-(4'-ethynylbiphenyl-2-yl)pyridine-3-carboxamide, (16.14) 2-chloro-N-[4'-(3,3-dimethylbut-1-yn-1-yl)biphenyl-2-yl]pyridine-3-carboxamide (known from EP-A 1 559 320), (16.15) 4-(difluoromethyl)-2-methyl-N-[4'-(trifluoromethyl)biphenyl-2-yl]-1,3-thiazole-5-carboxamide, (16.16) 5-fluoro-N-[4'-(3-hydroxy-3-methylbut-1-yn-1-yl)biphenyl-2-yl]-1,3-dimethyl-1H-pyrazole-4-carboxamide, (16.17) 2-chloro-N-[4'-(3-hydroxy-3-methylbut-1-yn-1-yl)biphenyl-2-yl]pyridine-3-carboxamide, (16.18) 3-(difluoromethyl)-N-[4'-(3-methoxy-3-methylbut-1-yn-1-yl)biphenyl-2-yl]-1-methyl-1H-pyrazole-4-carboxamide, (16.19) 5-fluoro-N-[4'-(3-methoxy-3-methylbut-1-yn-1-yl)biphenyl-2-yl]-1,3-dimethyl-1H-pyrazole-4-carboxamide, (16.20) 2-chloro-N-[4'-(3-methoxy-3-methylbut-1-yn-1-yl)biphenyl-2-yl]pyridine-3-carboxamide, (16.21) (5-bromo-2-methoxy-4-methylpyridin-3-yl)(2,3,4-trimethoxy-6-methylphenyl)methanone, (16.22) N-[2-(4-{[3-(4-chlorophenyl)prop-2-yn-1-yl]oxy}-3-methoxyphenyl)ethyl]-N2-(methylsulfonyl)valinamide (220706-93-4), (16.23) 4-oxo-4-[(2-phenylethyl)amino]butanoic acid and (16.24) but-3-yn-1-yl {6-[({[(Z)-(1-methyl-1H-tetrazol-5-yl)(phenyl)methylene]amino}oxy)methyl]pyridin-2-yl}carbamate.

All mixing partners mentioned in classes (1) to (16) can, if they are capable on the basis of their functional groups, optionally form salts with suitable bases or acids.

A mixture with other known active compounds, such as herbicides, fertilizers, growth regulators, safeners, semiochemicals, or else with agents for improving the plant properties, is also possible.

When used as insecticides, the active compounds according to the invention may also be present in their commercially available formulations and in the use forms, prepared from these formulations, as a mixture with synergists. Synergists are compounds which enhance the action of the active compounds, without any need for the synergist added to be active itself.

When used as insecticides, the active compounds according to the invention may also be present in their commercially available formulations and in the use forms, prepared from these formulations, as a mixture with inhibitors which reduce degradation of the active compound after use in the environment of the plant, on the surface of parts of plants or in plant tissues.

According to the invention, it is possible to treat all plants and plant parts. Plants are understood here to mean all plants and plant populations, such as wanted and unwanted wild plants or crop plants (including naturally occurring crop plants). Crop plants may be plants obtainable by conventional breeding and optimization methods or by biotechnological and gene-technological methods, or combinations of these methods, including the transgenic plants and including the plant cultivars protectable or not protectable by plant breeders' rights. Parts of plants shall be understood to mean all above-ground and below-ground parts and organs of plants, such as shoot, leaf, flower and root, examples including leaves, needles, stems, trunks, flowers, fruit bodies, fruits and seeds, and also roots, tubers and rhizomes. The plant parts also include harvested material and vegetative and generative propagation material, for example cuttings, tubers, rhizomes, slips and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and parts thereof in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (genetically modified organisms), and parts thereof are treated. The terms "parts" or "parts of plants" or "plant parts" have been explained above.

More preferably, plants of the plant cultivars which are commercially available or are in use are treated in accordance with the invention. Plant cultivars are understood to mean plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the treatment according to the invention may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, increased storage life and/or processability of the harvested products, which exceed the effects normally to be expected.

The preferred transgenic plants or plant cultivars (those obtained by genetic engineering) which are to be treated in accordance with the invention include all plants which, through the genetic modification, received genetic material which imparts particular advantageous useful traits to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, longer storage life and/or processability of the harvested products. Further and particularly emphasized examples of such properties are an improved defense of the plants against animal and microbial pests, such as against insects, mites, phytopathogenic fungi, bacteria and/or viruses, and also increased tolerance of the plants to certain herbicidally active ingredients. Examples of transgenic plants which may be mentioned are the important crop plants, such as cereals (wheat, rice), corn, soybeans, potatoes, sugar beet, tomatoes, peas and other types of vegetable, cotton, tobacco, oilseed rape and also fruit plants (with the fruits apples, pears, citrus fruits and grapes), with particular emphasis being given to corn, soybeans, potatoes, cotton, tobacco and oilseed rape. Traits that are emphasized in particular are the increased defense of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the improved defense of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain active herbicidal ingredients, for example imidazolinones, sulfonylureas, glyphosate or phosphinothricin (for example the "PAT" gene). The genes which impart the desired traits in question can also be present in combinations with one another in the transgenic plants. Examples of "Bt plants" include corn varieties, cotton varieties, soybean varieties and potato varieties which are sold under the trade names YIELD GARD® (for example corn, cotton, soybean), KnockOut® (for example corn), StarLink® (for example corn), Bollgard® (cotton), Nucotn® (cotton) and NewLeaf® (potato). Examples of herbicide-tolerant plants include corn varieties, cotton varieties and soybean varieties which are sold under the trade names Roundup Ready® (tolerance to glyphosate, for example corn, cotton, soybean), Liberty Link® (tolerance to phosphinothricin, for example oilseed rape), IMI® (tolerance to imidazolinones) and STS® (tolerance to sulfonylureas, for example corn). Herbicide-resistant plants (plants bred in a conventional manner for herbicide tolerance) which may be mentioned include the varieties sold under the name Clearfield® (for example corn). Of course, these statements also apply to plant cultivars which have these genetic traits or genetic traits which are still to be developed and will be developed and/or marketed in the future.

The plants listed can be treated in accordance with the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include: From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp.,

*Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., Pterolichus spp., *Psoroptes* spp., *Chorioptes* spp., Otodectes spp., *Sarcoptes* spp., Notoedres spp., Knemidocoptes spp., *Cytodites* spp. and *Laminosioptes* spp.

The active compounds of the formula (I) according to the invention are also suitable for controlling arthropods which attack agricultural livestock, for example cattle, sheep, goats, horses, pigs, donkeys, camels, buffaloes, rabbits, chickens, turkeys, ducks, geese, honey-bees, other domestic animals such as, for example, dogs, cats, caged birds, aquarium fish, and experimental animals, for example hamsters, guinea pigs, rats and mice. The control of these arthropods is intended to reduce cases of death and reduced productivity (of meat, milk, wool, hides, eggs, honey etc.), and so more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for livestock, poultry, domestic animals and the like, the active compounds of the formula (I) can be used as formulations (for example powders, emulsions, flowables) comprising the active compounds in an amount of 1 to 80% by weight, either directly or after 100 to 10 000-fold dilution, or they may be used as a chemical bath.

It has also been found that the compounds according to the invention have strong insecticidal action against insects which destroy industrial materials.

Preferred but nonlimiting examples include the following insects:

beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus;* dermapterans, such as *Sirex juvencus, Urocerus gigas, Urocerus gigas taignus, Urocerus* augur;

termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;* bristletails, such as *Lepisma saccarina.*

Industrial materials in the present connection are understood to mean inanimate materials, such as preferably plastics, adhesives, sizes, papers and cards, leather, wood, processed wood products and coating compositions.

The ready-to-use compositions may optionally also comprise other insecticides, and optionally one or more fungicides.

Moreover, the compounds according to the invention can be employed for protecting objects which come into contact with saltwater or brackish water, in particular hulls, screens, nets, buildings, moorings and signaling systems, against fouling.

In addition, the compounds according to the invention can be used as antifouling compositions, alone or in combinations with other active compounds.

The active compounds are also suitable for controlling animal pests in the domestic sector, in the hygiene sector and in the protection of stored products, especially insects, arachnids and mites, which are found in enclosed spaces, for example homes, factory halls, offices, vehicle cabins and the like. They can be used to control these pests alone or in combination with other active compounds and auxiliaries in domestic insecticide products. They are effective against sensitive and resistant species, and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Avicularii-dae, Araneidae.*

From the order of the Opiliones, for example, *Pseudoscorpiones chelifer, Pseudoscorpiones cheiridium,* Opiliones *phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai,* Leucophaea maderae, Panchlora spp., Parcoblatta spp., Periplaneta australasiae, Periplaneta americana, Periplaneta brunnea, Periplaneta fuliginosa, Supella longipalpa.

From the order of the Saltatoria, for example, Acheta domesticus.

From the order of the Dermaptera, for example, Forficula auricularia.

From the order of the Isoptera, for example, Kalotermes spp., Reticulitermes spp.

From the order of the Psocoptera, for example, Lepinatus spp., Liposcelis spp.

From the order of the Coleoptera, for example, Anthrenus spp., Attagenus spp., Dermestes spp., Latheticus oryzae, Necrobia spp., Ptinus spp., Rhizopertha dominica, Sitophilus granarius, Sitophilus oryzae, Sitophilus zeamais, Stegobium paniceum.

From the order of the Diptera, for example, Aedes aegypti, Aedes albopictus, Aedes taeniorhynchus, Anopheles spp., Calliphora erythrocephala, Chrysozona pluvialis, Culex quinquefasciatus, Culex pipiens, Culex tarsalis, Drosophila spp., Fannia canicularis, Musca domestica, Phlebotomus spp., Sarcophaga carnaria, Simulium spp., Stomoxys calcitrans, Tipula paludosa.

From the order of the Lepidoptera, for example, Achroia grisella, Galleria mellonella, Plodia interpunctella, Tinea cloacella, Tinea pellionella, Tineola bisselliella.

From the order of the Siphonaptera, for example, Ctenocephalides canis, Ctenocephalides felis, Pulex irritans, Tunga penetrans, Xenopsylla cheopis.

From the order of the Hymenoptera, for example, Camponotus herculeanus, Lasius fuliginosus, Lasius niger, Lasius umbratus, Monomorium pharaonis, Paravespula spp., Tetramorium caespitum.

From the order of the Anoplura, for example, Pediculus humanus capitis, Pediculus humanus corporis, Pemphigus spp., Phylloera vastatrix, Phthirus pubis.

From the order of the Heteroptera, for example, Cimex hemipterus, Cimex lectularius, Rhodinus prolixus, Triatoma infestans.

In the field of household insecticides, they are used alone or in combination with other suitable active compounds, such as phosphoric acid esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

Illustration of the Processes and Intermediates

The Preparation and Use Examples which follow illustrate the invention without limiting it.

Preparation Example 1: 2,2,2-Trifluoro-N'-{2-fluoro-4-methyl-5-[(2,2,2-trifluoroethyl)sulfinyl]phenyl}-N,N-dimethylethanimidamide (Ib-01)

Step 1: 2,2,2-Trifluoro-N-(2-fluoro-4-methylphenyl)acetamide (VI-1)

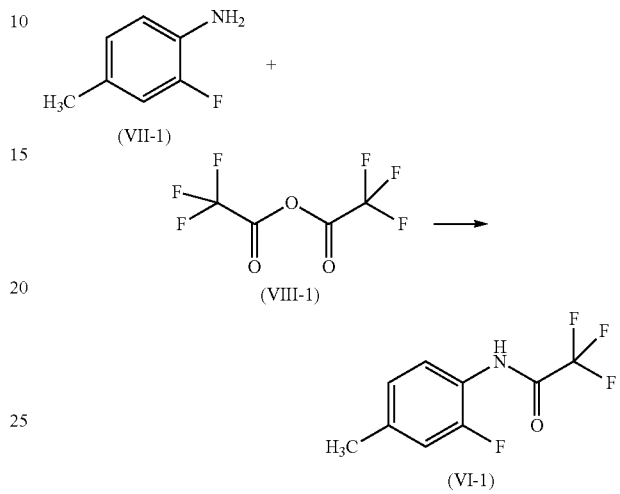

At 0° C., 27.5 g of 2-fluoro-4-methylaniline are initially charged in 300 ml of dichloromethane, 26.7 g of triethylamine are added and 50.8 g of trifluoroacetic anhydride are then added dropwise. The mixture is stirred at 0° C. for another 2 h and then concentrated by rotary evaporation. The residue is taken up in water and extracted twice with ethyl acetate. The combined organic phases are dried over sodium sulfate and filtered and the solvent is removed under reduced pressure. This gives 49.0 g (100% of theory) of the trifluoroacetamide (VI-1).

log P(HCOOH): 2.40

Step 2: 4-Fluoro-2-methyl-5-[(trifluoroacetyl)amino]benzenesulfonyl chloride (V-1)

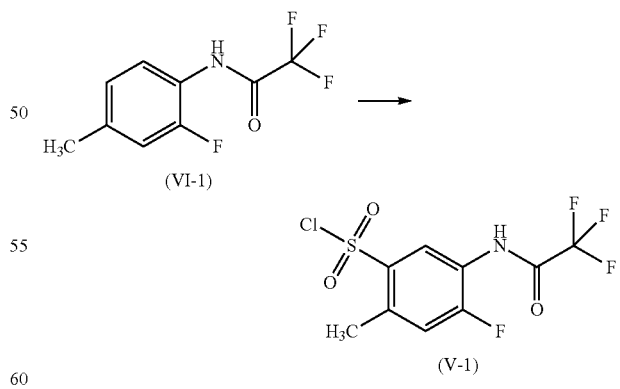

258 g of chlorosulfonic acid are initially charged, and 49 g of 2,2,2-trifluoro-N-(2-fluoro-4-methylphenyl)acetamide (VI-1) are added a little at a time at room temperature. The mixture is stirred at room temperature for another 16 h. With stirring, the mixture is added to ice and extracted twice with ethyl acetate. The combined organic phases are dried over sodium sulfate and filtered and the solvent is removed under reduced pressure. This gives 70.8 g of the chlorosulfonyl (V-1). The crude product is immediately reacted further.

Step 3: N,N'-[Disulfanediylbis(6-fluoro-4-methyl-benzene-3,1-diyl)]bis(2,2,2-trifluoroacetamide) (IV-1)

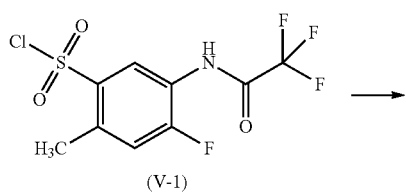
(V-1)

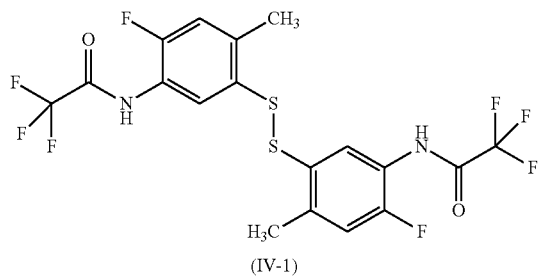
(IV-1)

298.8 g of sodium iodide are dissolved in 1000 ml of trifluoroacetic acid, and 70.8 g of 4-fluoro-2-methyl-5-[(trifluoroacetyl)amino]benzenesulfonyl chloride (V-1) are added at room temperature. The mixture is stirred at room temperature for 16 h and the solvent is then removed under reduced pressure. The residue is triturated with water and filtered off with suction. This gives 62.3 g (86% of theory) of the disulfide (IV-1) as a solid.

log P(HCOOH): 4.41

Step 4: 2,2,2-Trifluoro-N-{2-fluoro-4-methyl-5-[(2,2,2-trifluoroethyl)sulfanyl]phenyl}acetamide (III-1)

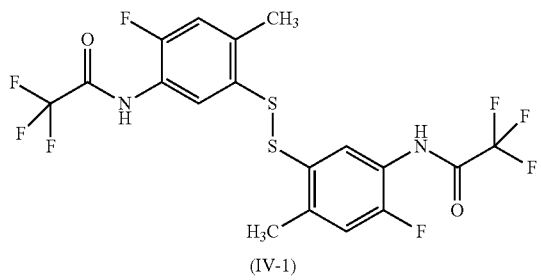
(IV-1)

+

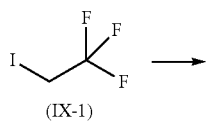
(IX-1)

-continued

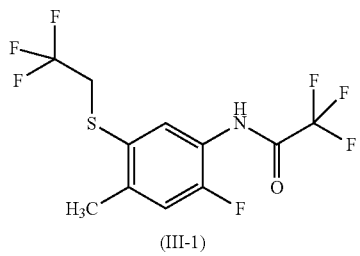
(III-1)

3.4 g of N,N'-[disulfanediylbis(6-fluoro-4-methylbenzene-3,1-diyl)]bis(2,2,2-trifluoroacetamide) (IV-1) are dissolved in 150 ml of N,N-dimethylformamide, and 1.86 g of potassium carbonate, 3.11 g of 1,1,1-trifluoroiodoethane (XVI-1), 2.39 g of Rongalite and a few drops of water are added. The reaction mixture is stirred at room temperature for 16 h. Most of the N,N-dimethylformamide is distilled off under reduced pressure. The residue is taken up in water and extracted twice with ethyl acetate. The combined organic phases are dried over sodium sulfate and filtered, and the solvent is then removed under reduced pressure. This gives 4.48 g (90% of theory) of the thioether (III-1).

log P(HCOOH): 3.31

Step 5: 2,2,2-Trifluoro-N-{2-fluoro-4-methyl-5-[(2,2,2-trifluoroethyl)sulfanyl]phenyl}ethanimidoyl chloride (II-1)

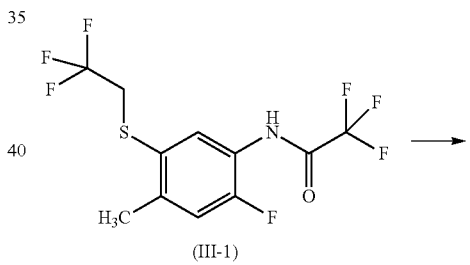
(III-1)

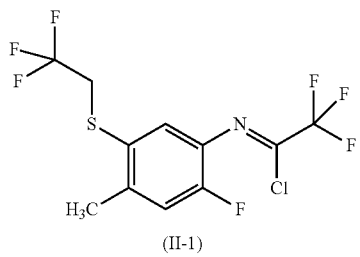
(II-1)

1 g of 2,2,2-trifluoro-N-{2-fluoro-4-methyl-5-[(2,2,2-trifluoroethyl)sulfanyl]phenyl}acetamide (III-1), 1.51 g of triethylamine and 4.01 g of diphenyl chlorophosphate in 20 ml of acetonitrile are heated under reflux for 16 h. After cooling, ethyl acetate is added and the precipitated solid is filtered off and discarded. The filtrate is adsorbed on silica gel and chromatographed using cyclohexane/ethyl acetate (98/2). Removal of the solvent affords 1 g of the imidoyl chloride (II-1).

Step 6: 2,2,2-Trifluoro-N'-{2-fluoro-4-methyl-5-[(2,2,2-trifluoroethyl)sulfanyl]phenyl}-N,N-dimethyl-ethanimidamide (Ia-01)

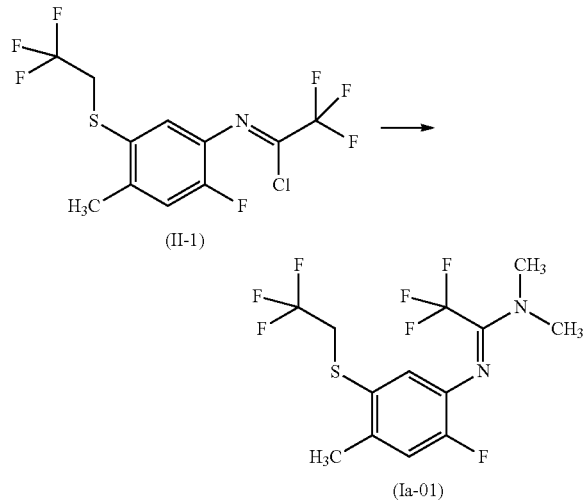

0.77 g of dimethylamine (2 M in THF) is initially charged in 40 ml of acetonitrile, and 1 g of 2,2,2-trifluoro-N-{2-fluoro-4-methyl-5-[(2,2,2-trifluoroethyl)sulfanyl]phenyl}ethanimidoyl chloride (II-1) dissolved in 10 ml of acetonitrile is added dropwise at room temperature. The reaction mixture is stirred at room temperature for 16 h and the solvent is then removed under reduced pressure. The residue is taken up in water and extracted twice with ethyl acetate. The combined organic phases are dried over sodium sulfate and filtered, and the solvent is then removed under reduced pressure. This gives 0.36 g (35% of theory) of the amidine (Ia-01).

log P(HCOOH): 4.48

Step 7: 2,2,2-Trifluoro-N'-{2-fluoro-4-methyl-5-[(2,2,2-trifluoroethyl)sulfinyl]phenyl}-N,N-dimethyl-ethanimidamide (Ib-01)

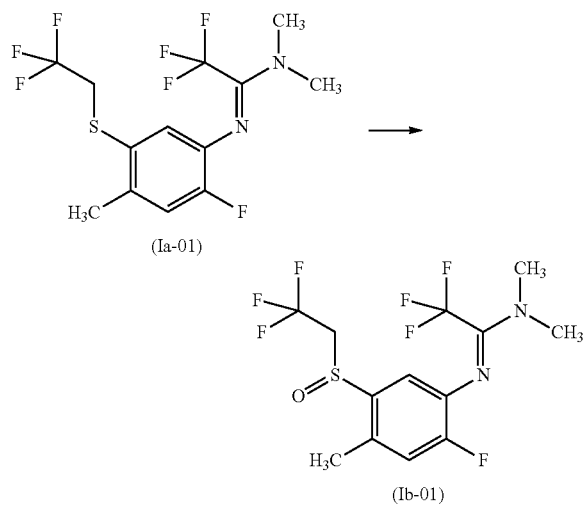

0.36 g of 2,2,2-trifluoro-N'-{2-fluoro-4-methyl-5-[(2,2,2-trifluoroethyl)sulfanyl]phenyl}-N,N-dimethylethanimidamide (Ia-01) is dissolved in 30 ml of dichloromethane, and 0.21 g of meta-chloroperbenzoic acid is added at room temperature. The reaction mixture is stirred at room temperature for another 16 h and then made alkaline using sodium carbonate solution. Excess meta-chloroperbenzoic acid is reduced with sodium thiosulfate. After phase separation, the solvent is removed under reduced pressure. The residue is chromatographed with cyclohexane/acetone (9/1). This gives 0.31 g (79% of theory) of the amidine (Ib-01).

log P(HCOOH): 3.15

Preparation Example 2:
5-Amino-4-fluoro-2-methylbenzenethiol (XI-1)

Step 1: S-(5-Acetamido-4-fluoro-2-methylphenyl)ethanethioate (XII-1)

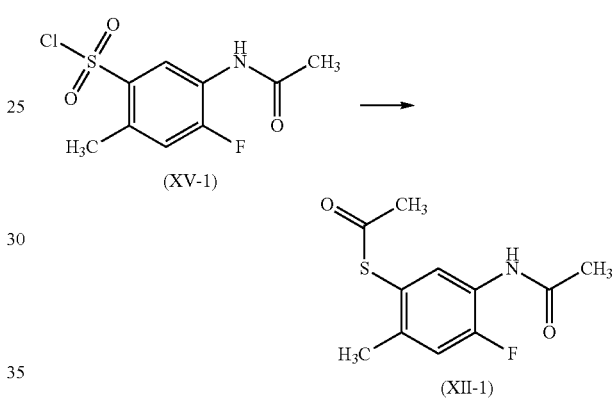

99.3 g of 5-acetamido-4-fluoro-2-methylbenzenesulfonyl chloride (XV-1) are suspended in 700 ml of glacial acetic acid, 0.9 g of iodine and 38.7 g of red phosphorus are added, and the mixture is stirred at reflux for 5 h. After cooling, the solid is filtered off and the filtrate is concentrated by rotary evaporation. The residue is triturated with water and filtered off with suction. This gives 57.6 g (67% of theory) of the thioate (XII-1) as a solid.

log P(HCOOH): 1.78

Step 2: 5-Amino-4-fluoro-2-methylbenzenethiol (XI-1)

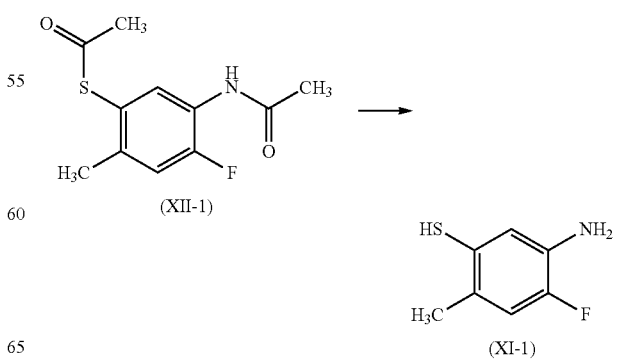

57.4 g of S-(5-acetamido-4-fluoro-2-methylphenyl) ethanethioate (XII-1) are dissolved in 750 ml of water and 96.6 g of potassium hydroxide. The reaction mixture is boiled at reflux for 16 hours. After cooling, the solution is adjusted to pH 2-3 using hydrochloric acid, and the precipitated solid is filtered off with suction. This gives 35.8 g (94% of theory) of the thiol (XI-1) as a solid.

log P(HCOOH): 3.70

Chiral Oxidation of (III) to (XVII)

Example 1: Synthesis of 2,2,2-trifluoro-N-{4-fluoro-2-methyl-5-[(2,2,2-trifluoroethyl)sulfinyl]phenyl}acetamide

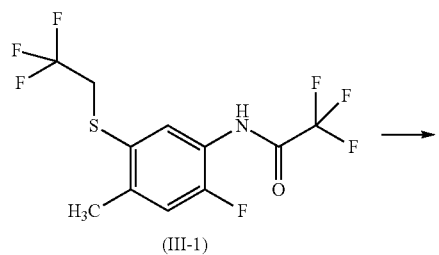

(III-1)

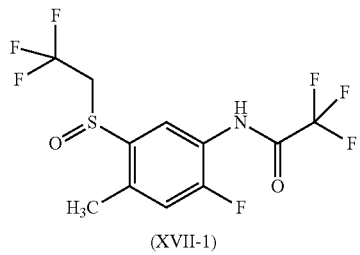

(XVII-1)

In a three-necked flask, 500 mg (1.49 mmol) of 2,2,2-trifluoro-N-{4-fluoro-2-methyl-5-[(2,2,2-trifluoroethyl)sulfanyl]phenyl}acetamide were dissolved in 5 g of chloroform and cooled to 15° C. A solution of 15.82 mg (0.06 mmol) of vanadium acetylacetonate and 29.84 mg (0.089 mmol) of (S)(2,4-di-tert-butyl-6-{(E)-[(1-hydroxy-3,3-dimethylbutan-2-yl)imino]methyl}phenol 1 g of chloroform was added to this mixture. After 5 minutes, a solution of 225.5 mg (1.79 mmol) of 30% strength H$_2$O$_2$ and 300 mg buffer solution pH 7 (KH$_2$PO$_4$/Na$_2$HPO$_4$) was metered in over 20 minutes. The progress of the reaction was monitored by HPLC. After a reaction time of 2 h, 100 mg of thiosulfate solution were added and most of the chloroform was evaporated under reduced pressure. 5 g of cyclohexane were added to the residue and the precipitated solid was filtered off.

This gave 1-{2,4-dimethyl-5-[(2,2,2-trifluoroethyl)sulfinyl]phenyl}-3-(trifluoromethyl)-1H-1,2,4-triazole (91.24% pure by HPLC) as a beige solid. The enantiomeric excess was determined by HPLC on a chiral phase (Daicel Chiracel OJ-RH 150) with a ratio of 25.90:74.10.

Chiral Oxidation of (Ia) to (Ib)

Example 1: Synthesis of N'-{2,4-dichloro-5-[(2,2,2-trifluoroethyl)sulfinyl]phenyl}-2,2,2-trifluoroethanimidamide

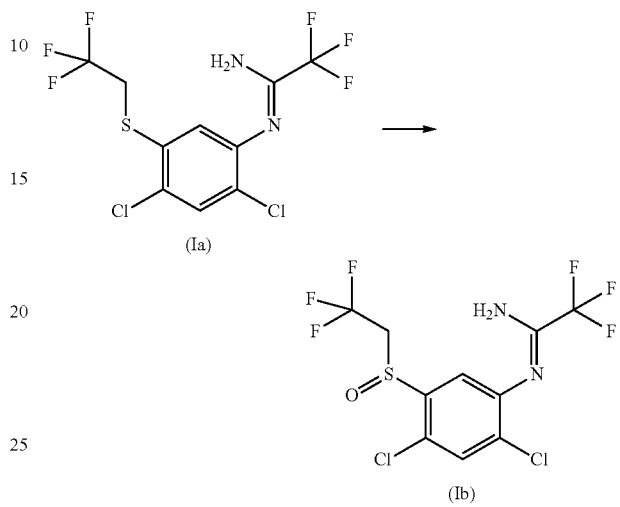

In a three-necked flask, 1 g (2.69 mmol) of N'-{2,4-dichloro-5-[(2,2,2-trifluoroethyl)sulfanyl]phenyl}-2,2,2-trifluoroethanimidamide was dissolved in 10 ml of chloroform and cooled to 15° C. A solution of 29 mg (0.10 mmol) of vanadium acetylacetonate and 54 mg (0.16 mmol) of (S)(2,4-di-tert-butyl-6-{(E)-[(1-hydroxy-3,3-dimethylbutan-2-yl)imino]methyl}phenol in 2 ml of chloroform was added to this mixture. A solution of 367 mg (3.23 mmol) of 30% strength H$_2$O$_2$ and 750 mg buffer solution pH 7 (KH$_2$PO$_4$/Na$_2$HPO$_4$) was metered in over 4 hours. The progress of the reaction was monitored by TLC. After a reaction time of 2 h, 128 mg of thiosulfate solution (1M) were added and the mixture was stirred overnight. The phases were separated and most of the chloroform (except for about 3 ml) was evaporated under reduced pressure. Cyclohexane was added to the residue and the precipitated solid was filtered off.

This gave 980 mg of N'-{2,4-dichloro-5-[(2,2,2-trifluoroethyl)sulfinyl]phenyl}-2,2,2-trifluoroethanimidamide (purity by HPLC >99%) as a solid. The enantiomeric excess was determined by HPLC on a chiral phase (Daicel Chiracel OD-RH 150) with a ratio of 89.63:10.37.

Preparation Example 3: N'-{4-Chloro-3-[(2,2,2-trifluoroethyl)sulfinyl]phenyl}-2,2,2-trifluoroethanimidamide (Ib-108)

Step 1: 1,1'-Disulfanediylbis(2-chloro-5-nitrobenzene)

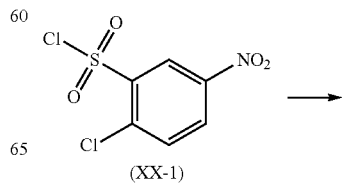

(XX-1)

-continued

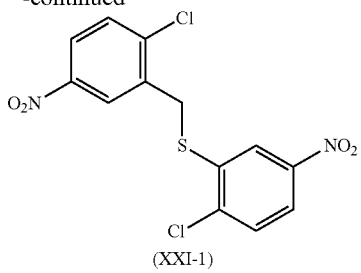
(XXI-1)

With vigorous stirring, 236.1 g (1.02 mol) of chlorosulfonic acid are added to 52.0 g (203.1 mmol) of 2-chloro-5-nitrobenzenesulfonyl chloride, and the mixture is stirred at room temperature overnight. After addition of 40% strength aqueous sodium bisulfite solution, the solid formed is filtered off with suction, washed with water and dried on a clay disk overnight. This gives 36.1 g (100% pure, 94% of theory) of the title compound as a gray-brown solid.

log P(HCOOH): 5.03; log P(neutral): 5.01; 1H-NMR (D6-DMSO, 400 MHz) δ ppm 8.40 (d, 2H), 8.18-8.16 (m, 2H), 7.91 (d, 2H); GC-MS: EI mass (m/z): 376 (2Cl) [M]+

Step 2: 3,3'-Disulfanediylbis(4-chloroaniline)

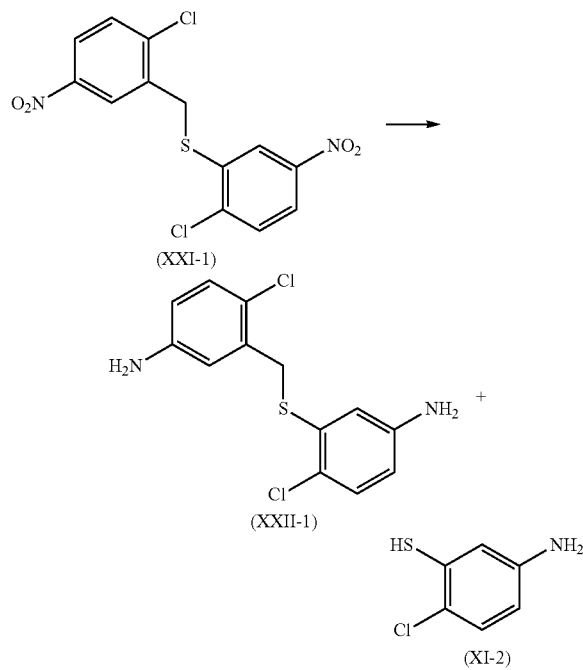

8.00 g (21.2 mmol) of 1,1'-disulfanediylbis(2-chloro-5-nitrobenzene) are dissolved in 150 ml of THF, 1.6 g of Raney nickel are added and the mixture is stirred at 50° C. under a hydrogen atmosphere (20 bar) for 72 h. Using THF, the reaction mixture is filtered through kieselguhr, and the filtrate is freed from the solvent under reduced pressure. This gives 6.64 g (90% pure, 89% of theory) of a mixture of 1,1'-disulfanediylbis(2-chloro-5-nitrobenzene) and 5-amino-2-chlorobenzenethiol which is alkylated without further purification.

1,1'-Disulfanediylbis(2-chloro-5-nitrobenzene)

log P(HCOOH): 3.31; log P(neutral): 3.35; 1H-NMR (D6-DMSO, 400 MHz) δ ppm 7.10 (d, 2H), 6.73 (d, 2H), 6.47-6.44 (m, 2H), 5.51 (broad, 4H); GC-MS: EI mass (m/z): 316 (2Cl) [M]+

5-Amino-2-chlorobenzenethiol log P(HCOOH): 1.64; log P(neutral): not measurable; 1H-NMR (D6-DMSO, 400 MHz) δ ppm 7.01 (d, 1H), 6.54 (d, 1H), 6.35-6.32 (m, 1H), 5.28 (broad, 3H); GC-MS: EI mass (m/z): 159 (1Cl) [M]+

Step 3: 4-Chloro-3-[(2,2,2-trifluoroethyl)sulfanyl]aniline

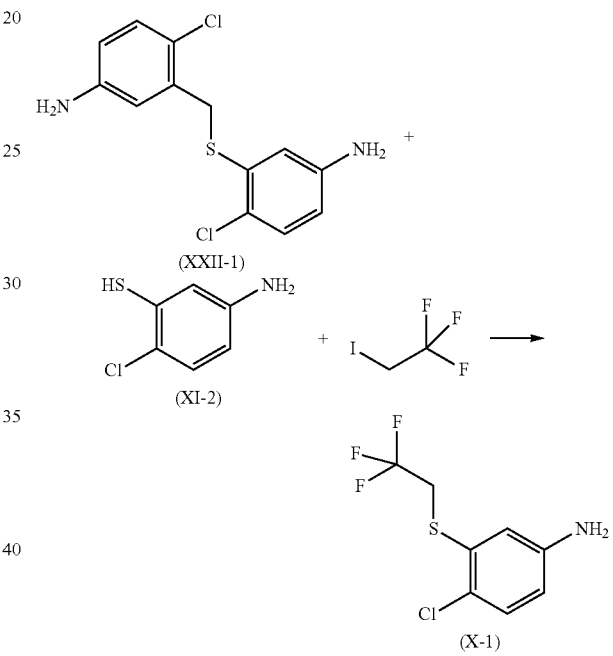

6.40 g of a mixture of disulfanediylbis(2-chloro-5-nitrobenzene) and 5-amino-2-chlorobenzenethiol (about 20 mmol) are initially charged in 100 ml of N,N-dimethylformamide, and 7.02 g (40.3 mmol) of sodium dithionite, 5.58 g (40.3 mmol) of potassium carbonate and 5.49 g (40.3 mmol) of Rongalit are added and the mixture is cooled to 0° C. 9.32 g of 1,1,1-trifluoro-2-iodoethane are added dropwise at 0° C. The reaction mixture is stirred at room temperature overnight. Most of the solvent is removed under reduced pressure, water is added to the residue and the mixture is extracted with ethyl acetate. The combined organic phases are washed successively with water and saturated aqueous sodium chloride solution, dried over magnesium sulfate, filtered and freed from the solvent under reduced pressure. Purification by column chromatography on silica gel by means of MPLC using the mobile phase cyclohexane/ethyl acetate gives 4.70 g (98% pure, 47% of theory) of the title compound as a yellow liquid.

log P(HCOOH): 2.64; log P(neutral): 2.69; 1H-NMR (D6-DMSO, 400 MHz) δ ppm 7.09 (d, 1H), 6.78 (d, 1H), 6.49-6.46 (m, 1H), 5.37 (broad, 2H), 3.90 (q, 2H); GC-MS: EI mass (m/z): 241 (1Cl) [M]+

Step 4: N-{4-Chloro-3-[(2,2,2-trifluoroethyl)sulfanyl]phenyl}-2,2,2-trifluoroacetamide

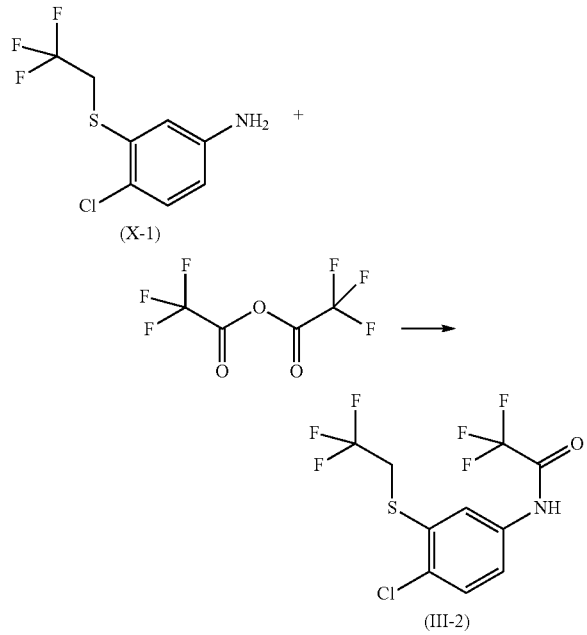

1.00 g (4.14 mmol) of 4-chloro-3-[(2,2,2-trifluoroethyl)sulfanyl]aniline is initially charged in 14 ml of dichloromethane, and 0.50 g (4.97 mmol) of triethylamine is added at 0° C. 0.96 g (4.55 mmol) of trifluoroacetic anhydride is added dropwise at 0° C. The reaction mixture is stirred at room temperature overnight, then washed with water and saturated aqueous sodium chloride solution, dried over magnesium sulfate, filtered and freed from the solvent under reduced pressure. Purification by column chromatography on silica gel by means of MPLC using the mobile phase cyclohexane/ethyl acetate gives 1.00 g (99% pure, 71% of theory) of the title compound as a colorless solid.

log P(HCOOH): 3.46; log P(neutral): 3.41; 1H-NMR (D6-DMSO, 400 MHz) δ ppm 11.43 (s, 1H), 7.91 (d, 1H), 7.63-7.69 (m, 1H), 7.56-7.58 (m, 1H), 4.05 (q, 2H); 1H-NMR (CDCl$_3$, 400 MHz) δ ppm 7.85 (broad, 1H), 7.82 (d, 1H), 7.52-7.45 (m, 2H), 3.53 (q, 2H); GC-MS: EI mass (m/z): 337 (1Cl) [M]+

Step 5: N-{4-Chloro-3-[(2,2,2-trifluoroethyl)sulfanyl]phenyl}-2,2,2-trifluoroethanimidoyl chloride

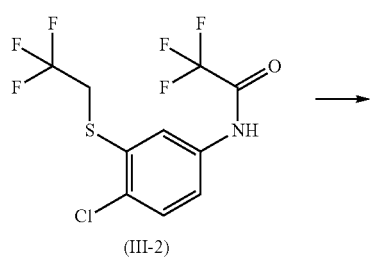

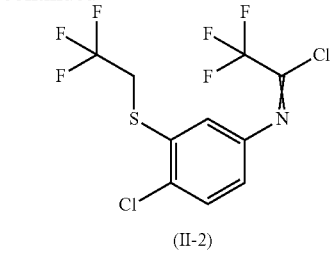

880 mg (2.61 mmol) of N-{4-chloro-3-[(2,2,2-trifluoroethyl)sulfanyl]phenyl}-2,2,2-trifluoroacetamide are initially charged in 17 ml of acetonitrile, 1.32 g (13.03 mmol) of triethylamine and 3.50 g (13.03 mmol) of diphenyl chlorophosphate are added at room temperature and the mixture is heated at reflux overnight. After cooling, ethyl acetate is added and the mixture is filtered and concentrated. The residue is directly subjected to purification by column chromatography on silica gel by MPLC using the mobile phase cyclohexane/ethyl acetate. This gives 640 mg (93% pure, 64% of theory) of the title compound as a yellow oil.

log P(HCOOH): 4.77; log P(neutral): 4.73; 1H-NMR (CDCl$_3$, 400 MHz) δ ppm 7.51 (d, 1H), 7.24 (d, 1H), 7.02-7.00 (m, 1H), 3.51 (q, 2H); GC-MS: EI mass (m/z): 355 (2Cl) [M]+

Step 6: N'-{4-Chloro-3-[(2,2,2-trifluoroethyl)sulfanyl]phenyl}-2,2,2-trifluoroethanimidamide (Ia-204)

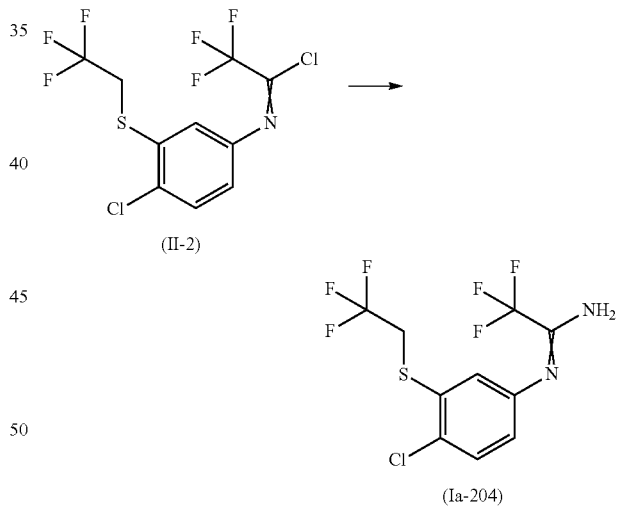

210 mg (0.59 mmol) of N-{4-chloro-3-[(2,2,2-trifluoroethyl)sulfanyl]phenyl}-2,2,2-trifluoroethanimidoyl chloride are initially charged in 5 ml of acetonitrile, and a solution of 241 mg (3.54 mmol) of 25% strength aqueous ammonia solution in 5 ml of acetonitrile is added. The reaction mixture is stirred at room temperature overnight and then concentrated. The residue is extracted with water and ethyl acetate. The combined organic phases are dried over magnesium sulfate, filtered and freed from the solvent under reduced pressure. Purification by column chromatography on silica gel by means of MPLC using the mobile phase cyclohexane/ethyl acetate gives 120 mg (100% pure, 60% of theory) of the title compound as a yellow oil.

log P(HCOOH): 3.10; log P(neutral): 3.10; 1H-NMR (D6-DMSO, 400 MHz) δ ppm 7.42 (d, 1H), 7.26 (broad, 2H), 7.05 (d, 1H), 6.75-6.72 (m, 1H), 4.13 (q, 2H)

Step 7: N'-{4-Chloro-3-[(2,2,2-trifluoroethyl)sulfinyl]phenyl}-2,2,2-trifluoroethanimidamide (Ib-108)

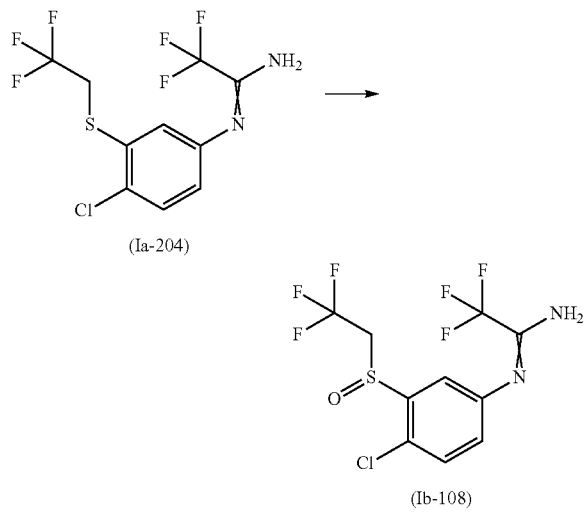

90 mg (0.27 mmol) of N'-{4-chloro-3-[(2,2,2-trifluoroethyl)sulfanyl]phenyl}-2,2,2-trifluoroethanimidamide are dissolved in 6 ml of dichloromethane, and 68 mg (0.29 mmol) of meta-chloroperbenzoic acid are added at 0° C. After two hours of stirring at 0° C., another 23 mg (0.13 mmol) are added. The reaction mixture is stirred at room temperature overnight and then diluted with dichloromethane and washed successively with 40% strength sodium bisulfite solution and saturated aqueous sodium bicarbonate. The organic phase is dried over magnesium sulfate, filtered and freed from the solvent under reduced pressure. Purification by column chromatography on silica gel by means of MPLC using the mobile phase cyclohexane/ethyl acetate gives 90 mg (95% pure, 91% of theory) of the title compound as a beige solid.

log P(HCOOH): 2.25; log P(neutral): 2.21; 1H-NMR (D6-DMSO, 400 MHz) δ ppm 7.57 (d, 1H), 7.42 (broad, 2H), 7.30 (d, 1H), 7.10-7.07 (m, 1H), 4.22-4.04 (m, 2H)

Preparation Example 4: N'-{2-Fluoro-4-methyl-5-[(2,2,2-trifluoroethyl)sulfanyl]phenyl}-N-methyl-4-(trifluoromethyl)benzenecarboximidamide (Ia-250)

Step 1: N-{2-Fluoro-4-methyl-5-[(2,2,2-trifluoroethyl)sulfanyl]phenyl}-4-(trifluoromethyl)benzamide

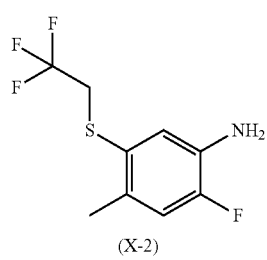 +

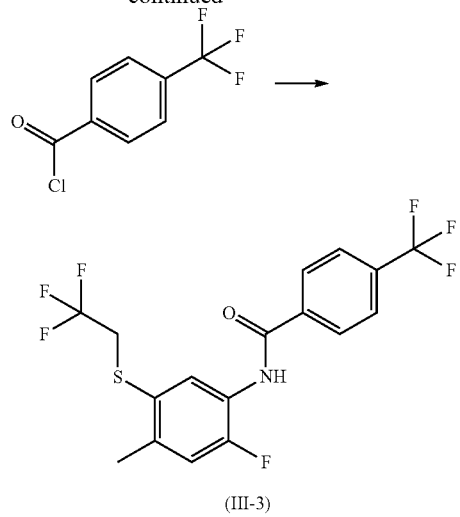

1.00 g (4.18 mmol) of 2-fluoro-4-methyl-5-[(2,2,2-trifluoroethyl)sulfanyl]aniline is initially charged in 25 ml of dichloromethane, 0.47 g (4.60 mmol) of triethylamine is added and the mixture is cooled to 0° C. 0.96 g (4.60 mmol) of 4-(trifluoromethyl)benzoyl chloride in 25 ml of dichloromethane is added dropwise at 0° C. The reaction mixture is stirred at room temperature overnight. 0.17 g (0.84 mmol) of 4-(trifluoromethyl)benzoyl chloride is added, and the mixture is stirred at room temperature for a further 3 h. The reaction mixture is diluted with dichloromethane, washed successively with semisaturated aqueous ammonium chloride solution and saturated aqueous sodium chloride solution, dried over magnesium sulfate, filtered and freed from the solvent under reduced pressure. The residue is triturated with petroleum ether, filtered off with suction and dried. This gives 1.69 g (95% pure, 93% of theory) of the title compound as a colorless solid.

log P(HCOOH): 4.20; log P(neutral): 4.17; 1H-NMR (D6-DMSO, 400 MHz) δ ppm 10.40 (s, 1H), 8.17 (d, 2H), 7.93 (d, 2H), 7.82 (d, 1H), 7.31 (d, 1H), 3.89 (q, 2H), 2.42 (s, 3H); 1H-NMR (CD$_3$CN, 400 MHz) δ ppm 8.70 (broad, 1H), 8.12 (d, 1H), 8.08 (d, 2H), 7.84 (d, 2H), 7.17 (d, 1H), 3.57 (q, 2H), 2.46 (s, 3H); GC-MS: EI mass (m/z): 411 [M]+

Step 2: N-{2-Fluoro-4-methyl-5-[(2,2,2-trifluoroethyl)sulfanyl]phenyl}-4-(trifluoromethyl)benzenecarboximidoyl chloride

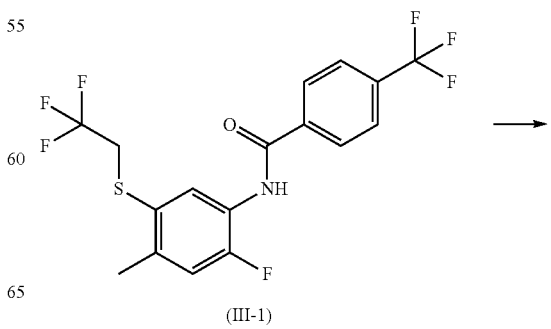

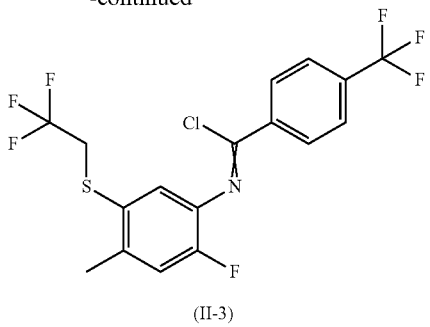

(II-3)

1.00 g (2.43 mmol) of N-{2-fluoro-4-methyl-5-[(2,2,2-trifluoroethyl)sulfanyl]phenyl}-4-(trifluoromethyl)benzamide is initially charged in 20 ml of dichloromethane, 0.51 g (2.43 mmol) of phosphorus pentachloride is added and the mixture is stirred at room temperature overnight. Another 0.51 g (2.43 mmol) of phosphorus pentachloride is added and the mixture is stirred at room temperature overnight. A further 0.51 g (2.43 mmol) of phosphorus pentachloride is added, and the reaction mixture is stirred at room temperature for 3 h and then filtered through silica gel and concentrated. This gives 0.91 g (74% pure, 65% of theory) of the title compound as a yellow oil which is directly reacted further.

1H-NMR (CD$_3$CN, 400 MHz) δ ppm 8.32 (d, 2H), 7.86 (d, 2H), 7.32 (d, 1H), 7.21 (d, 1H), 3.58 (q, 2H), 2.47 (s, 3H); GC-MS: EI mass (m/z): 429 (1Cl) [M]+

Step 3: N'-{2-Fluoro-4-methyl-5-[(2,2,2-trifluoroethyl)sulfanyl]phenyl}-N-methyl-4-(trifluoromethyl)benzenecarboximidamide

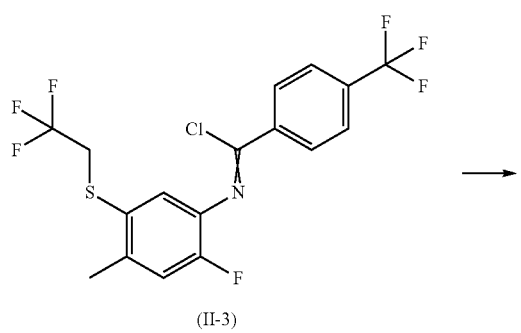

(Ia-150)

150 mg (4.65 mmol) of methylamine (2M in THF) are initially charged in 25 ml of acetonitrile, 400 mg (0.93 mmol) of N-{2-fluoro-4-methyl-5-[(2,2,2-trifluoroethyl)sulfanyl]phenyl}-4-(trifluoromethyl)benzenecarboximidoyl chloride in 25 ml of acetonitrile are added at 0° C. and the mixture is stirred at room temperature overnight and then concentrated. The residue is purified by column chromatography on silica gel by MPLC using the mobile phase cyclohexane/ethyl acetate. This gives 220 mg (99% pure, 56% of theory) of the title compound as a yellow solid.

log P(HCOOH): 1.96; log P(neutral): 4.08; 1H-NMR (D6-DMSO, 400 MHz) δ ppm 7.64 (d, 2H), 7.46 (d, 1H), 7.39 (d, 2H), 6.88 (d, 1H), 7.76 (d, 1H), 3.53 (q, 2H), 2.89 (d, 3H), 2.20 (s, 3H); GC-MS: EI mass (m/z): 424 [M]+

Preparation Example 5: 5-Chloro-N'-{2-fluoro-4-methyl-5-[(2,2,2-trifluoroethyl)sulfanyl]phenyl}-N,N-dimethylthiophene-2-carboximidamide (Ia-149)

Step 1: 5-Chloro-N'-{2-fluoro-4-methyl-5-[(2,2,2-trifluoroethyl)sulfanyl]phenyl}-N,N-dimethylthiophene-2-carboximidamide

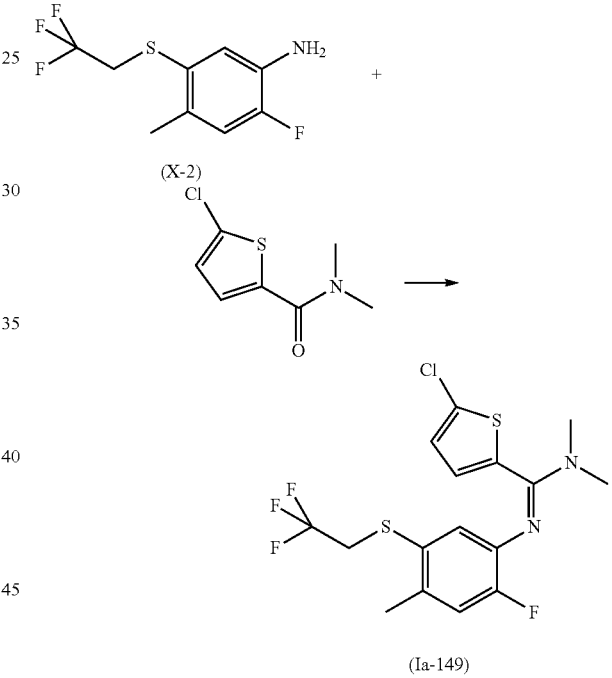

(Ia-149)

743 mg (4.85 mmol) of phosphoryl chloride are added to 200 mg (0.84 mmol) of 2-fluoro-4-methyl-5-[(2,2,2-trifluoroethyl)sulfanyl]aniline and 206 mg (1.09 mmol) of 5-chloro-N,N-dimethylthiophene-2-carboxamide, and the mixture is heated at reflux overnight. After cooling, the reaction mixture is poured into water, made alkaline with potassium carbonate and extracted with dichloromethane. The combined organic phases are dried over magnesium sulfate, filtered and freed from the solvent under reduced pressure. Purification by column chromatography on silica gel by means of MPLC using the mobile phase cyclohexane/ethyl acetate gives 165 mg (92% pure, 44% of theory) of the title compound as a red-brown oil.

log P(HCOOH): 2.11; log P(neutral): 4.89; 1H-NMR (D6-DMSO, 400 MHz) δ ppm 7.00 (d, 1H), 7.93 (d, 1H), 6.87-6.84 (m, 2H), 3.68 (q, 2H), 2.97 (broad, 6H), 2.23 (s, 3H)

Preparation Example 6: N'-{2-Fluoro-4-methyl-5-[(2,2,2-trifluoroethyl)sulfanyl]phenyl}-N,N,1-trimethyl-1H-pyrrole-2-carboximidamide (Ia-162)

Step 1: N'-{2-Fluoro-4-methyl-5-[(2,2,2-trifluoroethyl)sulfanyl]phenyl}-N,N,1-trimethyl-1H-pyrrole-2-carboximidamide

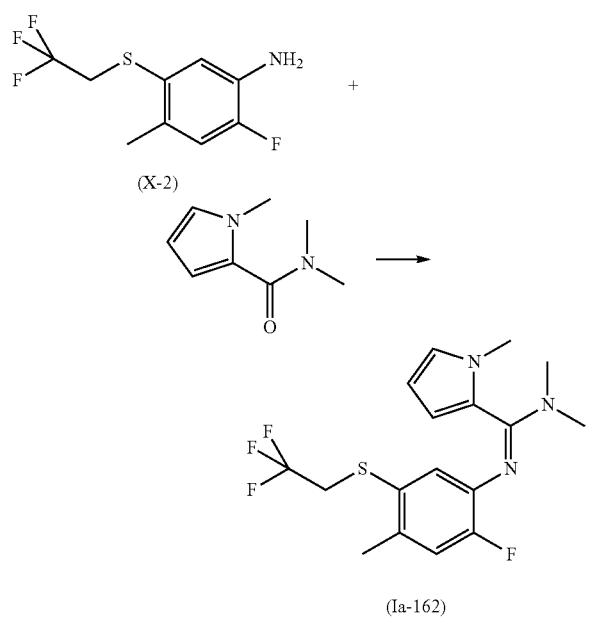

743 mg (4.85 mmol) of phosphoryl chloride are added to 200 mg (0.84 mmol) of 2-fluoro-4-methyl-5-[(2,2,2-trifluoroethyl)sulfanyl]aniline and 165 mg (1.09 mmol) of N,N,1-trimethyl-1H-pyrrole-2-carboxamide, and the mixture is heated at reflux overnight. After cooling, the reaction mixture is poured into water, made alkaline with potassium carbonate and extracted with dichloromethane. The combined organic phases are dried over magnesium sulfate, filtered and freed from the solvent under reduced pressure. Purification by column chromatography on silica gel by means of MPLC using the mobile phase cyclohexane/ethyl acetate gives 177 mg (99% pure, 56% of theory) of the title compound as a yellow oil.

log P(HCOOH): 1.67; log P(neutral): 4.11; 1H-NMR (D6-DMSO, 400 MHz) δ ppm 6.88 (d, 1H), 6.70-6.68 (m, 1H), 6.64 (d, 1H), 5.91-5.89 (m, 2H), 3.59 (q, 2H), 3.39 (s, 3H), 3.05 (broad, 3H), 2.77 (broad, 3H), 2.21 (s, 3H)

Preparation Example 7: N'-{2-Fluoro-4-methyl-5-[(2,2,2-trifluoroethyl)sulfanyl]phenyl}-N,N-dimethylfuran-2-carboximidamide (Ia-166)

Step 1: N'-{2-Fluoro-4-methyl-5-[(2,2,2-trifluoroethyl)sulfanyl]phenyl}-N,N-dimethylfuran-2-carboximidamide

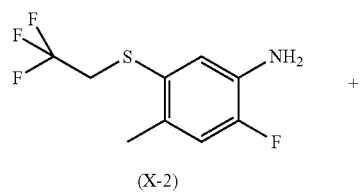

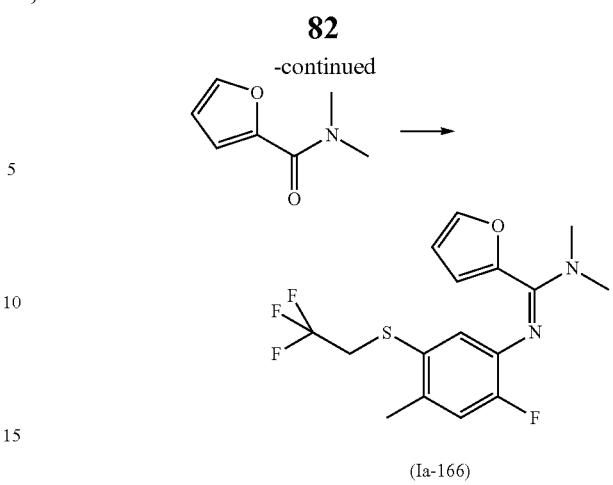

743 mg (4.85 mmol) of phosphoryl chloride are added to 200 mg (0.84 mmol) of 2-fluoro-4-methyl-5-[(2,2,2-trifluoroethyl)sulfanyl]aniline and 139 mg (1.09 mmol) of N,N-dimethyl-2-furanamide, and the mixture is heated at reflux overnight. After cooling, the reaction mixture is poured into water, made alkaline with potassium carbonate and extracted with dichloromethane. The combined organic phases are dried over magnesium sulfate, filtered and freed from the solvent under reduced pressure. Purification by column chromatography on silica gel by means of MPLC using the mobile phase cyclohexane/ethyl acetate gives 64 mg (98% pure, 21% of theory) of the title compound as a yellow oil.

log P(HCOOH): 1.57; log P(neutral): 3.94; 1H-NMR (D6-DMSO, 400 MHz) δ ppm 7.69-7.67 (m, 1H), 6.91 (d, 1H), 6.76 (d, 1H), 6.43-6.40 (m, 1H), 6.25 (d, 1H), 3.69 (q, 2H), 2.94 (s, 6H), 2.24 (s, 3H)

Preparation Example 8: 2-Methoxy-4-methyl-5-[(2,2,2-trifluoroethyl)sulfanyl]aniline Step 1:
5-Acetamido-4-methoxy-2-methylbenzenesulfonyl chloride

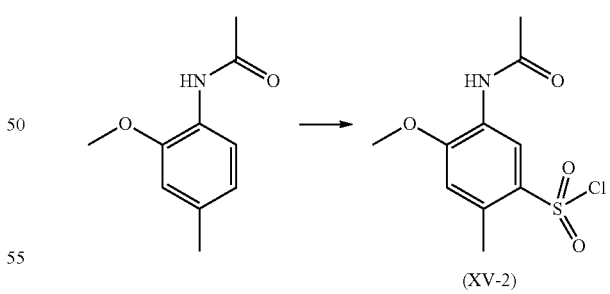

A little at a time, 19.5 g (108.8 mmol) of N-(2-methoxy-4-methylphenyl)acetamide [CAS-RN 89345-81-3] are added to 150 g (1287 mmol) of chlorosulfonic acid, and the mixture is stirred at 80° C. for another 4 h. After cooling, the mixture is added to ice-water and the solid obtained is filtered off with suction, giving 25.4 g of product (84.1% of theory, purity 100% according to 1H-NMR).

1H-NMR (D6-DMSO) δ ppm: 9.04 (s, 1H), 8.14 (s, 1H), 6.80 (s, 1H), 3.80 (s, 3H), 2.48 (s, 3H), 2.04 (s, 3H)

Step 2: N,N'-[Disulfanediylbis(6-methoxy-4-methyl-benzene-3,1-diyl)]diacetamide

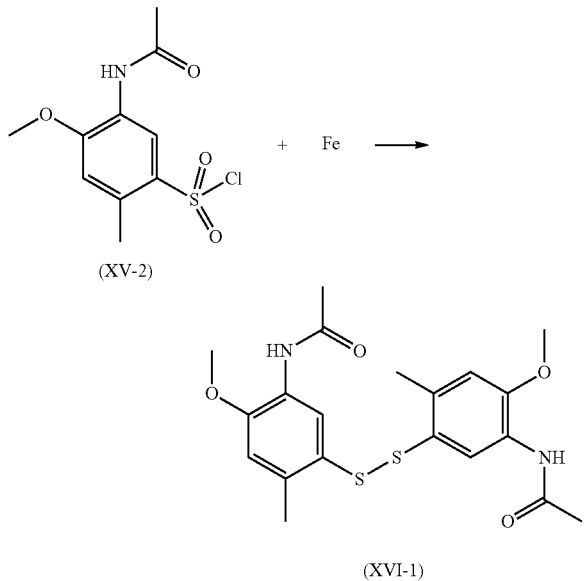

(XV-2)

(XVI-1)

25.3 g (91.1 mmol) of 5-acetamido-4-methoxy-2-methylbenzenesulfonyl chloride and 14.6 g (261.4 mmol) of iron powder in 400 ml of ethanol and 36.7 g of concentrated hydrochloric acid are heated under reflux for 12 h. After removal of the solvent under reduced pressure, the residue is triturated with water and filtered off with suction, giving 9.4 g of crude product (49.1% of theory, purity 86.4% according to LC/MS) as a light-brown solid.

log P(HCOOH): 2.73

Step 3: N-{2-Methoxy-4-methyl-5-[(2,2,2-trifluoroethyl)sulfanyl]phenyl}acetamide

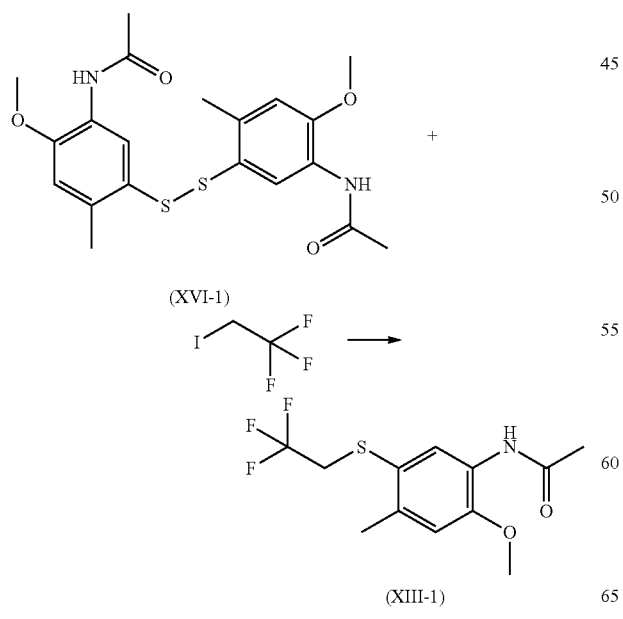

(XVI-1)

(XIII-1)

9.4 g (22.35 mmol) of N,N'-[disulfanediylbis(6-methoxy-4-methylbenzene-3,1-diyl)]diacetamide are initially charged in 60 ml of dimethylformamide, 6.5 g of sodium dithionite, 15.9 g of potassium carbonate and 5.45 g of sodium bisphosphate and 40 ml of water are added and the mixture is then stirred at 60° C. for 3 h. After cooling, 12.5 g (59.54 mmol) of 1,1,1-trifluoro-2-iodoethane are added and the mixture is stirred at 75° C. for a further 12 h. After removal of the solvent under reduced pressure, the residue that remains is acidified with concentrated hydrochloric acid and the precipitate formed is filtered off with suction. This leaves 5.3 g of product (80.8% of theory, purity >95% according to 1H-NMR).

1H-NMR (D6-DMSO) δ ppm: 9.15 (s, 1H), 8.14 (s, 1H), 6.98 (s, 1H), 3.83 (s, 3H), 3.69-3.61 (q, 2H), 2.40 (s, 3H), 2.06 (s, 3H)

Step 4: 2-Methoxy-4-methyl-5-[(2,2,2-trifluoroethyl)sulfanyl]aniline

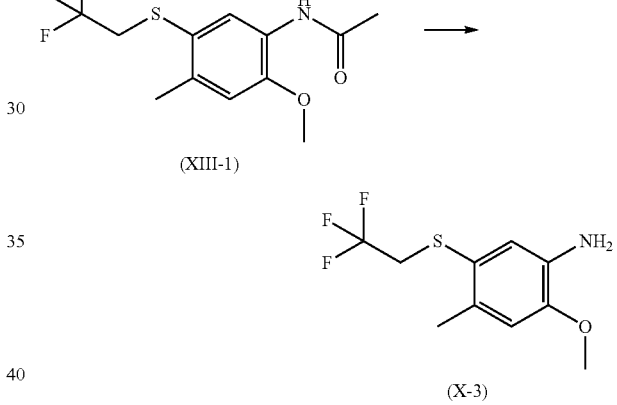

(XIII-1)

(X-3)

5.3 g (22.35 mmol) of N-{2-methoxy-4-methyl-5-[(2,2,2-trifluoroethyl)sulfanyl]phenyl}acetamide in 125 ml of 5 molar hydrochloric acid are stirred under reflux for 18 h. The reaction mixture is made alkaline with aqueous sodium hydroxide solution and extracted with dichloromethane. The organic phase is separated off, dried over sodium sulfate and freed from the solvent under reduced pressure. This leaves 3.6 g of product as a dark-orange oil (79.3% of theory, purity 96.8% according to LC/MS).

1H-NMR (D6-DMSO) δ ppm: 6.83 (s, 1H), 6.72 (s, 1H), 4.64 (broad, 2H), 3.75 (s, 3H), 3.64-3.56 (q, 2H), 2.30 (s, 3H)

Preparation Example 9: 3-[(2,2,2-Trifluoroethyl)sulfanyl]aniline

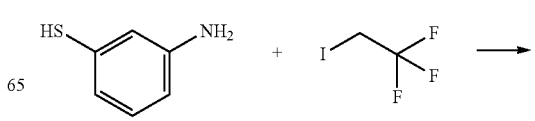

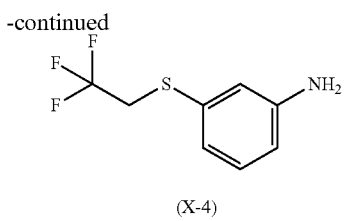

(X-4)

6.5 g (51.92 mmol) of 3-aminobenzenethiol are initially charged in 200 ml of acetonitrile, 13.7 g of potassium carbonate, 1.6 g of solid sodium hydroxide, 1 ml of dimethyl sulfoxide and 13 g (61.93 mmol) of 1,1,1-trifluoro-2-iodoethane are added and the mixture is stirred at 45° C. for 18 h. The reaction mixture is diluted with 250 ml of water and extracted with dichloromethane. The organic phase is separated off, dried over sodium sulfate and freed from the solvent under reduced pressure. This leaves 9.5 g of product as a brown oil (88.3% of theory, purity 97.9% according to LC/MS).

1H-NMR (D6-DMSO) δ ppm: 7.00-6.97 (m, 1H), 6.61 (m, 1H), 6.59 (m, 1H), 6.47-6.45 (m, 1H), 5.19 (broad, 2H), 3.88-3.80 (q, 2H)

log P(HCOOH): 2.01

Preparation Example 10:
N-(2,2-Difluoroethyl)cyclopropanecarboxamide (XXIV-1)

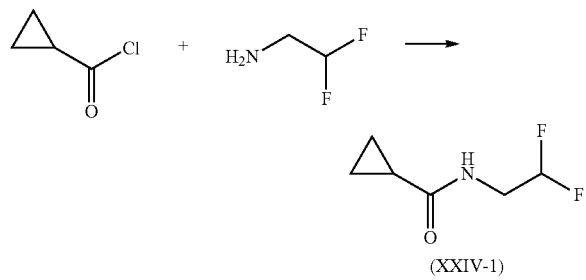

(XXIV-1)

14.4 g (137.75 mmol) of cyclopropanecarbonyl chloride are dissolved in 300 ml of anhydrous tetrahydrofuran. After the addition of 1 g of triethylamine, a solution of 16.8 g (207.24 mmol) of 2,2-difluoroethanamine in 50 ml of anhydrous tetrahydrofuran is added dropwise. After the end of the addition, the mixture is stirred at room temperature for another 18 h and subsequently at 40° C. for another 1 h. The mixture is diluted with 200 ml of water and extracted with dichloromethane. The combined organic phases are separated off, dried over sodium sulfate and freed from the solvent under reduced pressure. This leaves a residue of 18.9 g of product (92% of theory, purity 100% according to 1H-NMR) as a white solid.

1H-NMR (D6-DMSO) δ ppm: 8.46 (t, 1H), 5.99 (tt, 1H), 3.54-3.43 (m, 2H), 1.65-1.59 (m, 1H), 0.70-0.60 (m, 4H)

Preparation Example 11:
1-Fluorocyclopropanecarboxamide (XXIV-2)

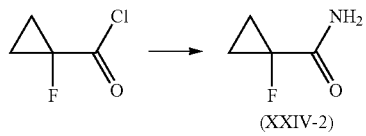

(XXIV-2)

A little at a time, 600 mg (4.9 mmol) of 1-fluorocyclopropanecarbonyl chloride [CAS-RN 149961-53-5] are added to 15 g of ammonium hydroxide (28-30% by weight strength solution of NH$_3$ in water), and the mixture is stirred at room temperature for another 18 h. The resulting precipitate is filtered off with suction, giving 470 mg of product (93.1% of theory, purity 100% according to 1H-NMR) as a white solid.

1H-NMR (D6-DMSO) δ ppm: 7.80 (broad, 1H), 7.58 (broad, 1H), 1.29-1.12 (m, 4H)

Preparation Example 12: (4-Chlorophenyl)(4,4-difluoropiperidin-1-yl)methanone (XXIV-3)

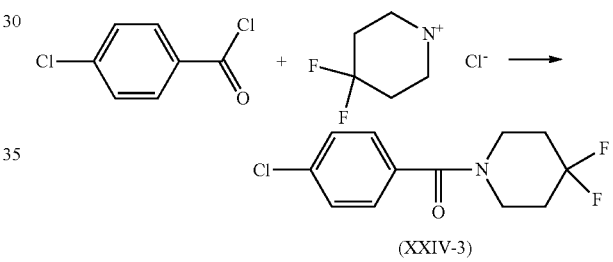

(XXIV-3)

470 mg (2.98 mmol) of 4,4-difluoropiperidinium chloride are initially charged in 35 ml of anhydrous toluene. After the addition of 1.4 g of triethylamine, 690 mg (3.94 mmol) of 4-chlorobenzoyl chloride are added a little at a time, and the mixture is stirred at 100° C. for a further 18 h. The reaction mixture is diluted with 250 ml of water and the organic phase is separated off, dried over sodium sulfate and freed from the solvent under reduced pressure. This leaves 480 mg of product as an orange oil (62% of theory, purity 88% according to LC/MS).

1H-NMR (D6-DMSO) δ ppm: 7.54-7.49 (m, 4H), 3.70 (m, 2H), 3.39 (m, 2H), 2.03 (m, 4H)

Preparation Example 13: N-{2-[3-Chloro-5-(trifluoromethyl)pyridin-2-yl]ethyl}cyclopropanecarboxamide (XXIV-4)

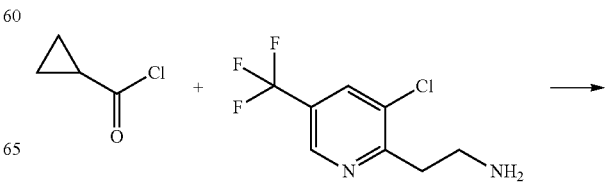

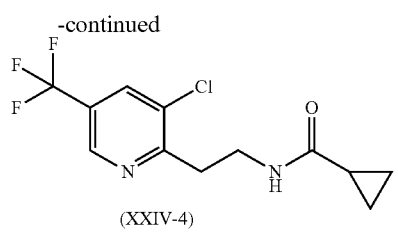

(XXIV-4)

550 mg (2.11 mmol) of 2-[3-chloro-5-(trifluoromethyl)pyridin-2-yl]ethanamine are initially charged in 20 ml of anhydrous dichloromethane. After the addition of 1 g of triethylamine, 270 mg (2.58 mmol) of cyclopropanecarbonyl chloride, dissolved in 5 ml of anhydrous dichloromethane, are added dropwise, and the mixture is then stirred at 50° C. for another 12 h. The reaction mixture is diluted with 50 ml of water and the organic phase is separated off, dried over magnesium sulfate and freed from the solvent under reduced pressure. This gives 450 mg of product as an orange solid (73% of theory, purity 87.1% according to LC/MS).

1H-NMR (D6-DMSO) δ ppm: 8.89 (d, 1H), 8.41 (d, 1H), 8.17 (t, 1H), 3.53-3.48 (m, 2H), 3.11 (t, 2H), 1.51-1.46 (m, 1H), 0.63-0.59 (m, 4H)

Preparation Example 14: 1-Fluoro-N'-{2-fluoro-4-methyl-5-[(2,2,2-trifluoroethyl)sulfinyl]phenyl}cyclopropanecarboximidamide (Ib-19)

Step 1: 1-Fluoro-N'-{2-fluoro-4-methyl-5-[(2,2,2-trifluoroethyl)sulfanyl]phenyl}cyclopropanecarboximidamide (Ia-27)

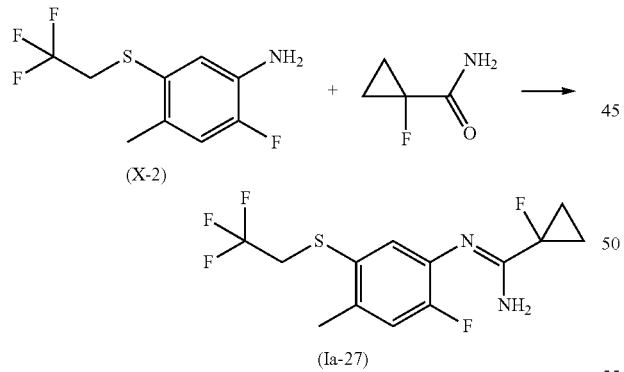

1.4 g (9.13 mmol) of phosphoryl chloride are added to 400 mg (1.67 mmol) of 2-fluoro-4-methyl-5-[(2,2,2-trifluoroethyl)sulfanyl]aniline and 470 mg (4.56 mmol) of 1-fluorocyclopropanecarboxamide, and the mixture is stirred at 95° C. for 18 h. The residue that remains after rotary evaporation is stirred with water, made alkaline with solid potassium carbonate and extracted with dichloromethane. The combined organic phases are separated off, dried over sodium sulfate and freed from the solvent under reduced pressure. This leaves 380 mg of product (70.1% of theory, purity 88.8% according to LC/MS) as residue.

log P(HCOOH): 1.2

Step 2: 1-Fluoro-N'-{2-fluoro-4-methyl-5-[(2,2,2-trifluoroethyl)sulfinyl]phenyl}cyclopropanecarboximidamide (Ib-19)

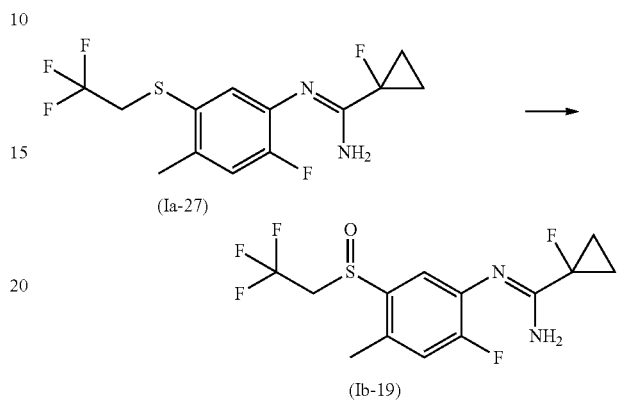

At 0-4° C., 310 mg (0.96 mmol) of 1-fluoro-N'-{2-fluoro-4-methyl-5-[(2,2,2-trifluoroethyl)sulfanyl]phenyl}cyclopropanecarboximidamide (Ia-27) are initially charged in 30 ml of trichloromethane. After the addition of 335 mg of buffer solution pH 7 (KH2PO4/Na2HPO4) and 65 mg of benzyltriethylammonium chloride, 230 mg (70% strength, 1.03 mmol) of m-chloroperbenzoic acid are added a little at a time at 0-4° C. and the reaction mixture is stirred at room temperature for 24 h. A 33% strength aqueous sodium bisulfite solution is added, and the mixture is then extracted twice with dichloromethane. The combined organic phases are washed with water, dried over sodium sulfate and filtered. After removal of the solvent under reduced pressure, the residue is purified by column chromatography using MPLC on RP(C-18) with water/acetonitrile. This gives 42 mg of product (12.9% of theory, purity 98.1% according to LC/MS).

Preparation Example 15: 2,2,2-Trifluoro-N'-{2-methoxy-4-methyl-5-[(2,2,2-trifluoroethyl)sulfanyl]phenyl}ethanimidamide (Ia-236)

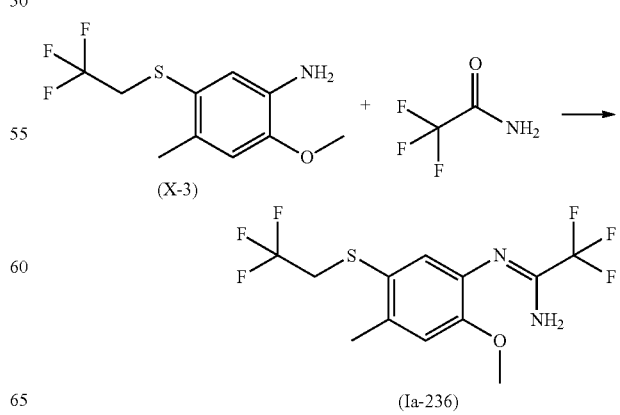

2.5 g (16.3 mmol) of phosphoryl chloride are added to 300 mg (1.19 mmol) of 2-methoxy-4-methyl-5-[(2,2,2-trifluoroethyl)sulfanyl]aniline and 400 mg (3.54 mmol) of trifluoroacetamide, and the mixture is stirred at 95° C. for 18 h. The residue that remains after rotary evaporation is stirred with water, made alkaline with solid potassium carbonate and extracted with dichloromethane. The combined organic phases are separated off, dried over sodium sulfate and freed from the solvent under reduced pressure. This leaves 61.3 mg of product (14.1% of theory, purity >95% according to 1H-NMR) as residue.

Preparation Example 16: N-[(4-Chlorophenyl)(morpholin-4-yl)methylene]-2-methoxy-4-methyl-5-[(2,2,2-trifluoroethyl)sulfanyl]aniline (Ia-268)

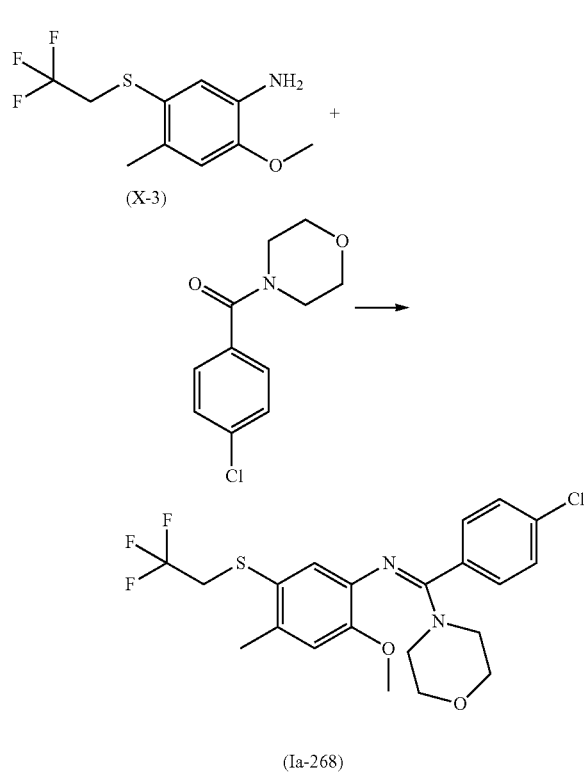

2.5 g (16.3 mmol) of phosphoryl chloride are added to 300 mg (1.19 mmol) of 2-methoxy-4-methyl-5-[(2,2,2-trifluoroethyl)sulfanyl]aniline and 360 mg (1.60 mmol) of (4-chlorophenyl)(morpholin-4-yl)methanone, and the mixture is stirred at 95° C. for 18 h. The residue that remains after rotary evaporation is stirred with water, made alkaline with solid potassium carbonate and extracted with dichloromethane. The combined organic phases are separated off, dried over sodium sulfate and freed from the solvent under reduced pressure. This leaves 247 mg of product (40.9% of theory, purity 90.9% according to LC/MS) as residue.

Preparation Example 17: N'-{2-Fluoro-4-methyl-5-[(2,2,2-trifluoroethyl)sulfinyl]phenyl}-N-methylpyridine-3-carboximidamide (Ib-28)

Step 1: N'-{2-Fluoro-4-methyl-5-[(2,2,2-trifluoroethyl)sulfanyl]phenyl}-N-methylpyridine-3-carboximidamide (Ia-61)

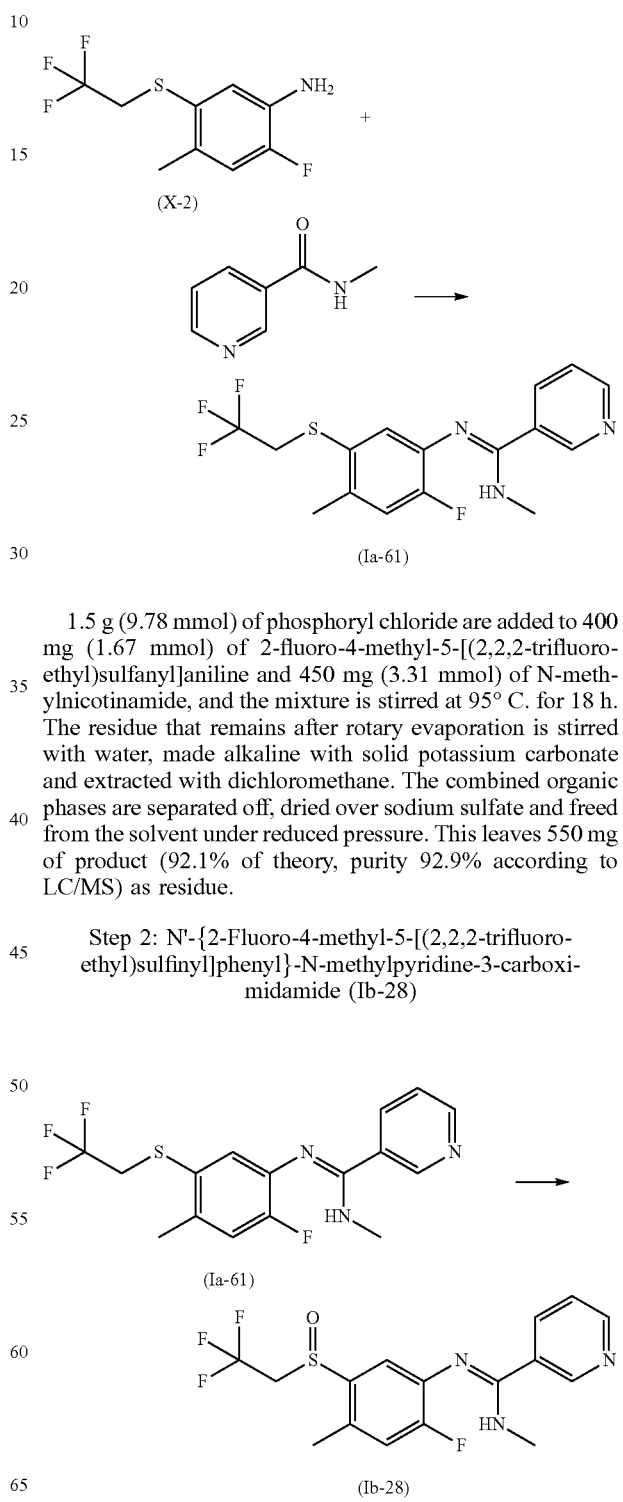

1.5 g (9.78 mmol) of phosphoryl chloride are added to 400 mg (1.67 mmol) of 2-fluoro-4-methyl-5-[(2,2,2-trifluoroethyl)sulfanyl]aniline and 450 mg (3.31 mmol) of N-methylnicotinamide, and the mixture is stirred at 95° C. for 18 h. The residue that remains after rotary evaporation is stirred with water, made alkaline with solid potassium carbonate and extracted with dichloromethane. The combined organic phases are separated off, dried over sodium sulfate and freed from the solvent under reduced pressure. This leaves 550 mg of product (92.1% of theory, purity 92.9% according to LC/MS) as residue.

Step 2: N'-{2-Fluoro-4-methyl-5-[(2,2,2-trifluoroethyl)sulfinyl]phenyl}-N-methylpyridine-3-carboximidamide (Ib-28)

At 0-4° C., 460 mg (1.29 mmol) of N'-{2-fluoro-4-methyl-5-[(2,2,2-trifluoroethyl)sulfanyl]phenyl}-N-methyl-pyridine-3-carboximidamide (Ia-61) are initially charged in 40 ml of trichloromethane. After the addition of 460 mg of buffer solution pH 7 (KH$_2$PO$_4$/Na$_2$HPO$_4$) and 90 mg of benzyltriethylammonium chloride, 320 mg (70%, 0.261 mmol) of m-chloroperbenzoic acid are added a little at a time at 0-4° C. and the reaction mixture is stirred at RT for 24 h. A 33% strength aqueous sodium bisulfite solution is added, and the mixture is then extracted twice with dichloromethane. The combined organic phases are washed with water, dried over sodium sulfate and filtered. After removal of the solvent under reduced pressure, the residue is purified by column chromatography using MPLC on RP(C-18) with water/acetonitrile. This gives 145 mg of product (30.2% of theory, purity 98.7% according to HPLC).

Preparation Example 18: N'-{2-Fluoro-4-methyl-5-[(2,2,2-trifluoroethyl)sulfinyl]phenyl}pyrazine-2-carboximidamide (Ib-62)

Step 1: N'-{2-Fluoro-4-methyl-5-[(2,2,2-trifluoroethyl)sulfanyl]phenyl}pyrazine-2-carboximidamide (Ia-117)

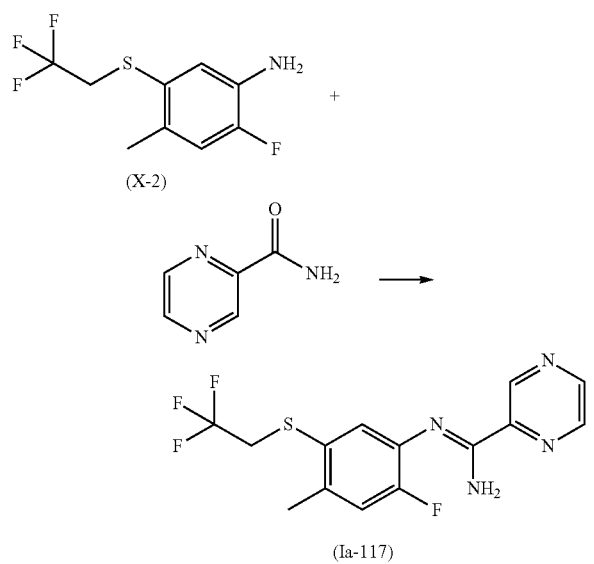

2 g (13.04 mmol) of phosphoryl chloride are added to 300 mg (1.25 mmol) of 2-fluoro-4-methyl-5-[(2,2,2-trifluoroethyl)sulfanyl]aniline and 190 mg (1.54 mmol) of pyrazinecarboxamide, and the mixture is stirred at 95° C. for 18 h. The residue that remains after rotary evaporation is stirred with water, made alkaline with solid potassium carbonate and extracted with dichloromethane. The combined organic phases are separated off, dried over sodium sulfate and freed from the solvent under reduced pressure. This leaves 365 mg of product (84.5% of theory, purity 91.2% according to LC/MS) as residue.

log P(HCOOH): 1.24

Step 2: N'-{2-Fluoro-4-methyl-5-[(2,2,2-trifluoroethyl)sulfinyl]phenyl}pyrazine-2-carboximidamide (Ib-62)

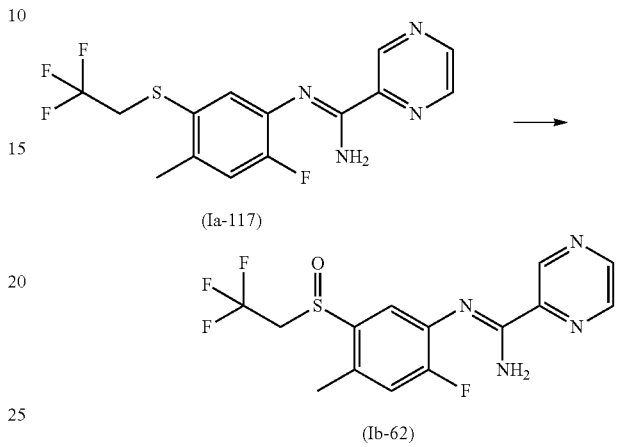

At 0-4° C., 305 mg (0.89 mmol) of N'-{2-fluoro-4-methyl-5-[(2,2,2-trifluoroethyl)sulfanyl]phenyl}pyrazine-2-carboximidamide (Ia-117) are initially charged in 30 ml of trichloromethane. After the addition of 320 mg of buffer solution pH 7 (KH$_2$PO$_4$/Na$_2$HPO$_4$) and 60 mg of benzyltriethylammonium chloride, 225 mg (70%, 1.04 mmol) of m-chloroperbenzoic acid are added a little at a time at 0-4° C. and the reaction mixture is stirred at RT for 24 h. A 33% strength aqueous bisulfite solution is added, and the mixture is then extracted twice with dichloromethane. The combined organic phases are washed with water, dried over sodium sulfate and filtered. After removal of the solvent under reduced pressure, the residue is adsorbed on RP(C-18) material. Purification by column chromatography using MPLC on RP(C-18) with water/acetonitrile gives 55 mg (17.2% of theory, purity 100% according to LC/MS) of product as a light-beige solid.

log P(HCOOH): 0.84 log P(neutral): 1.77

Preparation Example 19: 2-Fluoro-4-methyl-N-[1-(2,2,2-trifluoroethyl)pyrrolidin-2-ylidene]-5-[(2,2,2-trifluoroethyl)sulfinyl]aniline (Ib-115)

Step 1: N'-{2-Fluoro-4-methyl-5-[(2,2,2-trifluoroethyl)sulfanyl]phenyl}-N-(2,2,2 trifluoroethyl)cyclopropanecarboximidamide (Ia-145) and 2-fluoro-4-methyl-N-[1-(2,2,2-trifluoroethyl)pyrrolidin-2-ylidene]-5-[(2,2,2-trifluoroethyl)sulfanyl]aniline (Ia-189)

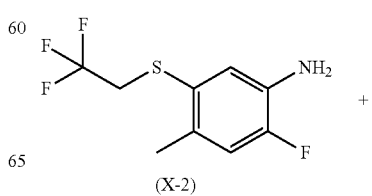

-continued

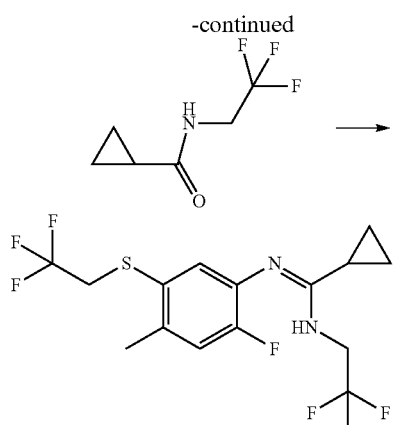

(Ia-145)

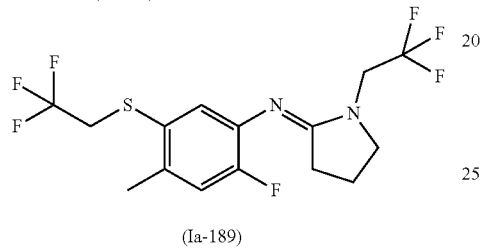

(Ia-189)

1.5 g (9.78 mmol) of phosphoryl chloride are added to 300 mg (1.25 mmol) of 2-fluoro-4-methyl-5-[(2,2,2-trifluoroethyl)sulfanyl]aniline and 430 mg (2.57 mmol) of N-(2,2,2-trifluoroethyl)cyclopropanecarboxamide, and the mixture is stirred at 95° C. for 18 h. The residue that remains after rotary evaporation is stirred with water, made alkaline with solid potassium carbonate and extracted with dichloromethane. The combined organic phases are separated off, dried over sodium sulfate and freed from the solvent under reduced pressure. This leaves 630 mg of crude product as an about 3:1 mixture of the isomers described above as residue.

Purification by column chromatography using MPLC on RP(C-18) with water/acetonitrile gives 239.8 mg (49.2% of theory, purity 80% according to 1H-NMR) of N'-{2-fluoro-4-methyl-5-[(2,2,2-trifluoroethyl)sulfanyl]phenyl}-N-(2,2,2-trifluoroethyl)cyclopropanecarboximidamide (Ia-145)

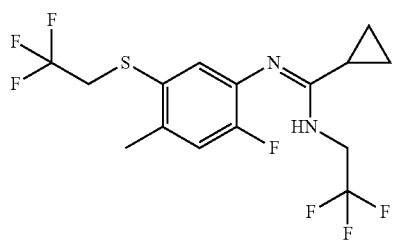

(Ia-145)

13C-NMR (D6-DMSO) δ ppm: 161.0, 153.5, 137.0, 133.9, 128.1, 127.2, 117.5, 41.0, 35.6, 19.6, 11.6, 6.2 log P(HCOOH): 1.99 log P(neutral): 4.12 and 72.4 mg (14.9% of theory, purity 100% according to HPLC) of 2-fluoro-4-methyl-N-[1-(2,2,2-trifluoroethyl)pyrrolidin-2-ylidene]-5-[(2,2,2-trifluoroethyl)sulfanyl]aniline (Ia-189).

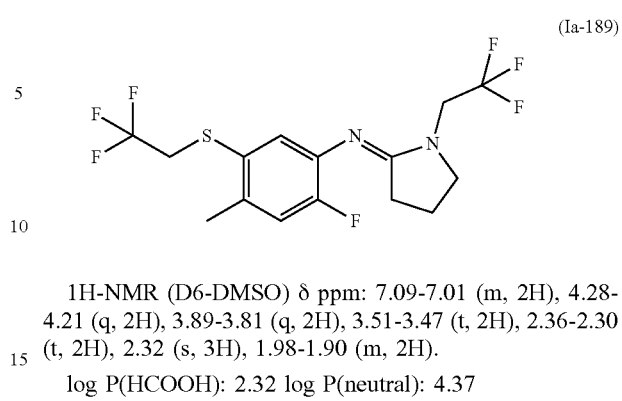

(Ia-189)

1H-NMR (D6-DMSO) δ ppm: 7.09-7.01 (m, 2H), 4.28-4.21 (q, 2H), 3.89-3.81 (q, 2H), 3.51-3.47 (t, 2H), 2.36-2.30 (t, 2H), 2.32 (s, 3H), 1.98-1.90 (m, 2H).

log P(HCOOH): 2.32 log P(neutral): 4.37

Step 2: 2-Fluoro-4-methyl-N-[1-(2,2,2-trifluoroethyl)pyrrolidin-2-ylidene]-5-[(2,2,2-trifluoroethyl)sulfinyl]aniline (Ib-115)

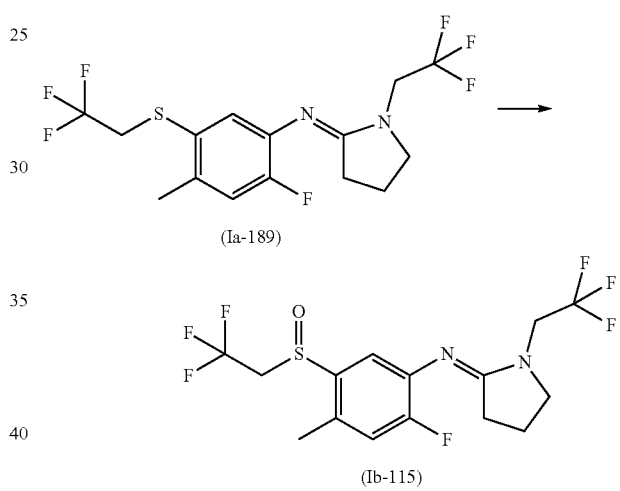

(Ib-115)

At 0-4° C., 900 mg (2.32 mmol) of 2-fluoro-4-methyl-N-[1-(2,2,2-trifluoroethyl)pyrrolidin-2-ylidene]-5-[(2,2,2-trifluoroethyl)sulfanyl]aniline (Ia-189) are initially charged in 40 ml of trichloromethane. After the addition of 850 mg of buffer solution pH 7 (KH$_2$PO$_4$/Na$_2$HPO$_4$) and 160 mg of benzyltriethylammonium chloride, 600 mg (77%, 2.68 mmol) of m-chloroperbenzoic acid are added a little at a time at 0-4° C. and the reaction mixture is stirred at RT for 24 h. A 33% strength aqueous sodium bisulfite solution is added, and the mixture is then extracted twice with dichloromethane. The combined organic phases are washed with water, dried over sodium sulfate and filtered. After removal of the solvent under reduced pressure, the residue is purified by column chromatography using MPLC on RP(C-18) with water/acetonitrile. This gives 70 mg of product (7.5% of theory, purity 95.2% according to LC/MS).

13C-NMR (D6-DMSO) δ ppm: 164.2, 155.6, 138.3, 136.0, 129.8, 125.1, 124.2, 119.9, 117.9, 56.8, 49.5, 44.4, 27.0, 19.5, 16.4

Preparation Example 20: 2,4-Dimethyl-N-[1,3-oxazolidin-2-ylidene]-5-[(2,2,2-trifluoroethyl)sulfanyl]aniline Step 1: 1-(2-Chloroethyl)-3-{2,4-dimethyl-5-[(2,2,2-trifluoroethyl)sulfanyl]phenyl}urea

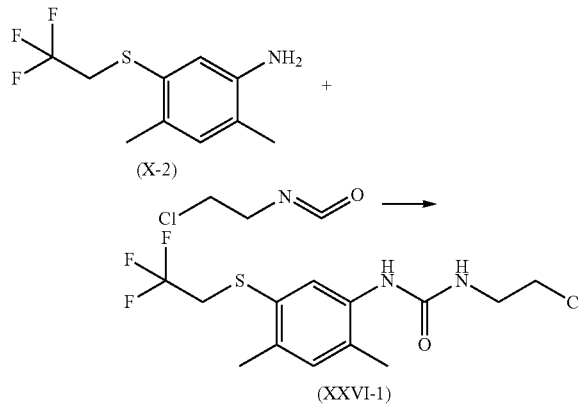

A little at a time, 1.45 g (6.16 mmol) of 2,4-dimethyl-5-[(2,2,2-trifluoroethyl)sulfanyl]aniline are added to a solution of 700 mg (6.63 mmol) of 2-chloroethyl isocyanate in 50 ml of tert-butyl methyl ether and a catalytic amount of 1,8-diazabicyclo[5.4.0]undec-7-ene (DBU) and subsequently stirred at room temperature for another 18 h. Under reduced pressure, almost all of the solvent is removed from the mixture, and the resulting white solid is filtered off with suction. This leaves 2.00 g of product (88.5% of theory, purity 94.4% according to LC/MS).

1H-NMR (D6-DMSO) δ ppm: 8.01 (s, 1H), 7.83 (s, 1H), 7.04 (s, 1H), 6.83 (t, 1H), 3.77-3.69 (q, 2H), 3.68-3.65 (m, 2H), 3.45-3.40 (m, 2H), 2.30 (s, 3H), 2.14 (s, 3H).

Step 2: 2,4-Dimethyl-N-[1,3-oxazolidin-2-ylidene]-5-[(2,2,2-trifluoroethyl)sulfanyl]aniline

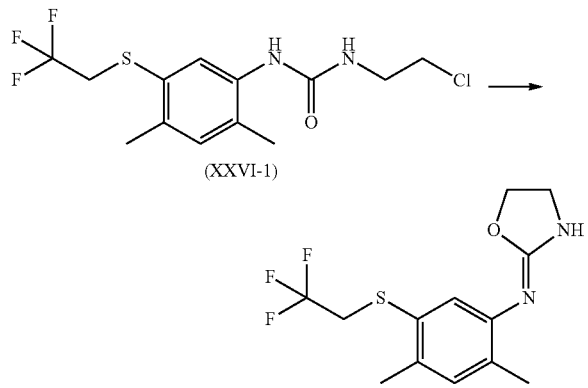

900 mg (2.64 mmol) of 1-(2-chloroethyl)-3-{2,4-dimethyl-5-[(2,2,2-trifluoroethyl)sulfanyl]phenyl}urea in a mixture of 15 ml of water and 20 ml of propionitrile with 4 g of potassium carbonate are heated under reflux for 18 h. Under reduced pressure, the mixture is freed from the solvent and the slurry of solids that remains is acidified with dilute hydrochloric acid. The mixture is then allowed to stand for 18 h, and the beige precipitate is then filtered off with suction. This gives 560 mg of crude product. Purification by column chromatography using a Biotage Isolera One and ethyl acetate/cyclohexane 2:1 v/v as mobile phase gives 130 mg of product (16.2% of theory, purity according to LC/MS 81.5%).

log P(HCOOH): 1.36

Preparation Example 21: 2-Fluoro-4-methyl-N-[1,3-thiazinan-2-ylidene]-5-[(2,2,2-trifluoroethyl)sulfanyl]aniline (Ia-279)

Step 1: 2-Fluoro-4-methyl-N-[(1,3-thiazinan-2-ylidene]-5-[(2,2,2-trifluoroethyl)sulfanyl]anilinium chloride (Ia-278)

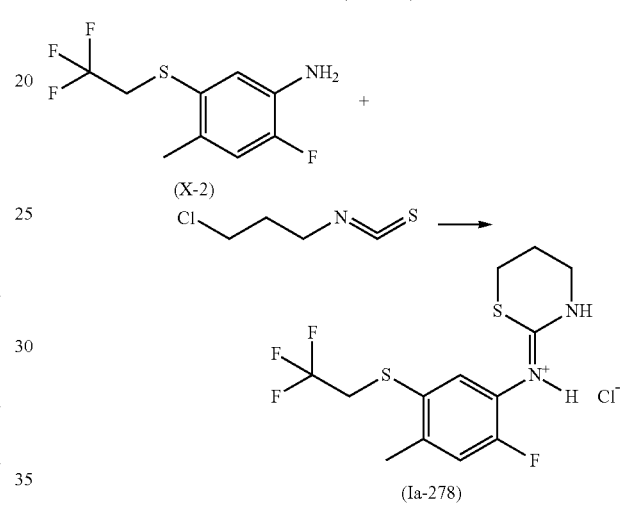

A little at a time, 1.61 g (6.72 mmol) of 2-fluoro-4-methyl-5-[(2,2,2-trifluoroethyl)sulfanyl]aniline are added to a solution of 1 g (7.37 mmol) of 3-chloropropyl isocyanate in 30 ml of tert-butyl methyl ether and a catalytic amount of 1,8-diazabicyclo[5.4.0]undec-7-ene (DBU) and subsequently stirred at room temperature for another 18 h. Under reduced pressure, the mixture is freed from the solvent. The residue that remains is a light-beige oil which slowly crystallizes. This leaves 2.3 g of product (91.3% of theory, purity 95% according to LC/MS).

13C-NMR (D6-DMSO) δ ppm: 166.0 (broad), 156.1, 142.1, 131.7, 129.4, 126.1, 120.6, 118.6, 41.3, 34.9, 26.6, 20.6 log P(HCOOH): 1.34

Step 2: 2-Fluoro-4-methyl-N-[1,3-thiazinan-2-ylidene]-5-[(2,2,2-trifluoroethyl)sulfanyl]aniline (Ia-279)

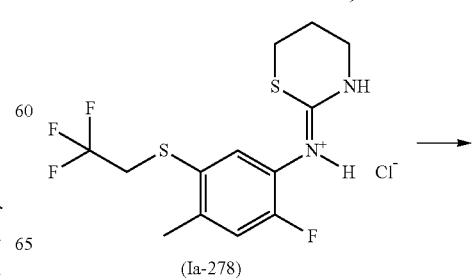

-continued

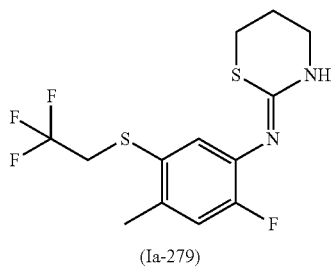

(Ia-279)

2.2 g (5.87 mmol) of 2-fluoro-4-methyl-N-[1,3-thiazinan-2-ylidene]-5-[(2,2,2-trifluoroethyl)sulfanyl]anilinium chloride (Ia-278) are dissolved in 50 ml of water and made alkaline with ammonium hydroxide (28-30% by weight solution of $NH_3$ in water). The mixture is extracted repeatedly with dichloromethane. The combined organic phases are separated off, dried over sodium sulfate and freed from the solvent under reduced pressure. This leaves a residue of 1.56 g of product (68.3% of theory, purity 100% according to 1H-NMR) as shiny amber crystals.

Preparation Example 22: 2-Fluoro-4-methyl-N-[1,3-thiazolidin-2-ylidene]-5-[(2,2,2-trifluoroethyl)sulfinyl]aniline Step 1: 1-(2-Chloroethyl)-3-{2-fluoro-4-methyl-5-[(2,2,2-trifluoroethyl)sulfanyl]phenyl}thiourea

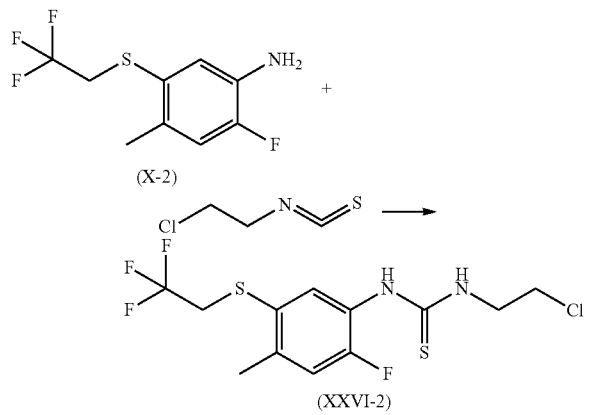

A little at a time, 1.9 g (7.94 mmol) of 2-fluoro-4-methyl-5-[(2,2,2-trifluoroethyl)sulfanyl]aniline are added to a solution of 1 g (8.22 mmol) of 2-chloroethyl isothiocyanate in 50 ml of tert-butyl methyl ether and a catalytic amount of 1,8-diazabicyclo[5.4.0]undec-7-ene (DBU) and subsequently stirred at room temperature for another 18 h. Under reduced pressure, almost all of the solvent is removed from the mixture, and the resulting white solid is filtered off with suction. This leaves 2.88 g of product (97.1% of theory, purity 100% according to 1H-NMR).

1H-NMR (D6-DMSO) δ ppm: 7.68-7.67 (m, 1H), 7.43-7.40 (m, 1H), 4.03-3.93 (m, 4H), 3.61 (t, 2H), 2.41 (s, 3H).

Step 2: 2-Fluoro-4-methyl-N-[1,3-thiazolidin-2-ylidene]-5-[(2,2,2-trifluoroethyl)sulfanyl]aniline (Ia-238)

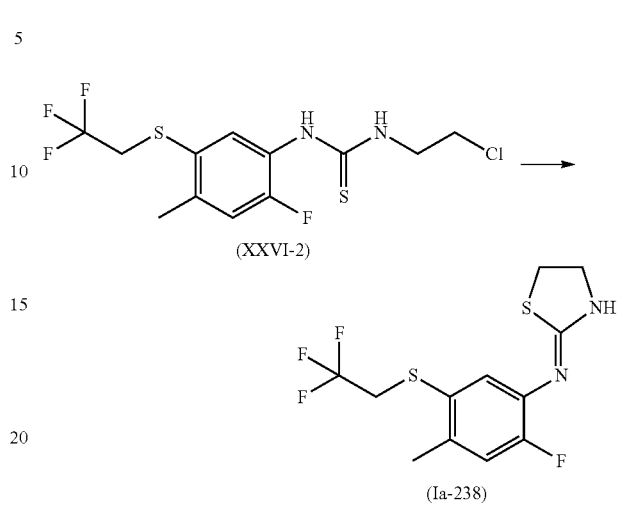

2.75 g (7.62 mmol) of 1-(2-chloroethyl)-3-{2-fluoro-4-methyl-5-[(2,2,2-trifluoroethyl)sulfanyl]phenyl}urea in a mixture of 3 ml of water and 100 ml of propionitrile with 2 g of potassium carbonate, 3.5 g of cesium carbonate, 0.1 g of sodium hydroxide and 0.1 g of potassium iodide are heated under reflux for 48 h. Under reduced pressure, the mixture is freed from the solvent and the slurry of solids that remains is neutralized with dilute hydrochloric acid. The mixture is extracted repeatedly with dichloromethane. The combined organic phases are separated off, dried over magnesium sulfate and freed from the solvent under reduced pressure. This gives 2.38 g of a brown oil as a crude product. Purification by column chromatography using a Biotage Isolera One using a 50 g Snap cartridge and ethyl acetate/cyclohexane 1:1 v/v as mobile phase gives 590 mg of product (23.9% of theory, purity according to LC/MS 92.9%).

13C-NMR (D6-DMSO) δ ppm: 163.3, 153.7, 134.8, 126.9 (broad), 126.9, 126.0, 117.0, 45.0 (broad), 35.5, 29.8, 19.4

Step 3: 2-Fluoro-4-methyl-N-[1,3-thiazolidin-2-ylidene]-5-[(2,2,2-trifluoroethyl)sulfinyl]aniline

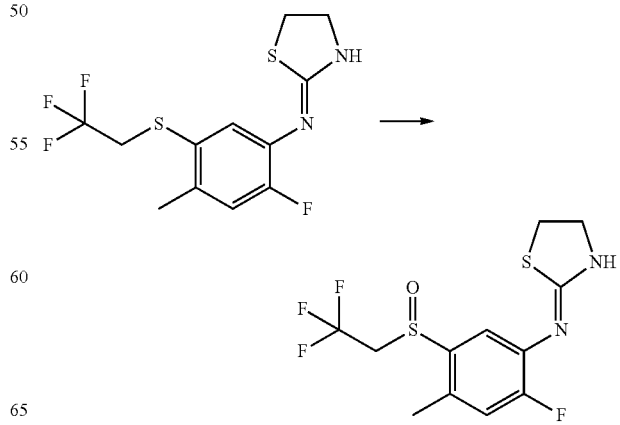

At 0-4° C., 99 mg (0.305 mmol) of 2-fluoro-4-methyl-N-[1,3-thiazolidin-2-ylidene]-5-[(2,2,2-trifluoroethyl)sulfanyl]aniline (Ia-238) are initially charged in 10 ml of trichloromethane. After the addition of 120 mg of buffer solution pH 7 (KH$_2$PO$_4$/Na$_2$HPO$_4$) and 20 mg of benzyltriethylammonium chloride, 80 mg (70%, 0.357 mmol) of m-chloroperbenzoic acid are added a little at a time at 0-4° C. and the reaction mixture is stirred at RT for 24 h. A 33% strength aqueous sodium bisulfite solution is added, and the mixture is then extracted twice with dichloromethane. The combined organic phases are washed with water, dried over sodium sulfate and filtered. After removal of the solvent under reduced pressure, the residue is purified by column chromatography using MPLC on RP(C-18) with water/acetonitrile. This gives 15 mg of product (14.4% of theory, purity 100% according to LC/MS).

13C-NMR (D6-DMSO) δ ppm: 165.3, 157.5, 137.2, 131.5, 125.6, 120.6, 119.5, 58.5, 46.4, 31.3 log P(HCOOH): 0.80

Preparation Example 23: 2-Fluoro-4-methyl-N-[(2E)-1-phenylpyrrolidin-2-ylidene]-5-[(2,2,2-trifluoroethyl)sulfinyl]aniline (Ib-55)

Step 1: 2-Fluoro-4-methyl-N-[(2E)-1-phenylpyrrolidin-2-ylidene]-5-[(2,2,2-trifluoroethyl)sulfanyl]aniline

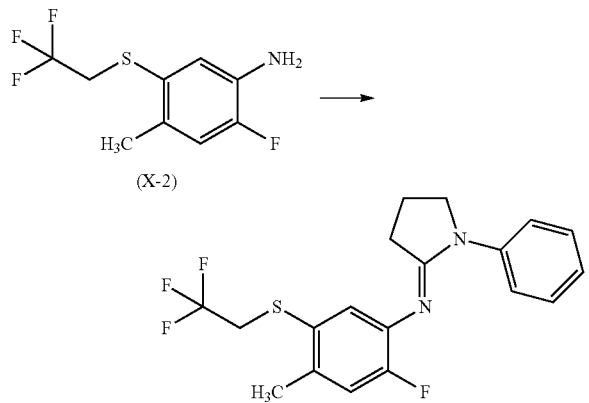

150 mg (0.63 mmol) of 2-fluoro-4-methyl-5-[(2,2,2-trifluoroethyl)sulfanyl]aniline and 202 mg (1.25 mmol) of N-phenyl-2-pyrrolidinone are initially charged. 0.29 ml (3.14 mmmol) of phosphoryl chloride is slowly added dropwise and the reaction mixture is stirred at 100° C. for 2 h. After cooling, the mixture is poured into ice-water, the pH is adjusted to 8-9 using aqueous sodium hydroxide solution and the mixture is extracted three times with ethyl acetate. The combined organic phases are washed with saturated sodium chloride solution, dried over sodium sulfate, filtered and concentrated. The residue is taken up in acetonitrile, adsorbed onto RP(C-18) and purified by MPLC on RP(C-18) using water/acetonitrile. Two fractions are isolated: 89 mg (98% pure, 37% of theory) and 65 mg (98% pure, 27% of theory) of the title compound.

log P(HCOOH): 1.83; log P(neutral): 4.92; 1H-NMR (D6-DMSO, 400 MHz) δ ppm 7.85 (d, 2H), 7.36 (dd, 2H), 7.12-7.09 (m, 3H), 3.92-3.84 (m, 4H), 2H under the DMSO peak, 2.33 (s, 3H), 2.05-1.97 (m, 2H)

Step 2: 2-Fluoro-4-methyl-N-[(2E)-1-phenylpyrrolidin-2-ylidene]-5-[(2,2,2-trifluoroethyl)sulfinyl]aniline (Ib-55)

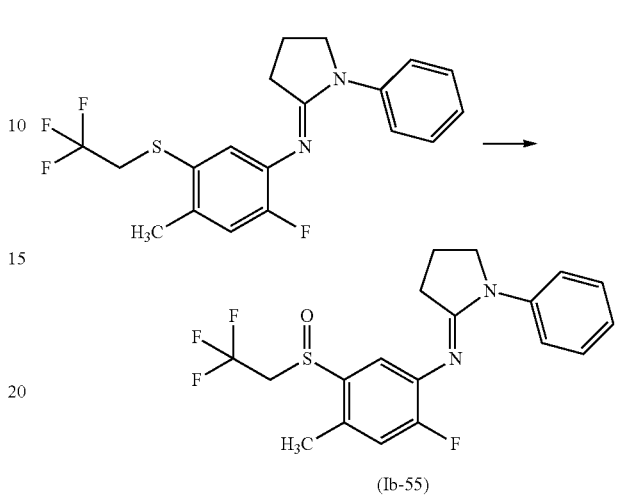

At 0-4° C., 89 g (0.23 mmol) of 2-fluoro-4-methyl-N-[(2E)-1-phenylpyrrolidin-2-ylidene]-5-[(2,2,2-trifluoroethyl)sulfanyl]aniline are initially charged in 3 ml of dichloromethane, 69 mg (0.28 mmol) of meta-chloroperbenzoic acid (70%) are added and the reaction mixture is stirred at room temperature for another 2 h. A 33% strength sodium thiosulfate solution (peroxide test carried out) and a saturated sodium bicarbonate solution are then added, and the mixture is extracted twice with dichloromethane. The combined organic phases are washed with a saturated sodium carbonate solution, dried over sodium sulfate and filtered, and the solvent is removed under reduced pressure. The residue comprises 98 mg (94% pure, 99% of theory) of the title compound as a brown oil.

log P(HCOOH): 1.27; log P(neutral): 3.47; 1H-NMR (D6-DMSO, 400 MHz) δ ppm 7.86 (d, 2H), 7.37 (m, 3H), 7.22 (d, 1H), 7.09 (dd, 1H), 4.14-4.02 (m, 2H), 3.73 (dd, 2H), 2.67-2.57 (m, 2H), 2.33 (s, 3H), 2.07-1.99 (m, 2H)

Preparation Example 24: 2-({2-Fluoro-4-methyl-5-[(2,2,2-trifluoroethyl)sulfinyl]phenyl}imino)-3-(2,2,2-trifluoroethyl)-1,3-thiazolidin-4-one (Ib-71)

Step 1.a: 1-{2-Fluoro-4-methyl-5-[(2,2,2-trifluoroethyl)sulfanyl]phenyl}-3-(2,2,2-trifluoroethyl)thiourea known from JP 2011-42611 (Example 250)

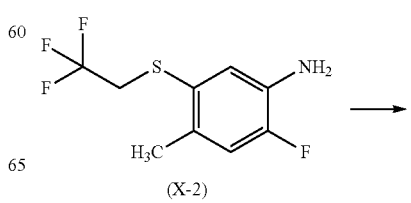

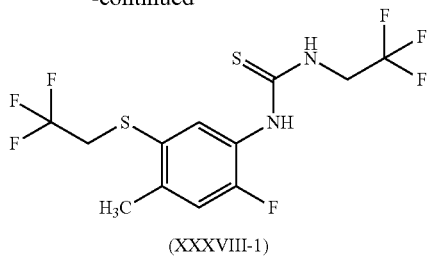

(XXXVIII-1)

1.00 g (4.18 mmol) of 2-fluoro-4-methyl-5-[(2,2,2-trifluoroethyl)sulfanyl]aniline is initially charged in 5 ml of dichloromethane, and 0.006 ml (0.042 mmol) of triethylamine is added. After the addition of 0.59 g (4.18 mmol) of 1,1,1-trifluoro-2-isothiocyanatoethane, the reaction mixture is stirred at room temperature overnight. The solvent is removed under reduced pressure, the residue is triturated with a little toluene and the insoluble fraction is filtered off with suction and dried. This gives 0.31 g (100% pure, 20% of theory) of the title compound as a white solid. Under reduced pressure, the filtrate is freed from the solvent. The residue of 1.30 g comprises the title compound in a purity of 77%.

log P(HCOOH): 3.32; log P(neutral): 3.24; 1H-NMR (D6-DMSO, 400 MHz) δ ppm 9.62 (bs, 1H), 8.34 (bs, 1H), 7.76 (d, 1H), 7.26 (d, 1H), 4.46-4.40 (m, 2H), 3.87 (q, 2H), 2.38 (s, 3H)

Step 2.a: 2-({2-Fluoro-4-methyl-5-[(2,2,2-trifluoroethyl)sulfanyl]phenyl}imino)-3-(2,2,2-trifluoroethyl)-1,3-thiazolidin-4-one (Ia-175)

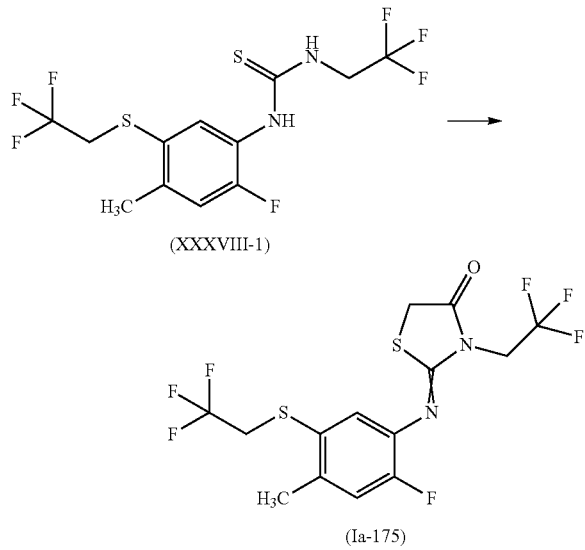

75 mg (97% pure, 0.19 mmol) of 1-{2-fluoro-4-methyl-5-[(2,2,2-trifluoroethyl)sulfanyl]phenyl}-3-(2,2,2-trifluoroethyl)thiourea and 27 mg (0.19 mmol) of bromoacetic acid are initially charged in 2 ml of toluene, and the mixture is stirred at reflux for 6 h. After cooling, a saturated sodium chloride solution is added to the reaction mixture and the organic phase is separated off, dried over sodium sulfate and freed from the solvent under reduced pressure. The residue is applied to RP(C-18) material and purified by means of MPLC on RP(C-18) using water/acetonitrile. 18 mg (100% pure, 23% of theory) of the title compound are isolated as a white solid.

log P(HCOOH): 4.09; log P(neutral): 3.99; 1H-NMR (D6-DMSO, 400 MHz) δ ppm 7.27 (d, 1H), 7.21 (d, 1H), 4.58 (q, 2H), 4.24 (s, 2H), 3.87 (q, 2H), 2.39 (s, 3H)

Step 3.a: 2-({2-Fluoro-4-methyl-5-[(2,2-trifluoroethyl)sulfinyl]phenyl}imino)-3-(2,2,2-trifluoroethyl)-1,3-thiazolidin-4-one (Ib-71)

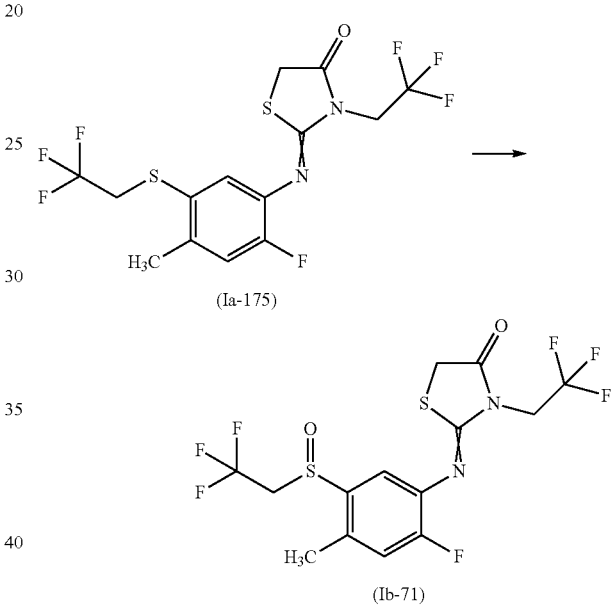

At 0-4° C., 136 g (0.32 mmol) of 2-({2-fluoro-4-methyl-5-[(2,2,2-trifluoroethyl)sulfanyl]phenyl}imino)-3-(2,2,2-trifluoroethyl)-1,3-thiazolidin-4-one are initially charged in 3 ml of dichloromethane, 84 mg (0.32 mmol) of meta-chloroperbenzoic acid (70%) are added and the reaction mixture is stirred at room temperature for another 2 h. A 33% strength sodium thiosulfate solution (peroxide test carried out) and a saturated sodium bicarbonate solution are then added, and the mixture is extracted twice with dichloromethane. The combined organic phases are washed with a saturated sodium carbonate solution, dried over sodium sulfate and filtered, and the solvent is removed under reduced pressure. The residue comprises 136 mg (100% pure, 96% of theory) of the title compound as a lightly colored oil which, over time, crystallizes to give a white solid.

log P(HCOOH): 2.93; log P(neutral): 2.87; 1H-NMR (D6-DMSO, 400 MHz) δ ppm 7.51 (d, 1H), 7.38 (d, 1H), 4.62-4.57 (m, 2H), 4.26-4.14 (m, 3H), 4.04-3.94 (m, 1H), 2.36 (s, 3H)

Alternatively, synthesis can be carried out as follows:

Step 1.b: 2-Fluoro-4-methyl-5-[(2,2,2-trifluoroethyl)sulfinyl]aniline

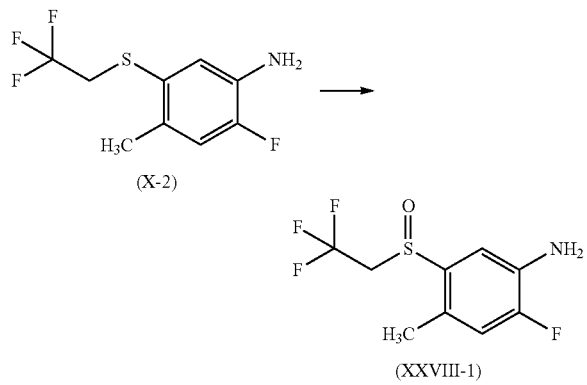

At 0-4° C., 5.00 g (0.21 mmol) of 2-fluoro-4-methyl-5-[(2,2,2-trifluoroethyl)sulfanyl]aniline are initially charged in 100 ml of dichloromethane, 6.18 g (0.25 mmol) of meta-chloroperbenzoic acid are added and the reaction mixture is stirred at room temperature for 2 h. A 33% strength sodium thiosulfate solution is then added (peroxide test carried out), and the mixture is extracted twice with dichloromethane. The combined organic phases are washed with a saturated sodium carbonate solution, dried over sodium sulfate and filtered, and the solvent is removed under reduced pressure. The residue comprises 5.10 g (90% pure, 86% of theory) of the title compound as a brown oil.

log P(HCOOH): 1.77; log P(neutral): 1.72; 1H-NMR (D6-DMSO, 400 MHz) δ ppm 7.26 (d, 1H), 7.02 (d, 1H), 5.45 (bs, 2H), 4.08-3.95 (m, 1H), 3.88-3.75 (m, 1H), 2.19 (s, 3H)

Step 2.b: 1-{2-Fluoro-4-methyl-5-[2,2,2-trifluoroethyl)sulfinyl]phenyl}-3-(2,2,2-trifluoroethyl)thiourea

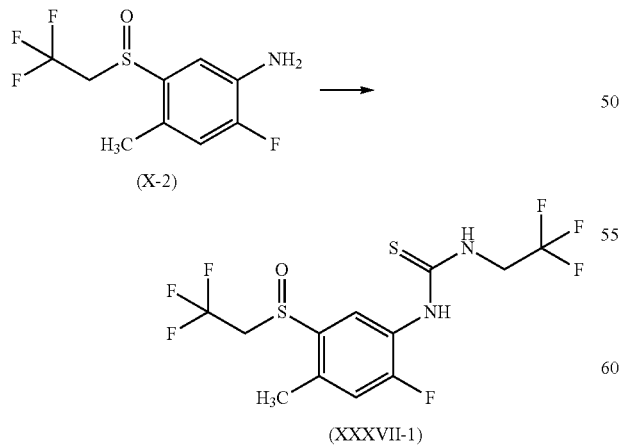

1.00 g (3.53 mmol) of 2-fluoro-4-methyl-5-[(2,2,2-trifluoroethyl)sulfanyl]aniline (90% pure) is initially charged in 5 ml of dichloromethane, and 0.005 ml (0.035 mmol) of triethylamine is added. After the addition of 0.50 g (3.53 mmol) of 1,1,1-trifluoro-2-isothiocyanatoethane, the reaction mixture is stirred at room temperature overnight. The insoluble fraction is filtered off with suction and dried. This gives 0.60 g (100% pure, 43% of theory) of the title compound as a white solid. Under reduced pressure, the filtrate is freed from the solvent. The residue of 0.81 g comprises the title compound in a purity of 54%.

log P(HCOOH): 2.34; log P(neutral): 2.30; 1H-NMR (D6-DMSO, 400 MHz) δ ppm 9.75 (bs, 1H), 8.50 (bs, 1H), 8.12 (bd, 1H), 7.36 (d, 1H), 4.52-4.40 (m, 1H), 4.21-4.15 (m, 1H), 4.05-3.95 (m, 1H), 2.36 (s, 3H)

Step 3.c: 2-({2-Fluoro-4-methyl-5-[(2,2,2-trifluoroethyl)sufinyl]phenyl}imino-3-(2,2,2-trifluoroethyl)-1,3-thiazolidin-4-one (Ib-71)

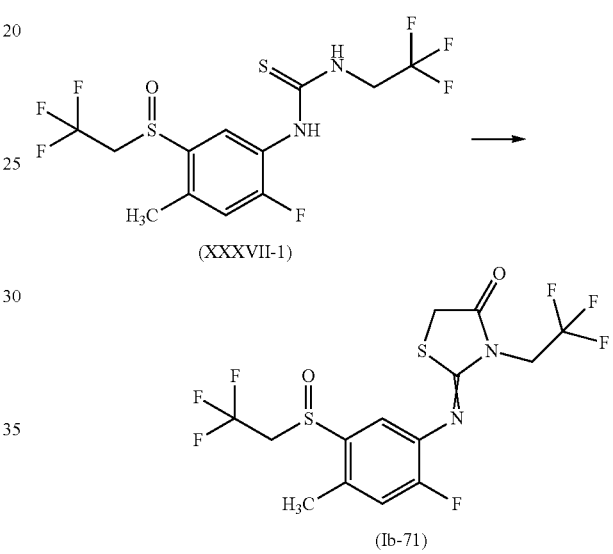

200 mg (0.51 mmol) of 1-{2-fluoro-4-methyl-5-[(2,2,2-trifluoroethyl)sulfinyl]phenyl}-3-(2,2,2-trifluoroethyl)thiourea and 70 mg (0.51 mmol) of bromoacetic acid are initially charged in 2 ml of toluene, and the mixture is stirred at reflux for 6 h. A saturated sodium chloride solution is added to the reaction mixture and the organic phase is separated off, dried over sodium sulfate and freed from the solvent under reduced pressure. The residue is applied to RP(C-18) material and purified by means of MPLC on RP(C-18) using water/acetonitrile. 63 mg (97% pure, 28% of theory) of the title compound are isolated as a white solid.

Preparation Example 25: Synthesis of 3,4-dimethyl-5-(methylsulfanyl)-1,2,4-thiadiazol-4-ium methylsulfate

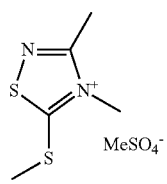

Step 1: 3,4-Dimethyl-1,2,4-thiadiazol-5(4H)-one

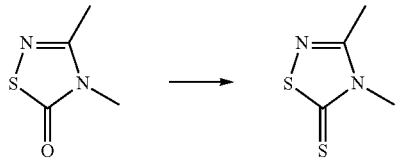

At 0° C., 6.13 g (27.6 mmol) of phosphorus pentasulfide are added to a solution of 1.80 g (13.80 mmol) of 3,4-dimethyl-1,2,4-thiadiazol-5(4H)-one (crude, prepared according to J. Chem. Soc. Perkin Trans. 1 1983, 4, 687-691) in xylene, and the mixture is then heated at 100° C. for 4 h. After aqueous work-up and chromatographic purification, 0.60 g (30% of theory) of the title compound is obtained.

Step 2: 3,4-Dimethyl-5-(methylsulfanyl)-1,2,4-thiadiazol-4-ium methylsulfate

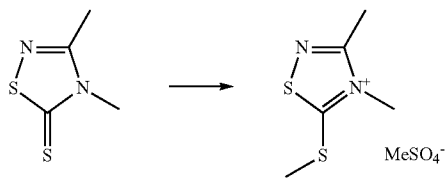

With stirring, 0.62 g (4.52 mmol) of dimethyl sulfate is added to a solution of 0.60 g (4.10 mmol) of 3,4-dimethyl-1,2,4-thiadiazole-5(4H)-thione in acetonitrile, and the mixture is stirred at reflux for 5 h. After cooling, the solvent is removed under reduced pressure and the residue obtained (1.50 g) is reacted further crude.

Preparation Example 26: N-(3,4-Dimethyl-1,2,4-thiadiazol-5(4H)-ylidene)-2,4-dimethyl-5-[(2,2,2-trifluoroethyl)sulfinyl]aniline (Ib-173)

Step 1: N-(3,4-Dimethyl-1,2,4-thiadiazol-5(4H)-ylidene)-2,4-dimethyl-5-[(2,2,2-trifluoroethyl)sulfanyl]aniline The preparation processes described above can be used to give the compounds of the formula (I)—for example the following compounds of the formula (I):

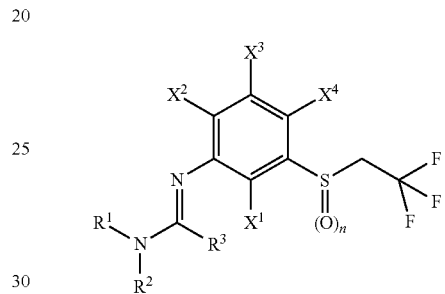

| Ex. | n | $R^1$ | $R^2$ | $R^3$ | $X^1$ | $X^2$ | $X^3$ | $X^4$ | log P |
|---|---|---|---|---|---|---|---|---|---|
| Ia-01 | 0 | CH | $CH_3$ | $CF_3$ | H | F | H | $CH_3$ | 4.48[a]; 4.5[b] |
| Ia-02 | 0 | propyl | H | $CF_3$ | H | F | H | $CH_3$ | 4.45[a]; 4.43[b] |
| Ia-03 | 0 | H | H | $CHF_2$ | H | F | H | $CH_3$ | 2.2[c] |
| Ia-04 | 0 | pyridin-2-ylmethyl | H | $CF_3$ | H | F | H | $CH_3$ | 3.68[a] |
| Ia-05 | 0 | propan-2-yl | H | $CF_3$ | H | F | H | $CH_3$ | 4.51[a]; 4.52[b] |
| Ia-06 | 0 | H | H | PD-F-heptyl | H | F | H | $CH_3$ | |
| Ia-07 | 0 | H | H | $CF_3$ | H | $CH_3$ | H | $CH_3$ | 3.36[a]; 3.4[b] |
| Ia-08 | 0 | pyridin-2-ylmethyl | pyridin-2-ylmethyl | $CF_3$ | H | F | H | $CH_3$ | |
| Ia-09 | 0 | $CH_3$ | H | $CF_3$ | H | $CH_3$ | H | F | 3.72[a]; 3.69[b] |
| Ia-10 | 0 | $CH_3$ | $CH_3$ | DD-F-hexyl | H | F | H | $CH_3$ | |
| Ia-11 | 0 | methylsulfonyl | H | $CF_3$ | H | F | H | $CH_3$ | 3.05[a] |
| Ia-12 | 0 | $CH_3$ | H | $CF_3$ | H | $CH_3$ | H | $CH_3$ | 3.95[a]; 4.01[b] |
| Ia-13 | 0 | $CH_3$ | H | $CF_3$ | H | F | H | $CH_3$ | 3.7[a]; 3.71[b] |
| Ia-14 | 0 | H | H | $CF_3$ | H | Cl | H | Cl | |
| Ia-15 | 0 | $CH_3$ | H | $CF_3$ | H | Cl | H | Cl | 4.2[a]; 4.2[b] |
| Ia-16 | 0 | (trifluoromethyl)sulfonyl | H | $CF_3$ | H | F | H | $CH_3$ | |
| Ia-17 | 0 | H | H | $CF_3$ | H | $CH_3$ | H | F | 3.16[a]; 3.14[b] |
| Ia-18 | 0 | ethyl | H | $CF_3$ | H | F | H | $CH_3$ | 4.12[a]; 4.12[b] |
| Ia-19 | 0 | $CH_3$ | H | $CF_3$ | H | H | H | $CF_3$ | |
| Ia-20 | 0 | $CH_3$ | H | $CF_3$ | H | Cl | H | $CH_3$ | |
| Ia-21 | 0 | H | H | $CF_3$ | H | F | H | $CH_3$ | 3.13[a]; 3.17[a]; 3.12[b] |
| Ia-22 | 0 | H | H | DD-F-hexyl | H | F | H | $CH_3$ | |
| Ia-23 | 0 | $CH_3$ | $CH_3$ | $CF_3$ | H | $CH_3$ | H | $CH_3$ | 4.87[a]; 4.87[b] |
| Ia-24 | 0 | $CH_3$ | $CH_3$ | $CF_3$ | H | $CH_3$ | H | F | 4.53[a]; 4.47[b] |
| Ia-25 | 0 | H | H | $CF_3$ | H | H | H | $CH_3$ | |
| Ia-26 | 0 | Cpr | H | $CF_3$ | H | F | H | $CH_3$ | 4.03[a]; 4.02[b] |
| Ib-01 | 1 | $CH_3$ | $CH_3$ | $CF_3$ | H | F | H | $CH_3$ | |
| Ib-02 | 1 | ethyl | H | $CF_3$ | H | F | H | $CH_3$ | |
| Ib-03 | 1 | propan-2-yl | | H | $CF_3$ | H | F | H | $CH_3$ |
| Ib-04 | 1 | $CH_3$ | H | $CF_3$ | H | $CH_3$ | H | $CH_3$ | 3.15[a]; 3.09[b] |
| Ib-05 | 1 | $CH_3$ | H | $CF_3$ | H | $CH_3$ | H | F | 2.86[a]; 2.79[b] |

-continued

| Ex. | n | $R^1$ | $R^2$ | $R^3$ | $X^1$ | $X^2$ | $X^3$ | $X^4$ | log P |
|---|---|---|---|---|---|---|---|---|---|
| Ib-06 | 1 | propyl | H | $CF_3$ | H | F | H | $CH_3$ | 3.24[a]; 3.17[b] |
| Ib-07 | 1 | $CH_3$ | H | $CF_3$ | H | F | H | $CH_3$ | 2.64[a]; 2.61[b] |
| Ib-08 | 1 | Cpr | H | $CF_3$ | H | F | H | $CH_3$ | 2.68[a]; 2.67[b] |
| Ib-09 | 1 | $CH_3$ | $CH_3$ | $CF_3$ | H | $CH_3$ | H | $CH_3$ | 3.23[a]; 3.19[b] |
| Ib-10 | 1 | $CH_3$ | H | $CF_3$ | H | H | H | $CF_3$ | 2.52[a]; 2.49[b] |
| Ib-11 | 1 | H | H | $CF_3$ | H | F | H | $CH_3$ | 2.77[a]; 2.71[b] |
| Ib-12 | 1 | H | H | $CF_3$ | H | $CH_3$ | H | $CH_3$ | 3.36[a]; 3.3[b] |
| Ib-13 | 1 | H | H | $CF_3$ | H | $CH_3$ | H | F | |
| Ib-14 | 1 | H | H | $CF_3$ | H | Cl | H | Cl | 2.05[a]; 2.02[b] |
| Ib-15 | 1 | $CH_3$ | $CH_3$ | $CF_3$ | H | $CH_3$ | H | F | 2.17[a]; 2.14[b] |
| Ib-16 | 1 | H | H | $CF_3$ | H | H | H | $CF_3$ | 2.2[a]; 2.19[b] |

Abbreviations:
PD-F-heptyl = pentadecafluoroheptyl; DD-F-hexyl = 1,1,2,2,3,3,4,4,5,5,6,6-dodecafluorohexyl; $CHF_2$ = difluoromethyl; Cpr = cyclopropyl; Cl = chlorine; F = fluorine. The logP values were determined in accordance with EEC Directive 79/831 Annex V.A8 by HPLC (High Performance Liquid Chromatography) using reversed-phase columns (C 18) by the following methods:
[a]The LC-MS determination in the acidic range is carried out at pH 2.7 using 0.1% aqueous formic acid and acetonitrile (contains 0.1% formic acid) as mobile phases; linear gradient from 10% acetonitrile to 95% acetonitrile. Also referred to as logP(HCOOH).
[b]The LC-MS determination in the neutral range is carried out at pH 7.8 using 0.001 molar aqueous ammonium bicarbonate solution and acetonitrile as mobile phases; linear gradient from 10% acetonitrile to 95% acetonitrile. Also referred to as logP(neutral).
[c]The determination in the acidic range is carried out at pH 2.3 using 0.1% aqueous phosphoric acid and acetonitrile as mobile phases; linear gradient from 10% acetonitrile to 95% acetonitrile.

Calibration is carried out using unbranched alkan-2-ones (having from 3 to 16 carbon atoms) with known log P values (the log P values are determined by the retention times using linear interpolation between two successive alkanones).

The lambda-max values were determined in the maxima of the chromatographic signals using the UV spectra from 200 nm to 400 nm.

NMR Data of Selected Examples

The NMR data for selected examples are listed either in conventional form (δ values, number of hydrogen atoms, multiplet splitting) or as NMR peak lists.

NMR peak list method:

When the 1H NMR data for selected examples are noted in the form of 1H NMR peak lists, first the δ value in ppm and then the signal intensity is listed for each signal peak, separated by a space. The δ value—signal intensity number pairs for different signal peaks are listed with separation from one another by semicolons.

The peak list for one example therefore takes the form of:
$\delta_1$ intensity$_1$; $\delta_2$ intensity$_2$; . . . ; $\delta_i$ intensity$_i$; . . . ; $\delta_n$ intensity$_n$ The solvent in which the NMR spectrum was recorded is listed in square brackets after the number of the example and before the NMR peak list or the conventional NMR interpretation list.

| Example number | 1H-NMR data |
|---|---|
| Ia-01 | 1H-NMR (D6-DMSO): 7.12 (d, 1H), 7.07 (d, 1H), 3.84-3.92 (m, 2H), 2.98 (broad, 6H), 2.33 (s, 3H) |
| Ia-02 | 1H-NMR (CDCl3): 7.03-7.09 (m, 1H), 6.91-6.93 (m, 1H), 5.29 (broad, 1H), 3.28-3.38 (m, 4H), 2.42 (s, 3H), 1.69 (broad, 2H), 1.01 (broad, 2H), 0.83-0.88 (m, 1H) |
| Ia-03 | 1H-NMR (D6-DMSO): 7.11-7.14 (m, 1H), 7.06-7.04 (m, 1H), 6.92-6.98 (broad, 2H), 6.30 (tt, 1H), 3.83-3.91 (q, 2H), 2.34 (s, 3H) |
| Ia-05 | [CDCl$_3$] 7.26 45.31; 7.09 0.35; 7.03 0.72; 6.93 0.95; 6.91 0.85; 5.09 0.50; 4.13 0.50; 3.30 1.93; 3.28 1.82; 2.42 16.00; 1.57 44.22; 1.43 0.36; 1.33 0.54; 1.29 4.62; 1.28 4.60; 1.26 1.33; 1.25 1.06; 1.25 1.27; 1.23 0.74; 1.08 0.47; 0.01 0.72; 0.00 24.21; −0.01 0.77 |
| Ia-07 | 1H-NMR (D6-DMSO): 7.10 (s, 1H), 6.98 (broad, 2H), 6.85 (s, 1H), 3.87 (q, 2H), 2.30 (s, 3H), 1.98 (s, 3H) |
| Ia-09 | [DMSO-D$_6$] 7.09 3.30; 7.07 3.26; 6.87 0.35; 6.85 0.33; 4.06 0.56; 4.04 1.74; 4.02 1.77; 4.00 0.62; 3.92 0.37; 3.86 1.00; 3.35 143.04; 3.34 312.18; 2.79 0.68; 2.78 0.62; 2.74 0.37; 2.73 0.35; 2.68 0.56; 2.67 0.68; 2.67 0.49; 2.54 0.38; 2.53 0.96; 2.51 54.21; 2.50 72.95; 2.34 0.46; 2.33 0.64; 2.33 0.79; 2.33 0.64; 2.32 0.46; 2.07 1.95; 2.04 0.35; 2.01 16.00; 1.99 8.08; 1.36 0.69; 1.24 0.46; 1.19 2.26; 1.17 4.49; 1.16 2.17; 0.88 0.50; 0.86 0.36; 0.00 9.11 |
| Ia-12 | [DMSO-D$_6$] 7.01 4.28; 4.03 0.82; 4.02 0.83; 3.79 0.35; 3.37 0.42; 3.34 331.71; 3.33 0.37; 3.32 2.34; 2.79 0.50; 2.62 0.35; 2.61 0.48; 2.61 0.35; 2.52 0.66; 2.52 0.84; 2.52 0.90; 2.51 23.83; 2.51 51.40; 2.50 70.93; 2.50 51.33; 2.50 23.51; 2.44 0.53; 2.39 0.35; 2.39 0.53; 2.38 0.38; 2.36 0.58; 2.33 0.49; 2.31 0.74; 2.28 16.00; 2.19 0.55; 1.99 3.80; 1.97 7.19; 1.19 0.93; 1.17 1.84; 1.16 0.90; 0.01 0.74; 0.00 23.54; −0.01 0.71 |
| Ia-13 | [CDCl$_3$] 7.26 51.97; 7.09 0.34; 7.04 0.43; 6.93 0.64; 6.92 0.56; 3.73 0.51; 3.72 0.51; 3.49 0.37; 3.30 1.06; 3.29 1.10; 3.29 0.94; 3.28 0.80; 3.01 1.54; 2.42 16.00; 2.36 0.92; 1.57 10.32; 1.26 0.76; 1.25 1.28; 1.23 0.63; 0.01 0.86; 0.00 28.20; −0.01 0.93 |
| Ia-14 | 1H-NMR (D6-DMSO): 7.67 (s, 1H), 7.15 (s, 1H), 4.16 (q, 2H) |
| Ia-15 | 1H-NMR (D6-DMSO): 8.30 (broad, 1H), 7.61 (s, 1H), 7.20 (s, 1H), 4.14 (q, 2H), 2.62 (broad, 3H) |
| Ia-17 | 1H-NMR (D6-DMSO): 7.15 (d, 1H), 7.10 (broad, 2H), 6.92 (d, 1H), 3.90 (q, 2H), 2.01 (s, 3H) |

| Example number | 1H-NMR data |
|---|---|
| Ia-18 | [CDCl$_3$] 7.26 18.05; 7.26 0.39; 7.25 0.35; 7.24 0.34; 7.04 0.64; 6.94 0.46; 6.93 1.00; 6.92 0.76; 6.91 0.76; 6.84 0.35; 6.82 0.33; 5.26 0.47; 3.45 1.08; 3.41 0.41; 3.39 0.32; 3.30 1.56; 3.28 1.39; 2.47 0.74; 2.42 16.00; 1.58 15.92; 1.29 1.95; 1.26 0.51; 1.25 0.43; 1.25 0.48; 1.09 0.37; 0.00 9.63; −0.01 0.33 |
| Ia-19 | 1H-NMR (CDCl3): 7.58 (d, 1H), 7.13 (s, 1H), 6.85 (d, 1H), 5.31 (broad, 1H), 3.45 (q, 2H), 2.93 (broad, 3H) |
| Ia-21 | 1H-NMR (D6-DMSO): 7.17 (d, 1H), 7.09 (d, 1H), 3.91 (q, 2H), 2.34 (s, 3H) |
| Ia-23 | 1H-NMR (D6-DMSO): 7.02 (s, 1H), 6.79 (s, 1H), 3.83 (q, 2H), 2.87 (broad, 6H), 2.28 (s, 3H), 1.96 (s, 3H) |
| Ia-24 | 1H-NMR (D6-DMSO): 7.09 (d, 1H), 6.86 (broad, 1H), 3.89 (q, 2H), 2.90 (broad, 3H), 2.00 (s, 3H) |
| Ia-25 | 1H-NMR (CDCl3): 7.72 (d, 1H), 7.24 (m, 1H), 6.96-6.99 (m, 1H), 4.98 (broad, 2H), 3.48 (q, 2H) |
| Ia-26 | [CDCl$_3$] 7.26 29.38; 6.94 1.54; 6.92 1.55; 3.73 0.38; 3.72 0.38; 3.49 0.34; 3.33 0.70; 3.32 0.83; 2.47 0.43; 2.42 16.00; 1.57 6.79; 1.26 0.58; 1.25 1.07; 1.23 0.54; 0.48 0.53; 0.43 0.39; 0.01 0.45; 0.00 15.80; −0.01 0.53 |

| Example number | 1H-NMR data |
|---|---|
| Ib-01 | 1H-NMR (D6-DMSO): 7.29 (d, 1H), 7.23 (d, 1H), 4.02-4.14 (m, 2H), 3.01 (broad, 6H), 2.31 (s, 3H) |
| Ib-02 | 1H-NMR (D6-DMSO): 8.30 (broad, 1H), 7.29 (d, 1H), 7.22 (d, 1H), 4.08-4.14 (m, 2H), 3.99 (broad, 2H), 2.31 (s, 3H), 1.11 (broad, 3H) |
| Ib-03 | 1H-NMR (D6-DMSO): 8.02 (broad, 1H), 7.28 (d, 1H), 7.21 (d, 1H), 4.08-4.14 (m, 2H), 3.96-4.00 (m, 1H), 2.31 (s, 3H), 1.12-1.17 (broad, 6H) |
| Ib-04 | 1H-NMR (D6-DMSO): 8.01 (broad, 1H), 7.00-7.20 (m, 2H), 3.70-4.10 (m, 2H), 2.80 (broad, 3H), 2.27 (s, 3H), 2.07 (s, 3H) |
| Ib-05 | [DMSO-D$_6$] 7.76 0.68; 7.75 0.68; 7.48 0.42; 7.46 0.41; 7.27 5.26; 7.26 5.26; 7.09 0.34; 7.02 0.49; 4.32 0.34; 4.30 0.38; 4.27 0.47; 4.26 0.80; 4.24 1.46; 4.22 2.04; 4.20 1.69; 4.18 0.75; 3.35 821.56; 3.34 2.15; 3.33 2.32; 3.17 0.58; 3.16 0.56; 2.81 0.80; 2.73 0.36; 2.62 0.57; 2.62 1.01; 2.62 1.31; 2.61 0.98; 2.61 0.52; 2.54 1.16; 2.52 3.60; 2.52 4.50; 2.52 5.20; 2.51 63.77; 2.51 130.55; 2.50 175.10; 2.50 122.46; 2.50 53.43; 2.48 0.53; 2.39 0.67; 2.39 1.11; 2.39 1.41; 2.38 1.11; 2.38 0.73; 2.37 6.18; 2.33 0.38; 2.31 0.37; 2.27 4.25; 2.11 16.00; 2.09 5.30; 2.08 1.22; 2.02 0.44; 1.91 0.99; 1.23 0.51; 1.14 1.46; 0.01 0.51; 0.00 12.92 |
| Ib-06 | 1H-NMR (D6-DMSO): 7.28 (d, 1H), 7.22 (d, 1H), 4.10-4.14 (m, 1H), 3.90-4.09 (m, 1H), 3.10-3.30 (broad, 2H), 2.31 (s, 3H), 1.51-1.56 (broad, 2H), 0.84-0.91 (broad, 3H) |
| Ib-07 | 1H-NMR (D6-DMSO): 7.30 (d, 1H), 7.22 (d, 1H), 3.99-4.15 (m, 2H), 2.66-2.73 (broad, 3H), 2.31 (s, 3H) |
| Ib-08 | [DMSO-D$_6$] 8.43 0.75; 7.39 0.32; 7.22 1.80; 7.20 1.79; 4.37 0.45; 4.13 0.35; 4.11 0.82; 4.09 0.84; 4.07 0.47; 4.05 0.32; 4.03 0.53; 4.02 0.49; 3.45 0.50; 3.44 0.51; 3.44 0.56; 3.43 0.58; 3.43 0.36; 3.42 0.38; 3.40 0.48; 3.40 0.57; 3.39 1.02; 3.38 1.14; 3.35 1478.79; 3.33 18.72; 2.62 0.34; 2.62 0.79; 2.62 1.07; 2.61 0.78; 2.61 0.36; 2.54 0.67; 2.52 1.59; 2.52 2.06; 2.52 2.16; 2.51 57.91; 2.51 127.88; 2.50 173.56; 2.50 123.42; 2.50 53.41; 2.39 0.33; 2.39 0.75; 2.39 1.04; 2.38 0.74; 2.38 0.33; 2.31 16.00; 2.08 2.40; 1.99 1.93; 1.23 0.45; 1.19 0.50; 1.17 1.09; 1.16 0.49; 1.07 0.79; 1.05 1.55; 1.04 0.73; 0.42 0.41; 0.41 0.44; 0.01 0.39; 0.00 13.49; −0.01 0.41 |
| Ib-09 | 1H-NMR (D6-DMSO): 7.12 (s, 1H), 7.03 (s, 1H), 4.03-4.07 (m, 2H), 2.91 (broad, 6H), 2.27 (s, 3H), 2.07 (s, 3H) |
| Ib-10 | 1H-NMR (CDCl3): 7.63-7.71 (m, 2H), 7.07 (d, 1H), 5.63 (broad, 1H), 3.25-3.58 (m, 2H), 2.94 (d, 3H) |
| Ib-11 | 1H-NMR (D6-DMSO): 7.37 (d, 1H), 7.28 (d, 1H), 4.03-4.10 (m, 2H), 2.34 (s, 3H) |
| Ib-12 | 1H-NMR (D6-DMSO): 7.19 (s, 1H), 7.17 (s, 1H), 3.96-4.04 (m, 2H), 2.30 (s, 3H), 2.07 (s, 3H) |
| Ib-13 | 1H-NMR (D6-DMSO): 7.31 (d, 1H), 7.10 (d, 1H), 4.23-4.29 (m, 1H), 4.13-4.18 (m, 1H), 2.10 (s, 3H) |
| Ib-14 | 1H-NMR (D6-DMSO): 7.87 (s, 1H), 7.54 (broad, 2H), 7.33 (s, 1H), 4.10-4.18 (m, 2H) |
| Ib-15 | 1H-NMR (D6-DMSO): 7.27 (d, 1H), 6.98 (d, 1H), 4.23 (m, 2H), 2.94 (broad, 6H), 2.09 (s, 3H) |

| Example number | Structure | Analytical data |
| --- | --- | --- |
| Ia-27 | 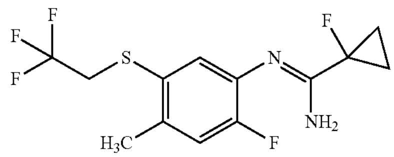 | 1H-NMR (D6-DMSO): 7.11-7.08 (m, 1H), 7.04-7.02 (m, 1H), 6.68 (broad, 2H), 3.89-3.81 (q, 2H), 2.33 (s, 3H), 1.37-1.30 (m, 4H) |
| Ia-28 | 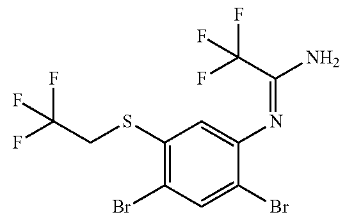 [SMILES: N/C(=N/c1cc(SCC(F)(F)F)c(Br)cc1Br)C(F)(F)F] | 1H-NMR (D6-DMSO): 7.87 (s, 1H), 7.60-7.27 (broad, 2H), 7.10 (s, 1H), 4.15 (q, 2H) |
| Ia-29 | 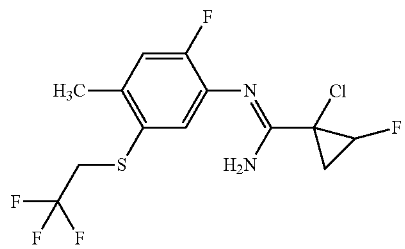 [SMILES: Cc1cc(F)c(/N=C(\N)C2(Cl)CC2F)cc1SCC(F)(F)F] | 1H-NMR (D6-DMSO): 7.10-7.07 (m, 1H), 7.00-6.98 (m, 1H), 6.60 (broad, 2H), 5.03 (m, 1H), 3.88-3.80 (q, 2H), 2.32 (s, 3H), 2.05-1.98 (m, 1H), 1.72-1.63 (m, 1H) |
| Ia-30 | 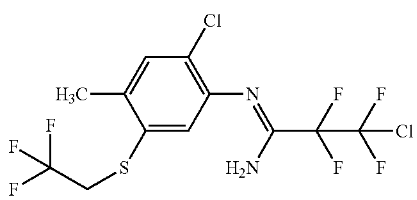 [SMILES: Cc1cc(Cl)c(/N=C(\N)C(F)(F)C(F)(F)Cl)cc1SCC(F)(F)F] | 1H-NMR (D6-DMSO): 7.37 (s, 1H), 7.26 (broad, 2H), 6.99 (s, 1H), 4.00-3.92 (q, 2H), 2.32 (s, 3H) |
| Ia-31 | 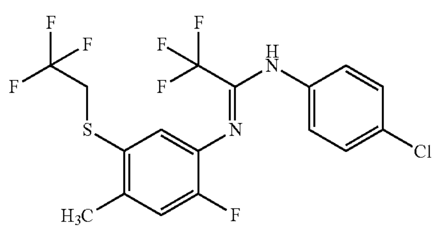 [SMILES: Cc1cc(F)c(/N=C(/Nc2ccc(Cl)cc2)C(F)(F)F)cc1SCC(F)(F)F] | logP(HCOOH) = 4.73. logP(neutral) = 4.67 |
| Ia-32 | 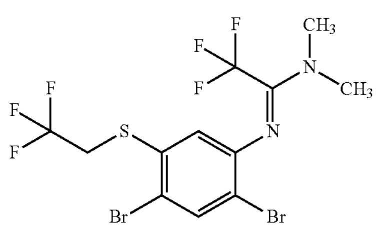 [SMILES: CN(C)/C(=N/c1cc(SCC(F)(F)F)c(Br)cc1Br)C(F)(F)F] | 1-H-NMR (D6-DMSO): 7.82 (s, 1H), 7.12 (s, 1H), 4.14 (q, 2H), 3.00 (s, 6H) |
| Ia-33 | 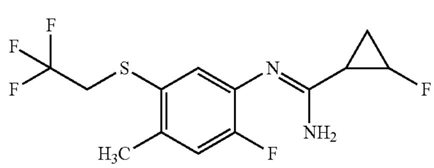 [SMILES: Cc1cc(F)c(/N=C(\N)C2CC2F)cc1SCC(F)(F)F] | 1H-NMR (D6-DMSO): 7.06-7.03 (m, 1H), 6.94-6.92 (m, 1H), 6.37 (broad, 2H), 4.93-4.76 (m, 1H), 3.86-3.78 (q, 2H), 2.31 (s, 3H), 2.09-2.05 (m, 1H), 1.42-1.24 (m, 2H) |

-continued

| Example number | Structure | Analytical data |
|---|---|---|
| Ia-34 | 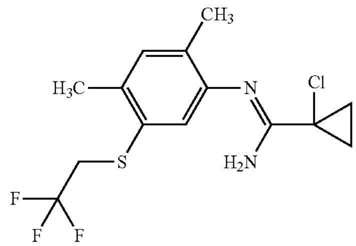 [SMILES: Cc1cc(C)c(SCC(F)(F)F)cc1/N=C(\N)C1(Cl)CC1] | 1H-NMR (D6-DMSO): 7.03 (s, 1H), 6.76 (s, 1H), 5.99 (broad, 2H), 3.86-3.78 (q, 2H), 2.29 (s, 3H), 1.91 (s, 3H), 1.59-1.55 (m, 2H), 1.29-1.26 (m, 2H) |
| Ia-35 | 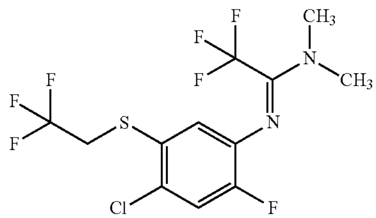 [SMILES: CN(C)/C(=N/c1cc(SCC(F)(F)F)c(Cl)cc1F)C(F)(F)F] | 1H-NMR (D6-DMSO): 7.48 (d, 1H), 7.20 (d, 1H), 4.05 (q, 2H), 3.01 (s, 6H) |
| Ia-36 | 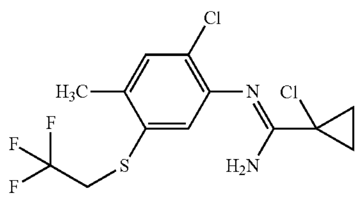 [SMILES: Cc1cc(Cl)c(/N=C(\N)C2(Cl)CC2)cc1SCC(F)(F)F] | 1H-NMR (D6-DMSO): 7.29 (m, 1H), 6.94 (m, 1H), 6.32 (broad, 2H), 3.97-3.89 (q, 2H), 2.29 (s, 3H), 1.60 (m, 2H), 1.28 (m, 2H) |
| Ia-37 | 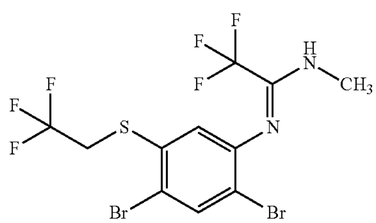 [SMILES: CN/C(=N/c1cc(SCC(F)(F)F)c(Br)cc1Br)C(F)(F)F] | 1H-NMR (D6-DMSO): 8.22 (broad, 1H), 7.82 (s, 1H), 7.16 (s, 1H), 4.13 (q, 2H), 2.65 (bs, 3H) |
| Ia-38 | 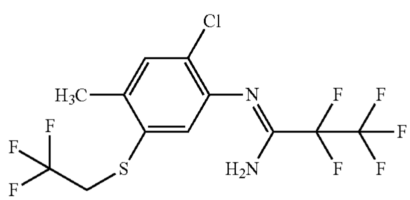 [SMILES: Cc1cc(Cl)c(/N=C(\N)C(F)(F)C(F)(F)F)cc1SCC(F)(F)F] | 1H-NMR (D6-DMSO): 7.37 (s, 1H), 7.32 (broad, 2H), 7.00 (s, 1H), 4.01-3.93 (q, 2H), 2.31 (s, 3H) |
| Ia-39 | 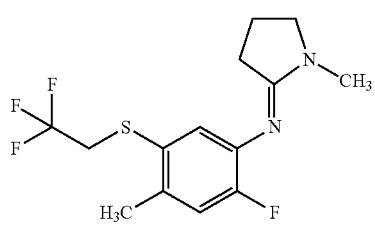 [SMILES: Cc1cc(F)c(/N=C2\CCCN2C)cc1SCC(F)(F)F] | 1H-NMR (D6-DMSO): 7.01 (m, 2H), 3.84 (q, 2H), 3.38-3.32 (m, 2H), 2.88 (s, 3H), 2.30 (s, 3H), 2.25 (t, 2H), 1.88 (q, 2H) |
| Ia-40 | 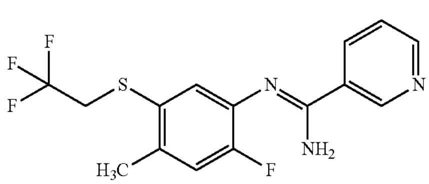 [SMILES: Cc1cc(F)c(/N=C(\N)c2cccnc2)cc1SCC(F)(F)F] | 1H-NMR (D6-DMSO): 9.12-9.11 (m, 1H), 8.68-8.67 (m, 1H), 8.32-8.28 (m, 1H), 7.50-7.47 (m, 1H), 7.17-7.12 (m, 2H), 6.79 (broad, 2H), 3.93-3.85 (q, 2H), 2.36 (s, 3H) |

| Example number | Structure | Analytical data |
|---|---|---|
| Ia-41 | 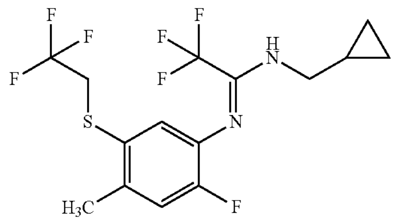 [SMILES: Cc1cc(F)c(/N=C(/NCC2CC2)C(F)(F)F)cc1SCC(F)(F)F] | logP(HCOOH) = 4.62 |
| Ia-42 | 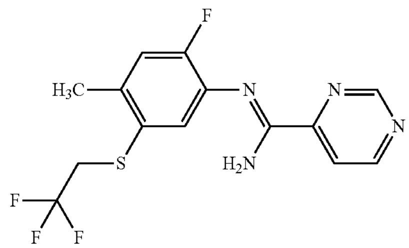 | 1H-NMR (D6-DMSO): 9.32 (m, 1H), 9.00-8.98 (m, 1H), 8.27-8.26 (m, 1H), 7.19-7.16 (m, 2H), 7.05-6.98 (broad, 2H), 3.93-3.85 (q, 2H), 2.37 (s, 3H) |
| Ia-43 | 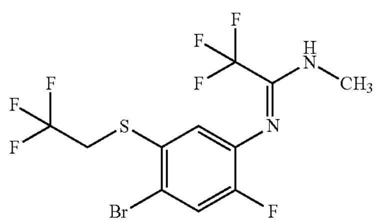 [SMILES: CN/C(=N/c1cc(SCC(F)(F)F)c(Br)cc1F)C(F)(F)F] | 1H-NMR (D6-DMSO): 8.32 (bs, 1H), 7.58 (d, 1H), 7.22-7.20 (m, 1H), 4.05 (q, 2H), 2.80-2.60 (broad, 3H) - peaks of the main isomer |
| Ia-44 | 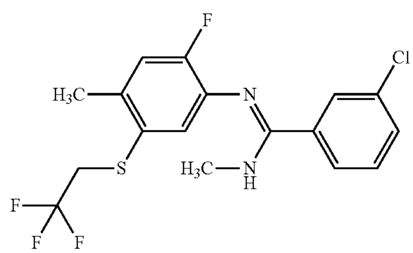 [SMILES: CN/C(=N\c1cc(SCC(F)(F)F)c(C)cc1F)c1cccc(Cl)c1] | 1H-NMR (D6-DMSO): 7.42-7.35 (m, 2H), 7.28-7.24 (m, 2H), 7.08-7.06 (m, 1H), 6.88-6.83 (m, 2H), 3.65-3.57 (q, 2H), 2.86-2.85 (d, 3H), 2.21 (s, 3H) |
| Ia-45 | 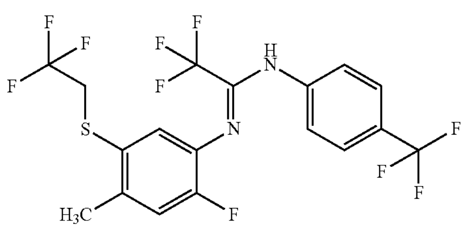 [SMILES: Cc1cc(F)c(/N=C(/Nc2ccc(C(F)(F)F)cc2)C(F)(F)F)cc1SCC(F)(F)F] | LogP (HCOOH) = 4.82. logP(neutral) = 4.71 |
| Ia-46 | 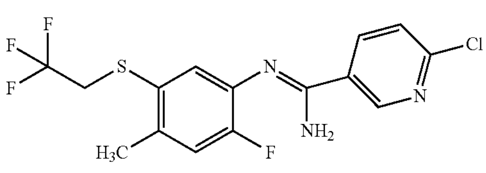 [SMILES: Cc1cc(F)c(/N=C(\N)c2ccc(Cl)nc2)cc1SCC(F)(F)F] | 1H-NMR (D6-DMSO): 8.94 (m, 1H), 8.37-8.34 (m, 1H), 7.63-7.61 (m, 1H), 7.17-7.12 (m, 2H), 6.86 (broad, 2H), 3.92-3.84 (q, 2H), 2.36 (s, 3H) |
| Ia-47 | 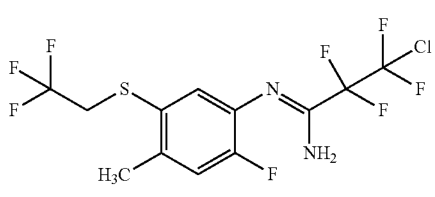 [SMILES: Cc1cc(F)c(/N=C(\N)C(F)(F)C(F)(F)Cl)cc1SCC(F)(F)F] | 1H-NMR (D6-DMSO): 7.35 (broad, 2H), 7.17-7.15 (m, 1H), 7.06-7.04 (m, 1H), 3.92-3.85 (q, 2H), 2.35 (s, 3H) |

-continued

| Example number | Structure | Analytical data |
|---|---|---|
| Ia-48 | 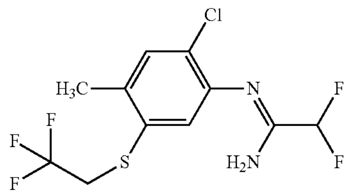 [SMILES: Cc1cc(Cl)c(/N=C(\N)C(F)F)cc1SCC(F)(F)F] | 1H-NMR (D6-DMSO): 7.34 (m, 1H), 6.99 (s, 1H), 6.84 (broad, 2H), 6.31 (t, 1H), 3.99-3.91 (q, 2H), 2.30 (s, 3H) |
| Ia-49 | 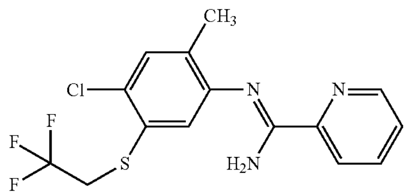 [SMILES: Cc1cc(Cl)c(SCC(F)(F)F)cc1/N=C(\N)c1ccccn1] | 1H-NMR (D6-DMSO): 8.63-8.64 (m, 1H), 8.34-8.32 (m, 1H), 7.98-7.94 (m, 1H), 7.59-7.55 (m, 1H), 7.36 (s, 1H), 7.02 (s, 1H), 6.60 (broad, 2H), 4.05-3.98 (q, 2H), 2.05 (s, 3H) |
| Ia-50 | 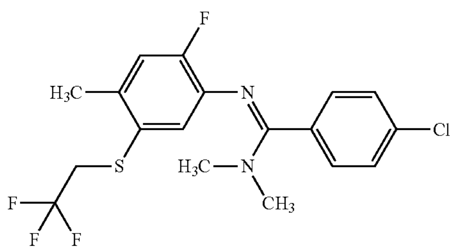 [SMILES: Cc1cc(F)c(/N=C(/c2ccc(Cl)cc2)N(C)C)cc1SCC(F)(F)F] | 1H-NMR (D6-DMSO): 7.51-6.74 (m, 6H), 3.64-3.56 (q, 2H), 2.98 (s, 3H), 2.89 (s, 3H), 2.18 (s, 3H) |
| Ia-51 | 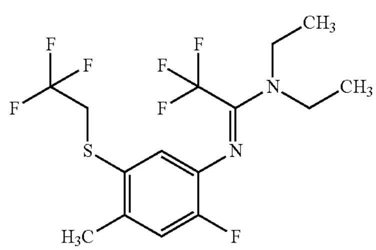 | 1H-NMR (D6-DMSO): 7.10 (d, 1H), 7.04 (d, 1H), 3.86 (q, 2H), 3.40-3.36 (m, 4H), 2.32 (s, 3H), 1.15-1.11 (m, 6H) |
| Ia-52 | 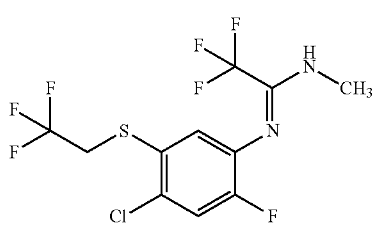 [SMILES: CN/C(=N/c1cc(SCC(F)(F)F)c(Cl)cc1F)C(F)(F)F] | 1H-NMR (D6-DMSO): 8.32 (bs, 1H), 7.49-7.44 (m, 1H), 7.32-7.21 (m, 1H), 4.04 (q, 2H), 2.70 (bs, 3H) |
| Ia-53 | 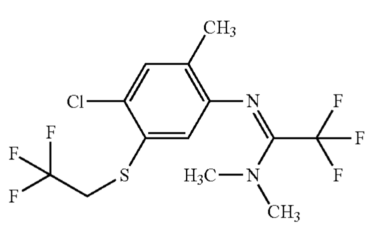 [SMILES: Cc1cc(Cl)c(SCC(F)(F)F)cc1/N=C(\N(C)C)C(F)(F)F] | 1H-NMR (D6-DMSO): 7.29 (s, 1H), 6.90 (s, 1H), 4.04-3.98 (q, 2H), 2.92 (broad, 6H), 1.98 (s, 3H) |
| Ia-54 | 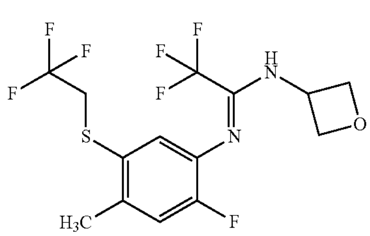 [SMILES: Cc1cc(F)c(/N=C(/NC2COC2)C(F)(F)F)cc1SCC(F)(F)F] | 1H-NMR (D6-DMSO): 8.86 (broad, 1H), 7.13-7.05 (broad, 2H), 4.77 (broad, 2H), 4.60 (broad, 2H), 4.40 (broad, 1H), 3.85 (broad, 2H), 2.33 (s, 3H) |

-continued

| Example number | Structure | Analytical data |
| --- | --- | --- |
| Ia-55 | 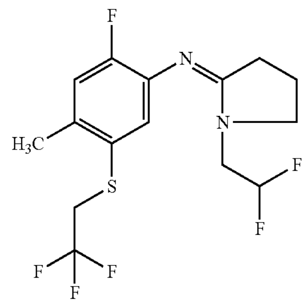 [SMILES: Cc1cc(F)c(/N=C2/CCCN2CC(F)F)cc1SCC(F)(F)F] | 1H-NMR (D6-DMSO): 7.08-7.04 (m, 2H), 6.23 (tt, 1H), 3.87-3.77 (m, 4H), 3.48-3.46 (t, 2H), 2.31 (s, 3H), 2.32-2.29 (t, 2H); 1.94-1.90 (m, 2H) |
| Ia-56 | 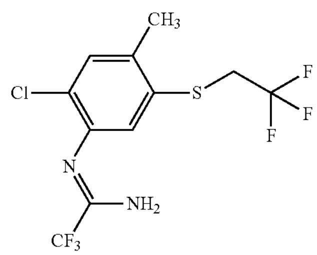 [SMILES: Cc1cc(Cl)c(/N=C(\N)C(F)(F)F)cc1SCC(F)(F)F] | 1H-NMR (D6-DMSO): 7.37 (s, 1H), 7.27 (broad, 2H), 7.03 (s, 1H), 4.03-3.95 (q, 2H), 2.31 (s, 3H) |
| Ia-57 | 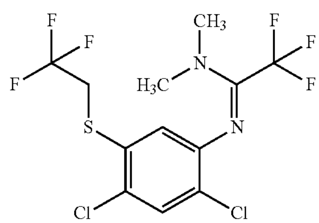 [SMILES: CN(C)/C(=N\c1cc(SCC(F)(F)F)c(Cl)cc1Cl)C(F)(F)F] | 1H-NMR (D6-DMSO): 7.62 (s, 1H), 7.17 (s, 1H), 4.17-4.12 (m, 2H), 3.00 (s, 6H) |
| Ia-58 | 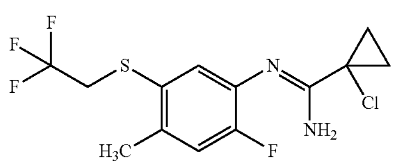 [SMILES: Cc1cc(F)c(/N=C(\N)C2(Cl)CC2)cc1SCC(F)(F)F] | 1H-NMR (D6-DMSO): 7.10-7.07 (m, 1H), 7.00-6.98 (m, 1H), 6.42 (broad, 2H), 3.88-3.80 (q, 2H), 2.32 (s, 3H), 1.57 (m, 2H), 1.29 (m, 2H) |
| Ia-59 | 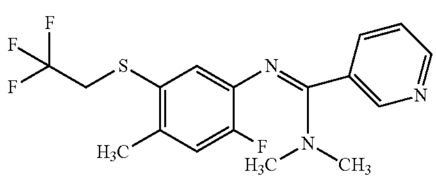 [SMILES: Cc1cc(F)c(/N=C(/c2cccnc2)N(C)C)cc1SCC(F)(F)F] | 1H-NMR (D6-DMSO): 8.46-8.44 (m, 1H), 8.32-8.31 (m, 1H), 7.60-7.58 (m, 1H), 7.33-7.30 (m, 1H), 6.83-6.80 (m, 2H), 3.69-3.61 (q, 2H), 3.01 (s, 3H), 2.93 (s, 3H), 2.17 (s, 3H) |
| Ia-60 | 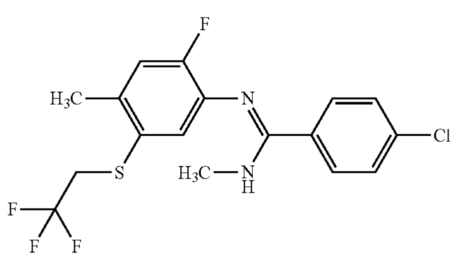 [SMILES: CN/C(=N\c1cc(SCC(F)(F)F)c(C)cc1F)c1ccc(Cl)cc1] | 1H-NMR (D6-DMSO): 7.37-7.32 (m, 3H), 7.19-7.17 (m, 2H), 6.88-6.85 (m, 1H), 6.80-6.78 (m, 1H), 3.64-3.56 (q, 2H), 2.86-2.85 (d, 3H), 2.21 (s, 3H) |
| Ia-61 | 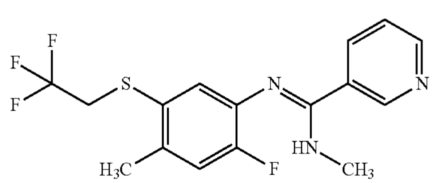 [SMILES: CN/C(=N\c1cc(SCC(F)(F)F)c(C)cc1F)c1cccnc1] | 1H-NMR (D6-DMSO): 8.47-8.46 (m, 1H), 8.36 (m, 1H), 7.57-7.55 (m, 1H), 7.51-7.48 (m, 1H), 7.30-7.27 (m, 1H), 6.89-6.83 (m, 2H), 3.70-3.62 (q, 2H), 2.89-2.88 (d, 3H), 2.20 (s, 3H) |

| Example number | Structure | Analytical data |
|---|---|---|
| Ia-62 | 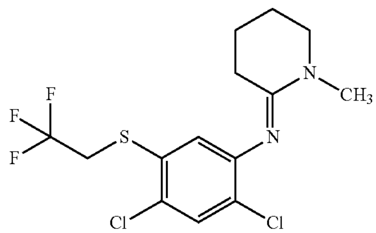 [SMILES: CN1CCCC/C1=N\c1cc(SCC(F)(F)F)c(Cl)cc1Cl] | 1H-NMR (D6-DMSO): 7.54 (s, 1H), 7.02 (broad, 1H), 4.11 (q, 2H), 3.28 (t, 2H), 2.96 (s, 3H), 2.08 (t, 2H), 1.77-1.71 (m, 2H), 1.62-1.56 (m, 2H) |
| Ia-63 | 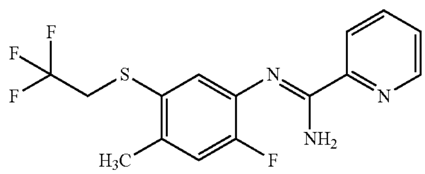 [SMILES: Cc1cc(F)c(/N=C(\N)c2ccccn2)cc1SCC(F)(F)F] | 1H-NMR (D6-DMSO): 8.65-8.64 (m, 1H), 8.31-8.29 (m, 1H), 7.98-7.94 (m, 1H), 7.59-7.56 (m, 1H), 7.17-7.14 (m, 2H), 6.80 (broad, 2H), 3.93-3.85 (q, 2H), 2.36 (s, 3H) |
| Ia-64 | 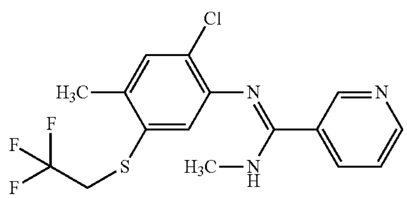 [SMILES: CN/C(=N\c1cc(SCC(F)(F)F)c(C)cc1Cl)c1cccnc1] | 1H-NMR (D6-DMSO): 8.46-8.45 (m, 1H), 8.37 (s, 1H), 7.57-7.55 (m, 1H), 7.49-7.48 (broad, 1H), 7.30-7.27 (m, 1H), 7.13 (s, 1H), 6.78 (s, 1H), 3.73-3.65 (q, 2H), 2.90-2.88 (d, 3H), 2.17 (s, 3H) |
| Ia-65 | 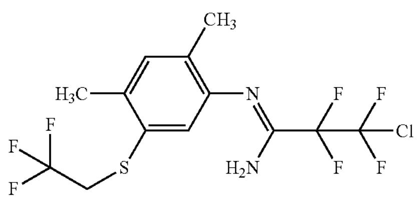 | 1H-NMR (D6-DMSO): 7.10 (s, 1H), 6.98 (broad, 2H), 6.83 (s, 1H), 3.89-3.81 (q, 2H), 2.31 (s, 3H), 1.98 (s, 3H) |
| Ia-66 | 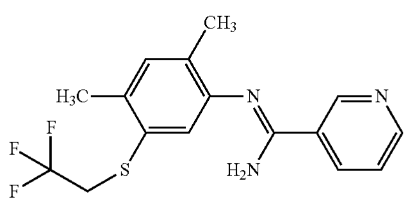 [SMILES: Cc1cc(C)c(SCC(F)(F)F)cc1/N=C(\N)c1cccnc1] | 1H-NMR (D6-DMSO): 9.14 (m, 1H), 8.67-8.66 (m, 1H), 8.33-8.30 (m, 1H), 7.50-7.46 (m, 1H), 7.10 (s, 1H), 6.91 (s, 1H), 6.41 (broad, 2H), 3.89-3.81 (q, 2H), 2.33 (s, 3H), 2.04 (s, 3H) |
| Ia-67 | 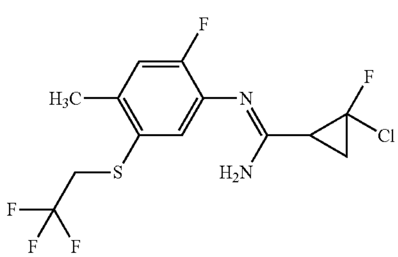 [SMILES: Cc1cc(F)c(/N=C(\N)C2CC2(F)Cl)cc1SCC(F)(F)F] | 1H-NMR (D6-DMSO): 7.09-7.06 (m, 1H), 6.94-6.92 (m, 1H), 6.53 (broad, 2H), 3.86-3.78 (m, 2H), 2.67 (m, 1H), 2.33 (s, 3H), 1.96-1.90 (m 1H), 1.76-1.70 (m, 1H) |
| Ia-68 | 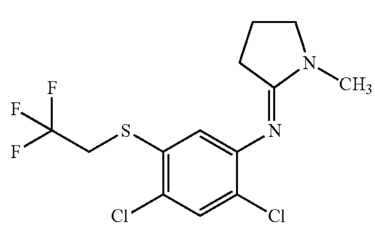 [SMILES: CN1CCC/C1=N\c1cc(SCC(F)(F)F)c(Cl)cc1Cl] | 1H-NMR (D6-DMSO): 7.53 (s, 1H), 7.10 (s, 1H), 4.11 (q, 2H), 3.39 (t, 2H), 2.90 (s, 3H), 2.26 (t, 2H), 1.90 (q, 2H) |

-continued

| Example number | Structure | Analytical data |
|---|---|---|
| Ia-69 | 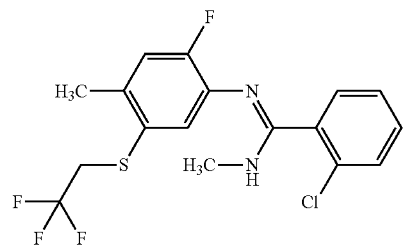 [SMILES: CN/C(=N\c1cc(SCC(F)(F)F)c(C)cc1F)c1ccccc1Cl] | 1H-NMR (D6-DMSO): 8.33 (broad, 1H), 7.50-7.24 (m, 4H), 6.88-6.85 (m, 1H), 6.76-6.73 (m, 1H), 3.49-3.45 (q, 2H), 2.89-2.88 (d, 3H), 2.18 (s, 3H) |
| Ia-70 | 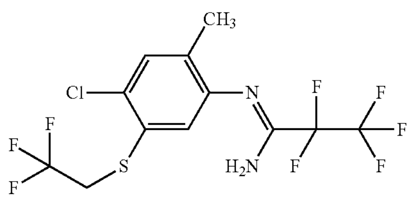 [SMILES: Cc1cc(Cl)c(SCC(F)(F)F)cc1/N=C(\N)C(F)(F)C(F)(F)F] | 1H-NMR (D6-DMSO): 7.36 (s, 1H), 7.22 (broad, 2H), 6.92 (s, 1H), 4.07-3.99 (q, 2H), 1.98 (s, 3H) |
| Ia-71 | 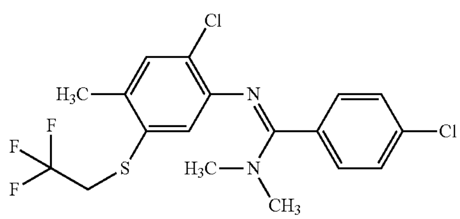 [SMILES: Cc1cc(Cl)c(/N=C(/c2ccc(Cl)cc2)N(C)C)cc1SCC(F)(F)F] | 1H-NMR (D6-DMSO): 7.35-7.32 (m, 2H), 7.19-7.16 (m, 2H), 7.09 (s, 1H), 6.70 (s, 1H), 3.68-3.60 (q, 2H), 2.90 (broad, 6H), 2.15 (s, 3H) |
| Ia-72 | 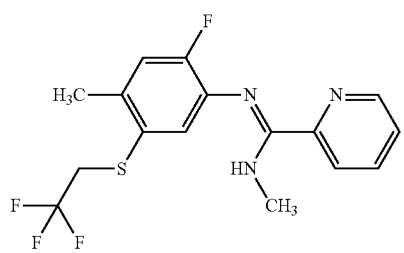 [SMILES: CN/C(=N\c1cc(SCC(F)(F)F)c(C)cc1F)c1ccccn1] | 1H-NMR (D6-DMSO): 8.55-8.54 (m, 1H), 8.04-7.96 (m, 2H), 7.72 (m, 1H), 7.60-7.57 (m, 1H), 7.37 (m, 1H), 6.93-6.90 (m, 1H), 3.63 (q, 2H), 2.83-2.81 (d, 3H), 2.24 (s, 3H) |
| Ia-73 | 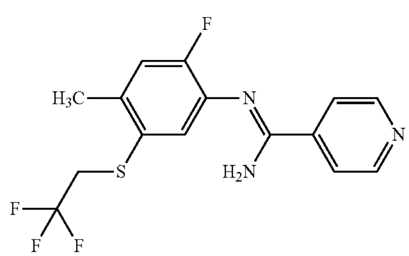 [SMILES: Cc1cc(F)c(/N=C(\N)c2ccncc2)cc1SCC(F)(F)F] | 1H-NMR (D6-DMSO): 8.69-8.68 (m, 2H), 7.90-7.89 (m, 2H), 7.17-7.11 (m, 2H), 6.85 (broad, 2H), 3.93-3.85 (q, 2H), 2.36 (s, 3H) |
| Ia-74 | 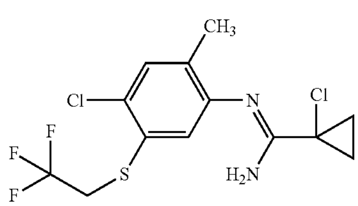 [SMILES: Cc1cc(Cl)c(SCC(F)(F)F)cc1/N=C(\N)C1(Cl)CC1] | 1H-NMR (D6-DMSO): 7.27 (s, 1H), 6.84 (s, 1H), 6.21 (broad, 2H), 4.04-3.94 (q, 2H), 1.93 (s, 3H), 1.30-1.15 (m, 4H) |

-continued
| Example number | Structure | Analytical data |
|---|---|---|
| Ia-75 | 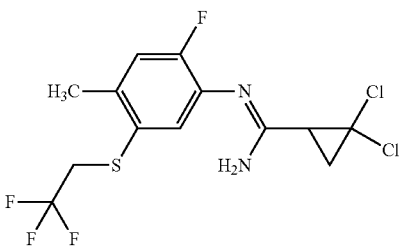 [SMILES: Cc1cc(F)c(/N=C(\N)C2CC2(Cl)Cl)cc1SCC(F)(F)F] | 1H-NMR (D6-DMSO): 7.09-7.06 (m, 1H), 6.94-6.92 (m, 1H), 6.65 (broad, 2H), 3.85-3.77 (q, 2H), 2.68-2.62 (m, 1H), 2.33 (s, 3H), 2.17-2.14 (m, 1H), 1.91-1.87 (m, 1H) |
| Ia-76 | 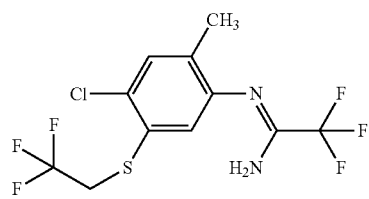 [SMILES: Cc1cc(Cl)c(SCC(F)(F)F)cc1/N=C(\N)C(F)(F)F] | 1H-NMR (D6-DMSO): 7.36 (m, 1H), 7.15 (broad, 2H), 6.95 (s, 1H), 4.08-4.00 (q, 2H), 1.99 (s, 3H) |
| Ia-77 | 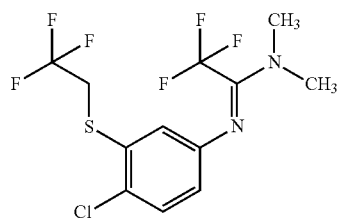 [SMILES: CN(C)/C(=N/c1ccc(Cl)c(SCC(F)(F)F)c1)C(F)(F)F] | 1H-NMR (D6-DMSO): 7.33 (d, 1H), 6.99 (d, 1H), 6.64-6.61 (m, 1H), 4.15-4.07 (m, 2H), 2.92 (s, 6H) |
| Ia-78 | 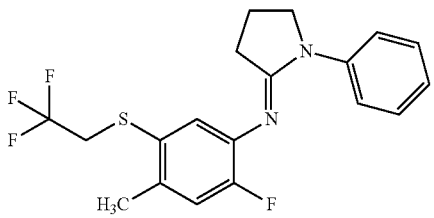 [SMILES: Cc1cc(F)c(/N=C2\CCCN2c2ccccc2)cc1SCC(F)(F)F] | 1H-NMR (D6-DMSO): 7.85 (d, 2H), 7.36 (dd, 2H), 7.12-7.09 (m, 3H), 3.92-3.84 (m, 4H), 2H under the DMSO peak, 2.33 (s, 3H), 2.05-1.97 (m, 2H) |
| Ia-79 | 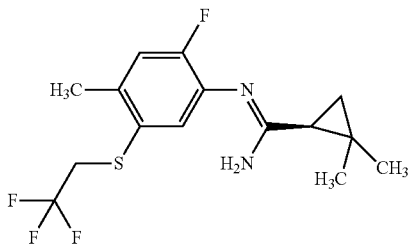 [SMILES: Cc1cc(F)c(/N=C(\N)[C@H]2CC2(C)C)cc1SCC(F)(F)F] | 1H-NMR (D6-DMSO): 7.05-7.01 (m, 2H), 6.10 (broad, 2H), 3.88-3.80 (q, 2H), 2.32 (s, 3H), 2.31 (s, 3H), 2.30 (s, 3H), 1.74 (m, 1H), 1.17 (m, 2H) |
| Ia-80 | 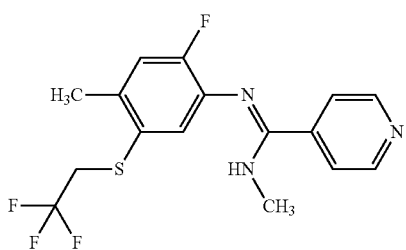 [SMILES: CN/C(=N\c1cc(SCC(F)(F)F)c(C)cc1F)c1ccncc1] | 1H-NMR (D6-DMSO): 8.49-8.48 (m, 2H), 7.51-7.49 (m, 1H), 7.15-7.14 (m, 2H), 6.87-6.85 (m, 2H), 3.69-3.61 (q, 2H), 2.88-2.87 (d, 3H), 2.20 (s, 3H) |

| Example number | Structure | Analytical data |
|---|---|---|
| Ia-81 | 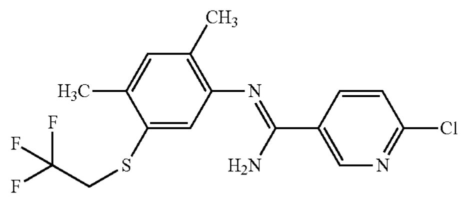 [SMILES: Cc1cc(C)c(SCC(F)(F)F)cc1/N=C(\N)c1ccc(Cl)nc1] | 1H-NMR (D6-DMSO): 8.95-8.96 (m, 1H), 8.36-8.39 (m, 1H), 7.61-7.63 (m, 1H), 7.10 (s, 1H), 6.91 (s, 1H), 6.49 (broad, 2H), 3.81-3.89 (q, 2H), 2.32 (s, 3H), 2.03 (s, 3H) |
| Ia-82 | 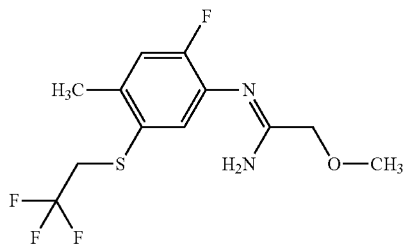 [SMILES: COC/C(N)=N/c1cc(SCC(F)(F)F)c(C)cc1F] | 1H-NMR (D6-DMSO): 7.09-7.06 (m, 1H), 7.01-6.99 (m, 1H), 6.19 (broad, 2H), 3.95 (s, 2H), 3.88-3.80 (q, 2H), 3.33 (s, 3H), 2.32 (s, 3H) |
| Ia-83 | 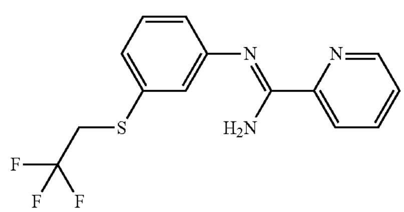 [SMILES: N/C(=N\c1cccc(SCC(F)(F)F)c1)c1ccccn1] | 1H-NMR (D6-DMSO): 8.64-8.63 (m, 1H), 8.30-8.28 (m, 1H), 7.98-7.93 (m, 1H), 7.58-7.55 (m, 1H), 7.33-7.29 (m, 1H), 7.13-7.11 (m, 1H), 7.02 (s, 1H), 6.84-6.82 (m, 1H), 6.64 (broad, 2H), 4.04-3.96 (q, 2H) |
| Ia-84 | 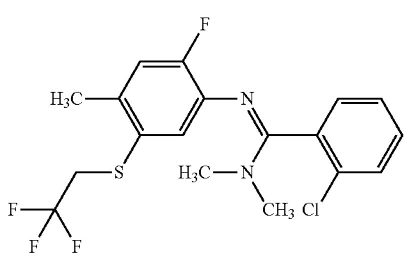 [SMILES: Cc1cc(F)c(/N=C(/c2ccccc2Cl)N(C)C)cc1SCC(F)(F)F] | 1H-NMR (D6-DMSO): 7.40-7.17 (m, 4H), 6.87-6.84 (m, 1H), 6.77-6.75 (m, 1H), 3.59-3.46 (m, 2H), 3.14 (broad, 3H), 2.71 (broad, 3H), 2.17 (s, 3H) |
| Ia-85 | 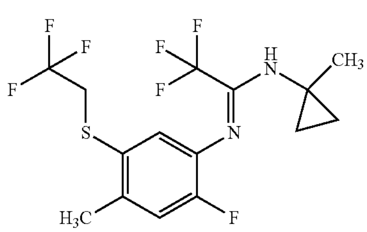 [SMILES: Cc1cc(F)c(/N=C(/NC2(C)CC2)C(F)(F)F)cc1SCC(F)(F)F] | 1H-NMR (D6-DMSO): 8.33 (broad, 1H), 7.11-7.06 (m, 2H), 3.83 (q, 2H), 2.33 (s, 3H), 1.34 (broad, 3H), 0.76 (broad, 2H), 0.57 (broad, 2H) |
| Ia-86 | 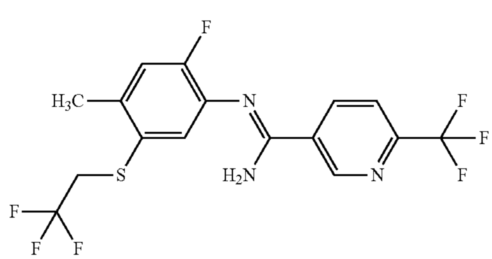 [SMILES: Cc1cc(F)c(/N=C(\N)c2ccc(C(F)(F)F)nc2)cc1SCC(F)(F)F] | 1H-NMR (D6-DMSO): 9.27-9.25 (m, 1H), 8.58-8.56 (m, 1H), 8.03-8.01 (m, 1H), 7.18-7.14 (m, 2H), 7.01 (broad, 2H), 3.93-3.85 (q, 2H), 2.37 (s, 3H) |

-continued

| Example number | Structure | Analytical data |
|---|---|---|
| Ia-87 | 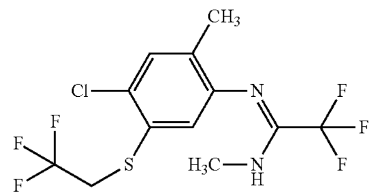 [SMILES: CN/C(=N\c1cc(SCC(F)(F)F)c(Cl)cc1C)C(F)(F)F] | 1H-NMR (D6-DMSO): 8.00 (broad, 1H), 7.28 (s, 1H), 6.95 (broad, 1H), 4.09-4.01 (q, 2H), 2.68-2.67 (broad, 3H), 2.00 (s, 3H) |
| Ia-88 | 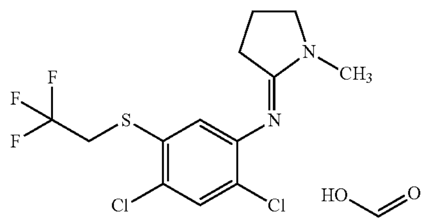 [SMILES: CN1CCC/C1=N\c1cc(SCC(F)(F)F)c(Cl)cc1Cl ; O=CO] | 1H-NMR (D6-DMSO): 7.53 (s, 1H), 7.102 (s, 1H), 4.12 (q, 2H), 3.39 (dd, 2H), 2.90 (s, 3H), 2.26 (dd, 2H), 1.90 (m, 2H) |
| Ia-89 | 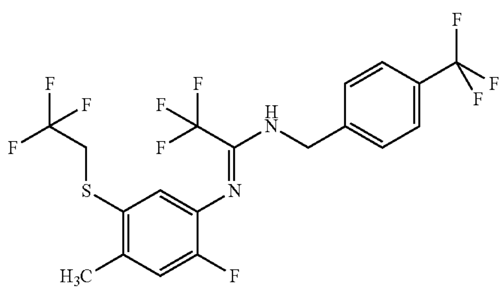 [SMILES: Cc1cc(F)c(/N=C(/NCc2ccc(C(F)(F)F)cc2)C(F)(F)F)cc1SCC(F)(F)F] | logP(HCOOH) = 5.15. logP(neutral) = 5.15 |
| Ia-90 | 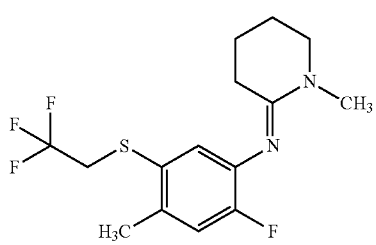 [SMILES: Cc1cc(F)c(/N=C2\CCCCN2C)cc1SCC(F)(F)F] | 1H-NMR (D6-DMSO): 7.03 (d, 1H), 6.93 (d, 1H), 3.84 (q, 2H), 3.25 (t, 2H), 2.94 (s, 3H), 2.30 (s, 3H), 2.10 (t, 2H), 1.76-1.70 (m, 2H), 1.60-1.54 (m, 2H) |
| Ia-91 | 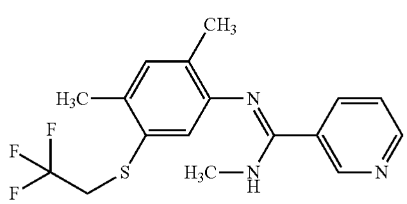 [SMILES: CN/C(=N\c1cc(SCC(F)(F)F)c(C)cc1C)c1cccnc1] | 1H-NMR (D6-DMSO): 8.44-8.43 (m, 1H), 8.32 (m, 1H), 7.51-7.48 (m, 1H), 7.28-7.21 (m, 2H), 6.89 (s, 1H), 6.41 (broad, 1H), 3.47-3.39 (q, 2H), 2.88 (broad, 3H), 2.17 (s, 3H), 2.07 (s, 3H) |
| Ia-92 | 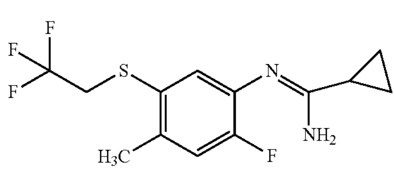 [SMILES: Cc1cc(F)c(/N=C(\N)C2CC2)cc1SCC(F)(F)F] | 1H-NMR (D6-DMSO): 7.04-7.01 (m, 1H), 6.93-6.91 (m, 1H), 6.12 (broad, 2H), 3.86-3.78 (q, 2H), 2.31 (s, 3H), 1.52 (m, 1H), 0.88-0.84 (m, 2H), 0.72-0.71 (m, 2H) |
| Ia-93 | 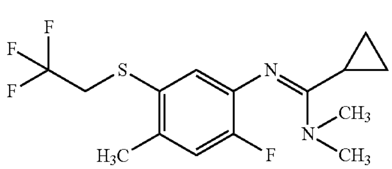 | 1H-NMR (D6-DMSO): 7.10-7.07 (m, 2H), 3.87-3.79 (q, 2H), 3.11 (broad, 6H), 2.34 (s, 3H), 1.69-1.68 (m, 1H), 0.68-0.66 (m, 2H), 0.33 (m, 2H) |

-continued

| Example number | Structure | Analytical data |
|---|---|---|
| Ia-94 | 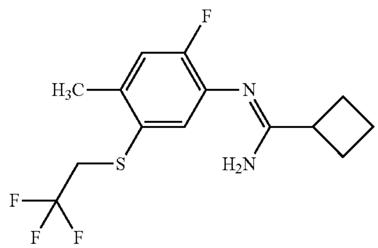 [SMILES: Cc1cc(F)c(/N=C(\N)C2CCC2)cc1SCC(F)(F)F] | 1H-NMR (D6-DMSO): 7.10-7.07 (m, 1H), 6.98-6.96 (m, 1H), 6.15 (broad, 2H), 3.88-3.81 (q, 2H), 3.12-3.08 (m, 1H), 2.33 (s, 3H), 2.37-1.71 (m, 6H) |
| Ia-95 | 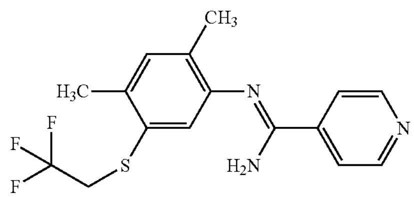 [SMILES: Cc1cc(C)c(SCC(F)(F)F)cc1/N=C(\N)c1ccncc1] | 1H-NMR (D6-DMSO): 8.69-8.67 (m, 2H), 7.92-7.91 (m, 2H), 7.11 (s, 1H), 6.90 (s, 1H), 6.47 (broad, 2H), 3.89-3.81 (q, 2H), 2.32 (s, 3H), 2.02 (s, 3H) |
| Ia-96 | 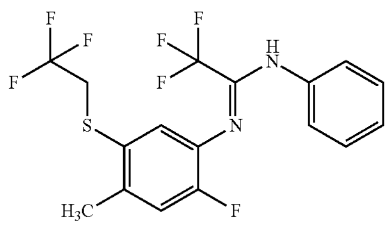 [SMILES: Cc1cc(F)c(/N=C(/Nc2ccccc2)C(F)(F)F)cc1SCC(F)(F)F] | logP(HCOOH) = 4.37, logP(neutral) = 4.37 |
| Ia-97 | 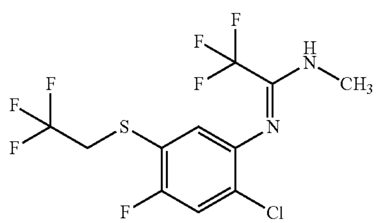 [SMILES: CN/C(=N/c1cc(SCC(F)(F)F)c(F)cc1Cl)C(F)(F)F] | 1H-NMR (D6-DMSO): 8.20 (bs, 1H), 7.48 (d, 1H), 7.32-7.17 (m, 1H), 3.98 (q, 2H), 2.90-2.50 (broad, 3H) |
| Ia-98 | 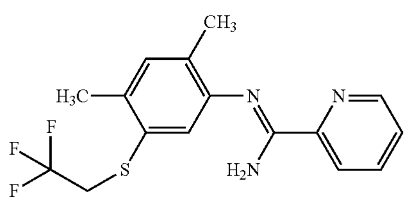 [SMILES: Cc1cc(C)c(SCC(F)(F)F)cc1/N=C(\N)c1ccccn1] | 1H-NMR (D6-DMSO): 8.64-8.63 (m, 1H), 8.35-8.33 (m, 1H), 7.98-7.93 (m, 1H), 7.58-7.54 (m, 1H), 7.11 (s, 1H), 6.94 (s, 1H), 6.41 (broad, 2H), 3.89-3.82 (q, 2H), 2.33 (s, 3H), 2.03 (s, 3H) |
| Ia-99 | 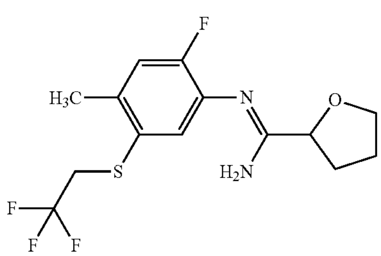 [SMILES: Cc1cc(F)c(/N=C(\N)C2CCCO2)cc1SCC(F)(F)F] | 1H-NMR (D6-DMSO): 7.09-7.02 (m, 2H), 6.22 (broad, 2H), 4.40-4.36 (t, 1H), 3.97-3.92 (m, 1H), 3.88-3.80 (q, 2H), 3.76-3.72 (m, 1H), 2.33 (s, 3H), 2.23-2.16 (m, 1H), 2.06-1.98 (m, 1H), 1.89-1.77 (m, 2H) |
| Ia-100 | 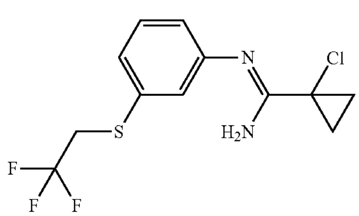 [SMILES: N/C(=N\c1cccc(SCC(F)(F)F)c1)C1(Cl)CC1] | 1H-NMR (D6-DMSO): 7.25-7.21 (m, 1H), 7.07-7.05 (m, 1H), 6.83 (m, 1H), 6.65-6.63 (m, 1H), 6.18 (broad, 2H), 4.00-3.92 (q, 2H), 1.55 (m, 2H), 1.26 (m, 2H) |

-continued

| Example number | Structure | Analytical data |
|---|---|---|
| Ia-101 | 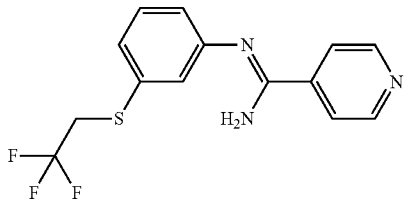 [SMILES: N/C(=N\c1cccc(SCC(F)(F)F)c1)c1ccncc1] | 1H-NMR (D6-DMSO): 8.69-8.67 (m, 2H), 7.91-7.89 (m, 2H), 7.32-7.29 (m, 1H), 7.12-7.10 (m, 1H), 6.98 (s, 1H), 6.79-6.77 (m, 1H), 6.65 (broad, 2H), 4.04-3.96 (q, 2H) |
| Ia-102 | 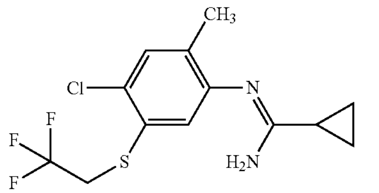 [SMILES: Cc1cc(Cl)c(SCC(F)(F)F)cc1/N=C(\N)C1CC1] | 1H-NMR (D6-DMSO): 7.24 (s, 1H), 6.79 (s, 1H), 5.95 (broad, 2H), 4.00-3.92 (q, 2H), 1.93 (s, 3H), 1.51 (broad, 1H), 0.89-0.86 (m, 2H), 0.73-0.70 (m, 2H) |
| Ia-103 | 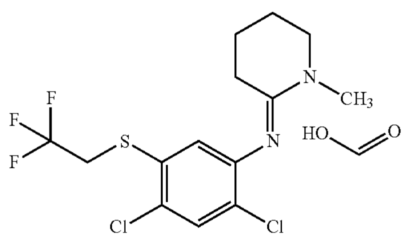 | 1H-NMR (D6-DMSO): 7.54 (bs, 1H), 7.02 (bs, 1H), 4.11 (q, 2H), 3.33 (dd, 2H), 2.96 (s, 3H), 2.08 (dd, 2H), 1.74 (m, 2H), 1.58 (m, 2H) |
| Ia-104 | 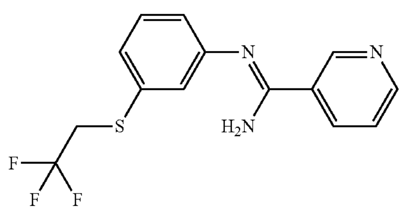 [SMILES: N/C(=N\c1cccc(SCC(F)(F)F)c1)c1cccnc1] | 1H-NMR (D6-DMSO): 9.12 (s, 1H), 8.67-8.66 (m, 1H), 8.31-8.29 (m, 1H), 7.50-7.46 (m, 1H), 7.32-7.28 (m, 1H), 7.12-7.10 (m, 1H), 6.99 (s, 1H), 6.80-6.78 (m, 1H), 6.66-6.59 (broad, 2H), 4.04-3.96 (q, 2H) |
| Ia-105 | 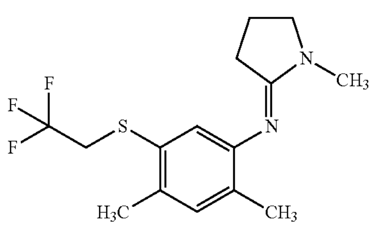 | 1H-NMR (D6-DMSO): 7.33 (bs, 1H), 7.20 (bs, 1H), 3.92 (q, 2H), 3.66 (bs, 2H), 3.34 (m, 2H), 3.13 (bs, 3H), 2.33 (bs, 3H), 2.16 (bs, 3H), 2.02-1.95 (m, 2H) |
| Ia-106 | 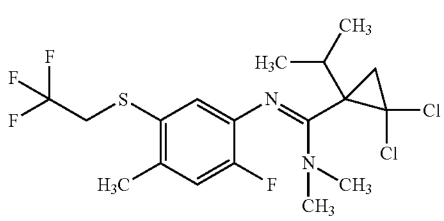 [SMILES: Cc1cc(F)c(/N=C(\N(C)C)C2(C(C)C)CC2(Cl)Cl)cc1SCC(F)(F)F] | 1H-NMR (D6-DMSO): 7.05 (m, 1H), 6.88 (m, 1H), 3.75 (q, 2H), 2.98 (s, 3H), 2.87 (s, 3H), 2.33 (s, 3H), 1.83 (m, 2H), 0.95-0.93 (m, 7H) |
| Ia-107 | 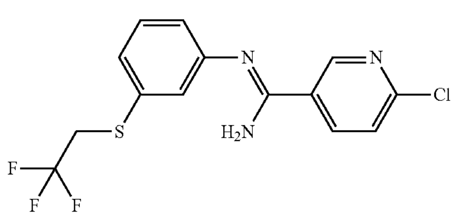 [SMILES: N/C(=N\c1cccc(SCC(F)(F)F)c1)c1ccc(Cl)nc1] | 1H-NMR (D6-DMSO): 8.94-8.93 (m, 1H), 8.41-8.34 (m, 2H), 7.82-7.80 (m, 1H), 7.63-7.61 (m, 1H), 7.32-7.28 (m, 1H), 6.99 (s, 1H), 6.68-6.65 (broad, 2H), 4.00 (q, 2H) |

-continued

| Example number | Structure | Analytical data |
|---|---|---|
| Ia-108 | 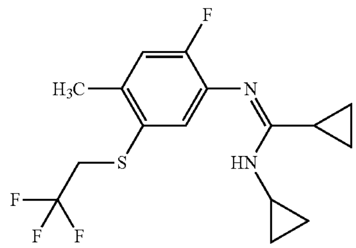 [SMILES: Cc1cc(F)c(/N=C(\NC2CC2)C2CC2)cc1SCC(F)(F)F] | 1H-NMR (D6-DMSO): 7.15-7.09 (m, 2H), 3.89-3.81 (q, 2H), 2.61 (m, 1H), 2.33 (s, 3H), 1.45 (m, 1H), 0.84-0.80 (m, 3H), 0.69-0.61 (m, 4H), 0.50 (m, 2H) |
| Ia-109 | 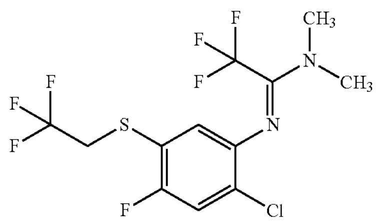 [SMILES: CN(C)/C(=N/c1cc(SCC(F)(F)F)c(F)cc1Cl)C(F)(F)F] | 1H-NMR (D6-DMSO): 7.48 (d, 1H), 7.15 (d, 1H), 4.00 (q, 2H), 2.98 (s, 6H) |
| Ia-110 | 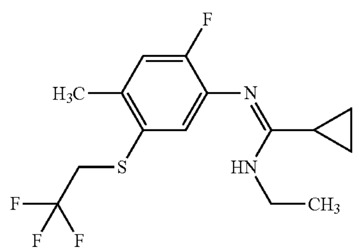 [SMILES: CCN/C(=N\c1cc(SCC(F)(F)F)c(C)cc1F)C1CC1] | 1H-NMR (D6-DMSO): 7.18 (d, 1H), 7.04-6.97 (m, 2H), 3.83 (q, 2H), 3.15 (m, 2H), 2.31 (s, 3H), 1.35 (m, 1H), 0.99 (t, 3H), 0.79-0.77 (m, 2H), 0.60-0.57 (m, 2H) |
| Ia-111 | 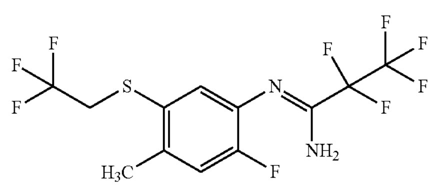 [SMILES: Cc1cc(F)c(/N=C(\N)C(F)(F)C(F)(F)F)cc1SCC(F)(F)F] | 1H-NMR (D6-DMSO): 7.40 (broad, 2H), 7.18-7.15 (m, 1H), 7.07-7.05 (m, 1H), 3.93-3.85 (q, 2H), 2.35 (s, 3H) |
| Ia-112 | 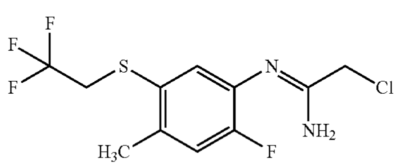 [SMILES: Cc1cc(F)c(/N=C(\N)CCl)cc1SCC(F)(F)F] | 1H-NMR (D6-DMSO): 7.14-7.12 (m, 1H), 7.06-7.04 (m, 1H), 6.75 (broad, 2H), 4.18 (s, 2H), 3.90-3.82 (q, 2H), 2.34 (s, 3H) |
| Ia-113 | 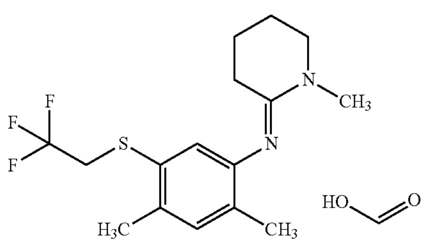 [SMILES: Cc1cc(C)c(SCC(F)(F)F)cc1/N=C1\CCCCN1C ; O=CO] | 1H-NMR (D6-DMSO): 8.15 (s, 1H), 7.33 (bs, 1H), 7.21 (d, 1H), 3.94 (q, 2H), 3.49 (broad, 2H), 3.19 (broad, 3H), 2.34 (s, 3H), 2.24-2.06 (m, 5H), 1.78 (broad, 2H), 1.61 (broad, 2H) |
| Ia-114 | 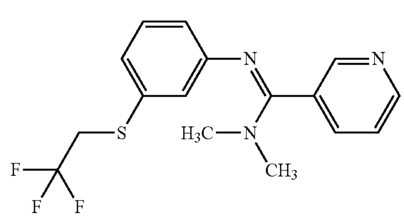 [SMILES: CN(C)/C(=N\c1cccc(SCC(F)(F)F)c1)c1cccnc1] | 1H-NMR (D6-DMSO): 8.44-8.42 (m, 1H), 8.31-8.30 (m, 1H), 7.60-7.58 (m, 1H), 7.32-7.29 (m, 1H), 6.96-6.92 (m, 1H), 6.79-6.77 (m, 1H), 6.60-6.59 (m, 1H), 6.41-6.38 (m, 1H), 3.79-3.71 (q, 2H), 3.00 (broad, 3H); 2.92 (broad, 3H) |

-continued

| Example number | Structure | Analytical data |
|---|---|---|
| Ia-115 | 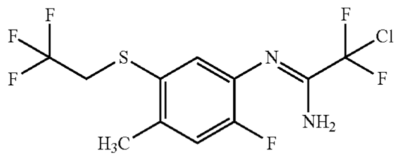 [SMILES: Cc1cc(F)c(/N=C(\N)C(F)(F)Cl)cc1SCC(F)(F)F] | 1H-NMR (D6-DMSO): 7.36-7.28 (broad, 2H), 7.17-7.15 (m, 1H), 7.09-7.06 (s, 1H), 3.94-3.86 (q, 2H), 2.34 (s, 3H) |
| Ia-116 | 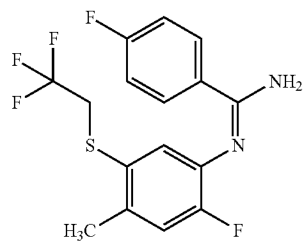 [SMILES: Cc1cc(F)c(/N=C(/N)c2ccc(F)cc2)cc1SCC(F)(F)F] | 1H-NMR (D6-DMSO): 8.04-8.01 (m, 2H), 7.29-7.25 (m, 2H), 7.14-7.09 (m, 2H), 6.61 (broad, 2H), 3.87 (q, 2H), 2.36 (s, 3H) |
| Ia-117 | 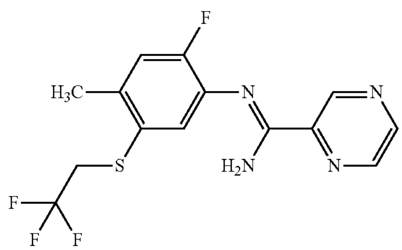 [SMILES: Cc1cc(F)c(/N=C(\N)c2cnccn2)cc1SCC(F)(F)F] | 1H-NMR (D6-DMSO): 9.45-9.44 (m, 1H), 8.83-8.82 (m, 1H), 8.72-8.71 (m, 1H), 7.20-7.16 (m, 2H), 6.98-6.92 (broad, 2H), 3.93-3.85 (q, 2H), 2.37 (s, 3H) |
| Ia-118 | 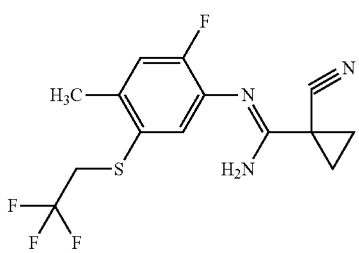 [SMILES: Cc1cc(F)c(/N=C(\N)C2(C#N)CC2)cc1SCC(F)(F)F] | 1H-NMR (D6-DMSO): 7.11-7.08 (m, 1H), 7.01-6.99 (m, 1H), 6.26 (broad, 2H), 3.90-3.82 (q, 2H), 2.32 (s, 3H), 1.66-1.56 (m, 4H) |
| Ia-119 | 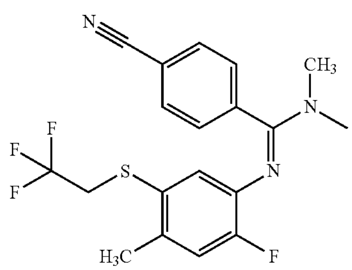 [SMILES: Cc1cc(F)c(/N=C(\c2ccc(C#N)cc2)N(C)C)cc1SCC(F)(F)F] | 1H-NMR (D6-DMSO): 7.77-7.75 (m, 2H), 7.36-7.34 (m, 2H), 6.83 (d, 1H), 6.74 (d, 1H), 3.57 (q, 2H), 3.10 (broad, 3H), 2.73 (broad, 3H), 2.17 (s, 3H) |
| Ia-120 | 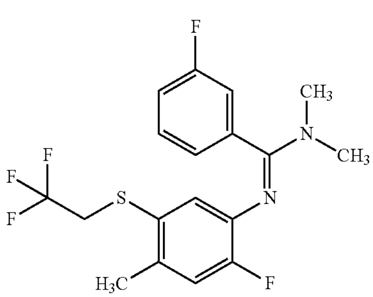 [SMILES: Cc1cc(F)c(/N=C(\c2cccc(F)c2)N(C)C)cc1SCC(F)(F)F] | 1H-NMR (D6-DMSO): 7.35-7.29 (m, 1H), 7.12-7.07 (m, 1H), 7.02-7.01 (m, 1H), 7.00-6.93 (m, 1H), 6.84-6.78 (m, 2H), 3.60 (q, 2H), 3.07 (broad, 3H), 2.73 (broad, 3H), 2.17 (s, 3H) |

-continued
| Example number | Structure | Analytical data |
|---|---|---|
| Ia-121 | 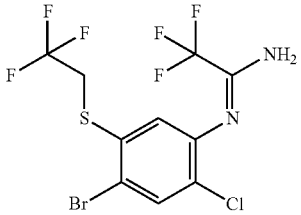 [SMILES: N/C(=N/c1cc(SCC(F)(F)F)c(Br)cc1Cl)C(F)(F)F] | 1H-NMR (D6-DMSO): 7.76 (s, 1H), 7.48-7.33 (broad, 2H), 7.13 (s, 1H), 4.20-4.12 (m, 2H) |
| Ia-122 | 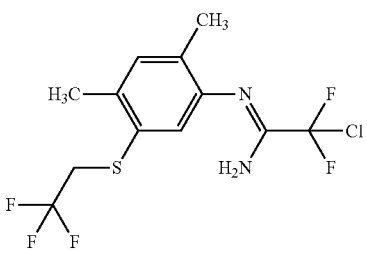 [SMILES: Cc1cc(C)c(SCC(F)(F)F)cc1/N=C(\N)C(F)(F)Cl] | 1H-NMR (D6-DMSO): 7.09 (s, 1H), 6.90 (broad, 2H), 6.84 (s, 1H), 3.90-3.82 (q, 2H), 2.31 (s, 3H), 1.99 (s, 3H) |
| Ia-123 | 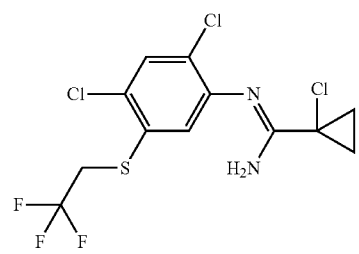 [SMILES: N/C(=N\c1cc(SCC(F)(F)F)c(Cl)cc1Cl)C1(Cl)CC1] | 1H-NMR (D6-DMSO): 7.56 (s, 1H), 7.04 (s, 1H), 6.53 (broad, 2H), 4.13-4.05 (q, 2H), 1.62-1.59 (m, 2H), 1.31-1.28 (m, 2H) |
| Ia-124 | 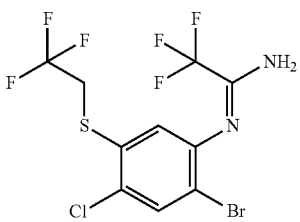 [SMILES: N/C(=N/c1cc(SCC(F)(F)F)c(Cl)cc1Br)C(F)(F)F] | 1H-NMR (D6-DMSO): 7.78 (s, 1H), 7.57-7.33 (broad, 1H), 7.12 (s, 1H), 4.19-4.11 (2H) |
| Ia-125 | 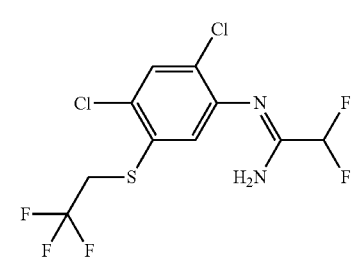 [SMILES: N/C(=N\c1cc(SCC(F)(F)F)c(Cl)cc1Cl)C(F)F] | 1H-NMR (D6-DMSO): 7.63 (s, 1H), 7.09 (s, 1H), 7.02-6.97 (broad, 2H), 6.34 (t, 1H), 4.16-4.09 (q, 2H) |
| Ia-126 | 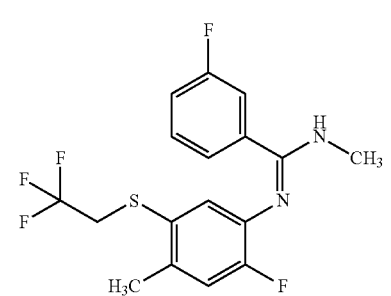 | 1H-NMR (D6-DMSO): 7.40-7.39 (m, 1H), 7.33-7.27 (m, 1H), 7.16-7.11 (m, 1H), 7.02-6.97 (m, 2H), 6.87-6.82 (t, 2H), 3.64-3.56 (q, 2H), 2.87-2.86 (m, 3H), 2.21 (s, 3H) |

-continued

| Example number | Structure | Analytical data |
|---|---|---|
| Ia-127 | 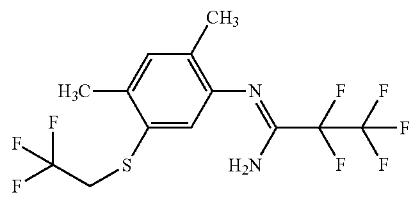 [SMILES: Cc1cc(C)c(SCC(F)(F)F)cc1/N=C(\N)C(F)(F)C(F)(F)F] | 1H-NMR (D6-DMSO): 7.10 (s, 1H), 7.05 (broad, 2H), 6.84 (s, 1H), 3.90-3.82 (q, 2H), 2.31 (s, 3H), 1.96 (s, 3H) |
| Ia-128 | 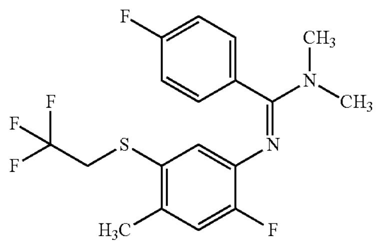 [SMILES: Cc1cc(F)c(/N=C(\c2ccc(F)cc2)N(C)C)cc1SCC(F)(F)F] | 1H-NMR (D6-DMSO): 7.19-7.16 (m, 2H), 7.13-7.08 (m, 2H), 6.82 (d, 1H), 6.72 (d, 1H), 3.58 (q, 2H), 3.01 (broad, 3H), 2.72 (broad, 3H), 2.17 (s, 3H) |
| Ia-129 | 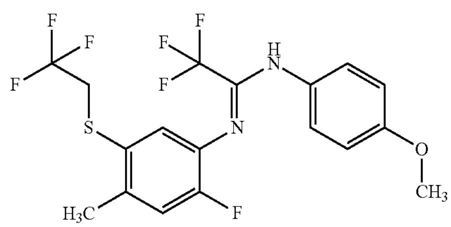 [SMILES: COc1ccc(N/C(=N/c2cc(SCC(F)(F)F)c(C)cc2F)C(F)(F)F)cc1] | logP(HCOOH) = 4.2, logP(neutral) = 4.2 |
| Ia-130 | 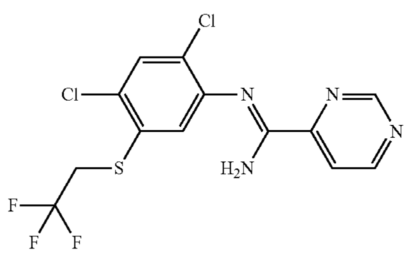 [SMILES: N/C(=N\c1cc(SCC(F)(F)F)c(Cl)cc1Cl)c1ccncn1] | 1H-NMR (D6-DMSO): 9.33 (m, 1H), 9.01-9.00 (m, 1H), 8.28-8.27 (m, 1H), 7.66 (s, 1H), 7.21 (s, 1H), 7.12-7.00 (broad, 2H), 4.16-4.08 (q, 2H) |
| Ia-131 | 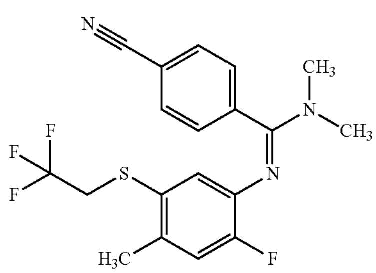 [SMILES: Cc1cc(F)c(/N=C(\c2ccc(C#N)cc2)N(C)C)cc1SCC(F)(F)F] | 1H-NMR (D6-DMSO): 7.77-7.75 (m, 2H), 7.36-7.34 (m, 2H), 6.83 (d, 1H), 6.74 (d, 1H), 3.58 (q, 2H), 3.10 (broad, 3H), 2.70 (broad, 3H), 2.17 (s, 3H) |
| Ia-132 | 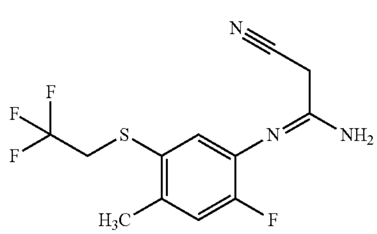 [SMILES: Cc1cc(F)c(N=C(N)CC#N)cc1SCC(F)(F)F] | 1H-NMR (D6-DMSO): 7.11-7.10 (m, 1H), 7.07-7.01 (m, 1H), 6.49 (broad, 2H), 3.88-3.83 (q, 2H), 3.65 (s, 2H), 2.33 (s, 3H) |

-continued

| Example number | Structure | Analytical data |
|---|---|---|
| Ia-133 | 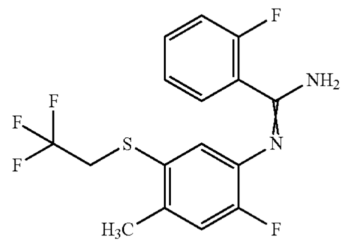 [SMILES: Cc1cc(F)c(N=C(N)c2ccccc2F)cc1SCC(F)(F)F] | 1H-NMR (D6-DMSO, 400 MHz): 7.58 (d, 1H), 7.18 (d, 1H), 4.06 (q, 2H), 3.01 (s, 6H) |
| Ia-134 | 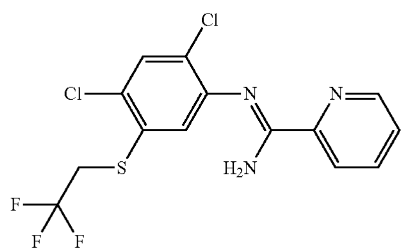 [SMILES: N/C(=N\c1cc(SCC(F)(F)F)c(Cl)cc1Cl)c1ccccn1] | 1H-NMR (D6-DMSO): 8.66-8.65 (m, 1H), 8.32-8.30 (m, 1H), 8.00-7.95 (m, 1H), 7.64 (s, 1H), 7.60-7.57 (m, 1H), 7.20 (s, 1H), 6.95 (broad, 2H), 4.16-4.08 (m, 2H) |
| Ia-135 | 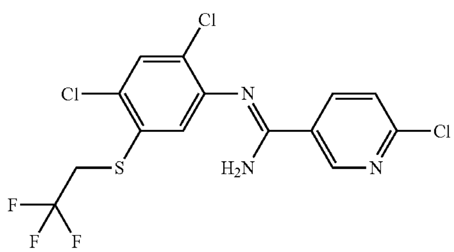 [SMILES: N/C(=N\c1cc(SCC(F)(F)F)c(Cl)cc1Cl)c1ccc(Cl)nc1] | 1H-NMR (D6-DMSO): 8.95 (broad, 1H), 8.38-8.32 (m, 1H), 7.64 (m, 2H), 7.19 (s, 1H), 6.94 (broad, 2H), 4.15-4.08 (q, 2H) |
| Ia-136 | 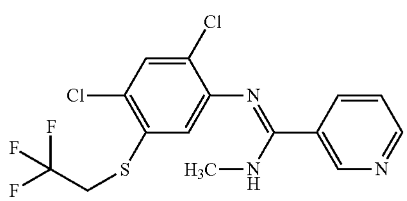 [SMILES: CN/C(=N\c1cc(SCC(F)(F)F)c(Cl)cc1Cl)c1cccnc1] | 1H-NMR (D6-DMSO): 8.47-8.45 (m, 1H), 8.35 (s, 1H), 7.56-7.54 (m, 1H), 7.39-7.38 (m, 1H), 7.31-7.27 (m, 1H), 7.15 (s, 1H), 6.54 (broad, 1H), 3.71-3.64 (q, 2H), 2.89-2.88 (d, 3H), 2.08 (s, 3H), |
| Ia-138 | 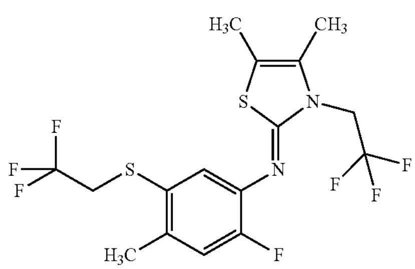 [SMILES: Cc1cc(F)c(/N=c2\sc(C)c(C)n2CC(F)(F)F)cc1SCC(F)(F)F] | 1H-NMR (D6-DMSO): 7.20-7.16 (m, 2H), 4.79 (q, 2H), 3.83 (q, 2H), 2.35 (s, 3H), 2.10 (s, 3H), 2.03 (s, 3H) |
| Ia-139 | 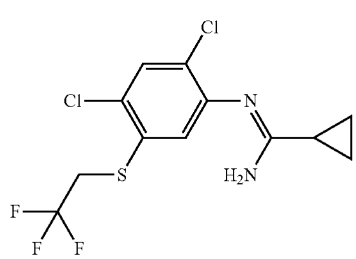 [SMILES: N/C(=N\c1cc(SCC(F)(F)F)c(Cl)cc1Cl)C1CC1] | 1H-NMR (D6-DMSO): 7.52 (s, 1H), 6.98 (s, 1H), 6.24-6.15 (broad, 2H), 4.11-4.03 (q, 2H), 1.51 (m, 1H), 0.92-0.88 (m, 2H), 0.76-0.71 (1H, 2H) |

| Example number | Structure | Analytical data |
|---|---|---|
| Ia-140 | 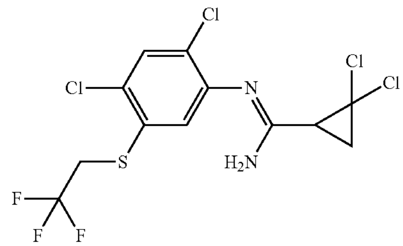 [SMILES: N/C(=N\c1cc(SCC(F)(F)F)c(Cl)cc1Cl)C1CC1(Cl)Cl] | 1H-NMR (D6-DMSO): 7.58 (s, 1H), 6.95 (s, 1H), 6.70 (broad, 2H), 4.07-4.00 (m, 2H), 2.17-2.14 (m, 1H), 1.95-1.93 (m, 1H) |
| Ia-141 | 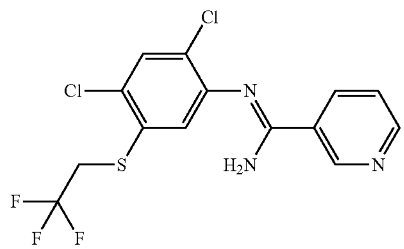 [SMILES: N/C(=N\c1cc(SCC(F)(F)F)c(Cl)cc1Cl)c1cccnc1] | 1H-NMR (D6-DMSO): 9.13 (m, 1H), 8.69 (m, 1H), 8.32 (m, 1H), 7.64 (s, 1H), 7.49 (m, 1H), 7.18 (s, 1H), 6.89 (broad, 2H), 4.16-4.08 (broad, 2H) |
| Ia-143 | 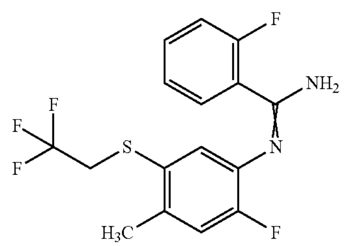 [SMILES: Cc1cc(F)c(N=C(N)c2ccccc2F)cc1SCC(F)(F)F] | logP(HCOOH) = 1.37. logP(neutral) = 3.25 |
| Ia-144 | 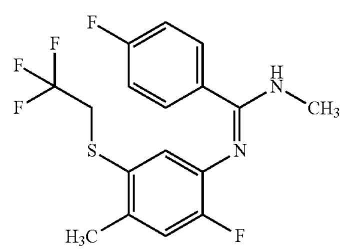 [SMILES: CN/C(=N/c1cc(SCC(F)(F)F)c(C)cc1F)c1ccc(F)cc1] | 1H-NMR (D6-DMSO): 7.34-7.33 (m, 1H), 7.23-7.20 (m, 2H), 7.12-7.07 (m, 2H), 6.85 (d, 1H), 6.77 (d, 1H), 3.58 (q, 2H), 2.86-2.85 (m, 3H), 2.21 (s, 3H) |
| Ia-145 | 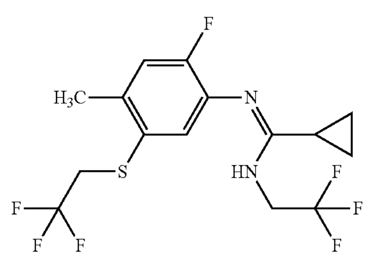 [SMILES: Cc1cc(F)c(/N=C(\NCC(F)(F)F)C2CC2)cc1SCC(F)(F)F] | 1H-NMR (D6-DMSO): 7.09-7.07 (m, 1H), 6.99-6.98 (m, 1H), 6.72 (broad, 1H), 3.85-3.79 (m, 4H), 2.33 (s, 3H), 1.41 (broad, 1H), 0.85-0.83 (m, 2H), 0.68-0.65 (m, 2H) |
| Ia-146 | 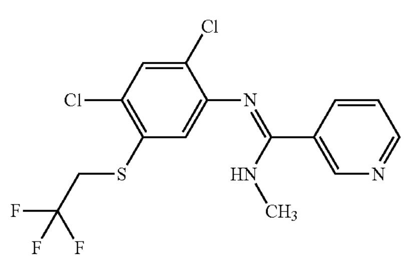 [SMILES: CN/C(=N\c1cc(SCC(F)(F)F)c(Cl)cc1Cl)c1cccnc1] | 1H-NMR (D6-DMSO): 8.50-8.49 (m, 1H), 8.41 (s, 1H), 7.71 (broad, 1H), 7.50-7.58 (m, 1H), 7.52-7.48 (m, 1H), 7.34-7.30 (m, 1H), 6.95 (broad, 1H), 3.96-3.88 (q, 2H), 2.92-2.90 (d, 3H) |

-continued

| Example number | Structure | Analytical data |
|---|---|---|
| Ia-147 | 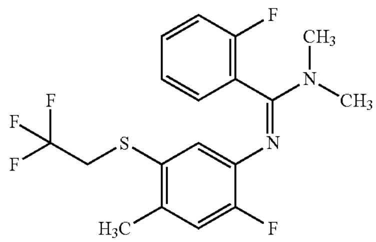 [SMILES: Cc1cc(F)c(/N=C(\c2ccccc2F)N(C)C)cc1SCC(F)(F)F] | 1H-NMR (D6-DMSO): 7.36-7.30 (m, 1H), 7.17-7.08 (m, 3H), 6.83 (d, 1H), 6.73 (d, 1H), 3.55 (q, 2H), 3.13 (broad, 3H), 2.76 (broad, 3H), 2.17 (s, 3H) |
| Ia-148 | 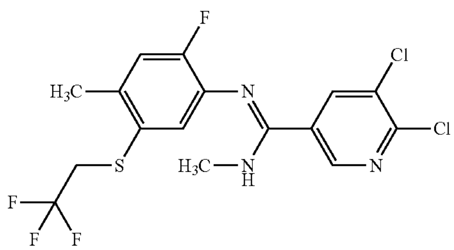 [SMILES: CN/C(=N\c1cc(SCC(F)(F)F)c(C)cc1F)c1cnc(Cl)c(Cl)c1] | 1H-NMR (D6-DMSO): 8.46-8.45 (m, 1H), 8.03 (s, 1H), 7.64-7.63 (q, 1H), 6.90-6.94 (m, 2H), 3.72-3.64 (q, 2H), 2.89 (d, 3H), 2.22 (s, 3H) |
| Ia-149 | 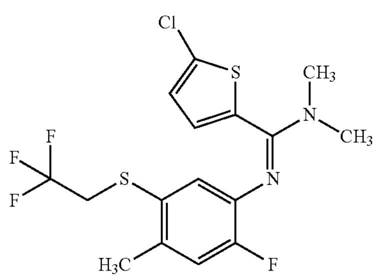 [SMILES: Cc1cc(F)c(/N=C(\c2ccc(Cl)s2)N(C)C)cc1SCC(F)(F)F] | 1H-NMR (D6-DMSO): 7.00 (m, 1H), 6.94-6.91 (d, 1H), 6.86-6.84 (m, 2H), 3.68 (q, 2H), 2.97 (s, 6H), 2.23 (s, 3H) |
| Ia-150 | 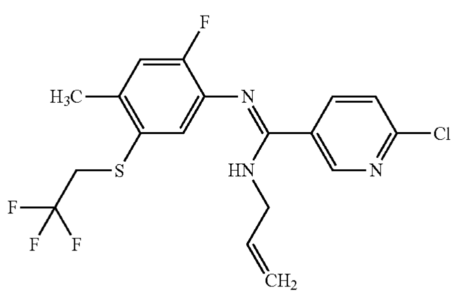 [SMILES: C=CCN/C(=N\c1cc(SCC(F)(F)F)c(C)cc1F)c1ccc(Cl)nc1] | 1H-NMR (D6-DMSO): 8.24-8.23 (m, 1H), 7.76 (broad, 1H), 7.66-7.63 (m, 1H), 7.45-7.43 (m, 1H), 6.90-6.87 (m, 2H), 6.03-5.97 (m, 1H), 5.32-5.28 (m, 1H), 5.16-5.13 (m, 1H), 4.02 (broad, 2H), 3.72-3.64 (q, 2H), 2.22 (s, 3H) |
| Ia-151 | 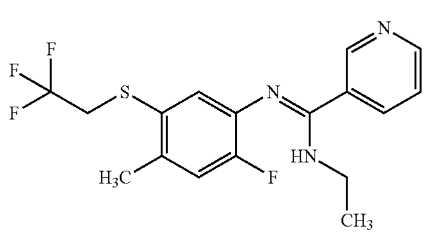 [SMILES: CCN/C(=N\c1cc(SCC(F)(F)F)c(C)cc1F)c1cccnc1] | 1H-NMR (D6-DMSO): 8.90 (m, 1H), 8.67 (m, 2H), 7.89-7.88 (m, 1H), 7.67-7.66 (m, 1H), 7.46-7.45 (m, 1H), 7.22-7.19 (m, 1H), 3.89-3.73 (m, 4H), 2.30 (s, 3H), 1.38-1.35 (t, 3H) |
| Ia-152 | 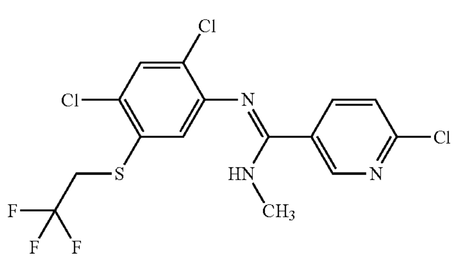 [SMILES: CN/C(=N\c1cc(SCC(F)(F)F)c(Cl)cc1Cl)c1ccc(Cl)nc1] | 1H-NMR (D6-DMSO): 8.25-8.20 (m, 2H), 7.73 (broad, 1H), 7.66-7.61 (m, 1H), 7.48-7.46 (m, 1H), 6.94 (broad, 1H), 3.97-3.89 (q, 2H), 2.91-2.90 (d, 3H) |

-continued

| Example number | Structure | Analytical data |
|---|---|---|
| Ia-153 | 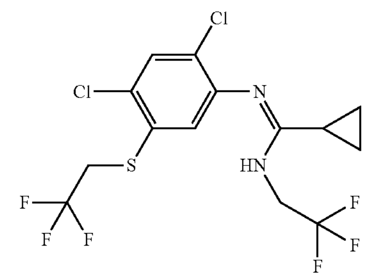 [SMILES: FC(F)(F)CN/C(=N\c1cc(SCC(F)(F)F)c(Cl)cc1Cl)C1CC1] | 1H-NMR (D6-DMSO): 8.58 (t, 1H), 7.60 (m, 1H), 7.10 (m, 1H), 4.10-3.87 (m, 4H), 1.38 (m, 1H), 0.88 (m, 2H), 0.71 (m, 2H) |
| Ia-155 | 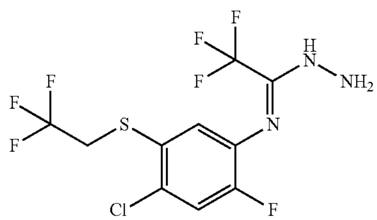 [SMILES: NN/C(=N/c1cc(SCC(F)(F)F)c(Cl)cc1F)C(F)(F)F] | 1H-NMR (D6-DMSO): 7.96 (bs, 1H), 7.48 (d, 1H), 7.33 (bs, 2H), 6.51 (d, 1H), 3.90-3.70 (m, 2H) |
| Ia-156 | 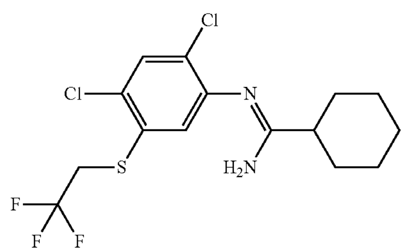 [SMILES: N/C(=N\c1cc(SCC(F)(F)F)c(Cl)cc1Cl)C1CCCCC1] | 1H-NMR (D6-DMSO): 7.54 (s, 1H), 6.98 (s, 1H), 6.10 (broad, 2H), 4.10-4.02 (q, 2H), 2.14 (m, 1H), 1.84-1.15 (m, 10H) |
| Ia-158 | 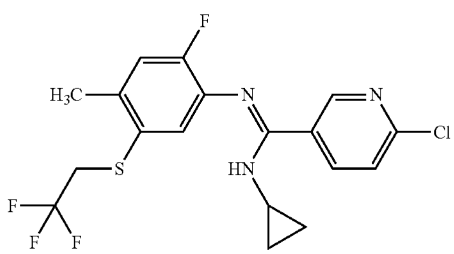 [SMILES: Cc1cc(F)c(/N=C(\NC2CC2)c2ccc(Cl)nc2)cc1SCC(F)(F)F] | 1H-NMR (D6-DMSO): 8.21-8.18 (m, 1H), 7.65-7.58 (m, 2H), 7.43-7.41 (m, 1H), 6.90-6.87 (m, 2H), 3.73-3.66 (q, 2H), 2.22 (s, 3H), 2.92 (m, 1H), 0.74-0.67 (m, 2H), 0.60-0.56 (m, 2H) |
| Ia-159 | 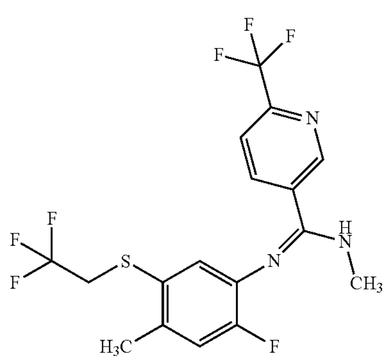 [SMILES: CN/C(=N/c1cc(SCC(F)(F)F)c(C)cc1F)c1ccc(C(F)(F)F)nc1] | 1H-NMR (D6-DMSO): 8.84 (m, 1H), 8.21-8.19 (m, 1H), 8.02-8.00 (m, 1H), 7.61-7.59 (m, 1H), 7.29-7.26 (m, 2H), 3.76-3.69 (q, 2H), 2.84 (broad, 3H), 2.30 (s, 3H) |

-continued
| Example number | Structure | Analytical data |
|---|---|---|
| Ia-160 | 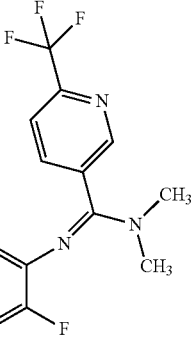 | 1H-NMR (D6-DMSO): 8.57 (m, 1H), 7.96-7.94 (m, 1H), 7.86-7.84 (m, 1H), 6.91-6.88 (m, 2H), 3.65-3.57 (q, 2H), 3.15 (broad, 3H), 2.80 (broad, 3H), 2.18 (s, 3H) |
| Ia-161 | 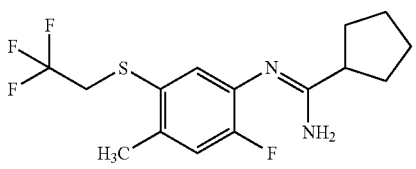 [SMILES: Cc1cc(F)c(/N=C(\N)C2CCCC2)cc1SCC(F)(F)F] | 1H-NMR (D6-DMSO): 7.08-7.05 (m, 1H), 6.98 (m, 1H), 6.20 (broad, 2H), 3.87-3.79 (q, 2H), 2.33 (s, 3H), 2.30 (m, 1H), 1.84-1.52 (m, 8H) |
| Ia-162 | 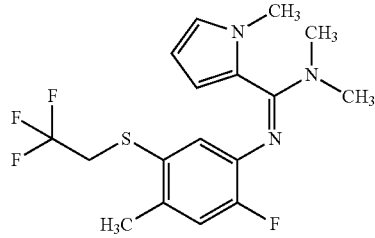 [SMILES: Cc1cc(F)c(/N=C(\c2cccn2C)N(C)C)cc1SCC(F)(F)F] | 1H-NMR (D6-DMSO): 6.88 (d, 1H), 6.70-6.69 (m, 1H), 6.63 (d, 1H), 5.91-5.89 (m, 2H), 3.58 (q, 2H), 3.39 (s, 3H), 3.05 (broad, 3H), 2.77 (broad, 3H), 2.21 (s, 3H) |
| Ia-163 | 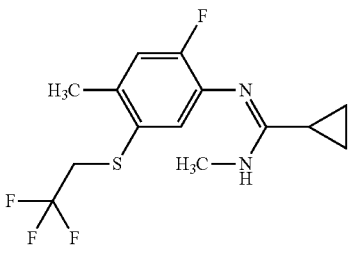 [SMILES: CN/C(=N\c1cc(SCC(F)(F)F)c(C)cc1F)C1CC1] | 1H-NMR (D6-DMSO): 7.05-6.99 (m, 2H), 6.24 (broad, 1H), 3.86-3.78 (q, 2H), 2.65-2.64 (d, 3H), 2.31 (s, 3H) 1.35 (m, 1H), 0.79-0.75 (m, 2H), 0.62-0.57 (m, 2H) |
| Ia-165 | 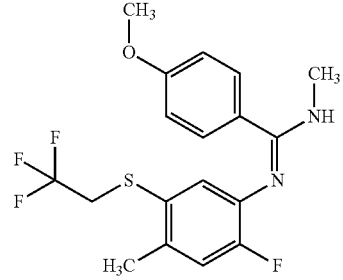 [SMILES: CN/C(=N/c1cc(SCC(F)(F)F)c(C)cc1F)c1ccc(OC)cc1] | logP(HCOOH) = 1.68. logP(neutral) = 3.49 |
| Ia-166 | 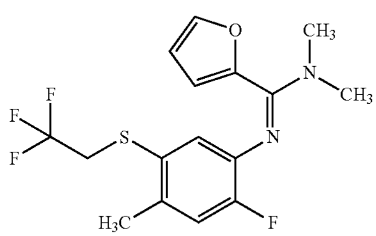 [SMILES: Cc1cc(F)c(/N=C(\c2ccco2)N(C)C)cc1SCC(F)(F)F] | 1H-NMR (D6-DMSO): 7.68 (m, 1H), 6.91 (d, 1H), 6.75 (d, 1H), 6.42-6.41 (m, 1H), 6.25-6.24 (m, 1H), 3.69 (q, 2H), 2.94 (s, 6H), 2.24 (s, 3H) |

-continued

| Example number | Structure | Analytical data |
|---|---|---|
| Ia-167 | 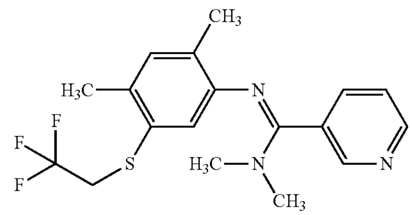 [SMILES: Cc1cc(C)c(SCC(F)(F)F)cc1/N=C(/c1cccnc1)N(C)C] | 1H-NMR (D6-DMSO): 8.42-8.40 (m, 1H), 8.29 (m, 1H), 7.59-7.56 (m, 1H), 7.30-7.27 (m, 1H), 6.83 (s, 1H) 2.04 (s, 3H), 6.42 (s, 1H), 2.13 (s, 3H), 3.51-3.43 (q, 2H), 2.92 (broad, 6H) |
| Ia-168 | 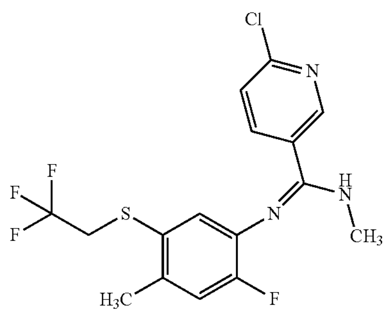 [SMILES: CN/C(=N/c1cc(SCC(F)(F)F)c(C)cc1F)c1ccc(Cl)nc1] | 1H-NMR (D6-DMSO): 8.35-8.33 (m, 1H), 7.76 (m, 1H), 7.54-7.52 (m, 1H), 7.25 (m, 1H), 7.07 (m, 2H), 3.74 (q, 2H), 3.07 (d, 3H), 2.27 (s, 3H) |
| Ia-169 | 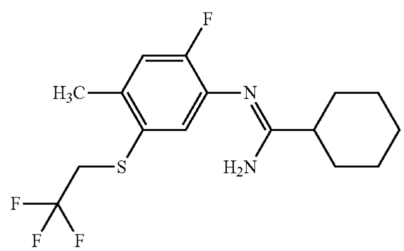 [SMILES: Cc1cc(F)c(/N=C(\N)C2CCCCC2)cc1SCC(F)(F)F] | 1H-NMR (D6-DMSO): 7.05-7.02 (m, 1H), 6.93-6.91 (m, 1H), 5.90 (broad, 2H), 3.85-3.77 (q, 2H), 2.3 (s, 3H), 2.16-2.10 (m, 1H), 1.83-1.15 (m, 10H) |
| Ia-171 | 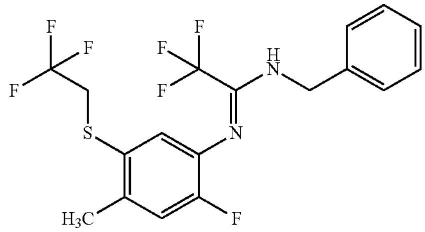 [SMILES: Cc1cc(F)c(/N=C(/NCc2ccccc2)C(F)(F)F)cc1SCC(F)(F)F] | 1H-NMR (D6-DMSO): 8.73 (broad, 1H), 7.32-7.25 (broad, 5H), 7.08-7.05 (m, 1H), 6.96-6.94 (m, 1H), 4.48 (broad, 2H) 3.78 (q, 2H), 2.32 (s, 3H) |
| Ia-172 | 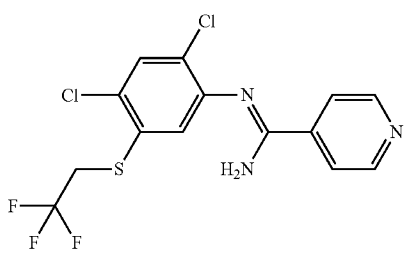 [SMILES: N/C(=N\c1cc(SCC(F)(F)F)c(Cl)cc1Cl)c1ccncc1] | 1H-NMR (D6-DMSO): 8.70 (m, 2H), 7.90-7.87 (m, 2H), 7.64 (m, 1H), 7.18 (s, 1H), 6.94 (broad, 2H), 4.15-4.08 (q, 2H) |
| Ia-173 | 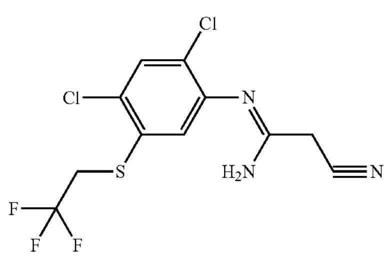 [SMILES: N#CC/C(N)=N/c1cc(SCC(F)(F)F)c(Cl)cc1Cl] | 1H-NMR (D6-DMSO): 7.60 (s, 1H), 7.06 (s, 1H), 6.63-6.54 (broad, 2H), 4.14-4.07 (q, 2H), 3.67 (s, 2H) |

| Example number | Structure | Analytical data |
|---|---|---|
| Ia-175 | 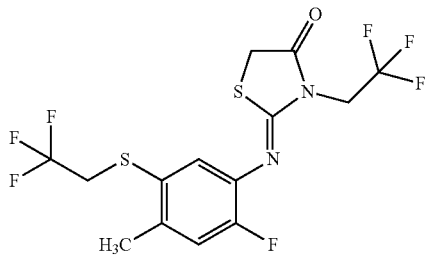 [SMILES: Cc1cc(F)c(/N=C2\SCC(=O)N2CC(F)(F)F)cc1SCC(F)(F)F] | 1H-NMR (D6-DMSO): 7.27 (d, 1H), 7.21 (d, 1H), 4.58 (q, 2H), 4.24 (s, 2H), 3.87 (q, 2H), 2.39 (s, 3H) |
| Ia-176 | 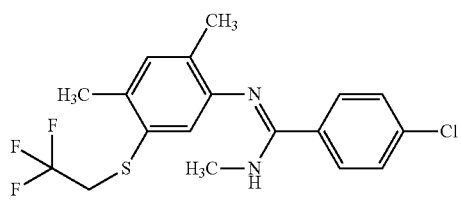 [SMILES: CN/C(=N\c1cc(SCC(F)(F)F)c(C)cc1C)c1ccc(Cl)cc1] | 1H-NMR (D6-DMSO): 7.31-7.29 (m, 2H), 7.14-7.08 (m, 3H), 6.89 (s, 1H), 6.36 (s, 1H), 3.41-3.33 (q, 2H), 2.85 (broad, 3H), 2.18 (s, 3H), 2.07 (s, 3H) |
| Ia-177 | 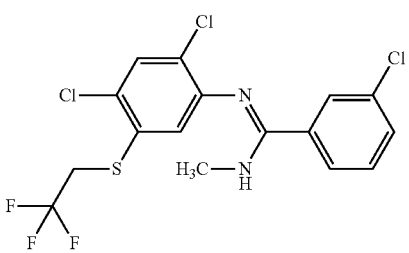 [SMILES: CN/C(=N\c1cc(SCC(F)(F)F)c(Cl)cc1Cl)c1cccc(Cl)c1] | 1H-NMR (D6-DMSO): 7.59-7.58 (m, 1H), 7.43 (s, 1H), 7.40-7.27 (m, 3H), 7.08-7.06 (m, 1H), 6.88 (s, 1H), 3.90-3.82 (q, 2H), 2.88-2.87 (d, 3H) |
| Ia-178 | 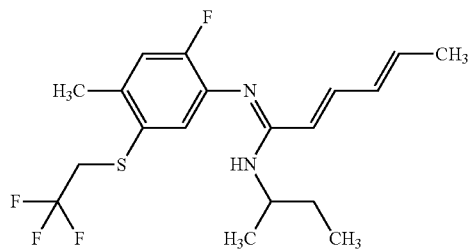 [SMILES: C/C=C/C=C/C(=N/c1cc(SCC(F)(F)F)c(C)cc1F)NC(C)CC] | 1H-NMR (D6-DMSO): 7.73 (m, 1H), 7.03-6.93 (m, 3H), 6.19-5.87 (m, 3H), 3.80-3.71 (m, 3H), 2.32 (s, 3H), 1.80-1.78 (d, 3H), 1.48 (m, 2H), 1.03-1.02 (d, 3H), 0.81 (t, 3H) |
| Ia-180 | 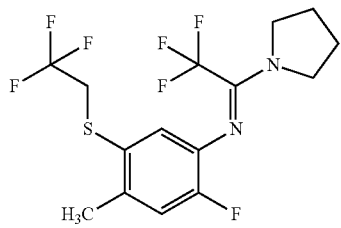 [SMILES: Cc1cc(F)c(/N=C(/N2CCCC2)C(F)(F)F)cc1SCC(F)(F)F] | 1H-NMR (D6-DMSO): 7.07-7.04 (m, 2H), 3.80 (q, 2H), 3.18 (broad, 4H), 2.33 (s, 3H), 1.84 (broad, 4H) |
| Ia-181 | 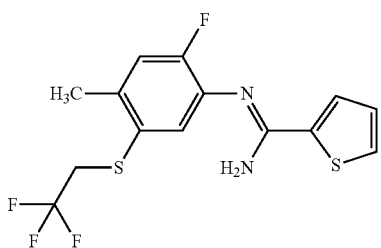 [SMILES: Cc1cc(F)c(/N=C(\N)c2cccs2)cc1SCC(F)(F)F] | 1H-NMR (D6-DMSO): 7.76 (m, 1H), 7.65-7.64 (m, 1H), 7.15-7.08 (m, 3H), 6.68 (broad, 2H), 3.92-3.84 (q, 2H), 2.35 (s, 3H) |

US 10,051,861 B2

-continued

| Example number | Structure | Analytical data |
|---|---|---|
| Ia-182 | 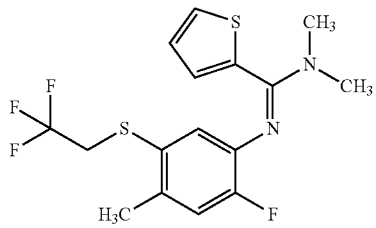 | 1H-NMR (D6-DMSO): 7.59-7.56 (m, 1H), 6.98-6.95 (m, 2H), 6.87 (d, 1H), 6.77 (d, 1H), 3.63 (q, 2H), 2.96 (s, 6H), 2.20 (s, 3H) |
| Ia-183 | 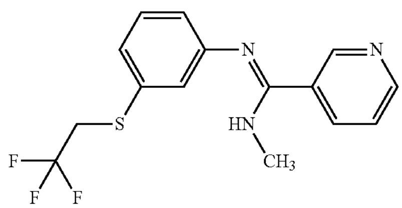 [SMILES: CN/C(=N\c1cccc(SCC(F)(F)F)c1)c1cccnc1] | 1H-NMR (D6-DMSO): 8.46-8.45 (m, 2H), 8.36 (s, 1H), 7.57-7.55 (m, 1H), 7.33-7.27 (m, 2H), 7.01-6.97 (m, 1H), 6.84-6.82 (m, 1H), 6.64 (s, 1H), 6.44-6.42 (m, 1H), 3.79-3.71 (q, 2H), 2.87-2.86 (d, 3H) |
| Ia-184 | 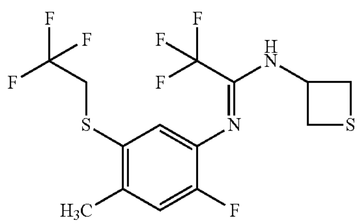 [SMILES: Cc1cc(F)c(/N=C(/NC2CSC2)C(F)(F)F)cc1SCC(F)(F)F] | 1H-NMR (D6-DMSO): 8.48 (broad, 1H), 7.11-7.01 (m, 2H), 4.90 (broad, 1H), 3.79 (q, 2H), 3.50 (broad, 2H), 3.18 (broad, 2H), 2.34 (s, 3H) |
| Ia-185 | 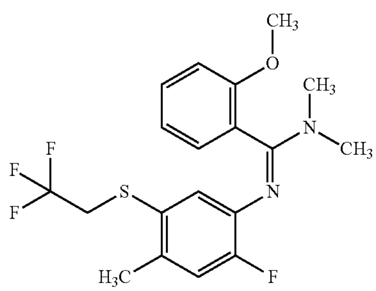 [SMILES: COc1ccccc1/C(=N\c1cc(SCC(F)(F)F)c(C)cc1F)N(C)C] | 1H-NMR (D6-DMSO): 7.25-7.21 (m, 1H), 6.96-6.90 (m, 2H), 6.84-6.81 (m, 2H), 6.60 (d, 1H), 3.73 (s, 3H), 3.50-3.37 (m, 2H), 3.10 (broad, 3H), 2.69 (broad, 3H), 2.17 (s, 3H) |
| Ia-186 | 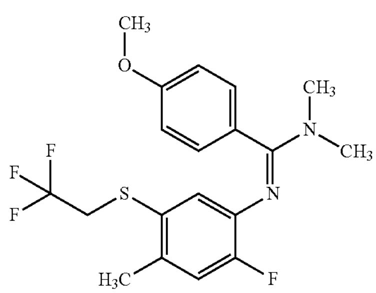 [SMILES: COc1ccc(/C(=N\c2cc(SCC(F)(F)F)c(C)cc2F)N(C)C)cc1] | 1H-NMR (D6-DMSO): 7.06-7.02 (m, 2H), 6.84-6.80 (m, 3H), 6.70 (d, 1H), 3.68 (s, 3H), 3.54 (q, 2H), 2.91 (broad, 6H), 2.17 (s, 3H) |
| Ia-187 | 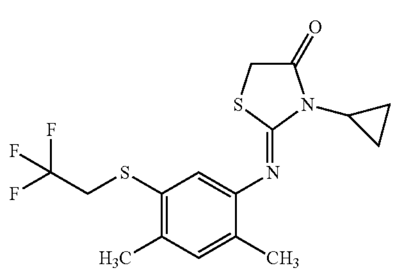 [SMILES: Cc1cc(C)c(SCC(F)(F)F)cc1/N=C1\SCC(=O)N1C1CC1] | 1H-NMR (D6-DMSO): 7.14 (s, 1H), 7.00 (s, 1H), 3.92 (s, 2H), 3.82 (q, 2H), 2.71 (septet, 1H), 2.33 (s, 3H), 2.06 (s, 3H), 1.00-0.90 (m, 4H) |

-continued
| Example number | Structure | Analytical data |
|---|---|---|
| Ia-188 | 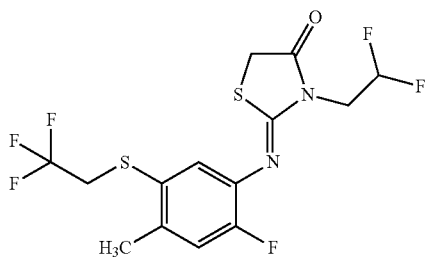 [SMILES: Cc1cc(F)c(/N=C2\SCC(=O)N2CC(F)F)cc1SCC(F)(F)F] | 1H-NMR (D6-DMSO): 7.28-7.25 (m, 2H), 6.32 (tt, 1H), 4.21-4.12 (m, 4H), 3.87 (q, 2H), 2.38 (s, 3H) |
| Ia-189 | 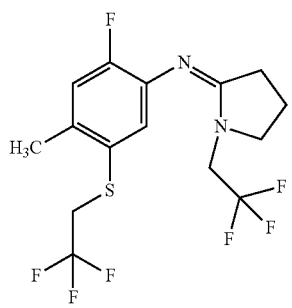 [SMILES: Cc1cc(F)c(/N=C2/CCCN2CC(F)(F)F)cc1SCC(F)(F)F] | 1H-NMR (D6-DMSO) 7.09-7.01 (m, 2H), 4.24 (q, 2H), 3.85 (q, 2H), 3.49 (t, 2H), 2.33 (t, 3H), 2.32 (s, 3H), 1.98-1.90 (m, 2H) |
| Ia-190 | 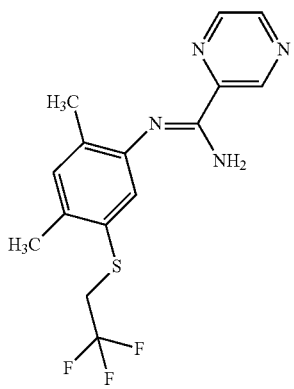 [SMILES: Cc1cc(C)c(SCC(F)(F)F)cc1/N=C(\N)c1cnccn1] | 1H-NMR (D6-DMSO): 9.49 (m, 1H), 8.81 (m, 1H), 8.71 (m, 1H), 7.13 (s, 1H), 6.98 (s, 1H), 6.53 (broad, 2H), 3.86 (q, 2H), 2.33 (s, 3H), 2.06 (s, 3H) |
| Ia-191 | 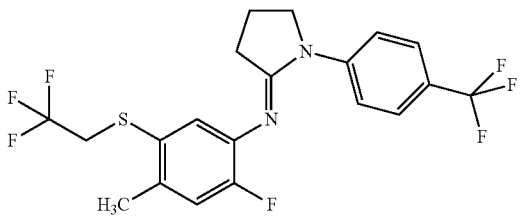 [SMILES: Cc1cc(F)c(/N=C2\CCCN2c2ccc(C(F)(F)F)cc2)cc1SCC(F)(F)F] | 1H-NMR (D6-DMSO): 8.15 (d, 2H), 7.72 (d, 2H), 7.14 (d, 2H), 3.95-3.85 (m, 2 × 2H), 2.54 (m, 2H), 2.34 (s, 3H), 2.04 (m, 2H) |
| Ia-192 | 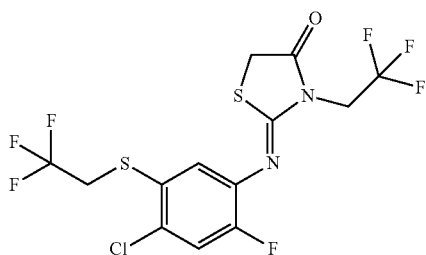 [SMILES: O=C1CS/C(=N\c2cc(SCC(F)(F)F)c(Cl)cc2F)N1CC(F)(F)F] | 1H-NMR (D6-DMSO): 7.67 (d, 1H), 7.36 (d, 1H), 4.59 (q, 2H), 4.27 (s, 2H), 4.06 (q, 2H) |

| Example number | Structure | Analytical data |
|---|---|---|
| Ia-193 | 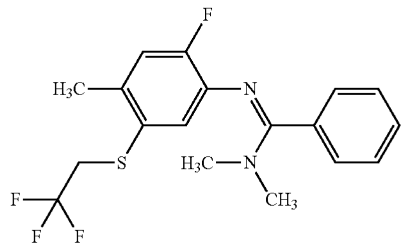 [SMILES: Cc1cc(F)c(/N=C(/c2ccccc2)N(C)C)cc1SCC(F)(F)F] | 1H-NMR (D6-DMSO): 7.30-7.25 (m, 3H), 7.13-7.11 (m, 2H), 6.81-6.78 (m, 1H), 6.73-6.71 (m, 1H), 3.54 (q, 2H), 3.08 (broad, 3H), 2.75 (broad, 3H), 2.16 (s, 3H) |
| Ia-194 | 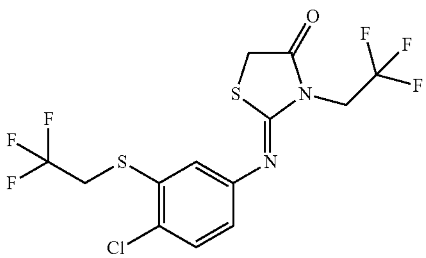 [SMILES: O=C1CS/C(=N\c2ccc(Cl)c(SCC(F)(F)F)c2)N1CC(F)(F)F] | 1H-NMR (D6-DMSO): 7.51 (d, 1H), 7.19 (d, 1H), 6.85 (dd, 1H), 4.57 (q, 2H), 4.21 (s, 2H), 4.12 (q, 2H) |
| Ia-195 | 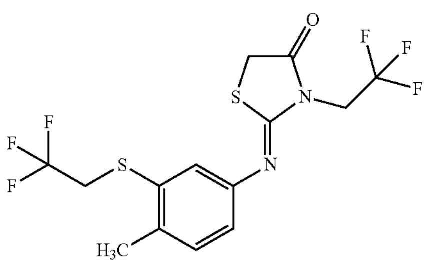 [SMILES: Cc1ccc(/N=C2\SCC(=O)N2CC(F)(F)F)cc1SCC(F)(F)F] | 1H-NMR (D6-DMSO): 7.27 (d, 1H), 7.09 (d, 1H), 6.79 (dd, 1H), 4.57 (q, 2H), 4.18 (s, 2H), 3.94 (q, 2H), 2.35 (s, 3H) |
| Ia-196 | 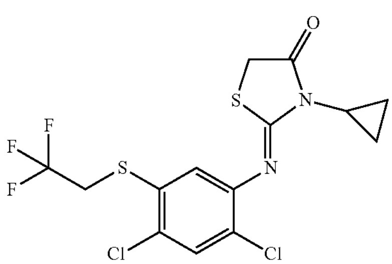 [SMILES: O=C1CS/C(=N\c2cc(SCC(F)(F)F)c(Cl)cc2Cl)N1C1CC1] | 1H-NMR (D6-DMSO): 7.76 (s, 1H), 7.35 (s, 1H), 4.13 (q, 2H), 4.02 (s, 2H), 2.71 (septet, 1H), 1.02-0.94 (m, 4H) |
| Ia-197 | 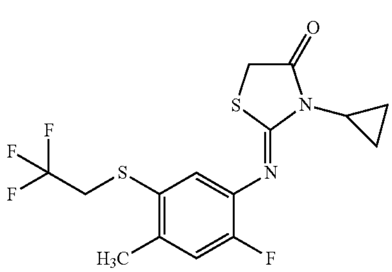 [SMILES: Cc1cc(F)c(/N=C2\SCC(=O)N2C2CC2)cc1SCC(F)(F)F] | 1H-NMR (D6-DMSO): 7.25-7.20 (m, 2H), 3.98 (s, 2H), 3.87 (q, 2H), 2.74-2.60 (m, 1H), 2.40 (s, 3H), 1.00-0.87 (m, 4H) |

-continued
| Example number | Structure | Analytical data |
|---|---|---|
| Ia-198 | 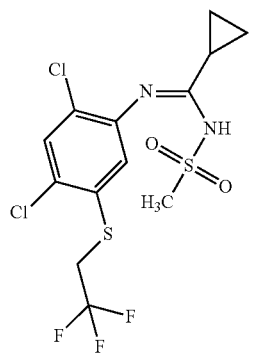 [SMILES: CS(=O)(=O)N/C(=N\c1cc(SCC(F)(F)F)c(Cl)cc1Cl)C1CC1] | 1H-NMR (D6-DMSO): 9.30 (broad, 1H), 7.85 (s, 1H), 7.75 (s, 1H), 4.21 (q, 2H), 2.87 (s, 3H), 1.20 (m, 2H), 1.05 (m, 2H) |
| Ia-199 | 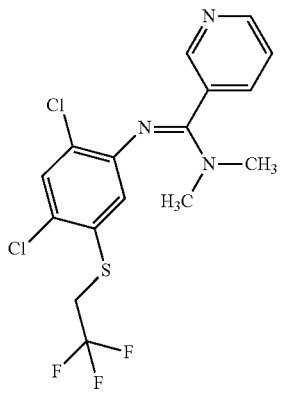 [SMILES: CN(C)/C(=N\c1cc(SCC(F)(F)F)c(Cl)cc1Cl)c1cccnc1] | 1H-NMR (D6-DMSO): 8.47-8.46 (m, 1H), 8.37-8.36 (m, 1H), 7.66-7.63 (m, 1H), 7.37 (s, 1H), 7.35-7.31 (m, 1H), 6.92 (s, 1H), 3.92 (q, 2H), 3.08 (broad, 3H), 2.85 (broad, 3H) |
| Ia-200 | 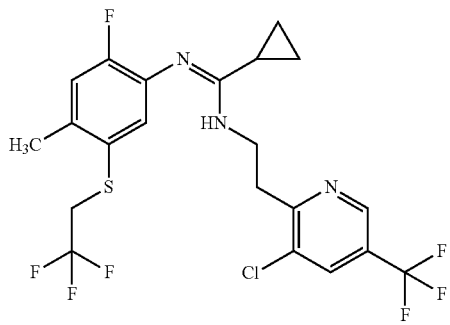 [SMILES: Cc1cc(F)c(/N=C(\NCCc2ncc(C(F)(F)F)cc2Cl)C2CC2)cc1SCC(F)(F)F] | 1H-NMR (D6-DMSO): 8.87 (s, 1H), 8.38 (m, 1H), 7.04-7.02 (m, 1H), 6.94 (s, 1H), 6.33 (broad, 1H), 3.79 (q, 2H), 3.63-3.58 (m, 2H), 3.23 (t, 2H), 2.31 (s, 3H), 1.34 (m, 1H), 0.76-0.72 (m, 2H), 0.60-0.55 (m, 2H) |
| Ia-201 | 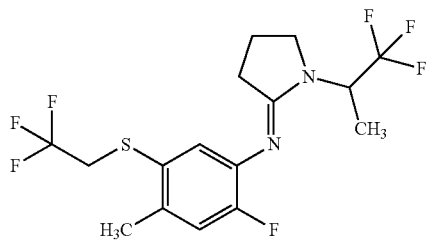 [SMILES: Cc1cc(F)c(/N=C2\CCCN2C(C)C(F)(F)F)cc1SCC(F)(F)F] | 1H-NMR (D6-DMSO): 7.10-7.05 (m, 2H), 5.14-5.06 (m, 1H), 3.89-3.81 (q, 2H), 3.51-3.49 (m, 2H), 2.32 (s, 3H), 2.30-2.28 (m, 2H), 1.98-1.89 (m, 2H), 1.38-1.36 (broad, 3H) |

| Example number | Structure | Analytical data |
|---|---|---|
| Ia-202 | 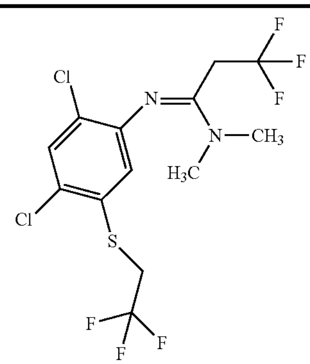 | 1H-NMR (D6-DMSO): 7.59 (s, 1H), 7.05 (s, 1H), 4.10 (q, 2H), 3.70 (s, 2H), 3.08 (broad, 6H) |
| Ia-203 | 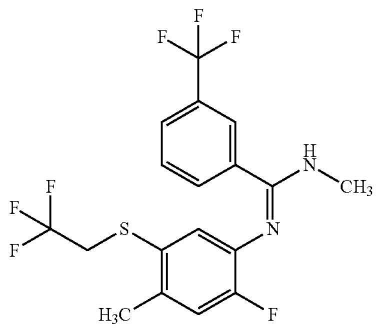 [SMILES: CN/C(=N/c1cc(SCC(F)(F)F)c(C)cc1F)c1cccc(C(F)(F)F)c1] | 1H-NMR (D6-DMSO): 7.66 (d, 1H) 7.55-7.41 (m, 4H), 6.87-6.83 (m, 2H), 3.56 (q, 2H), 2.89 (d, 3H), 2.19 (s, 3H) |
| Ia-204 | 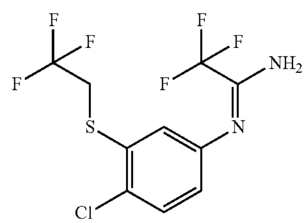 [SMILES: N/C(=N/c1ccc(Cl)c(SCC(F)(F)F)c1)C(F)(F)F] | 1H-NMR (D6-DMSO): 7.42 (d, 1H), 7.26 (broad, 2H), 7.05 (d, 1H), 6.75-6.72 (m, 1H), 4.13 (q, 2H) |
| Ia-205 | 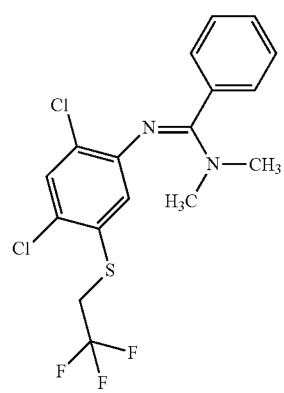 [SMILES: CN(C)/C(=N\c1cc(SCC(F)(F)F)c(Cl)cc1Cl)c1ccccc1] | 1H-NMR (D6-DMSO): 7.35 (s, 1H), 7.31-7.27 (m, 3H), 7.18-7.16 (m, 2H), 6.81 (s, 1H), 3.82 (q, 2H), 3.10 (broad, 3H), 2.82 (d, 3H) |
| Ia-206 | 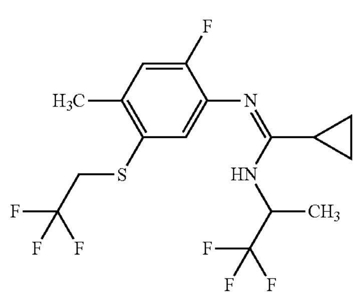 [SMILES: Cc1cc(F)c(/N=C(\NC(C)C(F)(F)F)C2CC2)cc1SCC(F)(F)F] | 1H-NMR (D6-DMSO): 7.09-7.06 (m, 1H), 7.01-6.99 (m, 1H), 6.47-6.44 (m, 1H), 3.85 (q, 2H), 2.65-2.59 (m, 2H), 2.33 (s, 3H), 1.41 (m, 1H), 1.27 (d, 3H), 0.96-0.61 (m, 4H) |

-continued
| Example number | Structure | Analytical data |
|---|---|---|
| Ia-207 | 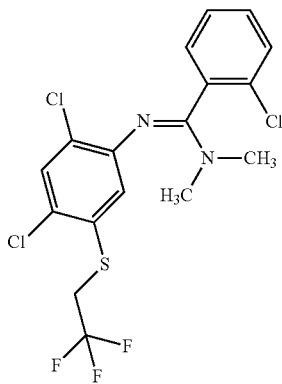 [SMILES: CN(C)/C(=N\c1cc(SCC(F)(F)F)c(Cl)cc1Cl)c1ccccc1Cl] | 1H-NMR (D6-DMSO): 7.45-6.76 (m, 6H), 3.86 (q, 2H), 3.17 (broad, 3H), 2.73 (broad, 3H) |
| Ia-208 | 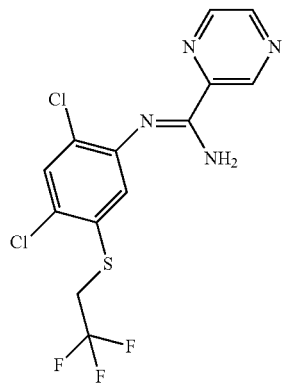 [SMILES: N/C(=N\c1cc(SCC(F)(F)F)c(Cl)cc1Cl)c1cnccn1] | 1H-NMR (D6-DMSO): 9.45 (s, 1H), 8.84 (m, 1H), 8.74-8.73 (m, 1H), 7.66 (s, 1H), 7.23 (s, 1H), 7.03 (broad, 2H), 4.12 (q, 2H) |
| Ia-209 | 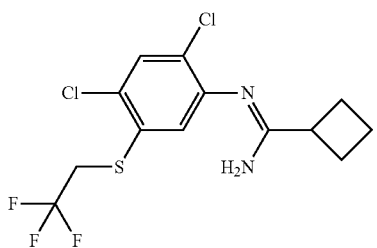 [SMILES: N/C(=N\c1cc(SCC(F)(F)F)c(Cl)cc1Cl)C1CCC1] | 1H-NMR (D6-DMSO): 7.61 (broad, 1H), 7.11 (broad, 1H), 6.20 (broad, 2H), 4.10 (q, 2H), 3.14 (m, 1H), 2.32-1.78 (m, 6H) |
| Ia-210 | 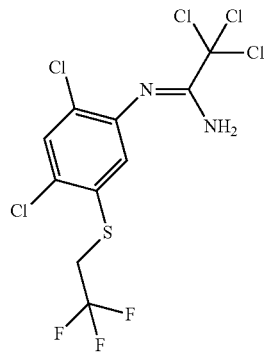 [SMILES: N/C(=N\c1cc(SCC(F)(F)F)c(Cl)cc1Cl)C(Cl)(Cl)Cl] | 1H-NMR (D6-DMSO): 7.65 (s, 1H), 7.15 (broad, 2H), 7.10 (s, 1H), 4.15 (q, 2H) |

-continued

| Example number | Structure | Analytical data |
|---|---|---|
| Ia-211 | 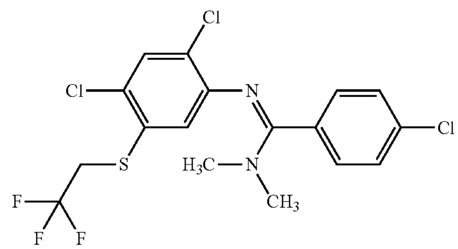 [SMILES: CN(C)/C(=N\c1cc(SCC(F)(F)F)c(Cl)cc1Cl)c1ccc(Cl)cc1] | 1H-NMR (D6-DMSO): 7.39-7.35 (m, 3H), 7.21-7.19 (m, 2H), 6.85 (s, 1H), 3.86 (q, 2H), 3.07 (broad, 3H), 2.79 (broad, 3H) |
| Ia-212 | 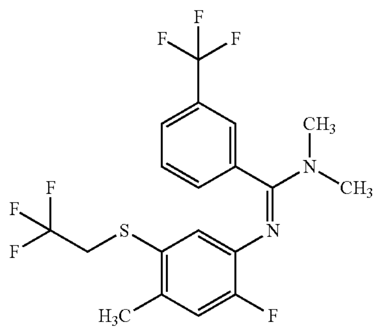 [SMILES: Cc1cc(F)c(/N=C(\c2cccc(C(F)(F)F)c2)N(C)C)cc1SCC(F)(F)F] | 1H-NMR (D6-DMSO): 7.63 (d, 1H), 7.54-7.46 (m, 2H), 7.42 (d, 1H), 6.83-6.78 (m, 2H), 3.56 (q, 2H), 3.11 (broad, 3H), 2.76 (broad, 3H), 2.16 (s, 3H) |
| Ia-213 | 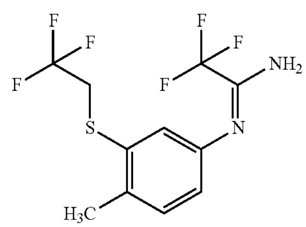 [SMILES: Cc1ccc(/N=C(/N)C(F)(F)F)cc1SCC(F)(F)F] | 1H-NMR (D6-DMSO): 7.20 (d, 1H), 7.10 (broad, 2H), 6.96 (d, 1H), 6.69-6.67 (m, 1H), 3.97 (q, 2H), 2.31 (s, 3H) |
| Ia-214 | 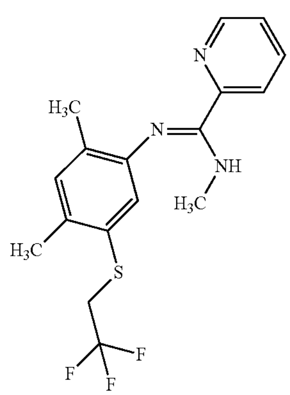 [SMILES: CN/C(=N\c1cc(SCC(F)(F)F)c(C)cc1C)c1ccccn1] | 1H-NMR (D6-DMSO): 8.56-8.55 (m, 1H), 7.69-7.68 (m, 2H), 7.38-7.22 (m, 3H), 6.93 (s, 1H), 3.48 (broad, 2H), 2.77 (broad, 3H), 2.22 (s, 3H), 2.06 (s, 3H) |
| Ia-215 | 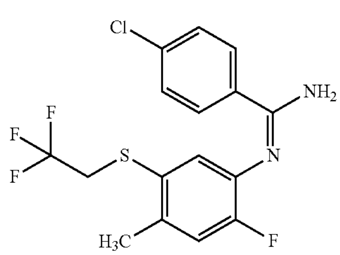 [SMILES: Cc1cc(F)c(/N=C(/N)c2ccc(Cl)cc2)cc1SCC(F)(F)F] | 1H-NMR (D6-DMSO): 7.99 (d, 2H), 7.51 (d, 2H), 7.14-7.09 (m, 2H), 6.65 (broad, 2H), 3.87 (q, 2H), 2.35 (s, 3H) |

-continued

| Example number | Structure | Analytical data |
|---|---|---|
| Ia-216 | 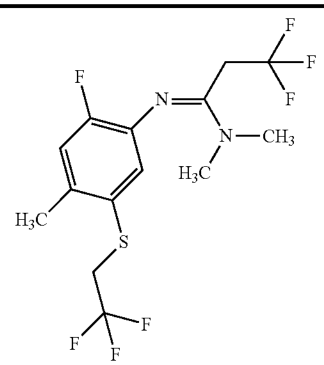 | 1H-NMR (D6-DMSO): 7.10-7.07 (m, 1H), 6.94-6.92 (m, 1H), 3.83 (q, 2H), 3.52 (q, 2H), 3.04 (broad, 6H), 2.32 (s, 3H) |
| Ia-217 | 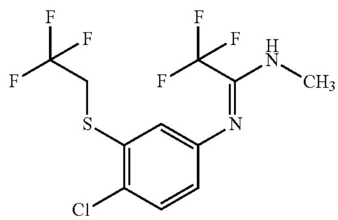 [SMILES: CN/C(=N/c1ccc(Cl)c(SCC(F)(F)F)c1)C(F)(F)F] | 1H-NMR (D6-DMSO): 8.05 (broad, 1H), 7.32 (d, 1H), 7.03 (broad, 1H), 6.65 (broad, 1H), 4.09 (q, 2H), 2.70 (broad, 3H) |
| Ia-218 | 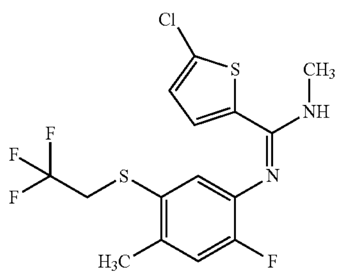 [SMILES: CN/C(=N/c1cc(SCC(F)(F)F)c(C)cc1F)c1ccc(Cl)s1] | 1H-NMR (D6-DMSO): 7.57 (d, 1H), 7.49 (broad, 1H), 7.17 (d, 1H), 7.05-6.99 (m, 2H), 3. |
| Ia-219 | 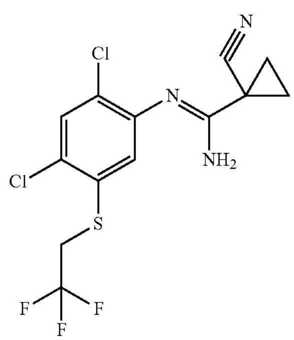 [SMILES: N#CC1(/C(N)=N/c2cc(SCC(F)(F)F)c(Cl)cc2Cl)CC1] | 1H-NMR (D6-DMSO): 7.58 (s, 1H), 7.07 (s, 1H), 6.40 (broad, 2H), 3.93 (q, 2H), 1.75-1.61 (m, 4H) |
| Ia-220 | 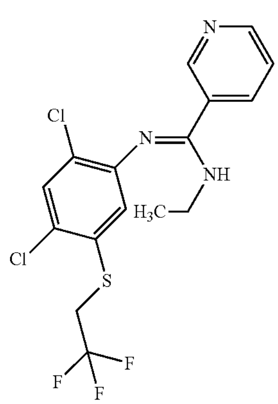 [SMILES: CCN/C(=N\c1cc(SCC(F)(F)F)c(Cl)cc1Cl)c1cccnc1] | 1H-NMR (D6-DMSO): 8.49-8.47 (m, 1H), 8.39 (m, 1H), 7.65 (t, 1H), 7.59-7.57 (m, 1H), 7.42 (s, 1H), 7.37-7.29 (m, 1H), 6.90 (s, 1H), 3.90 (q, 2H), 3.43-3.38 (m, 2H), 1.23 (t, 3H) |

| Example number | Structure | Analytical data |
|---|---|---|
| Ia-221 | 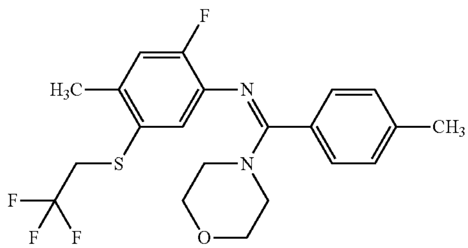 [SMILES: Cc1ccc(/C(=N/c2cc(SCC(F)(F)F)c(C)cc2F)N2CCOCC2)cc1] | 1H-NMR (D6-DMSO): 7.36-7.34 (m, 2H), 7.20-7.18 (m, 2H), 6.87-6.84 (m, 1H), 6.82-6.80 (m, 1H), 3.66-3.58 (m, 8H), 3.30 (broad, 2H), 2.19 (s, 3H) |
| Ia-222 | 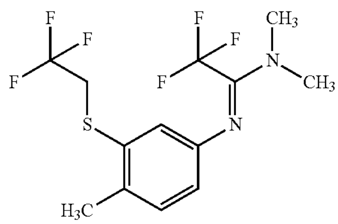 [SMILES: Cc1ccc(/N=C(/N(C)C)C(F)(F)F)cc1SCC(F)(F)F] | 1H-NMR (D6-DMSO): 7.10 (d, 2H), 6.89 (broad, 1H), 6.55 (d, 1H), 3.93 (q, 2H), 2.87 (broad, 6H), 2.29 (s, 3H) |
| Ia-223 | 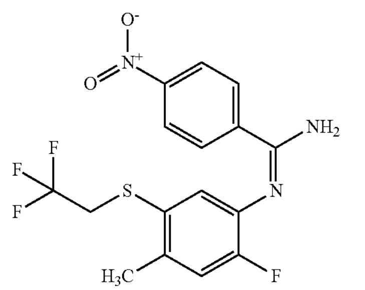 [SMILES: Cc1cc(F)c(/N=C(/N)c2ccc([N+](=O)[O-])cc2)cc1SCC(F)(F)F] | 1H-NMR (D6-DMSO): 8.30 (d, 2H), 8.21 (d, 2H), 7.17-7.13 (m, 2H), 6.89 (broad, 2H), 3.89 (q, 2H), 2.37 (s, 3H) |
| Ia-224 | 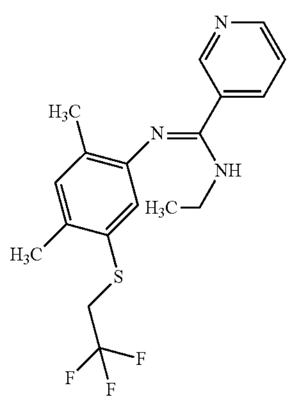 [SMILES: CCN/C(=N\c1cc(SCC(F)(F)F)c(C)cc1C)c1cccnc1] | 1H-NMR (D6-DMSO): 8.43-8.42 (m, 1H), 8.31 (m, 1H), 7.52-7.50 (m, 1H), 7.27-7.20 (m, 2H), 6.89 (s, 1H), 6.39 (s, 1H), 3.45-3.33 (m, 4H), 2.17 (s, 3H), 2.07 (s, 3H), 1.22 (t, 3H) |
| Ia-225 | 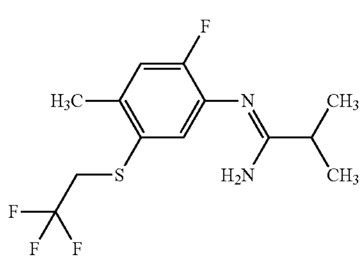 [SMILES: Cc1cc(F)c(/N=C(\N)C(C)C)cc1SCC(F)(F)F] | 1H-NMR (D6-DMSO): 7.07-7.04 (m, 1H), 6.95-6.94 (m, 1H), 5.95 (broad, 2H), 3.82 (q, 2H), 2.32 (s, 3H), 1.14 (d, 6H) |

-continued

| Example number | Structure | Analytical data |
|---|---|---|
| Ia-226 | 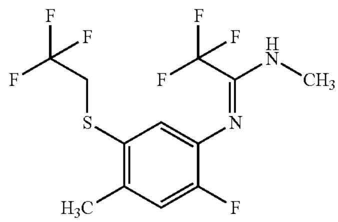 [SMILES: CN/C(=N/c1cc(SCC(F)(F)F)c(C)cc1F)C(F)(F)F] | 1H-NMR (D6-DMSO): 7.90 (broad, 1H), 7.09 (d, 1H), 6.89 (broad, 1H), 6.58 (broad, 1H), 4.03 (q, 2H) 2.76 (broad, 3H), 2.29 (s, 3H) |
| Ia-227 | 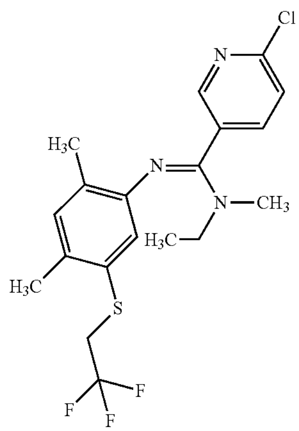 [SMILES: CCN(C)/C(=N\c1cc(SCC(F)(F)F)c(C)cc1C)c1ccc(Cl)nc1] | 1H-NMR (D6-DMSO): 8.15 (m, 1H), 7.68-7.65 (m, 1H), 7.42-7.40 (m, 1H), 6.86 (s, 1H), 6.45 (s, 1H), 3.52 (q, 2H), 2.92 (broad, 6H), 2.16 (s, 3H), 2.04 (s, 3H) |
| Ia-228 | 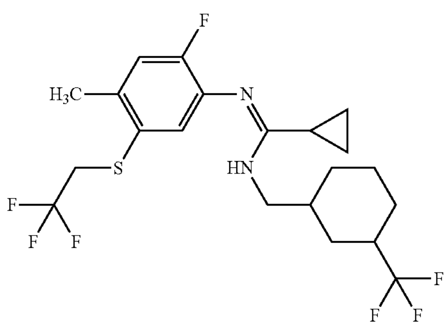 [SMILES: Cc1cc(F)c(/N=C(\NCC2CCCC(C(F)(F)F)C2)C2CC2)cc1SCC(F)(F)F] | 1H-NMR (D6-DMSO): 7.05-6.95 (m, 2H), 6.26 (broad, 1H), 3.80 (q, 2H), 3.09-3.01 (m, 2H), 2.32 (s, 3H), 2.22-0.60 (m, 15H) |
| Ia-229 | 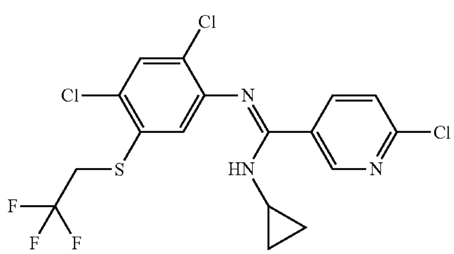 [SMILES: FC(F)(F)CSc1cc(/N=C(\NC2CC2)c2ccc(Cl)nc2)c(Cl)cc1Cl] | 1H-NMR (D6-DMSO): 8.32-8.27 (m, 1H), 7.82 (broad, 1H), 7.65 (m, 1H), 7.48-7.46 (m, 2H), 7.02 (broad, 1H), 3.97 (q, 2H), 2.83 (m, 1H), 0.69-0.61 (m, 4H) |
| Ia-230 | 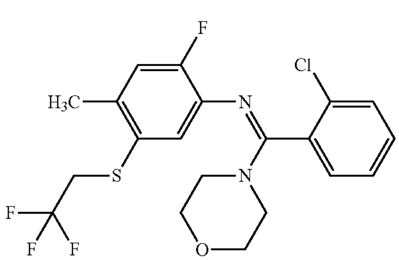 [SMILES: Cc1cc(F)c(/N=C(/c2ccccc2Cl)N2CCOCC2)cc1SCC(F)(F)F] | 1H-NMR (D6-DMSO): 7.40-7.23 (m, 4H), 6.89-6.86 (m, 1H), 6.81-6.79 (m, 1H), 3.65-3.49 (m, 8H), 3.02-3.00 (m, 2H), 2.18 (s, 3H) |

| Example number | Structure | Analytical data |
|---|---|---|
| Ia-231 | 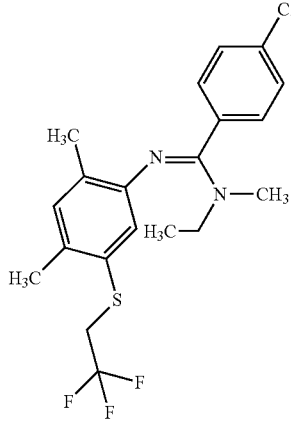 | 1H-NMR (D6-DMSO): 7.32-7.30 (m, 2H), 7.14-7.12 (m, 2H), 6.83 (s, 1H), 6.39 (s, 1H), 3.44 (q, 2H), 2.89 (broad, 6H), 2.15 (s, 3H), 2.04 (s, 3H) |
| Ia-232 | 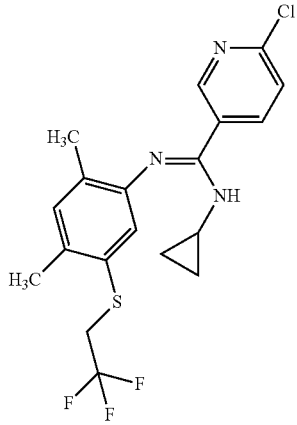 [SMILES: Cc1cc(C)c(SCC(F)(F)F)cc1/N=C(\NC1CC1)c1ccc(Cl)nc1] | 1H-NMR (D6-DMSO): 8.14 (m, 1H), 7.55-7.53 (m, 1H), 7.38-737 (m, 2H), 6.91 (s, 1H), 6.47 (s, 1H), 3.50 (q, 2H), 2.87 (m, 1H), 2.19 (s, 3H), 2.08 (s, 3H), 0.71 (m, 2H), 0.58 (m, 2H) |
| Ia-233 | 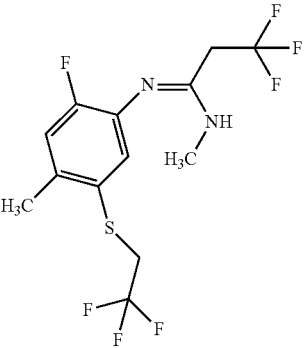 [SMILES: CN/C(CC(F)(F)F)=N\c1cc(SCC(F)(F)F)c(C)cc1F] | 1H-NMR (D6-DMSO): 7.26 (broad, 1H), 7.09-7.06 (m, 1H), 6.97-6.95 (m, 1H), 3.84 (q, 2H), 3.14 (q, 2H), 2.77 (d, 3H), 2.32 (s, 3H) |
| Ia-234 | 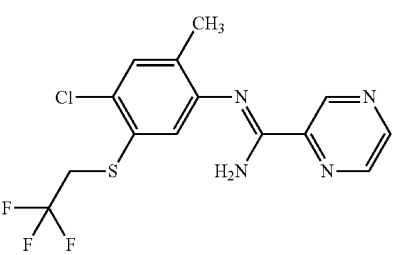 [SMILES: Cc1cc(Cl)c(SCC(F)(F)F)cc1/N=C(\N)c1cnccn1] | 1H-NMR (D6-DMSO): 9.50-9.49 (m, 1H), 8.83-8.82 (m, 1H), 8.72 (s, 1H), 7.37 (s, 1H), 7.07 (s, 1H), 6.75 (broad, 2H), 4.03 (q, 2H), 2.08 (s, 3H) |

| Example number | Structure | Analytical data |
|---|---|---|
| Ia-235 | 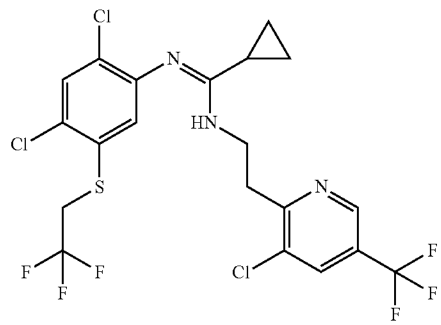 [SMILES: FC(F)(F)CSc1cc(/N=C(\NCCc2ncc(C(F)(F)F)cc2Cl)C2CC2)c(Cl)cc1Cl] | 1H-NMR (D6-DMSO): 8.88 (s, 1H), 8.39 (m, 1H), 7.54 (s, 1H), 7.05 (s, 1H), 6.53 (broad, 1H), 4.07 (q, 2H), 3.64-3.59 (m, 2H), 3.27 (t, 2H), 1.35-130 (m, 1H), 0.79-0.76 (m, 2H), 0.60-0.59 (m, 2H) |
| Ia-236 | 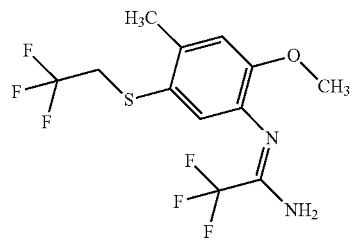 [SMILES: COc1cc(C)c(SCC(F)(F)F)cc1/N=C(/N)C(F)(F)F] | 1H-NMR (D6-DMSO): 6.96-6.92 (m, 4H), 3.75 (q, 2H), 3.73 (s, 3H), 2.39 (s, 3H) |
| Ia-237 | 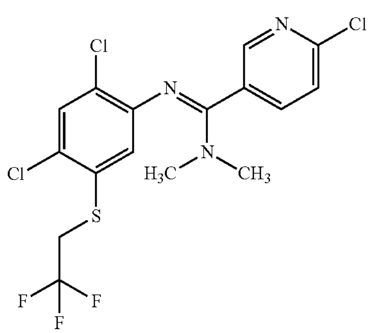 [SMILES: CN(C)/C(=N\c1cc(SCC(F)(F)F)c(Cl)cc1Cl)c1ccc(Cl)nc1] | 1H-NMR (D6-DMSO): 8.23-8.22 (m, 1H), 7.73-7.70 (m, 1H), 7.49-7.47 (m, 1H), 7.42 (s, 1H), 6.95 (s, 1H), 3.94 (q, 2H), 3.10 (broad, 3H), 2.83 (broad, 3H) |
| Ia-238 | 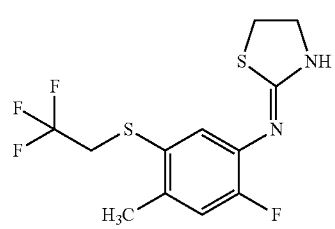 [SMILES: Cc1cc(F)c(/N=C2/NCCS2)cc1SCC(F)(F)F] | 1H-NMR (D6-DMSO): 7.78 (broad, 1H), 7.12-7.07 (m, 2H), 3.83-3.75 (m, 2H), 3.55 (broad, 2H), 3.29 (t, 2H), 2.33 (s, 3H) |
| Ia-239 | 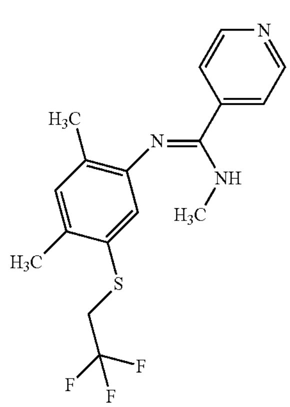 [SMILES: CN/C(=N\c1cc(SCC(F)(F)F)c(C)cc1C)c1ccncc1] | 1H-NMR (D6-DMSO): 8.46-8.45 (m, 2H), 7.19 (broad, 1H), 7.11 (m, 2H), 6.90 (s, 1H), 6.42 (broad, 1H), 3.44 (q, 2H), 2.87 (broad, 3H), 2.17 (s, 3H), 2.07 (s, 3H) |

-continued

| Example number | Structure | Analytical data |
| --- | --- | --- |
| Ia-240 | 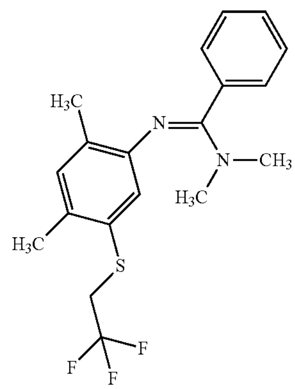 [SMILES: Cc1cc(C)c(SCC(F)(F)F)cc1/N=C(/c1ccccc1)N(C)C] | 1H-NMR (D6-DMSO): 7.28-7.22 (m, 3H), 7.10-7.08 (m, 2H), 6.81 (s, 1H), 6.37 (s, 1H), 3.36 (q, 2H), 2.90 (broad, 6H), 2.13 (s, 3H), 2.05 (s, 3H) |
| Ia-241 | 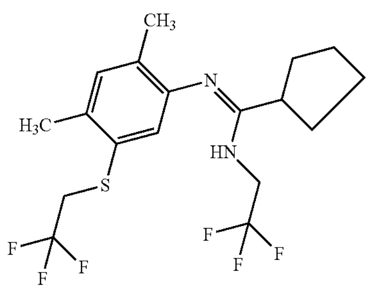 [SMILES: Cc1cc(C)c(SCC(F)(F)F)cc1/N=C(\NCC(F)(F)F)C1CCCC1] | 1H-NMR (D6-DMSO): 7.01 (s, 1H), 6.89 (t, 1H), 6.63 (s, 1H), 4.10-4.02 (m, 2H), 3.77 (q, 2H), 2.50 (m, 1H), 2.29 (s, 3H), 1.92 (s, 3H), 1.67-1.63 (m, 6H), 1.36-1.35 (m, 2H) |
| Ia-242 | 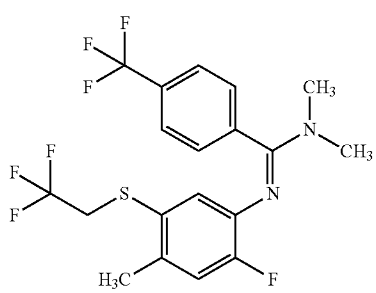 [SMILES: Cc1cc(F)c(/N=C(\c2ccc(C(F)(F)F)cc2)N(C)C)cc1SCC(F)(F)F] | 1H-NMR (D6-DMSO): 7.65 (d, 2H), 7.38 (d, 2H), 6.84 (d, 1H), 6.73 (d, 1H), 3.53 (q, 2H), 3.11 (broad, 3H), 2.73 (broad, 3H), 2.17 (s, 3H) |
| Ia-243 | 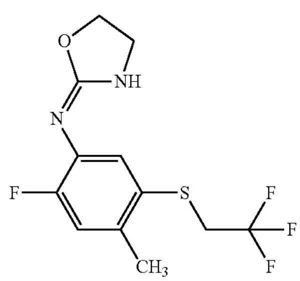 [SMILES: Cc1cc(F)c(/N=C2\NCCO2)cc1SCC(F)(F)F] | 1H-NMR (D6-DMSO): 7.65 (s, 1H), 7.20 (s, 1H), 7.03-7.01 (m, 1H), 4.36 (t, 2H), 3.80 (q, 2H), 3.50 (broad, 2H), 2.31 (s, 3H) |

-continued

| Example number | Structure | Analytical data |
|---|---|---|
| Ia-244 | 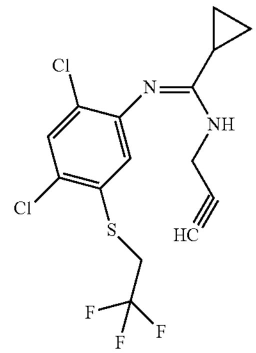 [SMILES: C#CCN/C(=N\c1cc(SCC(F)(F)F)c(Cl)cc1Cl)C1CC1] | 1H-NMR (D6-DMSO): 8.04 (s, 1H), 7.95 (s, 1H), 6.63 (s, 1H), 4.32 (q, 2H), 1.88 (s, 2H), 1.41-1.34 (m, 1H), 0.83-0.67 (m, 4H) |
| Ia-245 | 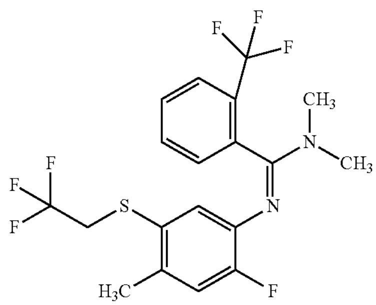 [SMILES: Cc1cc(F)c(/N=C(\c2ccccc2C(F)(F)F)N(C)C)cc1SCC(F)(F)F] | 1H-NMR (D6-DMSO): 7.68-7.60 (m, 2H), 7.54-7.49 (m, 1H), 7.40 (d, 1H), 6.85 (d, 1H), 6.66 (d, 1H), 3.55-3.43 (m, 2H), 3.12 (broad, 3H), 2.63 (broad, 3H), 2.17 (s, 3H) |
| Ia-247 | 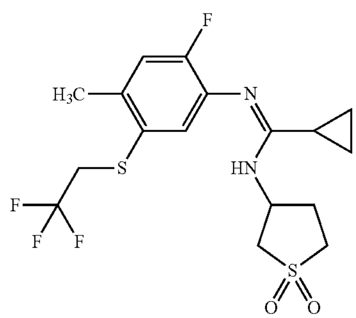 [SMILES: Cc1cc(F)c(/N=C(\NC2CCS(=O)(=O)C2)C2CC2)cc1SCC(F)(F)F] | 1H-NMR (D6-DMSO): 7.09-7.04 (m, 2H), 6.40-6.39 (m, 1H), 4.60-4.55 (m, 1H), 3.84 (q, 2H), 3.49-2.04 (m, 6H), 1.37-1.36 (m, 1H), 0.86-0.83 (m, 2H), 0.65-0.61 (m, 2H) |
| Ia-248 | 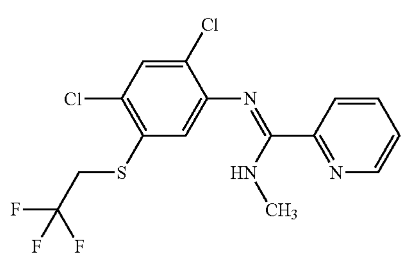 [SMILES: CN/C(=N\c1cc(SCC(F)(F)F)c(Cl)cc1Cl)c1ccccn1] | 1H-NMR (D6-DMSO): 8.56-8.55 (m, 1H), 7.79-7.75 (m, 2H), 7.47 (s, 1H), 7.42-7.39 (m, 2H), 6.86 (s, 1H), 3.89 (q, 2H), 2.81 (d, 3H) |
| Ia-249 | 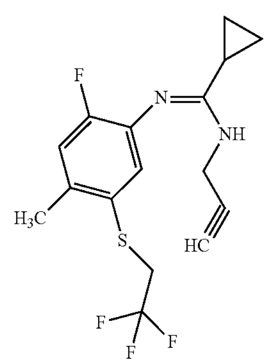 [SMILES: C#CCN/C(=N\c1cc(SCC(F)(F)F)c(C)cc1F)C1CC1] | 1H-NMR (D6-DMSO): 7.74-7.72 (m, 1H), 7.50-7.48 (m, 1H), 6.61 (s, 1H), 4.08 (q, 2H), 2.44 (s, 3H), 1.91 (s, 3H), 1.46-1.40 (m, 1H), 0.82-0.68 (m, 4H) |

-continued

| Example number | Structure | Analytical data |
|---|---|---|
| Ia-250 | 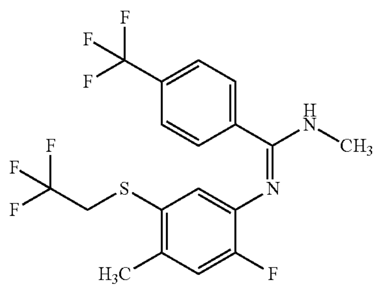 [SMILES: CN/C(=N/c1cc(SCC(F)(F)F)c(C)cc1F)c1ccc(C(F)(F)F)cc1] | 1H-NMR (D6-DMSO): 7.64 (d, 2H), 7.46 (d, 1H), 7.39 (d, 2H), 6.88 (d, 1H), 7.76 (d, 1H), 3.53 (q, 2H), 2.89 (d, 3H), 2.20 (s, 3H), |
| Ia-251 | 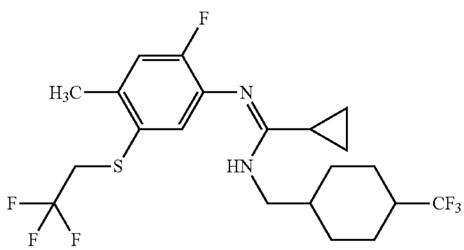 [SMILES: Cc1cc(F)c(/N=C(\NCC2CCC(C(F)(F)F)CC2)C2CC2)cc1SCC(F)(F)F] | logP(HCOOH) = 2.23 |
| Ia-252 | 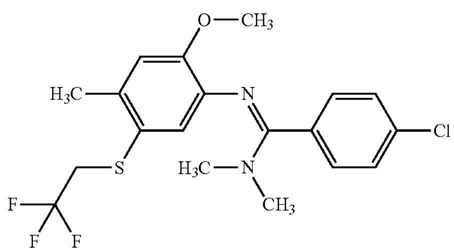 [SMILES: COc1cc(C)c(SCC(F)(F)F)cc1/N=C(/c1ccc(Cl)cc1)N(C)C] | 1H-NMR (D6-DMSO): 7.29-7.27 (m, 2H), 7.10-7.08 (m, 2H), 6.59 (m, 2H), 3.60 (s, 3H), 3.46 (q, 2H), 2.87 (broad, 6H), 2.22 (s, 3H) |
| Ia-253 | 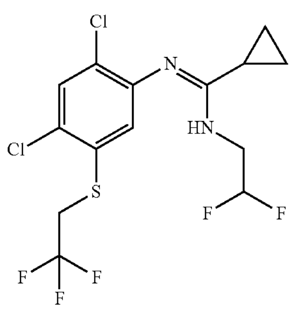 [SMILES: FC(F)CN/C(=N\c1cc(SCC(F)(F)F)c(Cl)cc1Cl)C1CC1] | 1H-NMR (D6-DMSO): 7.59 (s, 1H), 7.14 (s, 1H), 6.85 (broad, 1H), 6.20 (tt, 1H), 4.11 (q, 2H), 3.57-3.47 (m, 2H), 1.34 (m, 1H), 0.86-0.82 (m, 2H), 0.69-0.64 (m, 2H) |
| Ia-254 | 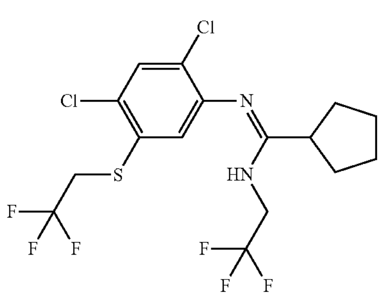 [SMILES: FC(F)(F)CN/C(=N\c1cc(SCC(F)(F)F)c(Cl)cc1Cl)C1CCCC1] | 1H-NMR (D6-DMSO): 7.58 (s, 1H), 7.27 (broad, 1H), 6.96 (s, 1H), 4.14-4.02 (m, 4H), 2.46-2.44 (m, 1H), 1.67-1.63 (m, 6H), 1.39-1.38 (m, 2H) |

-continued

| Example number | Structure | Analytical data |
|---|---|---|
| Ia-255 | 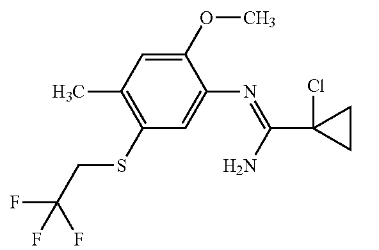 [SMILES: COc1cc(C)c(SCC(F)(F)F)cc1/N=C(\N)C1(Cl)CC1] | 1H-NMR (D6-DMSO): 6.87 (s, 1H), 6.81 (s, 1H), 5.98 (broad, 2H), 3.72 (q, 2H), 3.69 (s, 3H), 2.37 (s, 3H), 1.57-1.54 (m, 2H), 1.27-1.24 (m, 2H) |
| Ia-256 | 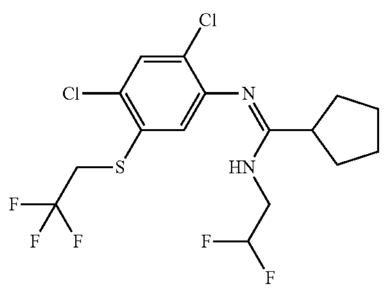 [SMILES: FC(F)CN/C(=N\c1cc(SCC(F)(F)F)c(Cl)cc1Cl)C1CCCC1] | 1H-NMR (D6-DMSO): 7.58 (s, 1H), 7.23 (broad, 1H), 7.04 (s, 1H), 6.23 (tt, 1H), 4.12 (q, 2H), 3.62-3.52 (m, 2H), 2.45-2.41 (m, 1H), 1.68-1.60 (m, 6H), 1.39-1.37 (m, 2H) |
| Ia-257 | 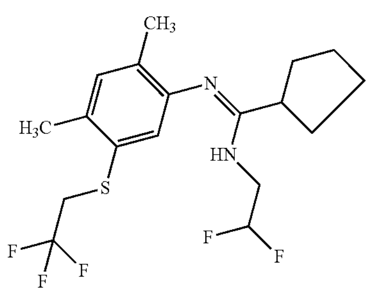 [SMILES: Cc1cc(C)c(SCC(F)(F)F)cc1/N=C(\NCC(F)F)C1CCCC1] | 1H-NMR (D6-DMSO): 7.00 (s, 1H), 6.79 (broad, 1H), 6.68 (s, 1H), 6.16 (tt, 1H), 3.78 (q, 2H), 3.57 (m, 2H), 2.49 (m, 1H), 2.28 (s, 3H), 1.93 (s, 3H), 1.68-1.61 (m, 6H), 1.35-1.34 (m, 2H) |
| Ia-258 | 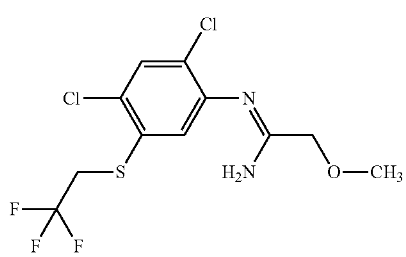 [SMILES: COC/C(N)=N/c1cc(SCC(F)(F)F)c(Cl)cc1Cl] | 1H-NMR (D6-DMSO): 7.56 (s, 1H), 7.05 (s, 1H), 6.32 (broad, 2H), 4.09 (q, 2H), 3.98-3.96 (m, 2H), 3.33 (s, 3H) |
| Ia-259 | 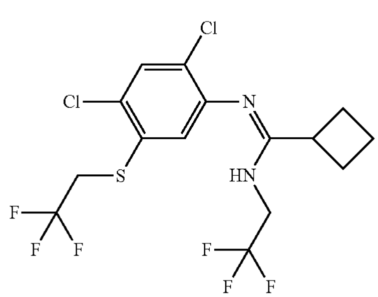 [SMILES: FC(F)(F)CN/C(=N\c1cc(SCC(F)(F)F)c(Cl)cc1Cl)C1CCC1] | 1H-NMR (D6-DMSO): 7.55 (s, 1H), 7.34 (broad, 1H), 6.99 (s, 1H), 4.14-4.02 (m, 4H), 3.26-3.17 (m, 1H), 2.12-1.56 (m, 6H) |

-continued
| Example number | Structure | Analytical data |
|---|---|---|
| Ia-260 | 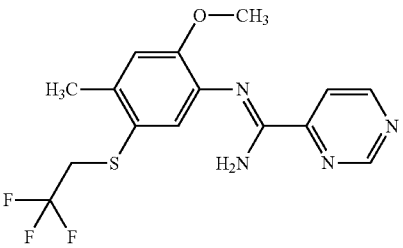 [SMILES: COc1cc(C)c(SCC(F)(F)F)cc1/N=C(\N)c1ccncn1] | 1H-NMR (D6-DMSO): 9.30-9.29 (m, 1H), 8.97-8.96 (m, 1H), 8.26-8.25 (m, 1H), 7.01 (s, 1H), 6.96 (s, 1H), 6.60 (broad, H), 3.75 (q, 2H), 3.73 (s, 3H), 2.42 (s, 3H) |
| Ia-261 | 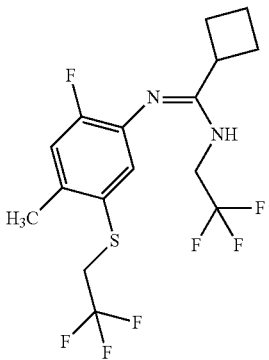 | 1H-NMR (D6-DMSO): 7.22 (t, 1H), 7.06-7.03 (m, 1H), 6.90-6.88 (m, 1H), 4.10-4.01 (m, 2H), 3.82 (q, 2H), 3.20-3.16 (m, 1H), 2.32 (s, 3H), 2.11-2.06 (m, 2H), 1.79-1.59 (m, 4H) |
| Ia-262 | 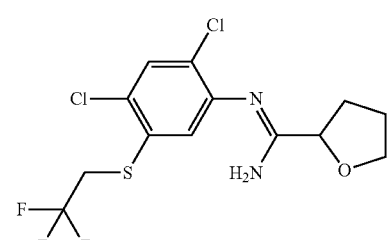 | 1H-NMR (D6-DMSO): 7.56 (s, 1H), 7.06 (s, 1H), 6.26 (broad, 2H), 4.39 (m, 1H), 4.09 (q, 2H), 3.98-3.92 (m, 1H), 3.77-3.75 (m, 1H), 2.17-2.08 (m, 2H), 1.92-1.86 (m, 2H) |
| Ia-263 | 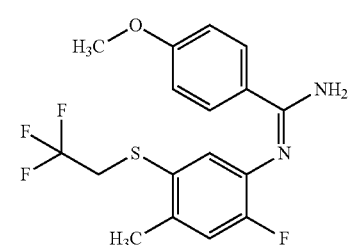 | 1H-NMR (D6-DMSO): 7.94 (d, 2H), 7.13-7.07 (m, 2H), 6.97 (d, 2H), 6.44 (broad, 2H), 3.86 (q, 2H), 3.81 (s, 3H), 2.35 (s, 3H) |
| Ia-264 | 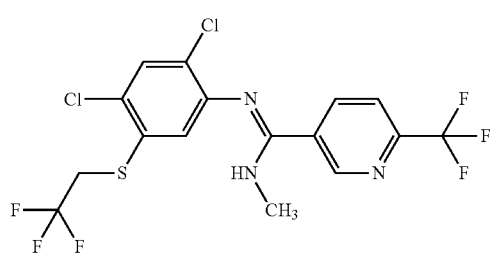 [SMILES: CN/C(=N\c1cc(SCC(F)(F)F)c(Cl)cc1Cl)c1ccc(C(F)(F)F)nc1] | 1H-NMR (D6-DMSO): 8.59 (s, 1H), 7.88-7.82 (m, 3H), 7.48 (s, 1H), 6.91 (s, 1H), 3.87 (q, 2H), 2, 93 (d, 3H) |

-continued

| Example number | Structure | Analytical data |
|---|---|---|
| Ia-265 | 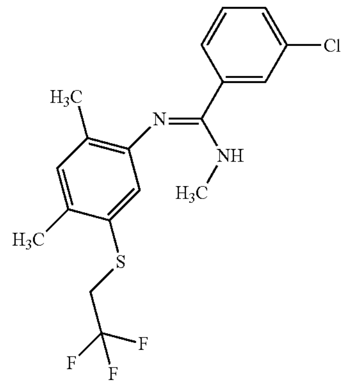 [SMILES: CN/C(=N\c1cc(SCC(F)(F)F)c(C)cc1C)c1cccc(Cl)c1] | 1H-NMR (D6-DMSO): 7.34-7.01 (m, 5H), 6.89 (s, 1H), 6.41 (s, 1H), 3.39 (q, 2H), 2.86 (broad, 3H), 2.18 (s, 3H), 2.07 (s, 3H) |
| Ia-266 | 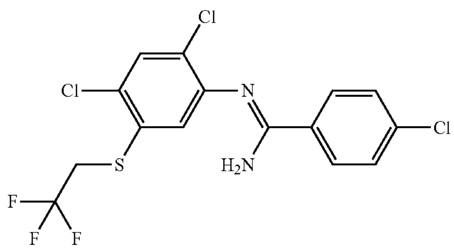 | 1H-NMR (D6-DMSO): 8.03-7.99 (m, 2H), 7.62 (s, 1H), 7.53-7.51 (m, 2H), 7.15 (s, 1H), 6.75 (broad, 2H), 4.13 (q, 2H) |
| Ia-267 | 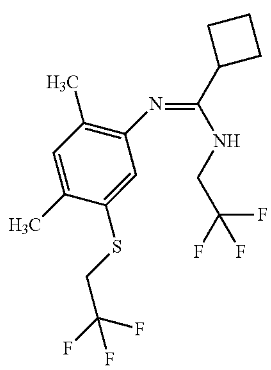 [SMILES: Cc1cc(C)c(SCC(F)(F)F)cc1/N=C(\NCC(F)(F)F)C1CCC1] | 1H-NMR (D6-DMSO): 7.02 (t, 1H), 6.98 (s, 1H), 6.63 (s, 1H), 4.11-4.02 (m, 2H), 3.78 (q, 2H), 3.14 (m, 1H), 2.28 (s, 3H), 2.12-2.04 (m, 2H), 1.91 (s, 3H), 1.75-1.59 (m, 4H) |
| Ia-268 | 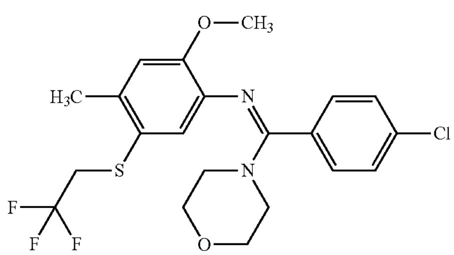 [SMILES: COc1cc(C)c(SCC(F)(F)F)cc1/N=C(/c1ccc(Cl)cc1)N1CCOCC1] | 1H-NMR (D6-DMSO): 7.30-7.28 (m, 2H), 7.14-7.11 (m, 2H), 6.64-6.62 (m, 2H), 3.63 (m, 6H), 3.59 (s, 3H), 3.48 (q, 2H), 3.34-3.29 (broad, 2H) 2.23 (s, 3H) |
| Ia-269 | 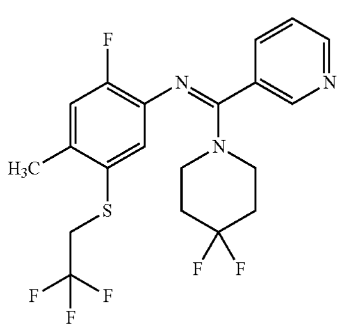 [SMILES: Cc1cc(F)c(/N=C(/c2cccnc2)N2CCC(F)(F)CC2)cc1SCC(F)(F)F] | 1H-NMR (D6-DMSO): 8.48-8.46 (m, 1H), 8.40-8.39 (m, 1H), 7.67-7.65 (m, 1H), 7.33-7.30 (m, 1H), 6.90-6.83 (m, 2H), 3.66 (q, 2H), 3.59-3.49 (m, 4H), 2.18 (s, 3H), 2.15-2.06 (m, 4H) |

| Example number | Structure | Analytical data |
|---|---|---|
| Ia-270 | 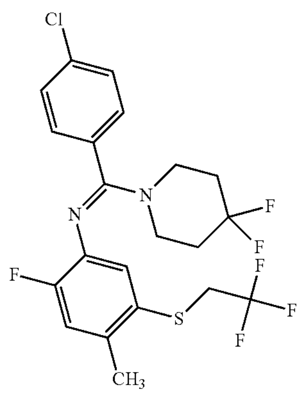 [SMILES: Cc1cc(F)c(/N=C(/c2ccc(Cl)cc2)N2CCC(F)(F)CC2)cc1SCC(F)(F)F] | 1H-NMR (D6-DMSO): 7.37-7.35 (m, 2H), 7.25-7.23 (m, 2H), 6.87-6.82 (m, 2H), 3.61 (q, 2H), 3.47 (m, 4H), 2.19 (s, 3H), 2.03 (m, 4H) |
| Ia-271 | 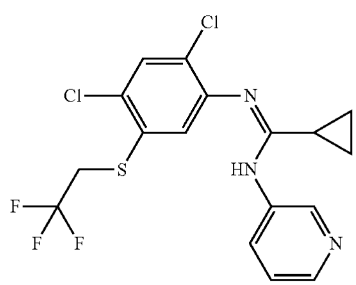 [SMILES: FC(F)(F)CSc1cc(/N=C(\Nc2cccnc2)C2CC2)c(Cl)cc1Cl] | 1H-NMR (D6-DMSO): 8.14 (m, 1H), 8.02 (m, 1H), 7.86-7.83 (m, 2H), 7.23-7.22 (m, 1H), 7.15-7.14 (m, 1H), 4.26-4.18 (m, 2H), 1.52 (m, 1H), 1.28 (m, 2H), 0.85-0.83 (m, 2H) |
| Ia-272 | 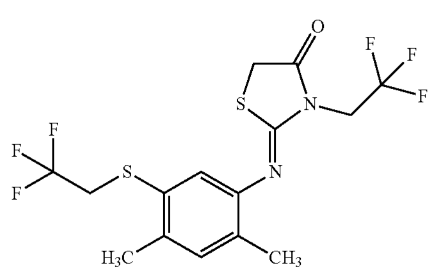 [SMILES: Cc1cc(C)c(SCC(F)(F)F)cc1/N=C1\SCC(=O)N1CC(F)(F)F] | 1H-NMR (D6-DMSO): 7.17 (s, 1H), 7.00 (s, 1H), 4.59 (q, 2H), 4.18 (s, 2H), 3.81 (q, 2H), 2.33 (s, 3H), 2.04 (s, 3H) |
| Ia-273 | 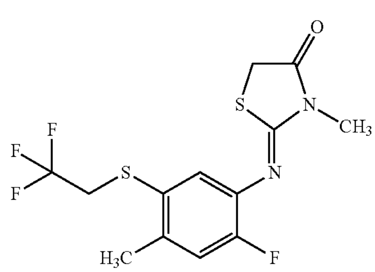 [SMILES: Cc1cc(F)c(/N=C2\SCC(=O)N2C)cc1SCC(F)(F)F] | 1H-NMR (D6-DMSO): 7.26-7.23 (m, 2H), 4.09 (s, 2H), 3.87 (q, 2H), 3.17 (s, 3H), 2.37 (s, 3H) |

| Example number | Structure | Analytical data |
|---|---|---|
| Ia-274 | 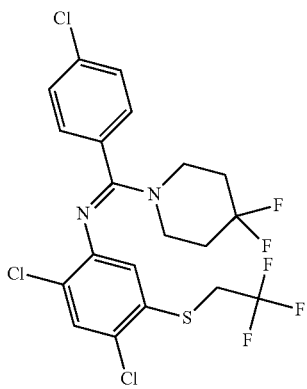 [SMILES: FC(F)(F)CSc1cc(/N=C(/c2ccc(Cl)cc2)N2CCC(F)(F)CC2)c(Cl)cc1Cl] | 1H-NMR (D6-DMSO): 7.44 (m, 1H), 7.39-7.37 (m, 2H), 7.28-7.26 (m, 2H), 6.92 (s, 1H), 3.90-3.83 (q, 2H), 3.60 (m, 4H), 2.06 (m, 4H) |
| Ia-275 | 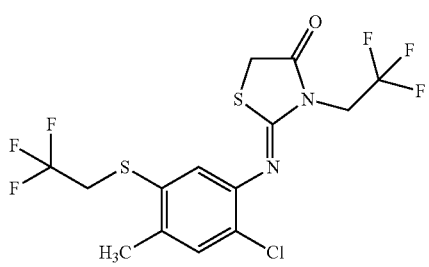 | 1H-NMR (D6-DMSO): 7.47 (s, 1H), 7.20 (s, 1H), 4.60 (q, 2H), 4.25 (s, 2H), 3.94 (q, 2H), 2.35 (s, 3H) |
| Ia-276 | 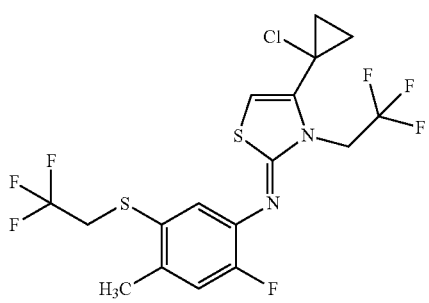 | 1H-NMR (D6-DMSO): 7.24-7.19 (m, 2H), 6.72 (s, 1H), 4.93 (q, 2H), 3.86 (q, 2H), 2.36 (s, 3H), 1.52-1.44 (m, 4H) |
| Ia-277 | 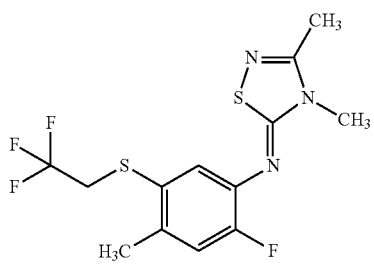 [SMILES: Cc1cc(F)c(/N=c2\snc(C)n2C)cc1SCC(F)(F)F] | 1H-NMR (D6-DMSO): 7.24-7.19 (m, 2H), 3.86 (q, 2H), 3.44 (s, 3H), 2.36 (s, 6H) |
| Ia-278 | 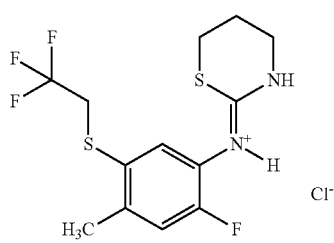 [SMILES: Cc1cc(F)c(/[NH+]=C2/NCCCS2)cc1SCC(F)(F)F ; [Cl-]] | 1H-NMR (D6-DMSO): 7.65-7.64 (m, 1H), 7.42-7.40 (m, 1H), 4.02-3.96 (q, 2H), 3.45 (t, 2H), 3.41 (broad, 1H), 3.27 (t, 2H), 2.41 (s, 3H), 2.09-2.05 (m, 2H) |

-continued
| Example number | Structure | Analytical data |
|---|---|---|
| Ia-279 | 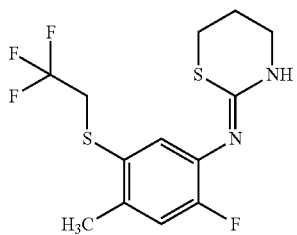 [SMILES: Cc1cc(F)c(/N=C2/NCCCS2)cc1SCC(F)(F)F] | 1H-NMR (D6-DMSO): 7.55 (broad, 1H), 7.05 (s, 1H), 7.02 (s, 1H), 3.83-3.75 (q, 2H), 3.26-3.23 (m, 2H), 2.97-2.94 (m, 2H), 2.31 (s, 3H), 1.96-1.90 (m, 2H). |
| Example number | Structure | Analytical data |
|---|---|---|
| Ib-17 | 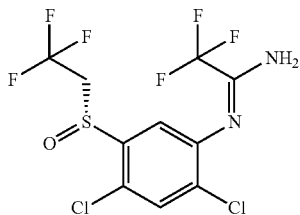 [SMILES: N/C(=N/c1cc([S@](=O)CC(F)(F)F)c(Cl)cc1Cl)C(F)(F)F] | 1H-NMR(D6-DMSO): 7.87(s, 1H), 7.54(broad, 2H), 7.33(s, 1H), 4.18-4.10(m, 2H) |
| Ib-18 | 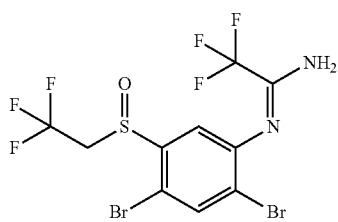 [SMILES: N/C(=N/c1cc(S(=O)CC(F)(F)F)c(Br)cc1Br)C(F)(F)F] | 1H-NMR(D6-DMSO): 8.10(s, 1H), 7.80-7.30(broad, 1H), 7.29(s, 1H), 4.16-4.05(m, 2H) |
| Ib-19 | 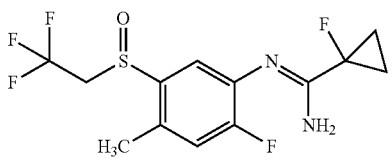 [SMILES: Cc1cc(F)c(/N=C(\N)C2(F)CC2)cc1S(=O)CC(F)(F)F] | 1H-NMR(D6-DMSO): 7.29-7.27(m, 1H), 7.18-7.15(m, 1H), 6.74(broad, 2H), 4.06-3.98(m, 2H), 2.30(s, 3H), 1.39-1.29(m, 4H) |
| Ib-20 | 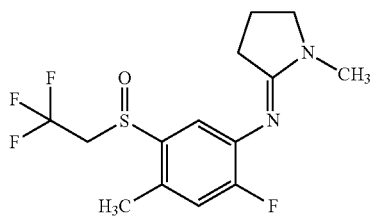 [SMILES: Cc1cc(F)c(/N=C2\CCCN2C)cc1S(=O)CC(F)(F)F] | 1H-NMR(D6-DMSO): 7.27(d, 1H), 7.14(d, 1H), 4.09-3.98(m, 2H), 3.34-3.33(m, 2H), 2.90(s, 3H), 2.38-2.22(m, 5H), 1.93-1.88(m, 2H) |
| Ib-21 | 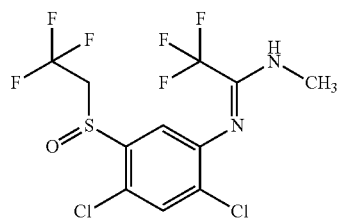 [SMILES: CN/C(=N/c1cc(S(=O)CC(F)(F)F)c(Cl)cc1Cl)C(F)(F)F] | logP(HCOOH) = 3.32, logP(neutral = 3.32) |

-continued

| Example number | Structure | Analytical data |
|---|---|---|
| Ib-22 | 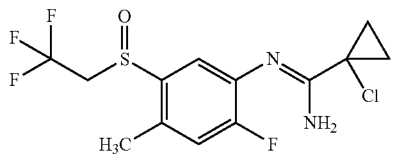 [SMILES: Cc1cc(F)c(/N=C(\N)C2(Cl)CC2)cc1S(=O)CC(F)(F)F] | 1H-NMR(D6DMSO): 7.27-7.24(m, 1H), 7.19-7.16(m, 1H), 6.57(broad, 2H), 4.05-3.97(m, 2H), 2.31(s, 3H), 1.57(m, 2H), 1.31-1.28(m, 2H) |
| Ib-23 | 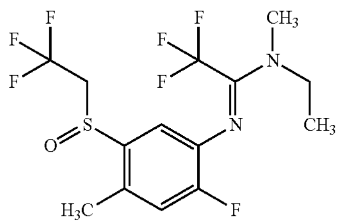 [SMILES: CCN(C)/C(=N/c1cc(S(=O)CC(F)(F)F)c(C)cc1F)C(F)(F)F] | 1H-NMR(D6-DMSO): 7.28(d, 1H), 7.21(d, 1H), 4.14-3.98(m, 2H), 3.48-3.43(m, 2H), 2.97(s, 3H), 2.31(s, 3H), 1.15(t, 3H) |
| Ib-24 | 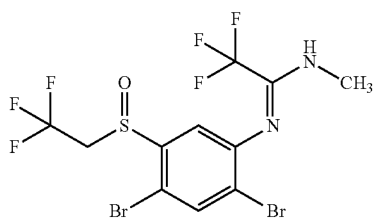 | 1H-NMR(D6-DMSO): 8.41(broad, 1H), 8.04(s, 1H), 7.27(s, 1H), 4.25-4.02(m, 2H), 2.66(broad, 3H) |
| Ib-25 | 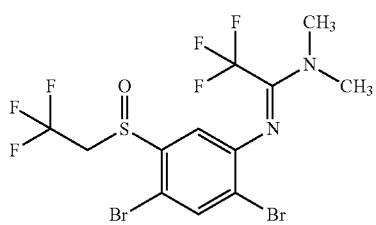 | 1H-NMR(D6-DMSO): 8.03(s, 1H), 7.22(s, 1H), 4.23-4.05(m, 2H), 3.03(broad, 3H) and 3H under the DMSO peak |
| Ib-26 | 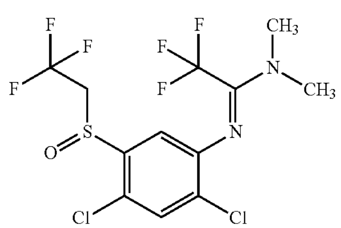 [SMILES: CN(C)/C(=N/c1cc(S(=O)CC(F)(F)F)c(Cl)cc1Cl)C(F)(F)F] | 1H-NMR(D6-DMSO): 7.83(s, 1H), 7.25(s, 1H), 4.16-4.12(m, 1H), 4.27-4.21(m, 1H), 3.04(s, 6H) |
| Ib-27 | 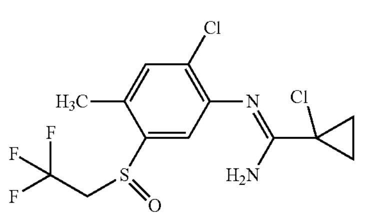 [SMILES: Cc1cc(Cl)c(/N=C(\N)C2(Cl)CC2)cc1S(=O)CC(F)(F)F] | 1H-NMR(D6-DMSO): 7.41(m, 1H), 7.23(m, 1H), 6.53(broad, 2H), 4.06-3.97(m, 2H), 2.29(s, 3H), 1.62-1.59(m, 2H), 1.32-1.29(m, 2H) |
| Ib-28 | 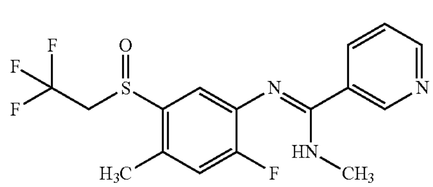 | 1H-NMR(D6-DMSO): 8.50-8.49(m, 1H), 8.38(broad, 1H), 7.66-7.60(m, 2H), 7.34-7.31(m, 1H), 7.16-7.14(m, 1H), 6.96-6.93(m, 1H), 3.97-3.88(m, 1H), 3.76-3.70(m, 1H), 2.91-2.90(d, 3H), 2.20(s, 3H) |

-continued

| Example number | Structure | Analytical data |
|---|---|---|
| Ib-29 | 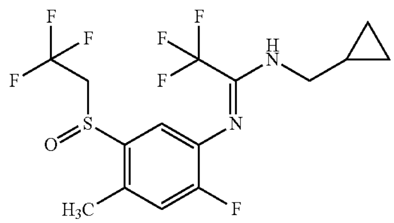 [SMILES: Cc1cc(F)c(/N=C(/NCC2CC2)C(F)(F)F)cc1S(=O)CC(F)(F)F] | 1H-NMR(D6-DMSO): 8.40(s, broad, 1H), 7.28(d, 1H), 7.21(d, 1H), 4.15-4.06(m, 1H), 4.00-3.94(m, 1H), 3.08(s, broad, 2H), 2.31(s, 3H), 1.09(s, broad, 1H), 0.46-0.44(m, 2H), 0.22(s, broad, 2H) |
| Ib-30 | 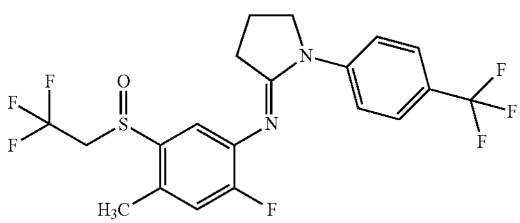 [SMILES: Cc1cc(F)c(/N=C2\CCCN2c2ccc(C(F)(F)F)cc2)cc1S(=O)CC(F)(F)F] | 1H-NMR(D6-DMSO): 8.12(d, 2H), 7.73(d, 2H), 7.41(d, 1H), 7.26(d, 1H), 4.15-4.05(m, 2H), 3.96(t, 2H), 2.69-2.50(m, 4H), 2.34(s, 3H), 2.09-2.02(m, 2H) |
| Ib-31 | 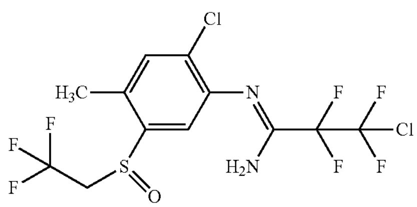 [SMILES: Cc1cc(Cl)c(/N=C(\N)C(F)(F)C(F)(F)Cl)cc1S(=O)CC(F)(F)F] | 1H-NMR(D6-DMSO): 7.50(s, 1H), 7.40(broad, 2H), 7.28(s, 1H), 4.10-4.02(q, 2H), 2.32(s, 3H) |
| Ib-32 | 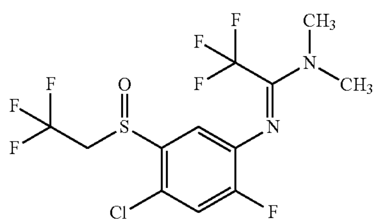 | 1H-NMR(D6-DMSO): 7.68(d, 1H), 7.32(d, 1H), 4.28-4.10(m, 2H), 3.05(s, 6H) |
| Ib-33 | 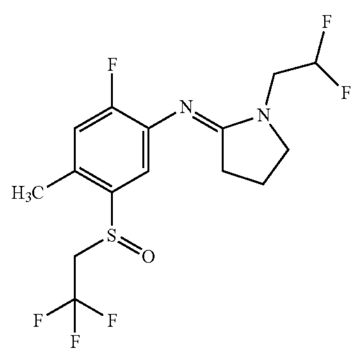 [SMILES: Cc1cc(F)c(/N=C2\CCCN2CC(F)F)cc1S(=O)CC(F)(F)F] | 1H-NMR(D6-DMSO): 7.33-7.31(m, 1H), 7.19-7.16(m, 1H), 6.26(tt, 1H), 4.12-3.98(m, 2H), 3.87-3.78(dt, 2H), 3.52-3.48(m, 2H), 2.35(m, 2H), 2.30(s, 3H), 1.98-1.90(m, 2H) |
| Ib-34 | 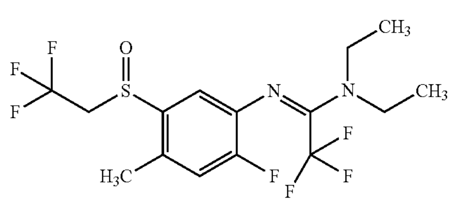 [SMILES: CCN(CC)/C(=N/c1cc(S(=O)CC(F)(F)F)c(C)cc1F)C(F)(F)F] | 1H-NMR(D6-DMSO): 7.27(d, 1H), 7.21(d, 1H), 4.15-3.98(m, 2H), 3.45-3.40(m, 4H), 2.30(s, 3H), 1.18-1.14(m, 6H) |

-continued

| Example number | Structure | Analytical data |
|---|---|---|
| Ib-35 | 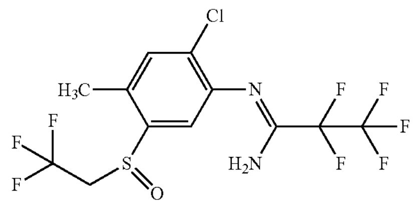 [SMILES: Cc1cc(Cl)c(/N=C(\N)C(F)(F)C(F)(F)F)cc1S(=O)CC(F)(F)F] | 1H-NMR (D6-DMSO): 7.51(s, 1H), 7.45(broad, 2H), 7.29(s, 1H), 4.11-4.01(m, 2H), 2.32(s, 3H) |
| Ib-36 | 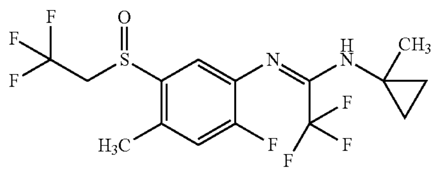 [SMILES: Cc1cc(F)c(/N=C(/NC2(C)CC2)C(F)(F)F)cc1S(=O)CC(F)(F)F] | 1H-NMR(D6-DMSO): 8.48(s, 1H), 7.30(d, 1H), 7.21(d, 1H), 4.15-3.95(m, 2H), 2.31(s, 3H), 1.33-1.24(m, 3H), 0.77(s, 2H), 0.57(s, 2H) |
| Ib-37 | 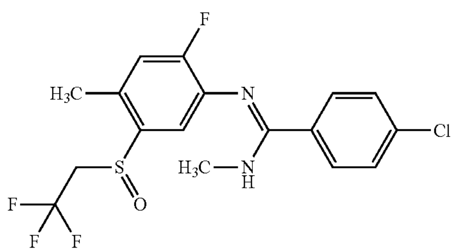 [SMILES: CN/C(=N\c1cc(S(=O)CC(F)(F)F)c(C)cc1F)c1ccc(Cl)cc1] | 1H-NMR(D6-DMSO): 7.52(broad, 1H), 7.37-7.35(m, 2H), 7.22-7.20(m, 2H), 7.06-7.04(m, 1H), 6.97-6.95(m, 1H), 3.92-3.83(m, 1H), 3.64-3.58(m, 1H), 2.89-2.88(d, 3H), 2.20(s, 3H) |
| Ib-38 | 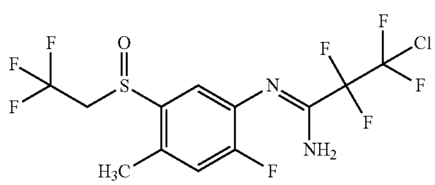 [SMILES: Cc1cc(F)c(/N=C(\N)C(F)(F)C(F)(F)Cl)cc1S(=O)CC(F)(F)F] | 1H-NMR(D6-DMSO): 7.50(broad, 2H), 7.34-7.32(m, 1H), 7.28-7.25(m, 1H), 4.21-4.02(m, 2H), 2.34(s, 3H) |
| Ib-39 | 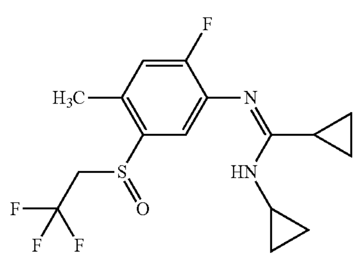 [SMILES: Cc1cc(F)c(/N=C(\NC2CC2)C2CC2)cc1S(=O)CC(F)(F)F] | 1H-NMR(D6-DMSO): 7.26-7.25(m, 1H), 7.13-7.11(m, 1H), 6.45(broad, 1H), 4.05-3.96(m, 2H), 2.29(s, 3H), 2.21-2.18(m, 1H), 1.87-1.84(m, 1H), 0.81-0.80(m, 2H), 0.66-0.54(m, 4H), 0.44(m, 2H) |
| Ib-40 | 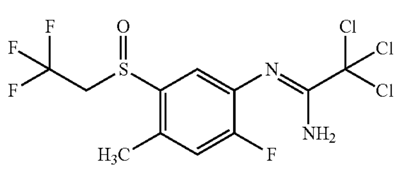 [SMILES: Cc1cc(F)c(/N=C(\N)C(Cl)(Cl)Cl)cc1S(=O)CC(F)(F)F] | 1H-NMR(D6-DMSO): 7.34-7.32(m, 1H), 7.29-7.26(m, 1H), 7.23(broad, 2H), 4.13-4.01(m, 2H), 2.34(s, 3H) |
| Ib-41 | 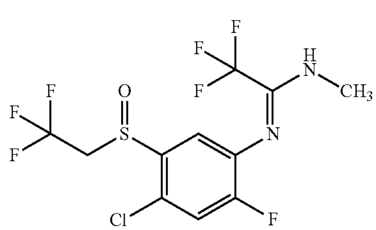 | 1H-NMR(D6-DMSO): 8.48(bs, 1H,), 7.68(d, 1H), 7.32(d, 1H), 4.28-4.05(m, 2H), 2.72(bs, 3H) |

| Example number | Structure | Analytical data |
|---|---|---|
| Ib-42 | 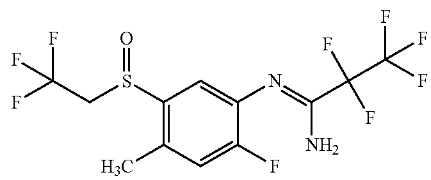 [SMILES: Cc1cc(F)c(/N=C(\N)C(F)(F)C(F)(F)F)cc1S(=O)CC(F)(F)F] | 1H-NMR(D6-DMSO): 7.55(broad, 2H), 7.35-7.33(m, 1H), 7.29-7.26(m, 1H), 4.12-4.01(m, 2H), 2.34(s, 3H) |
| Ib-43 | 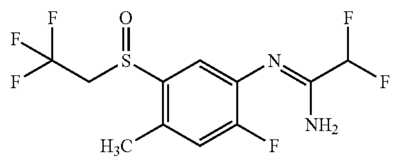 [SMILES: Cc1cc(F)c(/N=C(\N)C(F)F)cc1S(=O)CC(F)(F)F] | 1H-NMR(D6-DMSO): 8.22-8.20(m, 1H), 7.44-7.41(m, 1H), 6.49(tt, 1H), 4.21-3.93(m, 2H), 2.36(s, 3H) |
| Ib-44 | 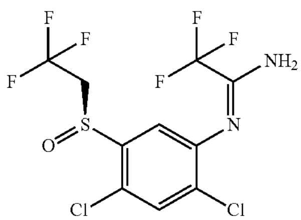 [SMILES: N/C(=N/c1cc([S@@](=O)CC(F)(F)F)c(Cl)cc1Cl)C(F)(F)F] | 1H-NMR(D6-DMSO): 7.87(s, 1H), 7.54(broad, 2H), 7.33(s, 1H), 4.18-4.10(m, 2H) |
| Ib-45 | 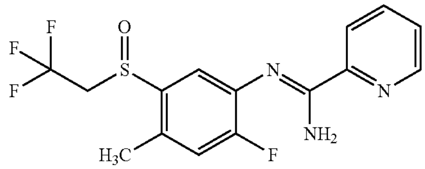 [SMILES: Cc1cc(F)c(/N=C(\N)c2ccccn2)cc1S(=O)CC(F)(F)F] | 1H-NMR(D6-DMSO): 8.66-8.65(m, 1H), 8.33-8.31(m, 1H), 8.00-7.95(m, 1H), 7.60-7.57(m, 1H), 7.46-7.44(m, H), 7.27-7.24(m, 1H), 6.95(broad, 2H), 4.11-4.03(q, 2H), 2.35(s, 3H) |
| Ib-46 | 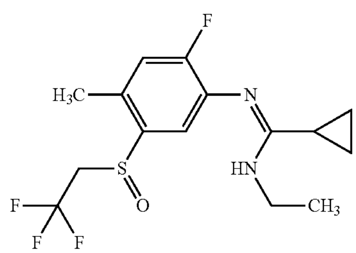 [SMILES: CCN/C(=N\c1cc(S(=O)CC(F)(F)F)c(C)cc1F)C1CC1] | 1H-NMR(D6-DMSO): 7.28-7.26(m, 1H), 7.15-7.12(m, 1H), 6.30(broad, 1H), 4.02(m, 2H), 3.19(m, 2H), 2.29(s, 3H), 1.90(m, 1H), 1.08(t, 3H), 0.85-0.81(m, 2H), 0.64-0.62(m, 2H) |
| Ib-47 | 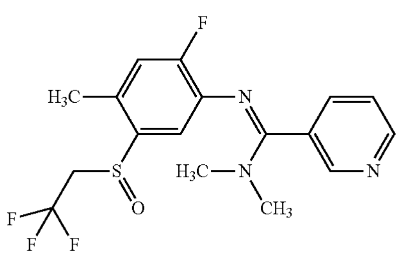 [SMILES: Cc1cc(F)c(/N=C(/c2cccnc2)N(C)C)cc1S(=O)CC(F)(F)F] | 1H-NMR(D6-DMSO): 8.48-8.46(m, 1H), 8.32(broad, 1H), 7.65(broad, 1H), 7.36-7.33(m, 1H), 7.07-7.05(m, 1H), 6.93-6.90(m, 1H), 3.92-3.83(m, 1H), 3.68-3.61(m, 1H), 3.13(broad, 3H), 281(broad, 3H), 2.16(s, 3H) |
| Ib-48 | 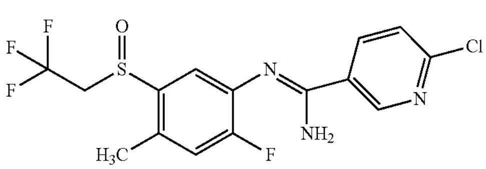 [SMILES: Cc1cc(F)c(/N=C(\N)c2ccc(Cl)nc2)cc1S(=O)CC(F)(F)F] | 1H-NMR(D6-DMSO): 8.96-8.95(m, 1H), 8.38-8.35(m, 1H), 7.65-7.63(m, 1H), 7.43-7.41(m, 1H), 7.27-7.24(m, 1H), 7.00(broad, 2H), 4.10-4.02(q, 2H), 2.35(s, 3H) |

-continued
| Example number | Structure | Analytical data |
|---|---|---|
| Ib-49 | 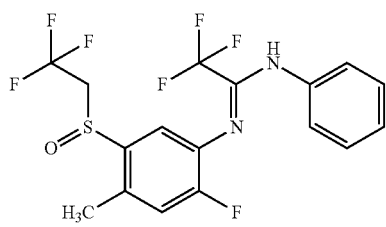 [SMILES: Cc1cc(F)c(/N=C(/Nc2ccccc2)C(F)(F)F)cc1S(=O)CC(F)(F)F] | logP(HCOOH) = 3.22, logP(neutral) = 3.12 |
| Ib-50 | 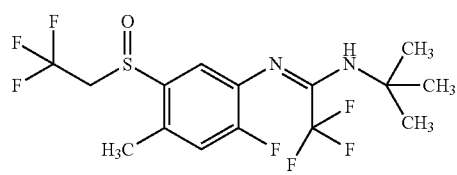 [SMILES: Cc1cc(F)c(/N=C(/NC(C)(C)C)C(F)(F)F)cc1S(=O)CC(F)(F)F] | 1H-NMR(D6-DMSO): 7.40(s, 1H), 7.25-7.19(m, 2H), 4.11-4.08(m, 1H), 4.00-3.97(m, 1H), 2.30(s, 3H), 1.42(s, 9H) |
| Ib-51 | 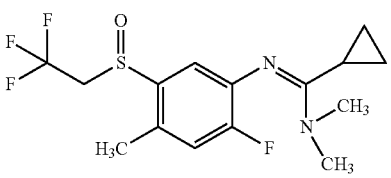 | 1H-NMR(D6-DMSO): 7.24-7.22(m, 1H), 7.11-7.08(m, 1H), 4.11-3.92(m, 2H), 3.08(s, 6H), 2.30(s, 3H), 1.66(m, 1H), 0.68-0.63(m, 2H), 0.32-0.30(m, 1H), 0.23-0.21(m, 1H) |
| Ib-52 | 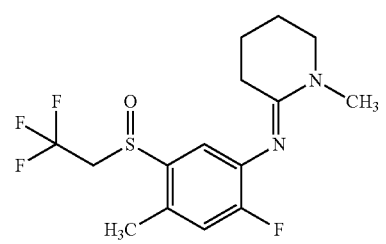 | 1H-NMR(D6-DMSO): 7.20(d, 1H), 7.13(d, 1H), 4.09-3.97(m, 2H), 3.32(s, 3H), 3.28(t, 2H), 2.22(s, 3H), 2.20-2.05(m, 2H), 1.78-1.72(m, 2H), 1.62-1.56(m, 2H) |
| Ib-53 | 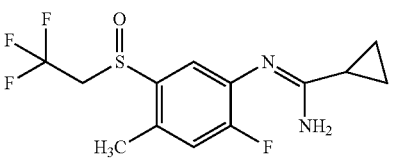 [SMILES: Cc1cc(F)c(/N=C(\N)C2CC2)cc1S(=O)CC(F)(F)F] | 1H-NMR(D6-DMSO): 7.15-7.12(m, 1H), 6.94-6.92(m, 1H), 4.06-3.88(m, 2H), 2.32(s, 3H), 1.55(m, 1H), 0.88-0.84(m, 2H), 0.74(m, 2H) |
| Ib-54 | 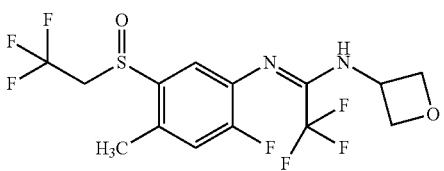 | 1H-NMR(D6-DMSO): 8.97(broad, 1H), 7.30-7.22(m, 2H), 4.77(broad, 2H), 4.59(broad, 3H), 4.19-4.07(m, 1H), 3.97(broad, 1H), 2.32(s, 3H) |
| Ib-55 | 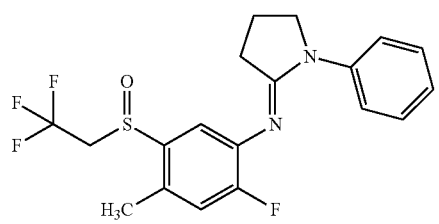 [SMILES: Cc1cc(F)c(/N=C2\CCCN2c2ccccc2)cc1S(=O)CC(F)(F)F] | 1H-NMR(D6-DMSO): 7.86(d, 2H), 7.37(m, 3H), 7.22(d, 1H), 7.09(dd, 1H), 4.14-4.02(m, 2H), 3.73(dd, 2H), 2.67-2.57(m, 2H), 2.33(s, 3H), 2.07-1.99(m, 2H) |

-continued

| Example number | Structure | Analytical data |
|---|---|---|
| Ib-56 | 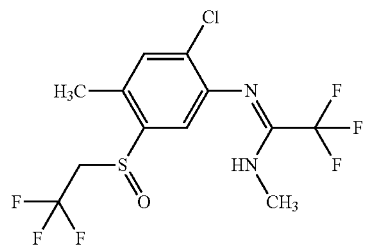 [SMILES: CN/C(=N\c1cc(S(=O)CC(F)(F)F)c(C)cc1Cl)C(F)(F)F] | 1H-NMR(D6-DMSO): 2.30(s, 3H), 2.62(broad, 3H), 4.17-3.95(m, 2H), 7.28(beit, 1H), 7.44(s, 1H), 8.22(broad, 1H) |
| Ib-57 | 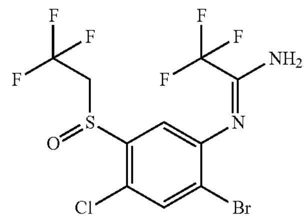 [SMILES: N/C(=N/c1cc(S(=O)CC(F)(F)F)c(Cl)cc1Br)C(F)(F)F] | 1H-NMR(D6-DMSO): 8.32(s, 1H), 7.40-7.36(broad, 1H), 7.29(s, 1H), 4.19-4.14(m, 2H) |
| Ib-58 | 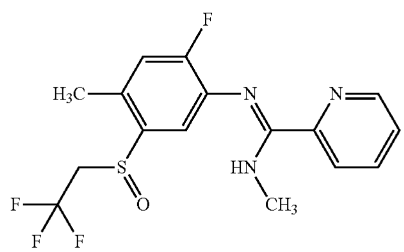 [SMILES: CN/C(=N\c1cc(S(=O)CC(F)(F)F)c(C)cc1F)c1ccccn1] | 1H-NMR(D6-DMSO): 8.56-8.55(m, 1H), 7.77-7.73(m, 1H), 7.69(broad, 1H), 7.41-7.38(m, 2H), 7.10-7.08(m, 1H), 7.02-6.99(m, 1H), 3.97-3.91(m, 1H), 3.73-3.67(m, 1H), 2.84-2.83(d, 3H), 2.23(s, 3H) |
| Ib-59 | 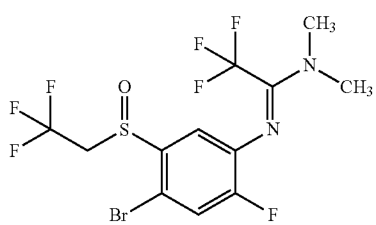 | 1H-NMR(D6-DMSO): 7.78(d, 1H), 7.32(d, 1H), 4.20-4.06(m, 2H), 3.05(s, 3H) |
| Ib-60 | 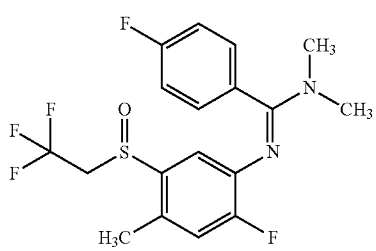 | 1H-NMR(D6-DMSO): 7.29-7.12(m, 4H), 6.97(d, 1H), 6.93(d, 1H), 3.88-3.79(m, 1H), 3.62-3.50(m, 1H), 3.11(broad, 3H), 2.79-2.77(broad, 3H), 2.17(s, 3H) |
| Ib-61 | 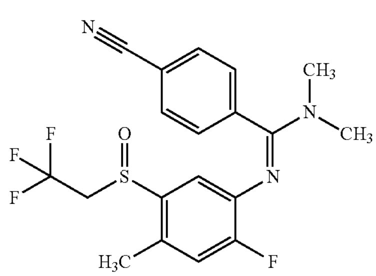 | 1H-NMR(D6-DMSO): 7.81-7.79(m, 2H), 7.46(broad, 1H), 7.29(broad, 1H), 6.98(d, 1H), 6.94(d, 1H), 3.88-3.79(m, 1H), 3.63-3.52(m, 1H), 3.14(broad, 3H), 2.76(broad, 3H), 2.16(s, 3H) |

| Example number | Structure | Analytical data |
|---|---|---|
| Ib-62 | 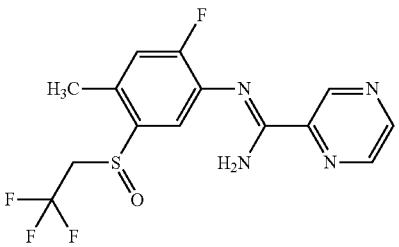 [SMILES: Cc1cc(F)c(/N=C(\N)c2cnccn2)cc1S(=O)CC(F)(F)F] | 1H-NMR(D6-DMSO): 9.46-9.45(m, 1H), 8.84(m, 1H), 8.74-8.73(m, 1H), 7.48-7.46(m, 1H), 7.29-7.26(m, 1H), 7.12(broad, 2H), 4.12-4.04(m, 2H), 2.36(s, 3H) |
| Ib-63 | 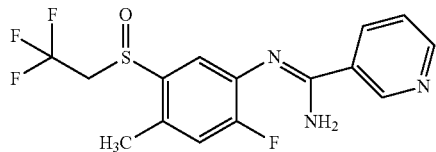 [SMILES: Cc1cc(F)c(/N=C(\N)c2cccnc2)cc1S(=O)CC(F)(F)F] | 1H-NMR(D6-DMSO): 9.13(s, 1H), 8.70-8.69(m, 1H), 8.32-8.30(m, 1H), 7.52-7.49(m, 1H), 7.43-7.41(m, 1H), 7.26-7.23(m, 1H), 6.94(broad, 2H), 4.11-4.03(m, 2H), 2.35(s, 3H) |
| Ib-64 | 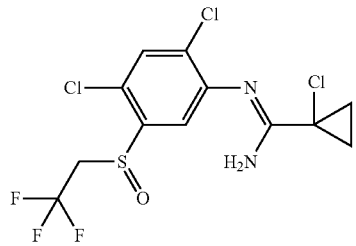 [SMILES: N/C(=N\c1cc(S(=O)CC(F)(F)F)c(Cl)cc1Cl)C1(Cl)CC1] | 1H-NMR(D6-DMSO): 7.84(m, 1H), 7.35(m, 1H), 6.85(broad, 2H), 4.16-4.08(m, 2H), 1.65(m, 2H), 1.37(m, 2H) |
| Ib-65 | 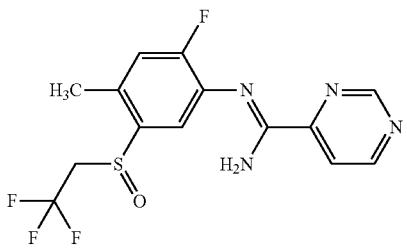 [SMILES: Cc1cc(F)c(/N=C(\N)c2ccncn2)cc1S(=O)CC(F)(F)F] | 1H-NMR(D6-DMSO): 9.34(m, 1H), 9.01-9.00(m, 1H), 8.28-8.27(m, 1H), 7.47-7.45(m, 1H), 7.29-7.25(m, 1H), 7.16(broad, 2H), 4.12-4.01(m, 2H), 2.36(s, 3H) |
| Ib-66 | 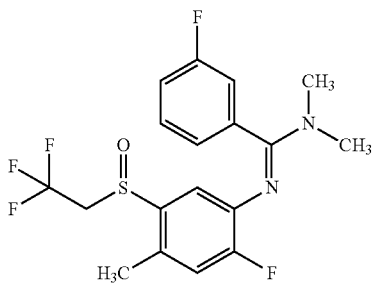 | 1H-NMR(D6-DMSO): 7.38-7.33(m, 1H), 7.15-7.10(m, 1H), 7.03(broad, 2H), 6.98-6.92(m, 2H), 3.89-3.82(m, 1H), 3.61-3.55(m, 1H), 3.12(broad, 3H), 2.83(broad, 3H), 2.17(s, 3H) |
| Ib-67 | 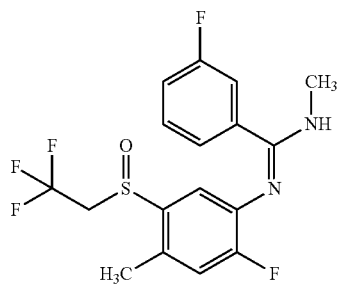 [SMILES: CN/C(=N/c1cc(S(=O)CC(F)(F)F)c(C)cc1F)c1cccc(F)c1] | 1H-NMR(D6-DMSO): 7.56-7.54(m, 1H), 7.36-7.30(m, 1H), 7.19-6.95(m, 5H), 3.94-3.85(m, 1H), 3.70-3.64(m, 1H), 2.89-2.88(m, 3H), 2.21(s, 3H) |

-continued

| Example number | Structure | Analytical data |
|---|---|---|
| Ib-68 | 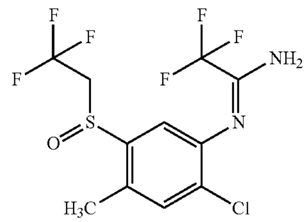 [SMILES: Cc1cc(Cl)c(/N=C(/N)C(F)(F)F)cc1S(=O)CC(F)(F)F] | 1H-NMR(D6-DMSO): 7.99(s, 1H), 7.63(broad, 2H), 7.32(s, 1H), 4.18-4.06(m, 2H) |
| Ib-69 | 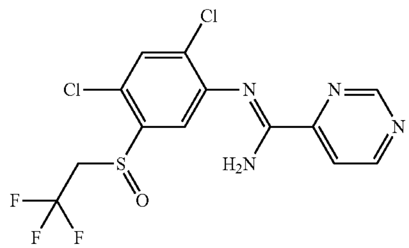 [SMILES: N/C(=N\c1cc(S(=O)CC(F)(F)F)c(Cl)cc1Cl)c1ccncn1] | 1H-NMR(D6-DMSO): 9.35(m, 1H), 9.03-9.02(m, 1H), 8.32-8.28(m, 1H), 7.87(s, 1H), 7.41(s, 1H), 7.08(broad, 2H), 4.19-4.11(m, 2H) |
| Ib-71 | 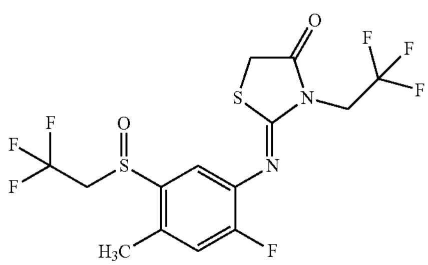 [SMILES: Cc1cc(F)c(/N=C2\SCC(=O)N2CC(F)(F)F)cc1S(=O)CC(F)(F)F] | 1H-NMR(D6-DMSO): 7.51(d, 1H), 7.38(d, 1H), 4.62-4.57(m, 2H), 4.26-4.14(m, 3H), 4.04-3.94(m, 1H), 2.36(s, 3H) |
| Ib-72 | 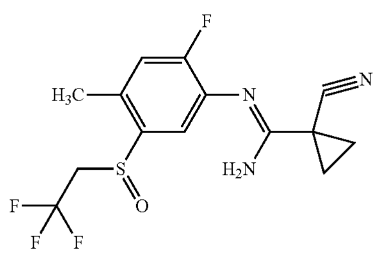 [SMILES: Cc1cc(F)c(/N=C(\N)C2(C#N)CC2)cc1S(=O)CC(F)(F)F] | 1H-NMR(D6-DMSO): 7.29-7.27(m, 1H), 7.21-7.18(m, 1H), 6.42(broad, 2H), 4.07-3.99(m, 2H), 2.32(s, 3H), 1.68-1.59(m, 4H) |
| Ib-73 | 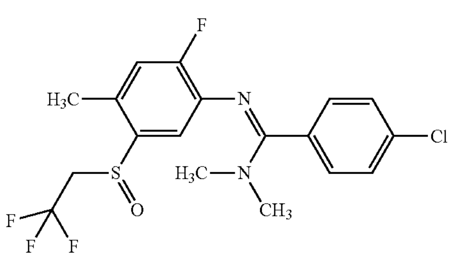 [SMILES: Cc1cc(F)c(/N=C(/c2ccc(Cl)cc2)N(C)C)cc1S(=O)CC(F)(F)F] | 1H-NMR(D6-DMSO): 7.3-6.93(m, 6H), 3.88-3.79(m, 1H), 3.58-3.47(m, 1H), 3.10(broad, 3H), 2.78(broad, 3H), 2.17(s, 3H) |
| Ib-74 | 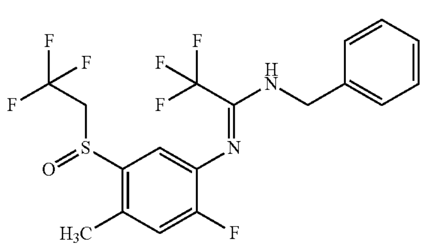 [SMILES: Cc1cc(F)c(/N=C(/NCc2ccccc2)C(F)(F)F)cc1S(=O)CC(F)(F)F] | 1H-NMR(D6-DMSO): 8.87(broad, 1H), 7.33-7.16(m, 7H), 4.47(broad, 2H), 4.12-4.06(m, 1H), 3.90(broad, 1H), 2.30(s, 3H) |

-continued

| Example number | Structure | Analytical data |
|---|---|---|
| Ib-75 | 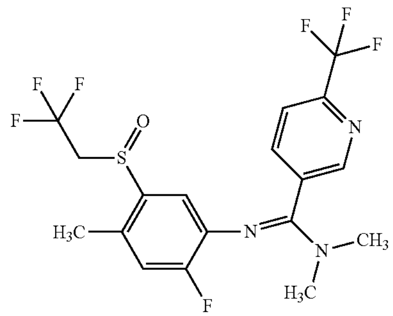 [SMILES: Cc1cc(F)c(/N=C(\c2ccc(C(F)(F)F)nc2)N(C)C)cc1S(=O)CC(F)(F)F] | 1H-NMR(D6-DMSO): 8.49(m, 1H), 8.09(m, 1H), 7.90-7.88(m, 1H), 7.03-6.96(m, 2H), 3.90-3.84(m, 1H), 3.56-3.50(m, 1H), 3.17(broad, 3H), 2.80(broad, 3H), 2.17(s, 3H) |
| Ib-76 | 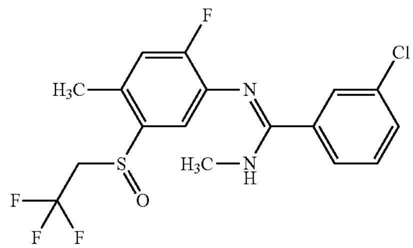 [SMILES: CN/C(=N\c1cc(S(=O)CC(F)(F)F)c(C)cc1F)c1cccc(Cl)c1] | 1H-NMR(D6-DMSO): 7.57-7.56(q, 1H) 7.40-7.38(m, 1H), 7.31-7.27(m, 2H), 7.13-7.08(m, 2H), 6.98-6.95(m, 1H), 3.92-3.83(m, 1H), 3.70-3.63(m, 1H), 2.89-2.87(d, 3H), 2.21(s, 3H) |
| Ib-77 | 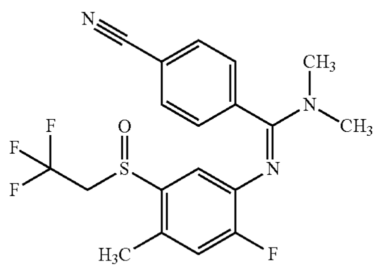 | 1H-NMR(D6-DMSO): 7.81-7.79(m, 2H), 7.46(broad, 1H), 7.29(broad, 1H), 6.98(d, 1H), 6.94(d, 1H), 3.88-3.79(m, 1H), 3.63-3.52(m, 1H), 3.14(broad, 3H), 2.75(broad, 3H), 2.16(2.3H) |
| Ib-78 | 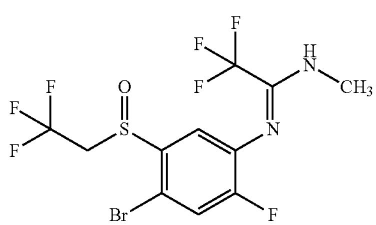 | 1H-NMR(D6-DMSO): 9.49(broad, 1H), 7.78(d, 1H), 7.33(d, 1H), 4.24-4.02(m, 2H), 2.73(broad, 3H) |
| Ib-79 | 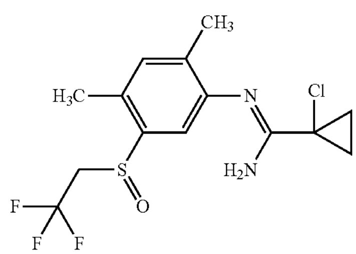 [SMILES: Cc1cc(C)c(S(=O)CC(F)(F)F)cc1/N=C(\N)C1(Cl)CC1] | 1H-NMR(D6-DMSO): 7.11(s, 1H), 7.08(s, 1H), 6.19(broad, 2H), 4.00-3.92(m, 2H), 2.27(s, 3H), 2.00(s, 3H), 1.58(m, 2H), 1.30-1.29(m, 2H) |
| Ib-80 | 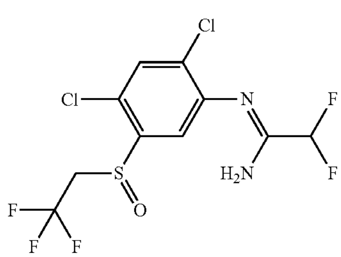 [SMILES: N/C(=N\c1cc(S(=O)CC(F)(F)F)c(Cl)cc1Cl)C(F)F] | 1H-NMR(D6-DMSO): 7.8(s, 1H), 7.30(s, 1H), 7.15(broad, 2H), 6.40(t, 1H), 4.18-4.10(m, 2H) |

-continued

| Example number | Structure | Analytical data |
|---|---|---|
| Ib-81 | 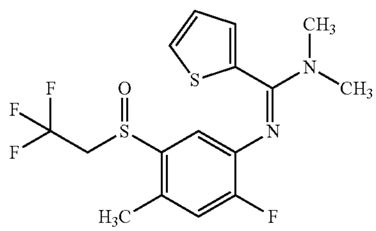 [SMILES: Cc1cc(F)c(/N=C(\c2cccs2)N(C)C)cc1S(=O)CC(F)(F)F] | 1H-NMR(D6-DMSO): 7.61-7.60(m, 1H), 7.04-6.97(m, 4H), 3.92-3.86(m, 1H), 3.65-3.52(m, 1H), 3.02(s, 6H), 2.20(s, 3H) |
| Ib-82 | 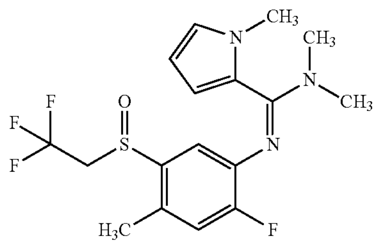 | 1H-NMR(D6-DMSO): 6.96-6.91(m, 2H), 6.70(broad, 1H), 5.90(broad, 2H), 3.83-3.74(m, 2H), 3.18(s, 6H), 2.21(broad, 6H) |
| Ib-83 | 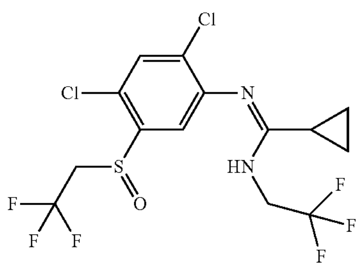 [SMILES: O=S(CC(F)(F)F)c1cc(/N=C(\NCC(F)(F)F)C2CC2)c(Cl)cc1Cl] | 1H-NMR(D6-DMSO): 7.78(s, 1H), 7.26(m, 1H), 7.01(broad, 1H), 4.22-4.01(m, 4H), 1.40-1.38(m, 1H), 0.96-0.86(m, 2H), 0.78-0.71(m, 2H) |
| Ib-84 | 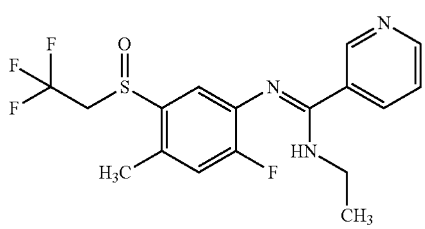 [SMILES: CCN/C(=N\c1cc(S(=O)CC(F)(F)F)c(C)cc1F)c1cccnc1] | 1H-NMR(D6-DMSO): 8.50-8.48(m, 1H), 8.38(m, 1H), 7.65-7.59(m, 2H), 7.33-7.30(m, 1H), 7.15-7.13(m, 1H), 6.95-6.92(m, 1H), 3.97-3.88(m, 1H), 3.79-3.70(m, 1H), 3.44-3.37(m, 2H), 2.20(s, 3H), 1.22(t, 3H) |
| Ib-85 | 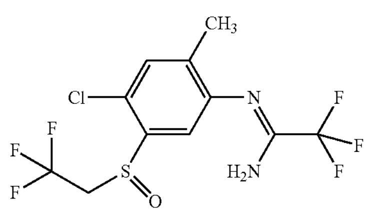 [SMILES: Cc1cc(Cl)c(S(=O)CC(F)(F)F)cc1/N=C(\N)C(F)(F)F] | 1H-NMR(D6-DMSO): 7.52-7.51(m, 1H), 7.3(broad, 2H), 7.18(s, 1H), 4.16-4.02(m, 2H), 2.10(s, 3H) |
| Ib-86 | 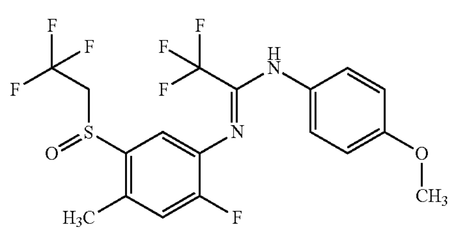 [SMILES: COc1ccc(N/C(=N/c2cc(S(=O)CC(F)(F)F)c(C)cc2F)C(F)(F)F)cc1] | logP(HCOOH) = 3.04, logP(neutral) = 3.05 |

| Example number | Structure | Analytical data |
|---|---|---|
| Ib-87 | 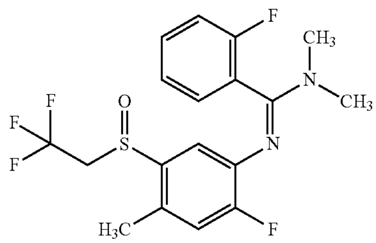 | 1H-NMR(D6-DMSO): 7.35-6.92(m, 6H), 3.85-3.79(m, 1H), 3.58-3.51(m, 1H), 3.16(broad, 3H), 2.79(broad, 3H), 2.16(s, 3H) |
| Ib-88 | 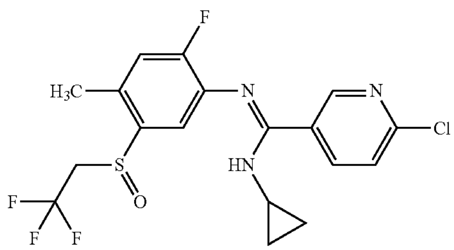 [SMILES: Cc1cc(F)c(/N=C(\NC2CC2)c2ccc(Cl)nc2)cc1S(=O)CC(F)(F)F] | 1H-NMR(D6-DMSO): 8.22(m, 1H), 7.80(m, 1H), 7.66(m, 1H), 7.48-7.46(m, 1H), 7.20-7.21(m, 1H), 7.01-6.98(m, 1H), 4.05-3.93(m, 1H), 3.80(m, 1H), 2.93(m, 1H), 2.22(s, 3H), 0.73(m, 2H), 0.59(m, 2H) |
| Ib-89 | 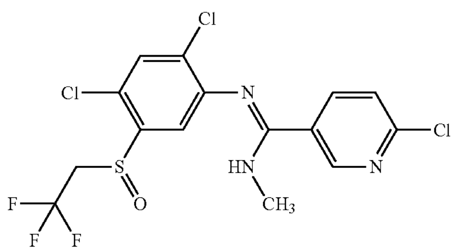 [SMILES: CN/C(=N\c1cc(S(=O)CC(F)(F)F)c(Cl)cc1Cl)c1ccc(Cl)nc1] | 1H-NMR(D6-DMSO): 8.28-8.27(m, 1H), 7.90(broad, 1H), 7.67-7.64(m, 2H), 7.50-7.48(m, 1H), 7.03(s, 1H), 4.17-4.05(m, 1H), 3.89-3.80(m, 1H), 2.92-2.91(d, 3H) |
| Ib-90 | 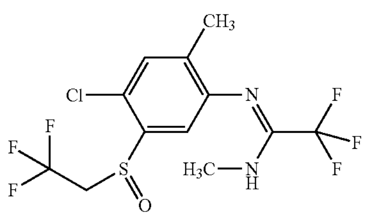 [SMILES: CN/C(=N\c1cc(S(=O)CC(F)(F)F)c(Cl)cc1C)C(F)(F)F] | 1H-NMR(D6-DMSO): 8.09(broad, 1H), 7.44(s, 1H), 7.12(broad, 1H), 4.18-4.05(m, 2H), 2.68-2.63(broad, 3H), 2.11(s, 3H) |
| Ib-91 | 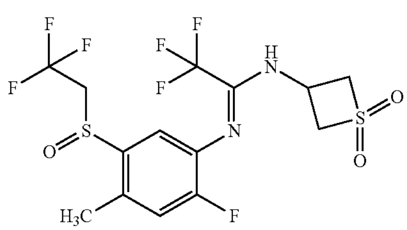 [SMILES: Cc1cc(F)c(/N=C(/NC2CS(=O)(=O)C2)C(F)(F)F)cc1S(=O)CC(F)(F)F] | 1H-NMR(D6-DMSO): 9.01(broad, 1H), 7.38(d, 1H), 7.24(d, 1H), 4.58-4.57(m, 2H), 4.35(broad, 3H), 4.16-4.09(m, 1H), 3.93(broad, 1H), 2.32(s, 3H) |
| Ib-92 | 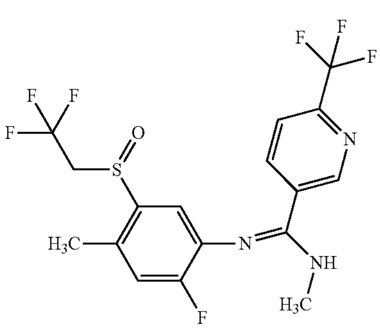 [SMILES: CN/C(=N/c1cc(S(=O)CC(F)(F)F)c(C)cc1F)c1ccc(C(F)(F)F)nc1] | 1H-NMR(D6-DMSO): 8.60(s, 1H), 7.84-7.81(m, 3H), 7.13-7.11(m, 1H), 7.02-6.99(m, 1H), 3.97-3.88(m, 1H), 3.67-3.61(m, 1H), 2.94-2.93(d, 3H), 2.21(s, 3H) |

-continued

| Example number | Structure | Analytical data |
|---|---|---|
| Ib-93 | 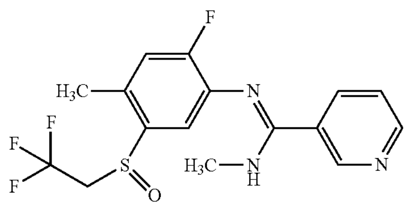 [SMILES: CN/C(=N\c1cc(S(=O)CC(F)(F)F)c(C)cc1F)c1cccnc1] | 1H-NMR(D6-DMSO): 8.46-8.45(m, 1H) 8.32(broad, 1H), 7.58-7.56(m, 1H), 7.37-7.29(m, 2H), 6.99(s, 1H), 6.66(s, 1H), 3.74-3.68(m, 2H), 2.91-2.90(d, 3H), 2.17(s, 3H), 2.15(s, 3H) |
| Ib-94 | 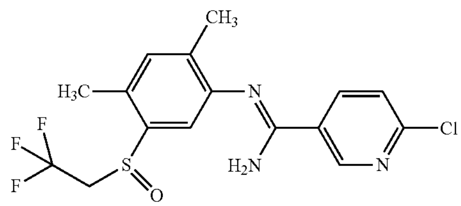 [SMILES: Cc1cc(C)c(S(=O)CC(F)(F)F)cc1/N=C(\N)c1ccc(Cl)nc1] | 1H-NMR(D6-DMSO): 8.98-8.97(m, 1H), 8.40-8.37(m, 1H), 7.71-7.68(m, 1H), 7.40-7.38(m, 1H), 7.26-7.24(m, 1H), 4.06-3.96(m, 2H), 2.33(s, 3H), 2.16(s, 3H) |
| Ib-95 | 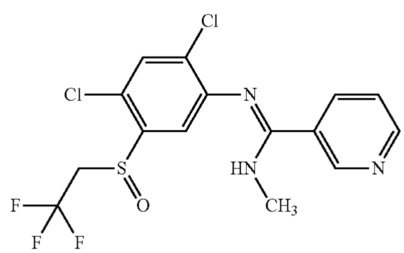 [SMILES: CN/C(=N\c1cc(S(=O)CC(F)(F)F)c(Cl)cc1Cl)c1cccnc1] | 1H-NMR(D6-DMSO): 8.53-8.51(m, 1H), 8.41(m, 1H), 7.85(q, 1H), 7.63(s, 1H), 7.62-7.59(m, 1H), 7.36-7.33(m, 1H), 7.00(s, 1H), 4.12-4.00(m, 1H), 3.86-3.75(m, 1H), 2.93-2.92(d, 3H) |
| Ib-96 | 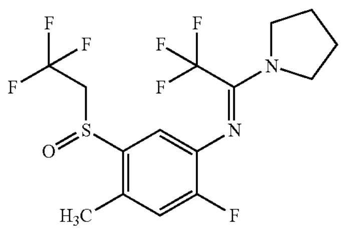 [SMILES: Cc1cc(F)c(/N=C(/N2CCCC2)C(F)(F)F)cc1S(=O)CC(F)(F)F] | 1H-NMR(D6-DMSO): 7.29(d, 1H), 7.21(d, 1H), 4.15-3.99(m, 2H), 3.41(broad, 4H), 2.31(s, 3H), 1.86(broad, 4H) |
| Ib-97 | 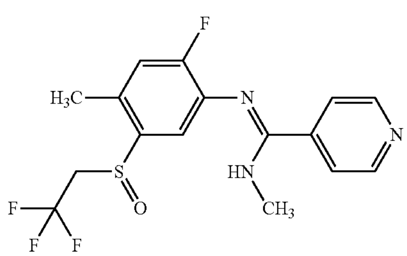 [SMILES: CN/C(=N\c1cc(S(=O)CC(F)(F)F)c(C)cc1F)c1ccncc1] | 1H-NMR(D6-DMSO): 8.52-8.50(m, 1H), 7.65-7.64(q, 1H), 7.19-7.12(m, 3H), 6.97-6.95(m, 1H), 3.96-3.87(m, 1H), 3.74-3.68(m, 1H), 2.90-2.89(d, 3H), 2.20(s, 3H) |
| Ib-98 | 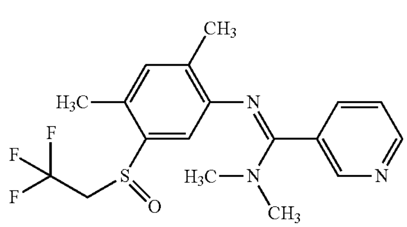 [SMILES: Cc1cc(C)c(S(=O)CC(F)(F)F)cc1/N=C(/c1cccnc1)N(C)C] | 1H-NMR(D6-DMSO): 8.44-8.43(m, 1H), 8.32-8.29(m ,1H), 7.60(m, 1H), 7.35-7.31(m, 1H), 6.94(s, 1H), 6.66(s, 1H), 3.70-3.64(m, 1H), 3.30-3.24(m, 1H), 2.96(broad, 6H), 2.14(s, 3H), 2.13(s, 3H) |

-continued

| Example number | Structure | Analytical data |
|---|---|---|
| Ib-99 | 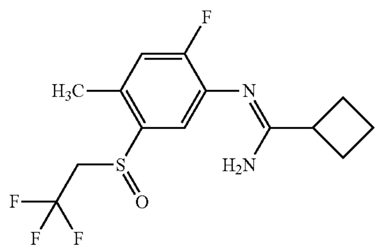 [SMILES: Cc1cc(F)c(/N=C(\N)C2CCC2)cc1S(=O)CC(F)(F)F] | 1H-NMR(D6-DMSO): 7.30-7.25(m, 1H), 7.09(m, 1H), 6.65(broad, 2H), 4.07-4.02(m, 2H), 2.97-2.93(m, 1H), 2.33(s, 3H), 2.22-1.71(m, 6H) |
| Ib-100 | 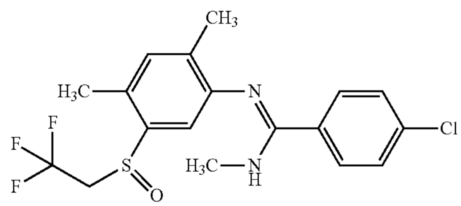 [SMILES: CN/C(=N\c1cc(S(=O)CC(F)(F)F)c(C)cc1C)c1ccc(Cl)cc1] | 1H-NMR(D6-DMSO): 7.35-7.15(m, 4H), 6.98-6.96(m, 2H), 6.61(s, 1H), 3.69-3.63(m, 1H), 3.22-3.17(m, 1H), 2.88(broad, 3H), 2.17(s, 3H), 2.16(s, 3H) |
| Ib-101 | 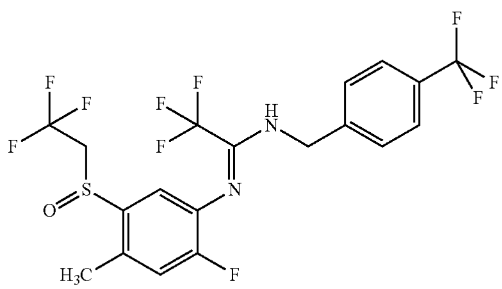 [SMILES: Cc1cc(F)c(/N=C(/NCc2ccc(C(F)(F)F)cc2)C(F)(F)F)cc1S(=O)CC(F)(F)F] | 1H-NMR(D6-DMSO): 8.98(broad, 1H), 7.72-7.70(m, 2H), 7.52-7.51(broad, 1H), 7.21-7.19(m, 3H), 4.56(broad, 2H), 4.13-4.06(m, 1H), 3.93-3.90(m, 1H), 2.28(s, 3H) |
| Ib-102 | 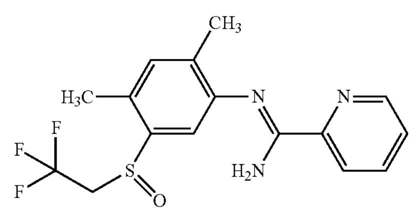 [SMILES: Cc1cc(C)c(S(=O)CC(F)(F)F)cc1/N=C(\N)c1ccccn1] | 1H-NMR(D6-DMSO): 8.66-8.64(m, 1H), 8.37-8.32(m, 1H), 7.99-7.95(m, 1H), 7.59-7.56(m, 1H), 7.27(s, 1H), 7.19(s, 1H), 6.60(broad, 2H), 4.05-3.97(m, 2H), 2.31(s, 3H), 2.13(s, 3H) |
| Ib-103 | 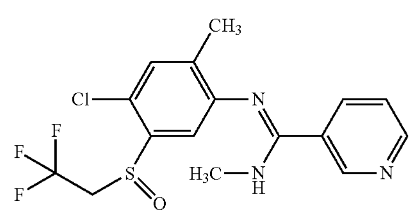 [SMILES: CN/C(=N\c1cc(S(=O)CC(F)(F)F)c(Cl)cc1C)c1cccnc1] | 1H-NMR(D6-DMSO): 8.50-8.49(m, 1H), 8.36(s, 1H), 7.58-7.57(m, 2H), 7.34-7.30(m, 2H), 6.68(broad, 1H), 3.91-3.82(m, 1H), 3.59-3.53(m, 1H), 2.92-2.91(d, 3H), 2.20(s, 3H) |
| Ib-104 | 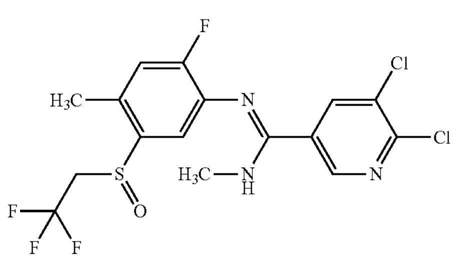 [SMILES: CN/C(=N\c1cc(S(=O)CC(F)(F)F)c(C)cc1F)c1cnc(Cl)c(Cl)c1] | 1H-NMR(D6-DMSO): 8.16-8.14(m, 2H), 7.78-7.77(broad, 1H), 7.23-7.21(m, 1H), 7.03-7.00(m, 1H), 4.02-3.93(m, 1H), 3.84-3.77(m, 1H), 2.91-2.90(d, 3H), 2.23(s, 3H) |

-continued

| Example number | Structure | Analytical data |
|---|---|---|
| Ib-105 | 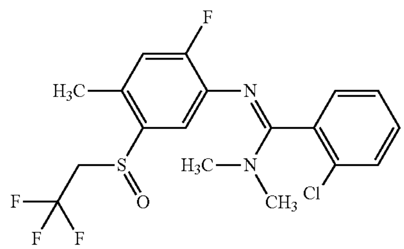 [SMILES: Cc1cc(F)c(/N=C(/c2ccccc2Cl)N(C)C)cc1S(=O)CC(F)(F)F] | 1H-NMR(D6-DMSO): 7.46-6.94(m, 6H), 3.85-3.74(m, 1H), 3.54-3.48(m, 1H), 3.17(broad, 3H), 2.74(broad, 3H), 2.15(s, 3H) |
| Ib-106 | 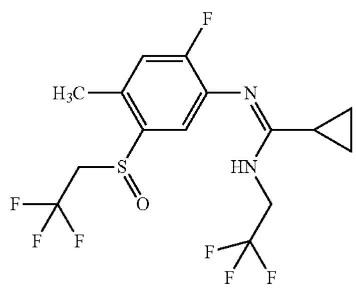 [SMILES: Cc1cc(F)c(/N=C(\NCC(F)(F)F)C2CC2)cc1S(=O)CC(F)(F)F] | 1H-NMR(D6-DMSO): 7.29-7.27(m, 1H), 7.20-7.17(m, 1H), 6.84(broad, 1H), 4.11-3.64(m, 4H), 2.30(s, 3H), 1.44-1.41(m, 1H), 0.91-0.84(m, 2H), 0.72-0.69(m, 2H) |
| Ib-107 | 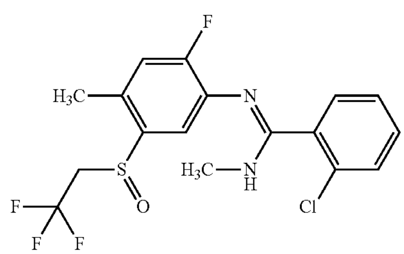 [SMILES: CN/C(=N\c1cc(S(=O)CC(F)(F)F)c(C)cc1F)c1ccccc1Cl] | 1H-NMR(D6-DMSO): 7.52-6.95(m, 7H), 3.82-3.72(m, 2H), 2.91-2.90(d, 3H), 2.18(s, 3H) |
| Ib-108 | 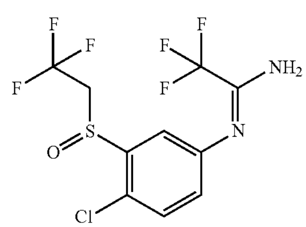 [SMILES: N/C(=N/c1ccc(Cl)c(S(=O)CC(F)(F)F)c1)C(F)(F)F] | 1H-NMR(D6-DMSO): 7.57(d, 1H), 7.42(broad, 2H), 7.30(d, 1H), 7.10-7.07(m, 1H), 4.22-4.04(m, 2H) |
| Ib-109 | 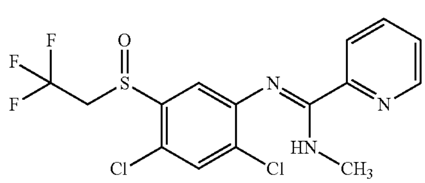 [SMILES: CN/C(=N\c1cc(S(=O)CC(F)(F)F)c(Cl)cc1Cl)c1ccccn1] | 1H-NMR(D6-DMSO): 8.57-8.55(m, 1H), 7.91(broad, 1H), 7.82-7.77(m, 1H), 7.66(s, 1H), 7.44-7.41(m, 2H), 6.96(s, 1H), 4.10-4.01(m, 1H), 3.87-3.78(m, 1H), 2.84-2.83(d, 3H) |
| Ib-110 | 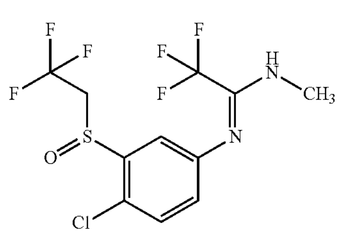 [SMILES: CN/C(=N/c1ccc(Cl)c(S(=O)CC(F)(F)F)c1)C(F)(F)F] | 1H-NMR(D6-DMSO): 8.14(broad, 1H), 7.48(d, 1H), 7.22(d, 1H), 7.03-7.00(m, 1H), 4.25-4.01(m, 2H), 3.67(broad, 3H) |

-continued

| Example number | Structure | Analytical data |
|---|---|---|
| Ib-111 | 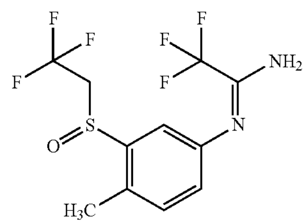 | 1H-NMR(D6-DMSO): 7.31-7.29(m, 2H), 7.25(broad, 2H), 6.98-6.95(m, 1H), 4.09-4.00(m ,2H), 2.33(s, 3H) |
| Ib-112 | 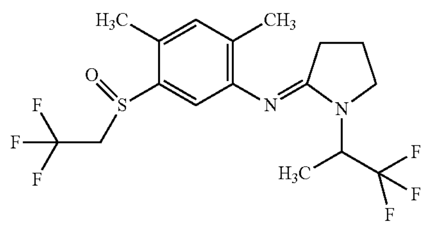 [SMILES: Cc1cc(C)c(S(=O)CC(F)(F)F)cc1/N=C1\CCCN1C(C)C(F)(F)F] | 1H-NMR(D6-DMSO): 7.09(m, 2H), 5.17-5.13(m, 1H), 4.03-3.93(m, 2H), 3.51-3.45(m, 1H), 3.32-3.30(m, 1H), 2.43-2.07(m, 2H), 2.27(s, 3H), 2.06(s, 3H), 1.95-1.88(m, 2H), 1.40-1.38(d, 3H) |
| Ib-113 | 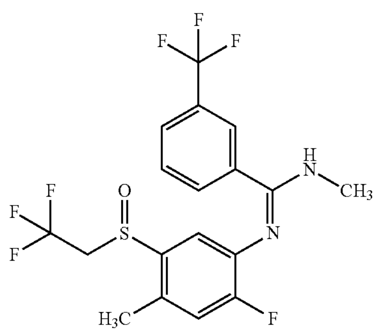 | 1H-NMR(D6-DMSO): 7.70-7.61(m, 2H), 7.57(s, 1H), 7.53-7.44(m, 2H), 7.12(d, 1H), 7.65(d, 1H), 3.87-3.77(m, 1H), 3.66-3.54(m, 1H), 2.90(d, 3H), 2.19(s, 3H) |
| Ib-114 | 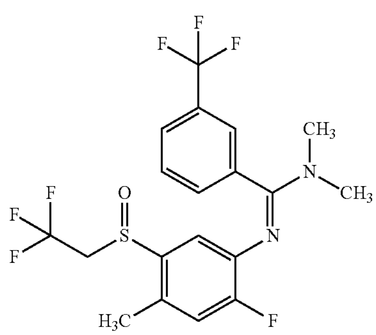 | 1H-NMR(D6-DMSO): 7.65(d, 2H), 7.54(t, 1H), 7.39(broad, 1H), 7.04(broad, 1H), 6.92(d, 1H), 3.83-3.70(m, 2H), 3.14(broad, 3H), 3.28(broad, 3H), 2.16(s, 3H) |
| Ib-115 | 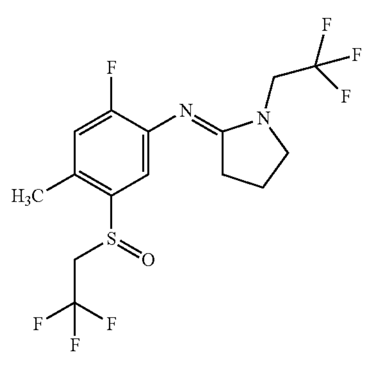 [SMILES: Cc1cc(F)c(/N=C2\CCCN2CC(F)(F)F)cc1S(=O)CC(F)(F)F] | 1H-NMR(D6-DMSO): 7.31-7.29(m, 1H), 7.20-7.17(m, 1H), 4.27(q, 2H), 4.12-4.00(m, 2H), 3.52(t, 2H), 2.47-2.25(m, 2H), 2.31(s, 3H), 2.00-1.92(m, 2H) |

-continued

| Example number | Structure | Analytical data |
|---|---|---|
| Ib-116 | 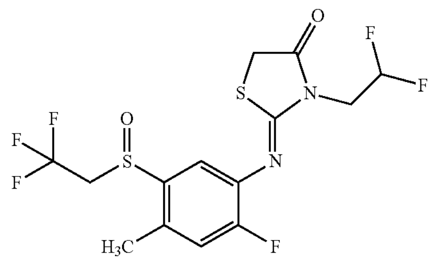 | 1H-NMR(D6-DMSO): 7.57(d, 1H), 7.37(d, 1H), 6.33(tt, 1H), 4.25-4.13(m, 5H), 4.01-3.89(m, 2H), 2.36(s, 3H) |
| Ib-117 | 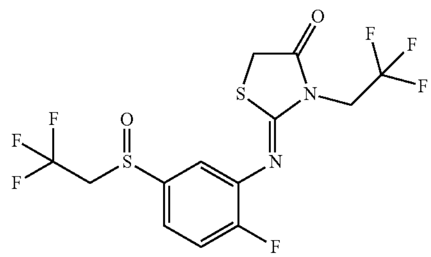 [SMILES: O=C1CS/C(=N\c2cc(S(=O)CC(F)(F)F)ccc2F)N1CC(F)(F)F] | 1H-NMR(D6-DMSO): 7.62-7.56(m, 2H), 7.50-7.48(m, 1H), 4.60(q, 2H), 4.27-4.00(m, 4H) |
| Ib-118 | 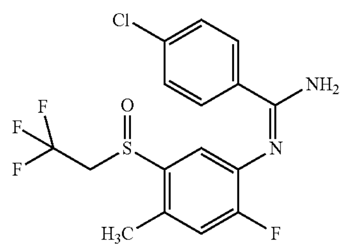 [SMILES: Cc1cc(F)c(/N=C(/N)c2ccc(Cl)cc2)cc1S(=O)CC(F)(F)F] | 1H-NMR(D6-DMSO): 8.00(d, 2H), 7.53(d, 2H), 7.39(d, 1H), 7.23(d, 1H), 6.80(broad, 2H), 4.06(q, 2H), 2.34(s, 3H) |
| Ib-119 | 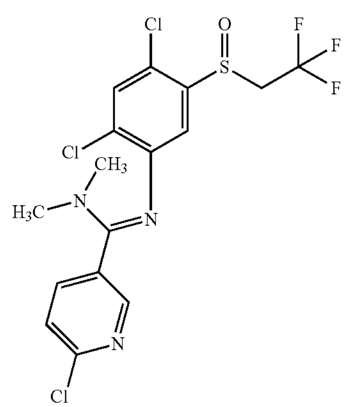 [SMILES: CN(C)/C(=N\c1cc(S(=O)CC(F)(F)F)c(Cl)cc1Cl)c1ccc(Cl)nc1] | 1H-NMR(D6-DMSO): 8.23(broad, 1H), 7.73-7.72(broad, 1H), 7.62(s, 1H), 7.52-7.50(m, 1H), 6.97(s, 1H), 4.14-4.02(m, 1H), 3.82-3.70(m, 1H), 3.00(broad, 6H) |
| Ib-120 | 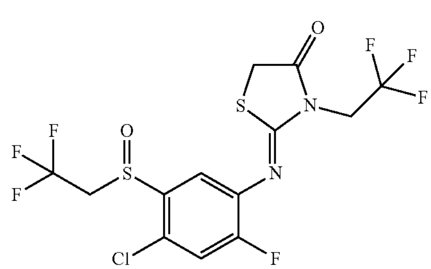 [SMILES: O=C1CS/C(=N\c2cc(S(=O)CC(F)(F)F)c(Cl)cc2F)N1CC(F)(F)F] | 1H-NMR(D6-DMSO): 7.86(d, 1H), 7.53(d, 1H), 4.60(q, 2H), 4.36-4.24(m, 3H), 4.17-4.06(m, 1H) |

-continued

| Example number | Structure | Analytical data |
|---|---|---|
| Ib-121 | 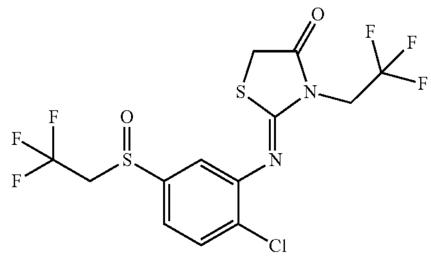 [SMILES: O=C1CS/C(=N\c2cc(S(=O)CC(F)(F)F)ccc2Cl)N1CC(F)(F)F] | 1H-NMR(D6-DMSO): 7.81(d, 1H), 7.56(dd, 1H), 7.47(d, 1H), 4.61(q, 2H), 4.31-4.07(m, 4H) |
| Ib-122 | 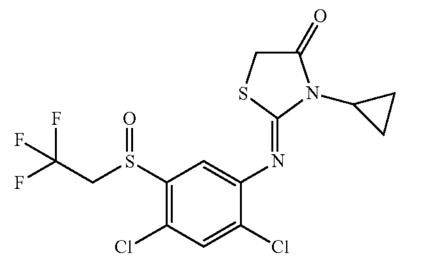 [SMILES: O=C1CS/C(=N\c2cc(S(=O)CC(F)(F)F)c(Cl)cc2Cl)N1C1CC1] | 1H-NMR(D6-DMSO): 7.96(s, 1H), 7.51(s, 1H), 4.36-4.24(m, 1H), 4.14-4.00(m, 3H), 2.75-2.70(m, 1H), 1.02-0.92(m, 4H) |
| Ib-123 | 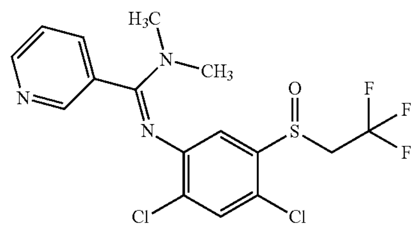 [SMILES: CN(C)/C(=N\c1cc(S(=O)CC(F)(F)F)c(Cl)cc1Cl)c1cccnc1] | 1H-NMR(D6-DMSO): 8.50-8.49(m, 1H), 8.36(m, 1H), 7.67-7.64(m, 1H), 7.60(s, 1H), 7.39-7.36(m, 1H), 6.96(s, 1H), 4.05-3.96(m, 1H), 3.78-3.66(m, 1H), 3.05(broad, 6H) |
| Ib-124 | 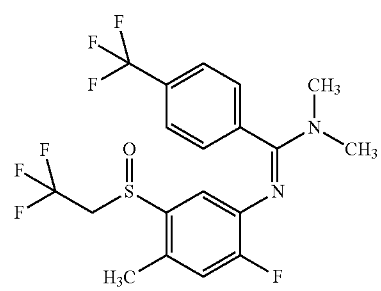 [SMILES: Cc1cc(F)c(/N=C(\c2ccc(C(F)(F)F)cc2)N(C)C)cc1S(=O)CC(F)(F)F] | 1H-NMR(D6-DMSO): 7.69(broad, 2H), 7.54(broad, 1H), 7.27(broad, 1H), 6.97-6.14(m, 2H), 3.84-3.70(m, 1H), 3.43-3.30(m, 1H), 3.15(broad, 3H), 2.77(broad, 3H), 2.16(s, 3H) |
| Ib-125 | 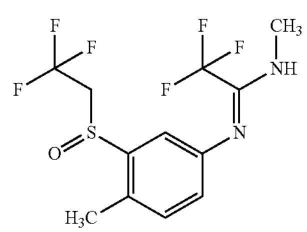 [SMILES: CN/C(=N/c1ccc(C)c(S(=O)CC(F)(F)F)c1)C(F)(F)F] | 1H-NMR(D6-DMSO): 8.02(broad, 1H), 7.22-7.17(m, 2H), 6.89(broad, 1H), 4.12-4.06(m, 1H), 3.92(broad, 1H), 2.76(broad, 3H), 2.30(s, 3H) |
| Ib-126 | 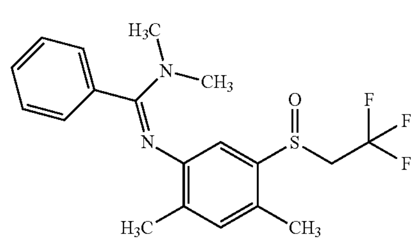 [SMILES: Cc1cc(C)c(S(=O)CC(F)(F)F)cc1/N=C(/c1ccccc1)N(C)C] | 1H-NMR(D6-DMSO): 7.27(m, 3H), 7.12(broad, 2H), 6.92(s, 1H), 6.62(s, 1H), 3.50(m, 2H), 2.93(broad, 6H), 2.16(s, 3H), 2.13(s, 3H) |

-continued

| Example number | Structure | Analytical data |
|---|---|---|
| Ib-127 | 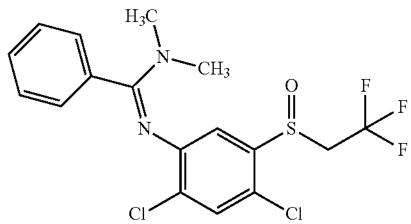 [SMILES: CN(C)/C(=N\c1cc(S(=O)CC(F)(F)F)c(Cl)cc1Cl)c1ccccc1] | 1H-NMR(D6-DMSO): 7.57(s, 1H), 7.34-7.30(m, 3H), 7.16(m, 2H), 6.86(s, 1H), 3.97-3.85(m, 1H), 3.61-3.49(m, 1H), 3.05(broad, 6H) |
| Ib-128 | 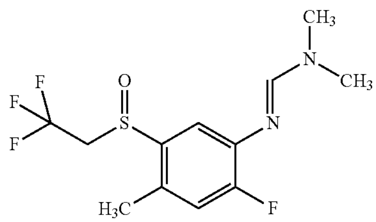 [SMILES: Cc1cc(F)c(/N=C/N(C)C)cc1S(=O)CC(F)(F)F] | 1H-NMR(D6-DMSO): 7.86(s, 1H), 7.44(d, 1H), 7.13(d, 1H), 4.10-3.98(m, 2H), 3.05(bs, 3H), 2.95(bs, 3H), 2.30(s, 3H) |
| Ib-129 | 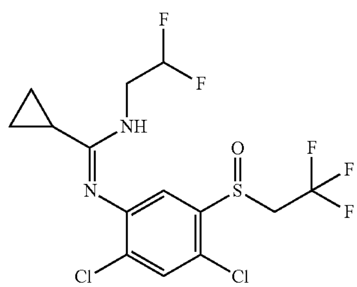 [SMILES: O=S(CC(F)(F)F)c1cc(/N=C(\NCC(F)F)C2CC2)c(Cl)cc1Cl] | 1H-NMR(D6-DMSO): 7.78(s, 1H), 7.34(s, 1H), 6.95(broad, 1H), 6.21(tt, 1H), 4.22-4.07(m, 2H), 3.59-3.52(m, 2H), 1.37(m, 1H), 0.90-0.87(m, 2H), 0.73-0.71(m, 2H) |
| Ib-130 | 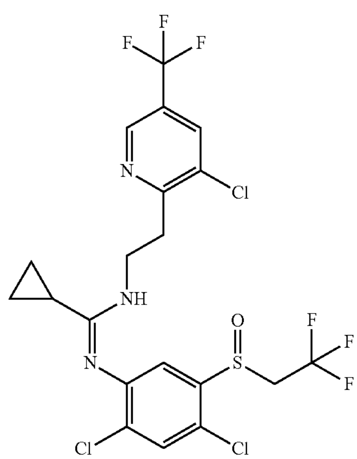 [SMILES: O=S(CC(F)(F)F)c1cc(/N=C(\NCCc2ncc(C(F)(F)F)cc2Cl)C2CC2)c(Cl)cc1Cl] | 1H-NMR(D6-DMSO): 8.88(s, 1H), 8.39(m, 1H), 7.73(s, 1H), 7.27(s, 1H), 6.66(m, 1H), 4.21-4.05(m, 2H), 3.68-3.59(m, 2H), 2.50(m, 2H), 1.34(m, 1H), 0.82-0.81(m, 2H), 0.68-0.66(m, 2H) |
| Ib-131 | 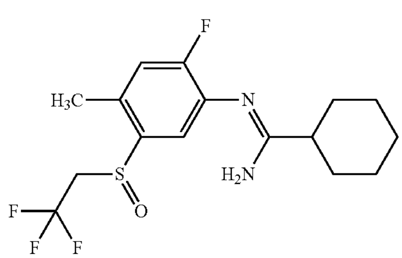 [SMILES: Cc1cc(F)c(/N=C(\N)C2CCCCC2)cc1S(=O)CC(F)(F)F] | 1H-NMR(D6-DMSO): 7.73-7.72(m, 1H), 7.45(m, 1H), 4.19-3.97(m, 2H), 2.40(s, 3H), 1.93-1.19(m, 10H) |

-continued

| Example number | Structure | Analytical data |
|---|---|---|
| Ib-132 | 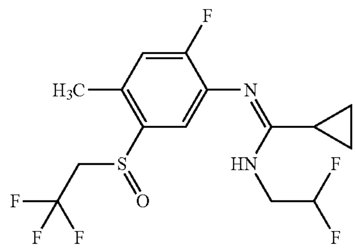 [SMILES: Cc1cc(F)c(/N=C(\NCC(F)F)C2CC2)cc1S(=O)CC(F)(F)F] | 1H-NMR(D6-DMSO): 7.35-7.33(m, 1H), 7.19-7.16(m, 1H), 6.75(broad, 1H), 6.15(tt, 1H), 4.11-3.96(m, 2H), 3.60-3.50(m, 2H), 2.31(s, 3H), 1.40(broad, 1H), 0.90-0.82(m, 2H), 0.73-0.67(m, 2H) |
| Ib-133 | 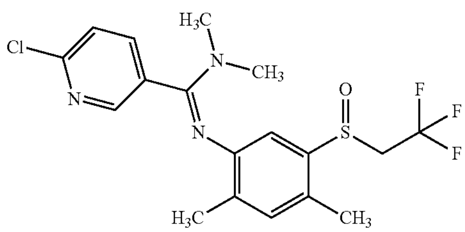 | 1H-NMR(D6-DMSO): 8.15(broad, 1H), 7.70(broad, 1H), 7.48-7.46(m, 1H), 6.96(s, 1H), 6.63(s, 1H), 3.77-3.71(m, 1H), 3.35-3.26(m, 1H), 2.96(broad, 6H), 2.15(s, 3H), 2.13(s, 3H) |
| Ib-134 | 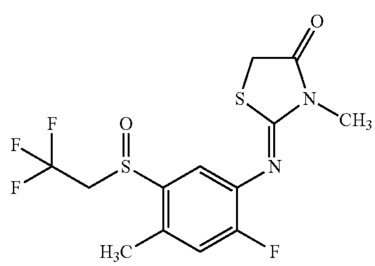 [SMILES: Cc1cc(F)c(/N=C2\SCC(=O)N2C)cc1S(=O)CC(F)(F)F] | 1H-NMR(D6-DMSO): 7.53(d, 1H), 7.36(d, 1H), 4.22-4.10(m, 3H), 4.04-3.92(m, 1H), 3.19(s, 3H), 2.35(s, 3H) |
| Ib-135 | 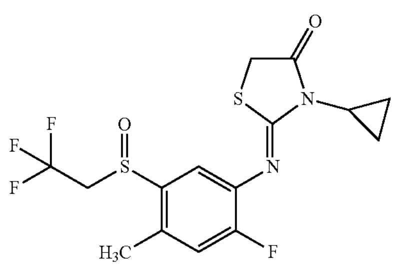 [SMILES: Cc1cc(F)c(/N=C2\SCC(=O)N2C2CC2)cc1S(=O)CC(F)(F)F] | 1H-NMR(D6-DMSO): 7.50(d, 1H), 7.35(d, 1H), 4.28-4.12(m, 1H), 4.02-3.91(m, 3H), 2.75-2.55(m, 1H), 2.35(s, 3H), 1.01-0.88(m, 4H) -peaks of the main isomer- |
| Ib-136 | 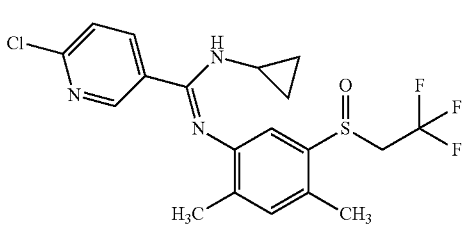 [SMILES: Cc1cc(C)c(S(=O)CC(F)(F)F)cc1/N=C(\NC1CC1)c1ccc(Cl)nc1] | 1H-NMR(D6-DMSO): 8.15(broad, 1H), 7.60-7.44(m, 3H), 7.01(s, 1H), 6.70(s, 1H), 3.79(m, 2H), 2.90(m, 1H), 2.19(s, 3H), 2.16(s, 3H), 0.72(m, 2H), 0.58(m, 2H) |
| Ib-137 | 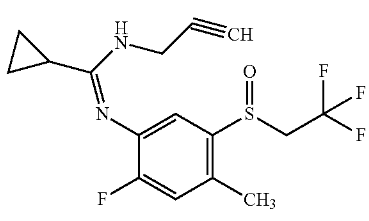 [SMILES: C#CCN/C(=N\c1cc(S(=O)CC(F)(F)F)c(C)cc1F)C1CC1] | 1H-NMR(D6-DMSO): 7.90-7.86(m, 1H), 7.65-7.63(m, 1H), 6.66(s, 1H), 4.30-4.16(m, 2H), 1.95(d, 2H), 1.41(m, 1H), 0.81-0.70(m, 4H) |

-continued
| Example number | Structure | Analytical data |
|---|---|---|
| Ib-138 | 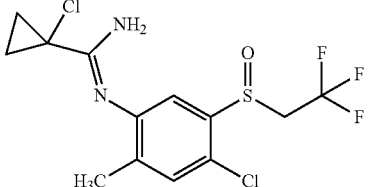 | 1H-NMR(D6-DMSO): 7.90(s, 1H), 7.41(s, 1H), 6.41(broad, 2H), 4.10-3.97(m, 2H), 2.04(s, 3H), 1.64-1.58(m, 2H), 1.32-1.29(m, 2H) |
| Ib-139 | 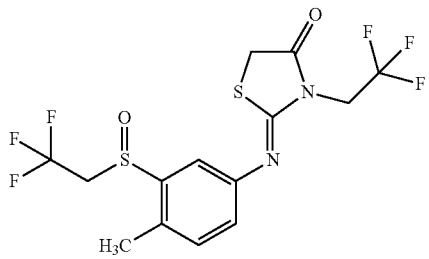 | 1H-NMR(D6-DMSO): 7.44(d, 1H), 7.37(d, 1H), 7.08(dd, 1H), 4.58(q, 2H), 4.23-4.11(m, 3H), 4.00-3.88(m, 1H), 2.35(s, 3H) |
| Ib-140 | 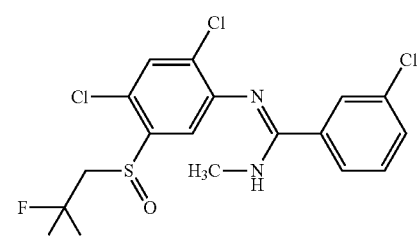 | 1H-NMR(D6-DMSO): 7.77(broad, 1H), 7.64(s, 1H), 7.43-7.41(m, 1H), 7.34-7.30(m, 2H), 7.09-7.07(m, 1H), 6.97(s, 1H), 4.08-3.96(m, 1H), 3.81-3.70(m, 1H), 2.90(d, 3H) |
| Ib-141 | 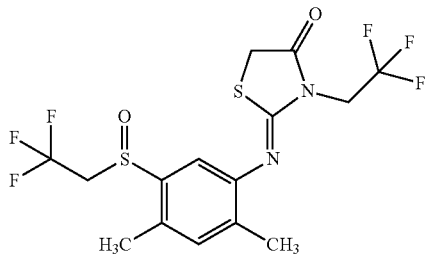 | 1H-NMR(D6-DMSO): 7.34(s, 1H), 7.26(s, 1H), 4.61(q, 2H), 4.20(s, 2H), 4.19-4.07(m, 1H), 3.91-3.79(m, 1H), 2.31(s, 3H), 2.14(s, 3H) |
| Ib-142 | 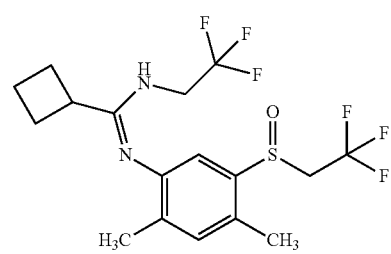 | 1H-NMR(D6-DMSO): 7.13(t, 1H), 7.07(s, 1H), 6.92(s, 1H), 4.15-3.88(m, 4H), 3.16-3.12(m, 1H), 2.26(s, 3H), 2.17-2.05(m, 2H), 2.00(s, 3H), 1.80-1.60(m, 4H) |
| Ib-143 | 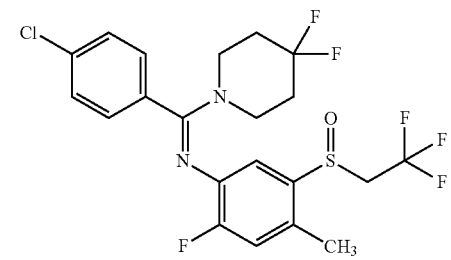 [SMILES: Cc1cc(F)c(/N=C(/c2ccc(Cl)cc2)N2CCC(F)(F)CC2)cc1S(=O)CC(F)(F)F] | 1H-NMR(D6-DMSO): 7.40-7.38(m, 2H), 7.29(broad, 2H), 7.10-7.08(m, 1H), 6.98-6.95(m, 1H), 3.94-3.82(m, 1H), 3.61-3.48(m, 1H), 3.31(broad, 4H), 2.18(s, 3H), 2.06(broad, 4H) |

-continued

| Example number | Structure | Analytical data |
|---|---|---|
| Ib-144 | 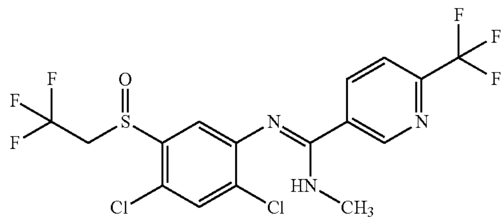 [SMILES: CN/C(=N\c1cc(S(=O)CC(F)(F)F)c(Cl)cc1Cl)c1ccc(C(F)(F)F)nc1] | 1H-NMR(D6-DMSO): 8.62(broad, 1H), 7.99(broad, 1H), 7.91-7.87(m, 2H), 7.67(s, 1H), 6.98(s, 1H), 4.15-4.03(m, 1H), 3.79-3.68(m, 1H), 2.96-2.95(d, 3H) |
| Ib-145 | 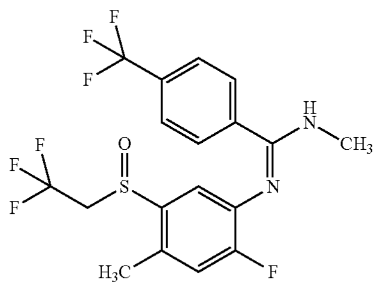 [SMILES: CN/C(=N/c1cc(S(=O)CC(F)(F)F)c(C)cc1F)c1ccc(C(F)(F)F)cc1] | 1H-NMR(D6-DMSO): 7.68(d, 2H), 7.63(d, 1H), 7.42(d, 2H), 7.02-7.96(m, 2H), 3.90-3.79(m, 1H), 3.52-3.40(m, 1H), 2.91(d, 3H), 2.20(s, 3H) |
| Ib-146 | 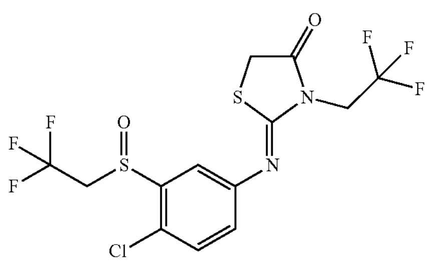 [SMILES: O=C1CS/C(=N\c2ccc(Cl)c(S(=O)CC(F)(F)F)c2)N1CC(F)(F)F] | 1H-NMR(D6-DMSO): 7.66(d, 1H), 7.45(d, 1H), 7.21(dd, 1H), 4.59(q, 2H), 4.30-4.21(m, 3H), 4.14-4.04(m, 1H) |
| Ib-147 | 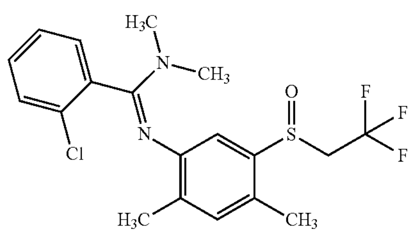 [SMILES: Cc1cc(C)c(S(=O)CC(F)(F)F)cc1/N=C(/c1ccccc1Cl)N(C)C] | 1H-NMR(D6-DMSO): 7.47-7.20(m, 4H), 6.94 (s, 1H), 6.80-6.76(m, 1H), 3.64-3.51(m, 1H), 3.19(broad, 3H), 3.06-2.97(m, 1H), 2.74(broad, 3H), 2.21(d, 3H), 2.13(s, 3H) |
| Ib-148 | 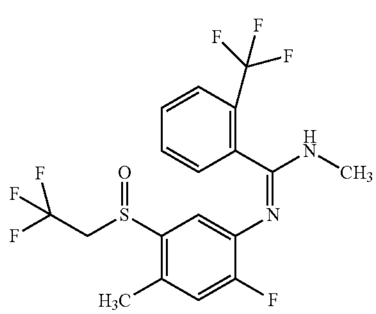 [SMILES: CN/C(=N/c1cc(S(=O)CC(F)(F)F)c(C)cc1F)c1ccccc1C(F)(F)F] | 1H-NMR(D6-DMSO): 7.70-7.43(m, 5H), 7.00-6.95(m, 2H), 3.90-3.70(m, 1H), 3.47-3.24(m, 1H), 2.89(d, 3H), 2.16(s, 3H) |
| Ib-149 | 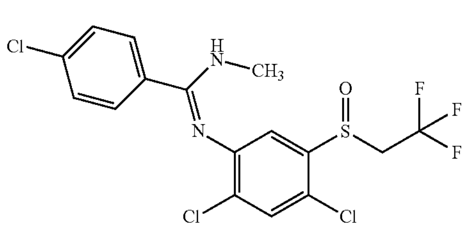 [SMILES: CN/C(=N\c1cc(S(=O)CC(F)(F)F)c(Cl)cc1Cl)c1ccc(Cl)cc1] | 1H-NMR(D6-DMSO): 7.73-7.72(broad, 1H), 7.63(s, 1H), 7.40-7.38(m, 2H), 7.22-7.20(m, 2H), 6.89(s, 1H), 4.05-3.96(m, 1H), 3.73-3.66(m, 1H), 2.91-2.90(d, 3H) |

-continued

| Example number | Structure | Analytical data |
|---|---|---|
| Ib-150 | 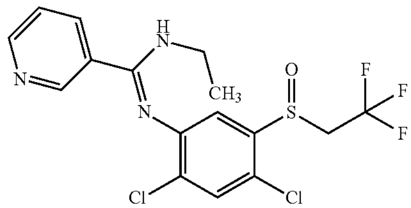 [SMILES: CCN/C(=N\c1cc(S(=O)CC(F)(F)F)c(Cl)cc1Cl)c1cccnc1] | 1H-NMR(D6-DMSO): 8.52-8.51(m, 1H), 8.40(m, 1H), 7.85(t, 1H), 7.63(s, 1H), 7.61-7.58(m, 1H), 7.35-7.32(m, 1H), 6.97(s, 1H), 4.11-4.00(m, 1H), 3.83-3.76(m, 1H), 3.43(m, 2H), 1.25(t, 3H) |
| Ib-151 | 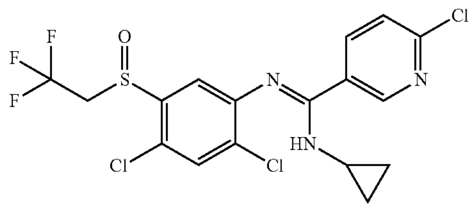 [SMILES: O=S(CC(F)(F)F)c1cc(/N=C(\NC2CC2)c2ccc(Cl)nc2)c(Cl)cc1Cl] | 1H-NMR(D6-DMSO): 8.33(broad, 1H), 7.98(broad, 1H), 7.72(broad, 1H), 7.66(s, 1H), 7.50-7.48(m, 1H), 7.13(broad, 1H), 4.16-4.07(m, 1H), 3.96-3.88(m, 1H), 2.77(broad, 1H), 0.66-0.62(m, 4H) |
| Ib-152 | 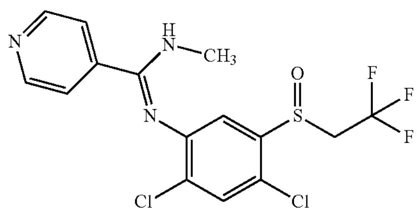 [SMILES: CN/C(=N\c1cc(S(=O)CC(F)(F)F)c(Cl)cc1Cl)c1ccncc1] | 1H-NMR(D6-DMSO): 8.55-8.53(m, 2H), 7.85-7.84(m, 1H), 7.64(s, 1H), 7.19-7.18(m, 2H), 6.97(s, 1H), 4.09-4.00(m, 1H), 3.83-3.74(m, 1H), 2.92-2.90(d, 3H) |
| Ib-153 | 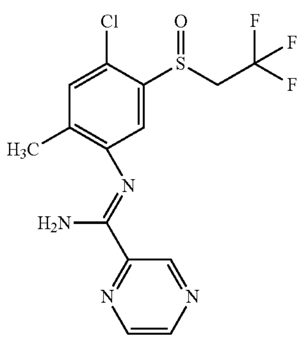 [SMILES: Cc1cc(Cl)c(S(=O)CC(F)(F)F)cc1/N=C(\N)c1cnccn1] | 1H-NMR(D6-DMSO): 9.50(s, 1H), 8.84-8.83(m, 1H), 8.74-8.73(m, 1H), 7.51(s, 1H), 7.30(s, 1H), 6.95(broad, 2H), 4.16-4.02(m, 2H), 2.18(s, 3H) |
| Ib-154 | 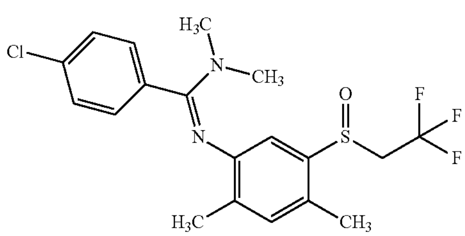 [SMILES: Cc1cc(C)c(S(=O)CC(F)(F)F)cc1/N=C(/c1ccc(Cl)cc1)N(C)C] | 1H-NMR(D6-DMSO): 7.36-7.34(m, 2H), 7.15(broad, 2H), 6.93(s, 1H), 6.60(s, 1H), 3.67-3.60(m, 1H), 3.21-3.14(m, 1H), 2.94(broad, 6H), 2.14(s, 6H) |
| Ib-155 | 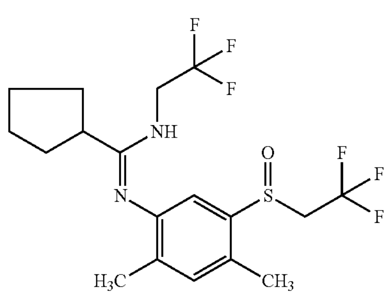 [SMILES: Cc1cc(C)c(S(=O)CC(F)(F)F)cc1/N=C(\NCC(F)(F)F)C1CCCC1] | 1H-NMR(D6-DMSO): 7.09(s, 1H), 6.99(t, 1H), 6.93(s, 1H), 4.13-3.84(m, 4H), 2.49(m, 1H), 2.26(s, 3H), 2.00(s, 3H), 1.68-1.67(broad, 6H), 1.38-1.37(broad, 2H) |

| Example number | Structure | Analytical data |
|---|---|---|
| Ib-156 | 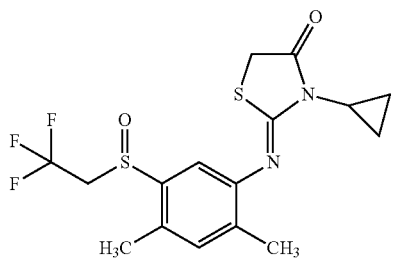 | 1H-NMR(D6-DMSO): 7.32(s, 1H), 7.24(s, 1H), 4.14-4.05(m, 1H), 3.94(s, 2H), 3.91-3.82(m, 1H), 2.73(septet, 1H), 2.31(s, 3H), 2.15(s, 3H), 1.02-0.90(m, 4H) |
| Ib-157 | 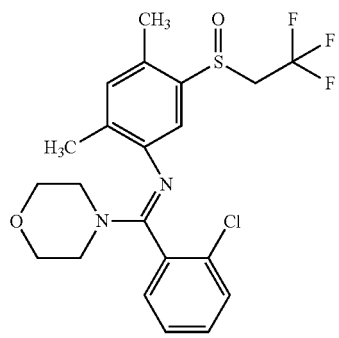 [SMILES: Cc1cc(C)c(S(=O)CC(F)(F)F)cc1/N=C(/c1ccccc1Cl)N1CCOCC1] | 1H-NMR(D6-DMSO): 7.45-6.96(m, 6H), 3.86-3.47(m, 8H), 3.03(m, 2H), 2.16(s, 3H) |
| Ib-158 | 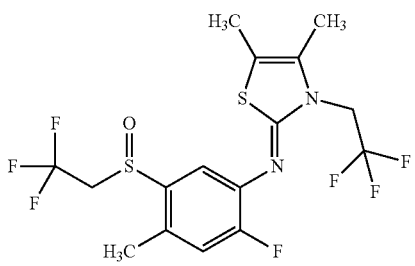 [SMILES: Cc1cc(F)c(/N=c2\sc(C)c(C)n2CC(F)(F)F)cc1S(=O)CC(F)(F)F] | 1H-NMR(D6-DMSO): 7.54(d, 1H), 7.27(d, 1H), 4.82(q, 2H), 4.17-4.07(m, 1H), 4.02-3.93(m, 1H), 2.32(s, 3H), 2.12(s, 3H), 2.05(s, 3H) |
| Ib-159 | 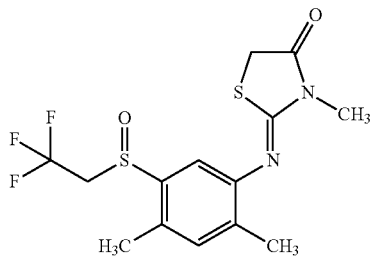 | 1H-NMR(D6-DMSO): 7.34(s, 1H), 7.24(s, 1H), 4.14-4.05(m, 3H), 3.87-3.81(m, 1H), 3.20(s, 3H), 2.31(s, 3H), 2.15(s, 3H) |
| Ib-160 | 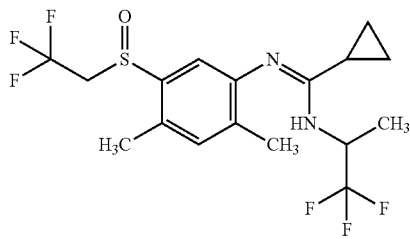 [SMILES: Cc1cc(C)c(S(=O)CC(F)(F)F)cc1/N=C(\NC(C)C(F)(F)F)C1CC1] | 1H-NMR(D6-DMSO): 7.10-7.09(m, 2H), 6.25-6.23(m, 1H), 5.10-5.00(m, 1H), 4.03-3.87(m, 2H), 2.26(s, 3H), 2.05(s, 3H), 1.36-1.33(m, 1H), 1.29-1.28(d, 3H), 1.01-0.96(m, 1H), 0.82-0.76(m, 1H), 0.68-0.61(m, 2H) |

-continued

| Example number | Structure | Analytical data |
|---|---|---|
| Ib-161 | 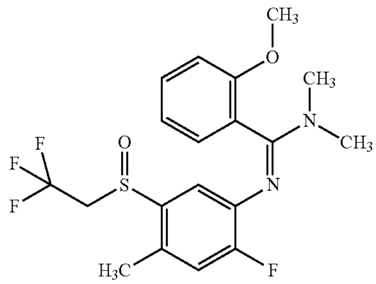 [SMILES: COc1ccccc1/C(=N\c1cc(S(=O)CC(F)(F)F)c(C)cc1F)N(C)C] | logP(HCOOH) = 1.28, logP(neutral) = 2.95 |
| Ib-162 | 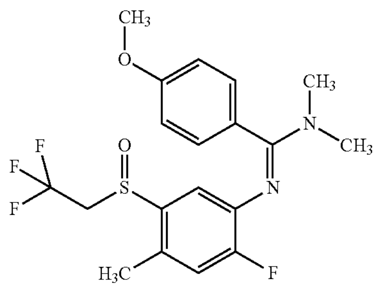 [SMILES: COc1ccc(/C(=N\c2cc(S(=O)CC(F)(F)F)c(C)cc2F)N(C)C)cc1] | 1H-NMR(D6-DMSO): 7.91-7.89(m, 2H), 7.72-7.70(m, 1H), 7.57-7.53(m, 1H), 6.94-6.84(m, 2H), 3.84-3.72(m, 1H), 3.69(s, 3H), 3.44-3.32(m, 1H), 2.95(broad, 6H), 2.17(s, 3H) |
| Ib-163 | 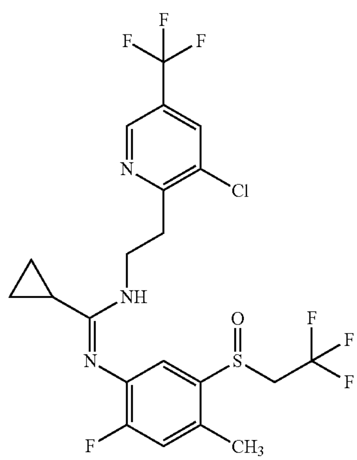 [SMILES: Cc1cc(F)c(/N=C(\NCCc2ncc(C(F)(F)F)cc2Cl)C2CC2)cc1S(=O)CC(F)(F)F] | 1H-NMR(D6-DMSO): 8.87(m, 1H), 8.38(m, 1H), 7.28-7.26(m, 1H), 7.14-7.12(m, 1H), 6.45(m, 1H), 4.10-3.93(m, 2H), 3.63-3.60(m, 2H), 3.25(t, 2H), 2.29(s, 3H), 1.36(m, 1H), 0.78-0.75(m, 2H), 0.63-0.61(m, 2H) |
| Ib-165 | 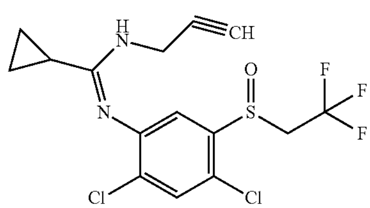 [SMILES: C#CCN/C(=N\c1cc(S(=O)CC(F)(F)F)c(Cl)cc1Cl)C1CC1] | 1H-NMR(D6-DMSO): 8.30(s, 1H), 7.89-7.88(m, 1H), 6.69(s, 1H), 4.43-4.29(m, 2H), 1.94-1.91(d, 2H), 1.39(m, 1H), 0.81-0.74(m, 4H) |
| Ib-166 | 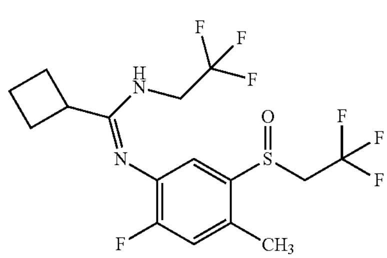 [SMILES: Cc1cc(F)c(/N=C(\NCC(F)(F)F)C2CCC2)cc1S(=O)CC(F)(F)F] | 1H-NMR(D6-DMSO): 7.35(broad, 1H), 7.17-7.13(m, 2H), 4.12-3.98(m, 4H), 3.21-3.16(m, 1H), 2.30(s, 3H), 2.16-2.09(m, 2H), 1.84-1.61(m, 4H) |

-continued

| Example number | Structure | Analytical data |
|---|---|---|
| Ib-167 | 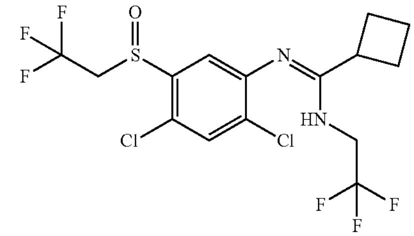 [SMILES: O=S(CC(F)(F)F)c1cc(/N=C(\NCC(F)(F)F)C2CCC2)c(Cl)cc1Cl] | 1H-NMR(D6-DMSO): 7.74(s, 1H), 7.50(broad, 1H), 7.12(s, 1H), 4.24-4.07(m, 4H), 3.23-3.14(m, 1H), 2.18-1.59(m, 6H) |
| Ib-168 | 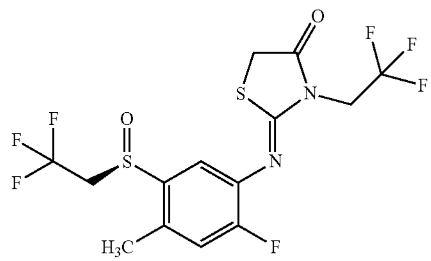 [SMILES: Cc1cc(F)c(/N=C2\SCC(=O)N2CC(F)(F)F)cc1[S@](=O)CC(F)(F)F] | 1H-NMR(D6-DMSO): 7.51(d, 1H), 7.38(d, 1H), 4.62-4.57(m, 2H), 4.26-4.14(m, 3H), 4.04-3.94(m, 1H), 2.36(s, 3H) |
| Ib-169 | 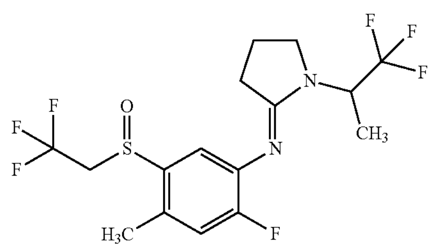 | 1H-NMR(D6-DMSO): 7.31-7.29(m, 1H), 7.20-7.17(m, 1H), 5.14-5.10(m, 1H), 4.12-4.01(m, 2H), 3.55-3.49(m, 2H), 2.47-2.28(m, 2H), 2.30(s, 3H), 1.96-1.92(m, 2H), 1.39-1.38(d, 3H) |
| Ib-170 | 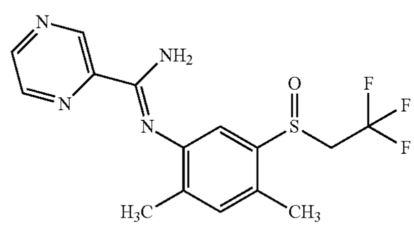 [SMILES: Cc1cc(C)c(S(=O)CC(F)(F)F)cc1/N=C(\N)c1cnccn1] | 1H-NMR(D6-DMSO): 9.51(d, 1H), 8.83-8.82(d, 1H), 8.73(s, 1H), 7.30(s, 1H), 7.21(s, 1H), 6.75(broad, 2H), 4.06-3.97(m, 2H), 2.32(s, 3H), 2.15(s, 3H) |
| Ib-171 | 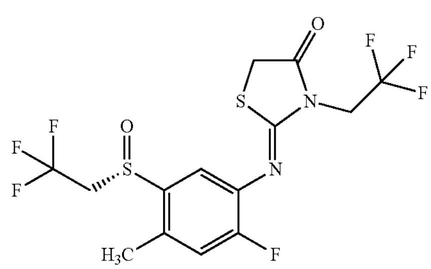 | 1H-NMR(D6-DMSO): 7.51(d, 1H), 7.38(d, 1H), 4.62-4.57(m, 2H), 4.26-4.14(m, 3H), 4.04-3.94(m, 1H), 2.36(s, 3H) |
| Ib-172 | 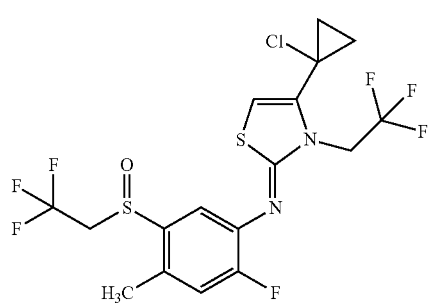 | 1H-NMR(D6-DMSO): 7.55(d, 1H), 7.31(d, 1H), 6.76(s, 1H), 4.96(q, 2H), 4.18-3.95(m, 2H), 2.33(s, 3H), 1.53-1.45(m, 4H) |

| Example number | Structure | Analytical data |
|---|---|---|
| Ib-173 | ![structure] | 1H-NMR(D6-DMSO): 7.37(s, 1H), 7.22(s, 1H), 4.12-4.06(m, 1H), 3.89-3.82(m, 2H), 3.47(s, 3H), 2.37(s, 3H), 2.29(s, 3H), 2.20(s, 3H) |
| Ib-174 | ![structure] | 1H-NMR(D6-DMSO): 7.55(d, 1H), 7.53(d, 1H), 4.19-4.13(m, 1H), 4.00-3.93(m, 1H), 3.45(s, 3H), 2.38(s, 3H), 2.33(s, 3H) |

The intensity of sharp signals correlates with the height of the signals in a printed example of an NMR spectrum in cm and shows the true ratios of the signal intensities. In the case of broad signals, several peaks or the middle of the signal and their relative intensities may be shown in comparison to the most intense signal in the spectrum.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of 1H NMR peaks show the usual solvent peaks, for example peaks of DMSO in DMSO-$d_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

If, as a result of the δ-value being rounded to two digits after the comma, there are signals having the same δ-value, their intensities after addition give the same image that would also be observed in the printout of a classic NMR in the region of this δ-value.

The preparation processes described above can be used to obtain the compounds of the formula (II), for example the following compounds of the formula (II):

N-{2-Chloro-4-fluoro-5-[(2,2,2-trifluoroethyl)sulfanyl]phenyl}-2,2,2-trifluoroethanimidoyl chloride (II-4)

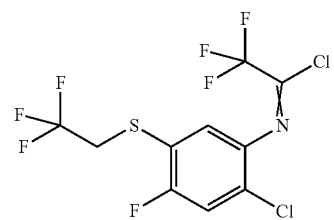 [SMILES: Fc1cc(Cl)c(N=C(Cl)C(F)(F)F)cc1SCC(F)(F)F]

GC-MS: EI mass (m/z): 373 (2Cl) [M]$^+$

The preparation processes described above can be used to obtain the compounds of the formula (III), for example the following compounds of the formula (III):

2,2,2-Trifluoro-N-{4-fluoro-2-methyl-5-[(2,2,2-trifluoroethyl)sulfanyl]phenyl}acetamide (III-4)

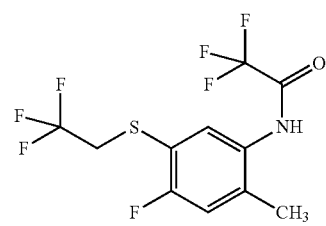 [SMILES: Cc1cc(F)c(SCC(F)(F)F)cc1NC(=O)C(F)(F)F]

log P(HCOOH): 3.16; log P(neutral): 3.1; 1H-NMR (D6-DMSO, 400 MHz) δ ppm 11.05 (s, 1H), 7.59 (d, 1H), 7.31 (d, 1H), 3.96 (q, 2H), 2.17 (s, 3H)

N-{4-Bromo-2-chloro-5-[(2,2,2-trifluoroethyl)sulfanyl]phenyl}-2,2,2-trifluoroacetamide (III-5)

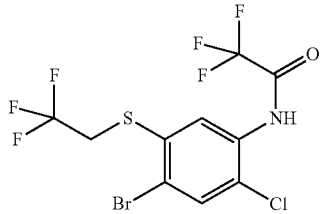 [SMILES: O=C(Nc1cc(SCC(F)(F)F)c(Br)cc1Cl)C(F)(F)F]

log P(HCOOH): 3.78; 1H-NMR (D6-DMSO, 400 MHz) δ ppm 4.17-4.24 (m, 2H), 7.79 (s, 1H), 8.01 (s, 1H), 11.45 (s, 1H)

N-{2,4-Dibromo-5-[(2,2,2-trifluoroethyl)sulfanyl]phenyl}-2,2,2-trifluoroacetamide (III-6)

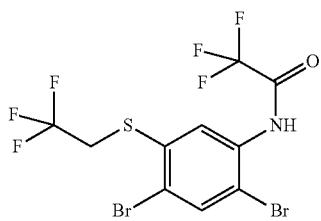 [SMILES: O=C(Nc1cc(SCC(F)(F)F)c(Br)cc1Br)C(F)(F)F]

log P(HCOOH): 3.81; 1H-NMR (D6-DMSO, 400 MHz) δ ppm 11.21 (s, 1H), 7.90 (s, 1H), 7.56 (s, 1H), 3.99 (q, 2H)

N-{2-Chloro-4-fluoro-5-[(2,2,2-trifluoroethyl)sulfanyl]phenyl}-2,2,2-trifluoroacetamide (III-7)

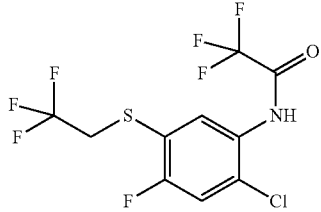 [SMILES: O=C(Nc1cc(SCC(F)(F)F)c(F)cc1Cl)C(F)(F)F]

log P(HCOOH): 3.33; log P(neutral): 3.11; 1H-NMR (D6-DMSO, 400 MHz) δ ppm 11.39 (s, 1H), 7.85 (d, 1H), 7.76 (d, 1H), 4.08 (q, 2H)

N-{4-Chloro-2-fluoro-5-[(2,2,2-trifluoroethyl)sulfanyl]phenyl}-2,2,2-trifluoroacetamide (III-8)

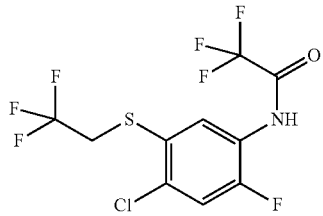 [SMILES: O=C(Nc1cc(SCC(F)(F)F)c(Cl)cc1F)C(F)(F)F]

log P(HCOOH): 3.34; log P(neutral): 3.14; 1H-NMR (D6-DMSO, 400 MHz) δ ppm 11.47 (bs, 1H), 7.85 (d, 1H), 7.76 (d, 1H), 4.09 (q, 2H)

N-{4-Bromo-2-chloro-5-[(2,2,2-trifluoroethyl)sulfanyl]phenyl}-2,2,2-trifluoroacetamide (III-9)

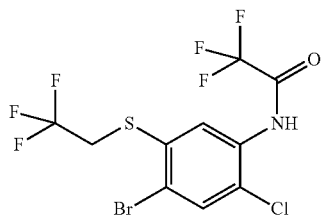 [SMILES: O=C(Nc1cc(SCC(F)(F)F)c(Br)cc1Cl)C(F)(F)F]

log P(HCOOH): 3.46; log P(neutral): 3.11; 1H-NMR (D6-DMSO, 400 MHz) δ ppm 11.46 (s, 1H), 7.87 (d, 1H), 7.82 (d, 1H), 4.11 (q, 2H)

The preparation processes described above can be used to obtain the compounds of the formula (IV), for example the following compounds of the formula (IV):

N,N'-[Disulfanediylbis(4-fluoro-6-methylbenzene-3,1-diyl)]bis(2,2,2-trifluoroacetamide) (IV-2)

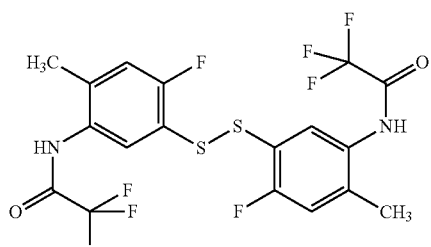

log P(HCOOH): 4.0; log P(neutral): 3.92; 1H-NMR (D6-DMSO, 400 MHz) δ ppm 11.04 (s, 2H), 7.62 (d, 2H), 7.32 (d, 2H), 2.19 (s, 6H)

253

N,N'-[Disulfanediylbis(4-bromo-6-chlorobenzene-3,1-diyl)]bis(2,2,2-trifluoroacetamide) (IV-3)

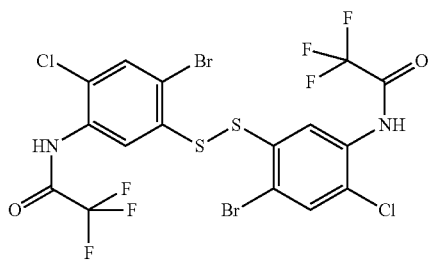 [SMILES: O=C(Nc1cc(SSc2cc(NC(=O)C(F)(F)F)c(Cl)cc2Br)c(Br)cc1Cl)C(F)(F)F]

log P(HCOOH): 5.42

N,N'-[Disulfanediylbis(4,6-dibromobenzene-3,1-diyl)]bis(2,2,2-trifluoroacetamide) (IV-4)

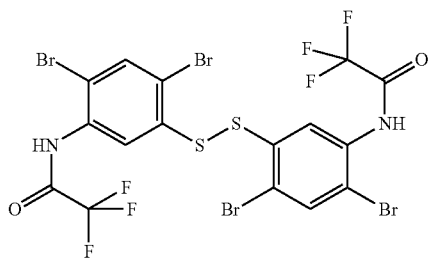 [SMILES: O=C(Nc1cc(SSc2cc(NC(=O)C(F)(F)F)c(Br)cc2Br)c(Br)cc1Br)C(F)(F)F]

log P(HCOOH): 5.62; log P(neutral): 4.49; 1H-NMR (D6-DMSO, 400 MHz) δ ppm 11.38 (s, 2H), 8.18 (s, 2H), 7.77 (d, 2H)

N,N'-[Disulfanediylbis(6-chloro-4-fluorobenzene-3,1-diyl)]bis(2,2,2-trifluoroacetamide) (IV-5)

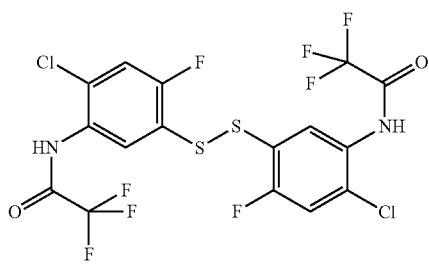 [SMILES: O=C(Nc1cc(SSc2cc(NC(=O)C(F)(F)F)c(Cl)cc2F)c(F)cc1Cl)C(F)(F)F]

log P(HCOOH): 4.45; log P(neutral): 3.81; 1H-NMR (D6-DMSO, 400 MHz) δ ppm 11.37 (s, 2H), 7.88 (d, 2H), 7.80 (d, 2H)

254

N,N'-[Disulfanediylbis(4-chloro-6-fluorobenzene-3,1-diyl)]bis(2,2,2-trifluoroacetamide) (IV-6)

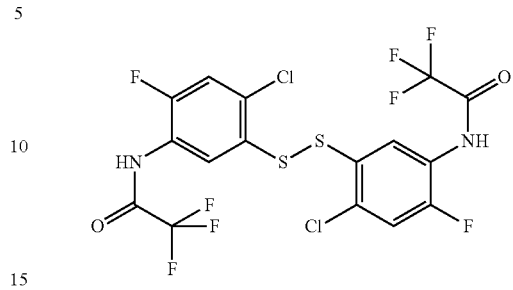

log P(HCOOH): 4.60; log P(neutral): 3.82; 1H-NMR (D6-DMSO, 400 MHz) δ ppm 11.44 (s, 2H), 7.95 (d, 2H), 7.83 (d, 2H)

N,N'-[Disulfanediylbis(4-bromo-6-fluorobenzene-3,1-diyl)]bis(2,2,2-trifluoroacetamide) (IV-7)

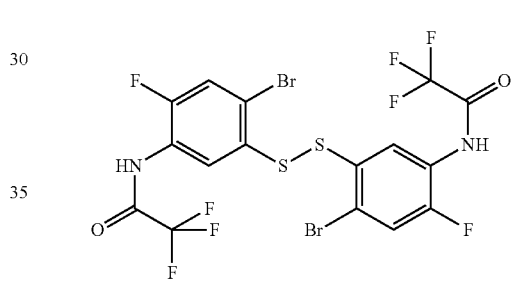

log P(HCOOH): 4.76; log P(neutral): 4.02; 1H-NMR (D6-DMSO, 400 MHz) δ ppm 11.44 (s, 2H), 7.95-7.89 (m, 4H)

The preparation processes described above can be used to obtain the compounds of the formula (V), for example the following compounds of the formula (V):

2-Fluoro-4-methyl-5-[(trifluoroacetyl)amino]benzenesulfonyl chloride (V-2)

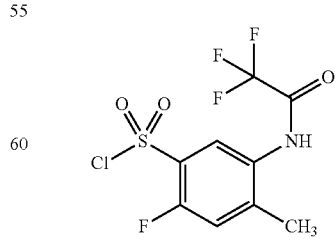

1H-NMR (D6-DMSO, 400 MHz) δ ppm 10.98 (s, 1H), 7.48 (d, 1H), 7.12 (d, 1H), 2.15 (s, 3H)

2,4-Dibromo-5-[(trifluoroacetyl)amino]benzenesulfonyl chloride (V-3)

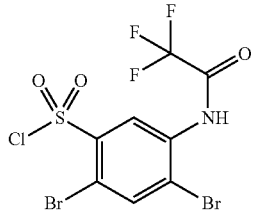 [SMILES: O=C(Nc1cc(S(=O)(=O)Cl)c(Br)cc1Br)C(F)(F)F]

1H-NMR (D6-DMSO, 400 MHz) δ ppm 9.20 (bs, 1H), 8.56 (s, 1H), 8.36 (s, 1H)

4-Chloro-2-fluoro-5-[(trifluoroacetyl)amino]benzenesulfonyl chloride (V-4)

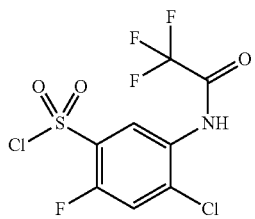 [SMILES: O=C(Nc1cc(S(=O)(=O)Cl)c(F)cc1Cl)C(F)(F)F]

1H-NMR (D6-DMSO, 400 MHz) δ ppm 11.30 (s, 1H), 7.72-7.67 (m, 1H), 7.59-7.55 (d, 1H)

2-Bromo-4-fluoro-5-[(trifluoroacetyl)amino]benzenesulfonyl chloride (V-5)

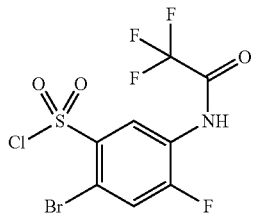 [SMILES: O=C(Nc1cc(S(=O)(=O)Cl)c(Br)cc1F)C(F)(F)F]

1H-NMR (D6-DMSO, 400 MHz) δ ppm 9.38 (bs, 1H), 8.00-7.97 (m, 1H), 7.68 (d, 1H)

The preparation processes described above can be used to obtain the compounds of the formula (VI), for example the following compounds of the formula (VI):

2,2,2-Trifluoro-N-(4-fluoro-2-methylphenyl)acetamide (VI-2)

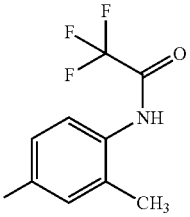

log P(HCOOH): 2.2; log P(neutral): 2.19; 1H-NMR (D6-DMSO, 400 MHz) δ ppm 10.97 (s, 1H), 7.28-7.30 (m, 1H), 7.19-7.21 (m, 1H), 7.08-7.11 (m, 1H), 2.18 (s, 3H)

N-(4-Bromo-2-chlorophenyl)-2,2,2-trifluoroacetamide (VI-3)

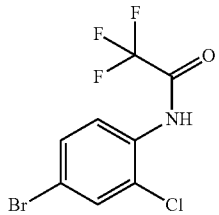 [SMILES: O=C(Nc1ccc(Br)cc1Cl)C(F)(F)F]

log P(HCOOH): 3.01; log P(neutral): 2.81; 1H-NMR (D6-DMSO, 400 MHz) δ ppm 11.35 (s, 1H), 7.92 (d, 1H), 7.65 (dd, 1H), 7.45 (d, 1H)

N-(2,4-Dibromophenyl)-2,2,2-trifluoroacetamide (VI-4)

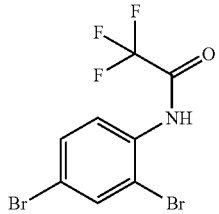

log P(HCOOH): 3.10; log P(neutral): 2.89; 1H-NMR (D6-DMSO, 400 MHz) δ ppm 11.36 (s, 1H), 8.04 (d, 1H), 7.69 (dd, 1H), 7.43 (d, 1H)

N-(2-Chloro-4-fluorophenyl)-2,2,2-trifluoroacetamide (VI-5)

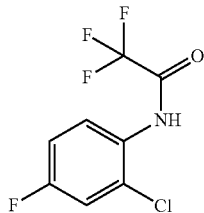

log P(HCOOH): 2.46; log P(neutral): 2.31; 1H-NMR (D6-DMSO, 400 MHz) δ ppm 11.29 (s, 1H), 7.64 (dd, 1H), 7.53 (dd, 1H), 7.35-7.30 (m, 1H)

N-(4-Chloro-2-fluorophenyl)-2,2,2-trifluoroacetamide (VI-6)

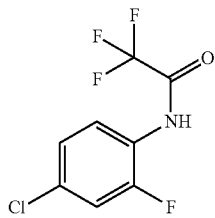 [SMILES: O=C(Nc1ccc(Cl)cc1F)C(F)(F)F]

log P(HCOOH): 2.53; log P(neutral): 2.40; 1H-NMR (D6-DMSO, 400 MHz) δ ppm 11.29 (s, 1H), 7.62 (dd, 1H), 7.55 (dd, 1H), 7.37 (dd, 1H)

N-(4-Bromo-2-fluorophenyl)-2,2,2-trifluoroacetamide (VI-7)

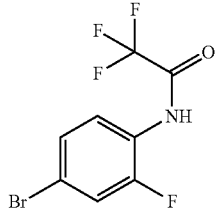

log P(HCOOH): 2.73; log P(neutral): 2.51; 1H-NMR (D6-DMSO, 400 MHz) δ ppm 11.36 (s, 1H), 7.74 (d, 1H), 7.52-7.46 (m, 2H)

The preparation processes described above can be used to obtain the compounds of the formula (X), for example the following compounds of the formula (X):

4-Chloro-2-fluoro-5-[(2,2,2-trifluoroethyl)sulfanyl]aniline (X-6)

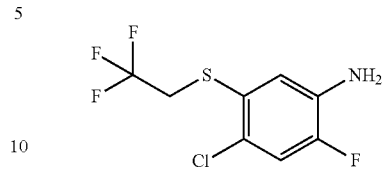

11.0 g (30.9 mmol) of N-{4-chloro-2-fluoro-5-[(2,2,2-trifluoroethyl)sulfanyl]phenyl}-2,2,2-trifluoroacetamide in 150 ml of dioxane are added carefully to a solution of 10.3 ml (186 mmol) of sulfuric acid (96% strength) in 100 ml of water. The reaction mixture is then heated under reflux overnight. After cooling, the solution is adjusted to pH 7 using a saturated sodium bicarbonate solution and a little sodium carbonate and extracted three times with ethyl acetate. The combined organic phases are washed with a saturated sodium chloride solution, dried over sodium sulfate, filtered and concentrated. The residue comprises 8.27 g (96% pure, 99% of theory) of the title compound as a black oil/solid mixture.

log P(HCOOH): 3.02; log P(neutral): 3.00; 1H-NMR (D6-DMSO, 400 MHz) δ ppm 7.27 (d, 1H), 7.04 (d, 1H), 5.46 (bs, 2H), 3.85 (q, 2H)

2-Chloro-5-[(2,2,2-trifluoroethyl)sulfanyl]aniline (X-7)

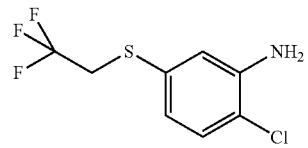 [SMILES: Nc1cc(SCC(F)(F)F)ccc1Cl]

log P(HCOOH): 3.00; log P(neutral): 2.95; 1H-NMR (D6-DMSO, 400 MHz) δ ppm 7.16 (d, 1H), 6.89 (d, 1H), 6.68-6.65 (m, 1H), 5.48 (broad, 2H), 3.89 (q, 2H); GC-MS: EI mass (m/z): 241 (1Cl) [M]+

2-Fluoro-5-[(2,2,2-trifluoroethyl)sulfanyl]aniline (X-8)

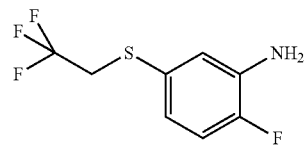 [SMILES: Nc1cc(SCC(F)(F)F)ccc1F]

log P(HCOOH): 2.57; log P(neutral): 2.53; 1H-NMR (D6-DMSO, 400 MHz) δ ppm 7.01-6.97 (m, 1H), 6.92-6.89 (m, 1H), 6.69-6.64 (m, 1H), 5.31 (broad, 2H), 3.82 (q, 2H); GC-MS: EI mass (m/z): 225 [M]+

The preparation processes described above can be used to obtain the compounds of the formula (XXI), for example the following compounds of the formula (XXI):

1,1'-Disulfanediylbis(4-chloro-3-nitrobenzene) (XXI-2)

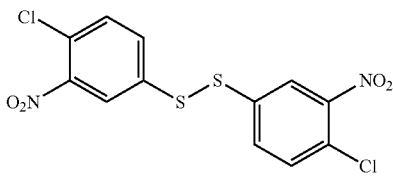 [SMILES: O=[N+]([O-])c1cc(SSc2ccc(Cl)c([N+](=O)[O-])c2)ccc1Cl]

log P(HCOOH): 4.58; log P(neutral): 4.58; 1H-NMR (D6-DMSO, 400 MHz) δ ppm 8.29 (d, 2H), 7.89-7.86 (m, 2H), 7.81 (d, 2H); GC-MS: EI mass (m/z): 376 (2Cl) [M]+

1,1'-Disulfanediylbis(4-fluoro-3-nitrobenzene) (XXI-3)

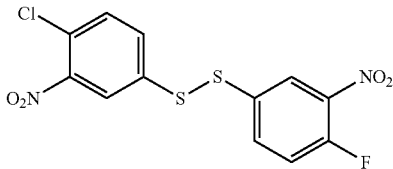

log P(HCOOH): 3.83; log P(neutral): 3.79; 1H-NMR (D6-DMSO, 400 MHz) δ ppm 8.32-8.29 (m, 2H), 8.03-7.97 (m, 2H), 7.69-7.63 (m, 2H); GC-MS: EI mass (m/z): 344 [M]+

1,1'-Disulfanediylbis(2,4-dichloro-5-nitrobenzene) (XXI-4)

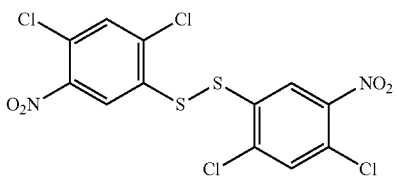 [SMILES: O=[N+]([O-])c1cc(SSc2cc([N+](=O)[O-])c(Cl)cc2Cl)c(Cl)cc1Cl]

log P(HCOOH): 5.69; log P(neutral): 5.64; 1H-NMR (D6-DMSO, 400 MHz) δ ppm 8.33 (s, 2H), 8.21 (s, 2H)

The preparation processes described above can be used to obtain the compounds of the formula (XXII), for example the following compounds of the formula (XXII):

3,3'-Disulfanediylbis(6-chloroaniline) (XXII-2)

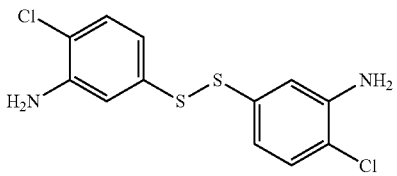

log P(HCOOH): 3.84; log P(neutral): 3.83; 1H-NMR (D6-DMSO, 400 MHz) δ ppm 7.18 (d, 2H), 6.94 (d, 2H), 6.65-6.62 (m, 2H), 5.59 (broad, 4H); GC-MS: EI mass (m/z): 316 (2Cl) [M]+

3,3'-Disulfanediylbis(6-fluoroaniline) (XXII-3)

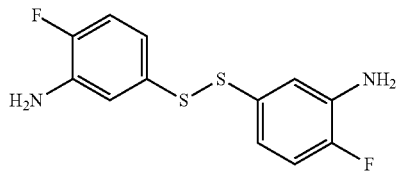 [SMILES: Nc1cc(SSc2ccc(F)c(N)c2)ccc1F]

log P(HCOOH): 2.98; log P(neutral): 2.97; 1H-NMR (D6-DMSO, 400 MHz) δ ppm 7.02-6.95 (m, 2H), 6.95-6.82 (m, 2H), 6.62-6.57 (m, 2H), 5.40 (broad, 4H); GC-MS: EI mass (m/z): 284 [M]+

3,3'-Disulfanediylbis(4,6-dichloroaniline) (XXII-4)

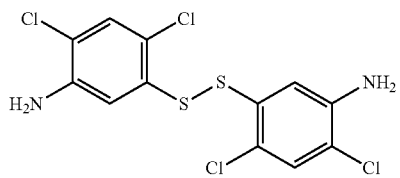

log P(HCOOH): 5.14; log P(neutral): 4.95; 1H-NMR (D6-DMSO, 400 MHz) δ ppm 7.41 (s, 2H), 6.95 (s, 2H), 5.78 (broad, 4H); GC-MS: EI mass (m/z): 386 (4Cl) [M]+

The preparation processes described above can be used to obtain the compounds of the formula (XXIV), for example the following compounds of the formula (XXIV):

1-Chloro-2-fluorocyclopropanecarboxamide (XXIV-1)

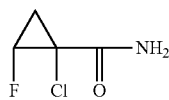

1H-NMR (D6-DMSO) δ ppm: 7.84 (broad, 1H), 7.75 (broad, 1H), 5.05-4.86 (m, 1H), 1.89-1.81 (m, 1H), 1.69-1.60 (m, 1H)

N-(2,2,2-Trifluoroethyl)cyclopentanecarboxamide (XXIV-2)

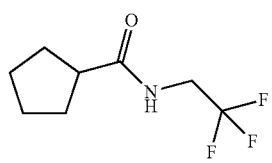 [SMILES: O=C(NCC(F)(F)F)C1CCCC1]

1H-NMR (D6-DMSO) δ ppm: 8.43 (broad, 1H), 3.92-3.83 (m, 2H), 3.08-3.07 (m, 1H), 2.67-2.59 (m, 1H), 1.79-1.49 (m, 7H)

N-(2,2-Difluoroethyl)cyclopentanecarboxamide (XXIV-3)

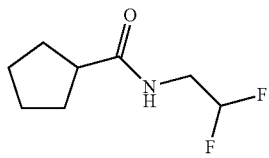 [SMILES: O=C(NCC(F)F)C1CCCC1]

1H-NMR (D6-DMSO) δ ppm: 8.18 (t, 1H), 5.97 (tt, 1H), 3.50-3.40 (m, 2H), 3.08-3.06 (m, 1H), 2.64-2.57 (m, 1H), 1.78-1.45 (m, 7H)

N-(1,1,1-Trifluoropropan-2-yl)cyclopropanecarboxamide (XXIV-4)

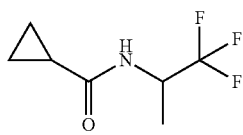

1H-NMR (D6-DMSO) δ ppm: 8.62-8.60 (d, 1H), 4.62-4.55 (m, 1H), 1.63-1.59 (m, 1H), 1.24-1.23 (d, 3H), 0.72-0.70 (m, 4H)

(3-Pyridyl)(4,4-difluoropiperidin-1-yl)methanone (XXIV-5)

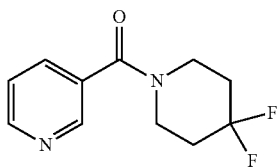 [SMILES: O=C(c1cccnc1)N1CCC(F)(F)CC1]

1H-NMR (D6-DMSO) δ ppm: 8.67-8.66 (m, 2H), 7.90-7.87 (m, 1H), 7.51-7.48 (m, 1H), 3.73 (m, 2H), 3.42 (m, 2H), 2.06 (m, 4H)

(2-Chlorophenyl)(4,4-difluoropiperidin-1-yl)methanone (XXIV-6)

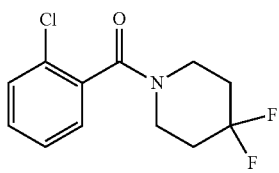 [SMILES: O=C(c1ccccc1Cl)N1CCC(F)(F)CC1]

1H-NMR (D6-DMSO) δ ppm: 7.56-7.53 (m, 1H), 7.49-7.41 (m, 3H), 3.90-3.84 (m, 1H), 3.70-3.64 (m, 1H), 3.34-3.22 (m, 2H), 2.15-1.90 (m, 4H)

Use Examples

Phaedon Test (PHAECO Spray Treatment)

Solvents: 78.0 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. disks of Chinese cabbage leaves (*Brassica pekinensis*) are sprayed with an active compound preparation of the desired concentration and, after drying, populated with larvae of the mustard beetle (*Phaedon cochleariae*).

After 7 days, the effect in % is determined. 100% means that all beetle larvae have been killed; 0% means that none of the beetle larvae have been killed.

In this test, for example, the following compounds from the Preparation Examples show an efficacy of 100% at an application rate of 500 g/ha: Ia-02, Ia-04, Ia-05, Ia-13, Ia-14, Ia-15, Ia-18, Ia-19, Ib-02, Ib-10, Ib-11, Ib-14, Ib-16

*Tetranychus* Test, OP-Resistant (TETRUR Spray Treatment)

Solvents: 78.0 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. disks of bean leaves (*Phaseolus vulgaris*) which are infested by all stages of the greenhouse red spider mite (*Tetranychus urticae*) are sprayed with an active compound preparation of the desired concentration.

After 6 days, the effect in % is determined. 100% here means that all of the spider mites have been killed; 0% means that none of the spider mites have been killed.

In this test, for example, the following compounds of the Preparation Examples show an efficacy of 80% at an application rate of 500 g/ha: Ia-09, Ia-17, Ib-04, Ib-05

In this test, for example, the following compounds of the Preparation Examples show an efficacy of 100% at an application rate of 500 g/ha: Ia-02, Ia-03, Ia-05, Ia-07, Ia-12, Ia-13, Ia-15, Ia-18, Ia-23, Ia-26, Ib-02, Ib-03, Ib-06, Ib-07, Ib-08, Ib-09, Ib-12, Ib-13, Ib-15

*Meloidogyne incognita* Test (MELGIN)

Solvents: 80.0 parts by weight of acetone

To prepare a suitable active compound preparation, 1 part by weight of active compound is mixed with the stated amounts of solvent and the concentrate is diluted with water to the desired concentration.

Containers are filled with sand, solution of active compound, *Meloidogyne incognita* egg/larvae suspension and lettuce seeds. The lettuce seeds germinate and the plants develop. On the roots, galls are formed.

After 14 days, the nematicidal efficacy in % is determined by the formation of galls. 100% means that no galls have been found; 0% means that the number of galls on the treated plants corresponds to the untreated control.

In this test, for example, the following compound from the Preparation Examples shows an efficacy of 90% at an application rate of 20 ppm: Ia-07

In this test, for example, the following compound from the Preparation Examples shows an efficacy of 100% at an application rate of 20 ppm: Ib-02

Lucilia cuprina (48 h)

Solvent: dimethyl sulfoxide 10 mg of active compound are dissolved in 0.5 ml of dimethyl sulfoxide. To prepare a suitable formulation, the active compound solution is diluted with water to the concentration desired in each case. About 20 Lucilia cuprina larvae are introduced into a test tube which contains about 1 cm$^3$ of horse meat and 0.5 ml of the preparation of active compound to be tested. After 48 hours, the efficacy of the active compound preparation is determined as % larvae mortality.

In this test, for example, the following compounds of the Preparation Examples show an effect of 100% at an application rate of 100 ppm: Ia-21, Ib-11

Boophilus microplus Test (BOOPMI Injection)

Solvent: dimethyl sulfoxide

To produce a suitable preparation of active compound, 10 mg of active compound are mixed with 0.5 ml of solvent, and the concentrate is diluted with solvent to the desired concentration. The solution of active compound is injected into the abdomen (Boophilus microplus), and the animals are transferred into dishes and kept in a climatized room. The activity is assessed by laying of fertile eggs.

After 7 days, the effect in % is determined. 100% means that none of the ticks has laid any fertile eggs.

In this test, for example, the following compound from the Preparation Examples shows an efficacy of 80% at an application rate of 20 g/animal: Ia-04

In this test, for example, the following compounds of the Preparation Examples show an efficacy of 100% at an application rate of 20 g/animal: Ia-01, Ia-21, Ia-22, Ib-01, Ib-10, Ib-11, Ib-14, Ib-16

Unless indicated otherwise, the test solution in the examples below was prepared as follows:

1 part by weight of active compound is mixed with the stated amounts of a solvent and emulsifier mixture (3 parts by weight of dimethylformamide as solvent and 1 part by weight of polyoxyethylene alkyl phenyl ether as emulsifier) and the solution is diluted with water to the desired concentration.

Spider Mite Test (Tetranychus urticae)

50 to 100 adult spider mites are placed onto the leaves of a kidney bean plant at the two-leaf stage growing in a pot having a diameter of 6 cm.

After one day, using a paint spray gun, the plant is sprayed with a sufficient amount of the active compound preparation of the desired concentration and placed in a greenhouse. After 7 days, the acaricidal effect is determined. 100% here means that all of the spider mites have been killed; 0% means that none of the spider mites have been killed.

In this test, for example, the following compounds of the Preparation Examples show an efficacy of 100% at an active compound concentration of 100 ppm:

Ia-21, Ia-01, Ib-11, Ib-01, Ia-06, Ia-14, Ia-15, Ib-14, Ia-20, Ia-25, Ia-19, Ib-16 and Ib-10

Cucrbit Leaf Beetle Test (Aulacophora Femoralis)

Cucumber leaves are dipped into the test solution of the appropriate concentration and then air-dried. The leaves are then inserted into a plastic dish filled with sterile soil and five Aulacophora femoralis larvae at the second larval stage. The dishes are placed in a climatized room at 25° C.

After 7 days, the effect in % is determined. 100% means that all beetle larvae have been killed; 0% means that none of the beetle larvae have been killed.

In this test, for example, the following compounds of the Preparation Examples show an efficacy of 100% at an active compound concentration of 500 ppm:

Ia-21, Ib-11, Ib-01, Ib-14, Ib-16 and Ib-10

Boophilus microplus—Dip Test (BOOPMI Dip)

Test animals: cattle ticks (Boophilus microplus) Parkhurst strain, SP-resistant

Solvent: dimethyl sulfoxide 10 mg of active compound are dissolved in 0.5 ml of dimethyl sulfoxide. To prepare a suitable formulation, the active compound solution is diluted with water to the concentration desired in each case.

This active compound preparation is pipetted into tubes. 8-10 adult engorged female cattle ticks (Boophilus microplus) are transferred into a further tube with holes. The tube is immersed into the active compound formulation, and all ticks are completely wetted. After the liquid has run out, the ticks are transferred on filter disks into plastic dishes and stored in a climate-controlled room.

The activity is assessed after 7 days by laying of fertile eggs. Eggs whose fertility is not visible from the outside are stored in a climate-controlled cabinet until the larvae hatch after about 42 days. An efficacy of 100% means that none of the ticks has laid any fertile eggs; 0% means that all eggs are fertile.

In this test, for example, the following compounds of the Preparation Examples show an efficacy of 100% at an application rate of 100 ppm: Ia-189, Ib-115, Ib-33

Boophilus microplus—Injection Test (BOOPMI Inj)

Solvent: dimethyl sulfoxide

To produce a suitable preparation of active compound, 10 mg of active compound are mixed with 0.5 ml of solvent, and the concentrate is diluted with solvent to the desired concentration.

1 µl of the active compound solution is injected into the abdomen of 5 engorged adult female cattle ticks (Boophilus microplus). The animals are transferred into dishes and kept in a climate-controlled room.

The activity is assessed after 7 days by laying of fertile eggs. Eggs whose fertility is not visible from the outside are stored in a climate-controlled cabinet until the larvae hatch after about 42 days. An efficacy of 100% means that none of the ticks has laid any fertile eggs; 0% means that all eggs are fertile.

In this test, for example, the following compounds of the Preparation Examples show an efficacy of 100% at an application rate of 20 µg/animal: Ia-01, Ia-115, Ia-116, Ia-118, Ia-120, Ia-13, Ia-189, Ia-206, Ia-21, Ia-22, Ia-27, Ia-34, Ia-39, Ia-44, Ia-50, Ia-66, Ia-80, Ib-01, Ib-02, Ib-03, Ib-07, Ib-10, Ib-108, Ib-11, Ib-115, Ib-12, Ib-14, Ib-14, Ib-16, Ib-17, Ib-18, Ib-19, Ib-20, Ib-33, Ib-35, Ib-38, Ib-40, Ib-47, Ib-48, Ib-58, Ib-59, Ib-68, Ib-85

In this test, for example, the following compounds of the Preparation Examples show an efficacy of 90% at an application rate of 20 µg/animal: Ib-44

In this test, for example, the following compounds of the Preparation Examples show an efficacy of 80% at an application rate of 20 µg/animal: Ia-04, Ib-24, Ib-89

Cooperia curticei Test (COOPCU)

Solvent: dimethyl sulfoxide

To produce a suitable preparation of active compound, 10 mg of active compound are mixed with 0.5 ml of dimethyl sulfoxide, and the concentrate is diluted with "Ringer solution" to the desired concentration.

Vessels containing the active compound preparation of the desired concentration are populated with about 40 nematode larvae (Cooperia curticei).

After 5 days, the kill in % is determined. 100% means that all of the larvae have been killed; 0% means that none of the larvae have been killed.

In this test, for example, the following compounds of the Preparation Examples show an efficacy of 100% at an application rate of 100 ppm: Ia-220

*Lucilia cuprina* Test (LUCICU)

Solvent: dimethyl sulfoxide

To produce a suitable preparation of active compound, 10 mg of active compound are mixed with 0.5 ml of dimethyl sulfoxide, and the concentrate is diluted with water to the desired concentration.

About 20 L1 larvae of the Australian sheep blowfly (*Lucilia cuprina*) are transferred into a test vessel containing minced horsemeat and the active compound preparation of the desired concentration.

After 2 days, the kill in % is determined. 100% means that all larvae have been killed; 0% means that no larvae have been killed.

In this test, for example, the following compounds of the Preparation Examples show an efficacy of 100% at an application rate of 100 ppm: Ia-21, Ib-11

In this test, for example, the following compounds of the Preparation Examples show an efficacy of 90% at an application rate of 100 ppm: Ia-13

In this test, for example, the following compounds of the Preparation Examples show an efficacy of 80% at an application rate of 100 ppm: Ib-02

*Myzus persicae*—Spray Test (MYZUPE)

Solvents: 78 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

disks of Chinese cabbage leaves (*Brassica pekinensis*) infested by all stages of the green peach aphid (*Myzus persicae*) are sprayed with an active compound preparation of the desired concentration.

After 6 days, the effect in % is determined. 100% here means that all of the aphids have been killed; 0% means that none of the aphids have been killed.

In this test, for example, the following compounds of the Preparation Examples show, at an application rate of 500 g/ha, an effect of 100%: Ia-206, Ia-228, Ib-44

In this test, for example, the following compounds of the Preparation Examples show, at an application rate of 500 g/ha, an effect of 90%: Ia-34, Ia-116, Ib-123

In this test, for example, the following compounds of the Preparation Examples show, at an application rate of 100 g/ha, an effect of 80%: Ib-42

*Phaedon cochleariae*—Spray Test (PHAECO)

Solvents: 78.0 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

disks of Chinese cabbage leaves (*Brassica pekinensis*) are sprayed with an active compound preparation of the desired concentration and, after drying, populated with larvae of the mustard beetle (*Phaedon cochleariae*).

After 7 days, the effect in % is determined. 100% means that all beetle larvae have been killed; 0% means that none of the beetle larvae have been killed.

In this test, for example, the following compounds of the Preparation Examples show, at an application rate of 500 g/ha, an effect of 100%: Ia-02, Ia-04, Ia-05, Ia-13, Ia-14, Ia-15, Ia-18, Ia-19, Ia-27, Ia-28, Ia-29, Ia-31, Ia-35, Ia-36, Ia-38, Ia-45, Ia-78, Ia-79, Ia-115, Ia-118, Ia-121, Ia-135, Ia-139, Ia-149, Ia-162, Ia-191, Ia-202, Ia-209, Ia-229, Ib-02, Ib-10, Ib-11, Ib-14, Ib-16, Ib-17, Ib-20, Ib-20, Ib-27, Ib-39, Ib-43, Ib-44, Ib-56, Ib-57, Ib-68, Ib-78, Ib-83, Ib-101, Ib-110, Ib-111, Ib-115

In this test, for example, the following compounds of the Preparation Examples show, at an application rate of 500 g/ha, an effect of 83%: Ia-33, Ia-92, Ia-130, Ia-134, Ia-171, Ia-204, Ia-207, Ia-210, Ib-18, Ib-30, Ib-108, Ib-137, Ib-143

*Tetranychus urticae*—Spray Test, OP-Resistant (TETRUR)

Solvents: 78.0 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

disks of bean leaves (*Phaseolus vulgaris*) which are infested by all stages of the greenhouse red spider mite (*Tetranychus urticae*) are sprayed with an active compound preparation of the desired concentration.

After 6 days, the effect in % is determined. 100% here means that all of the spider mites have been killed; 0% means that none of the spider mites have been killed.

In this test, for example, the following compounds of the Preparation Examples show an efficacy of 100% at an application rate of 500 g/ha: Ia-01, Ia-02, Ia-03, Ia-04, Ia-05, Ia-06, Ia-07, Ia-08, Ia-11, Ia-12, Ia-13, Ia-14, Ia-15, Ia-16, Ia-18, Ia-19, Ia-20, Ia-21, Ia-22, Ia-23, Ia-25, Ia-26, Ia-27, Ia-28, Ia-29, Ia-30, Ia-31, Ia-32, Ia-33, Ia-34, Ia-35, Ia-36, Ia-37, Ia-38, Ia-39, Ia-40, Ia-41, Ia-42, Ia-43, Ia-44, Ia-46, Ia-47, Ia-48, Ia-49, Ia-50, Ia-51, Ia-52, Ia-53, Ia-54, Ia-55, Ia-56, Ia-57, Ia-60, Ia-61, Ia-64, Ia-65, Ia-66, Ia-67, Ia-69, Ia-70, Ia-71, Ia-72, Ia-73, Ia-74, Ia-75, Ia-76, Ia-77, Ia-78, Ia-79, Ia-80, Ia-81, Ia-82, Ia-83, Ia-84, Ia-85, Ia-86, Ia-87, Ia-89, Ia-93, Ia-94, Ia-95, Ia-96, Ia-97, Ia-98, Ia-99, Ia-100, Ia-115, Ia-116, Ia-119, Ia-120, Ia-121, Ia-122, Ia-123, Ia-124, Ia-125, Ia-126, Ia-127, Ia-129, Ia-130, Ia-131, Ia-132, Ia-133, Ia-134, Ia-135, Ia-136, Ia-138, Ia-139, Ia-140, Ia-141, Ia-141, Ia-143, Ia-144, Ia-145, Ia-146, Ia-147, Ia-148, Ia-150, Ia-151, Ia-152, Ia-153, Ia-156, Ia-158, Ia-161, Ia-162, Ia-163, Ia-165, Ia-166, Ia-187, Ia-188, Ia-189, Ia-191, Ia-193, Ia-194, Ia-195, Ia-197, Ia-201, Ia-202, Ia-203, Ia-205, Ia-206, Ia-207, Ia-208, Ia-209, Ia-210, Ia-211, Ia-213, Ia-214, Ia-217, Ia-221, Ia-222, Ia-224, Ia-225, Ia-226, Ia-227, Ia-230, Ia-233, Ia-234, Ia-236, Ia-238, Ia-239, Ia-242, Ia-247, Ia-249, Ia-272, Ia-275, Ia-276, Ib-02, Ib-03, Ib-06, Ib-07, Ib-08, Ib-09, Ib-10, Ib-11, Ib-12, Ib-13, Ib-14, Ib-15, Ib-16, Ib-17, Ib-19, Ib-20, Ib-21, Ib-22, Ib-24, Ib-25, Ib-26, Ib-27, Ib-28, Ib-29, Ib-30, Ib-31, Ib-32, Ib-33, Ib-34, Ib-35, Ib-36, Ib-37, Ib-38, Ib-39, Ib-40, Ib-42, Ib-43, Ib-45, Ib-46, Ib-47, Ib-48, Ib-49, Ib-50, Ib-51, Ib-52, Ib-53, Ib-56, Ib-57, Ib-58, Ib-59, Ib-61, Ib-62, Ib-63, Ib-64, Ib-65, Ib-68, Ib-69, Ib-71, Ib-72, Ib-75, Ib-76, Ib-78, Ib-79, Ib-80, Ib-81, Ib-82, Ib-83, Ib-84, Ib-85, Ib-86, Ib-87, Ib-88, Ib-89, Ib-90, Ib-92, Ib-93, Ib-94, Ib-95, Ib-97, Ib-98, Ib-99, Ib-100, Ib-108, Ib-109, Ib-110, Ib-112, Ib-113, Ib-114, Ib-115, Ib-117, Ib-118, Ib-119, Ib-120, Ib-121, Ib-123, Ib-125, Ib-126, Ib-127, Ib-129, Ib-130, Ib-131, Ib-132, Ib-135, Ib-137, Ib-138, Ib-139, Ib-140, Ib-141, Ib-148, Ib-151, Ib-160, Ib-169, Ib-174

In this test, for example, the following compounds of the Preparation Examples show an efficacy of 90% at an application rate of 500 g/ha: Ia-59, Ia-62, Ia-63, Ia-68, Ia-83, Ia-88, Ia-91, Ia-92, Ia-101, Ia-102, Ia-103, Ia-104, Ia-105, Ia-106, Ia-107, Ia-117, Ia-118, Ia-128, Ia-149, Ia-155, Ia-159, Ia-160, Ia-167, Ia-168, Ia-169, Ia-171, Ia-172, Ia-173, Ia-175, Ia-176, Ia-177, Ia-178, Ia-180, Ia-190, Ia-192, Ia-196, Ia-204, Ia-205, Ia-212, Ia-215, Ia-216, Ia-218, Ia-219, Ia-220, Ia-223, Ia-228, Ia-229, Ia-231, Ia-232, Ia-235, Ia-237, Ia-240, Ia-241, Ia-243, Ia-244, Ia-245, Ia-248, Ia-250, Ia-251, Ia-252, Ia-253, Ia-254, Ia-255, Ia-256, Ia-257, Ia-258, Ia-259, Ia-260, Ia-261, Ia-262, Ia-263, Ia-264, Ia-265, Ia-266, Ia-267, Ia-268, Ia-269, Ia-270, Ia-278, Ib-01, Ib-23, Ib-41, Ib-54, Ib-60, Ib-66, Ib-67, Ib-73, Ib-74, Ib-77, Ib-91, Ib-96, Ib-101, Ib-102, Ib-103, Ib-104, Ib-111, Ib-116, Ib-122, Ib-124, Ib-128, Ib-133, Ib-134, Ib-136, Ib-142, Ib-143, Ib-144, Ib-145, Ib-146, Ib-147, Ib-149, Ib-150, Ib-152, Ib-153, Ib-154, Ib-155, Ib-156, Ib-157, Ib-158, Ib-166, Ib-167, Ib-172

In this test, for example, the following compounds of the Preparation Examples show an efficacy of 80% at an application rate of 500 g/ha: Ia-09, Ia-17, Ia-45, Ia-90, Ia-108, Ia-109, Ib-04, Ib-05, Ib-18

In this test, for example, the following compounds of the Preparation Examples show an efficacy of 100% at an application rate of 100 g/ha: Ia-58

In this test, for example, the following compounds of the Preparation Examples show an efficacy of 90% at an application rate of 100 g/ha: Ia-181

Tetranychus urticae—Spray Test, OP-Resistant (TET-RUR)

Solvents: 7 parts by weight of dimethylformamide
Emulsifier: 2 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. If the addition of ammonium salts or/and penetrants is required, these are in each case added in a concentration of 1000 ppm to the solution of the preparation.

Bean plants (Phaseolus vulgaris) which are heavily infested by all stages of the greenhouse red spider mite (Tetranychus urticae) are treated by spraying with the active compound preparation of the desired concentration.

After 7 days, the effect in % is determined. 100% here means that all of the spider mites have been killed; 0% means that none of the spider mites have been killed.

In this test, for example, the following compounds of the Preparation Examples show an efficacy of 90% at an application rate of 100 ppm: Ib-44

In this test, for example, the following compounds of the Preparation Examples show an efficacy of 100% at an application rate of 20 ppm: Ib-168

In this test, for example, the following compounds of the Preparation Examples show an efficacy of 80% at an application rate of 20 ppm: Ib-159.

The invention claimed is:
1. A process for preparing compounds of the formula (Ia-g)

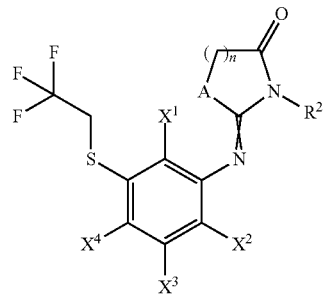

in which
n represents the number 0 or 1,
A represents oxygen or sulfur,
$X^1$, $X^2$, $X^3$, $X^4$ independently of one another represent hydrogen, halogen, hydroxy, amino, OCN, SCN, $SF_5$, trialkylsilyl, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, hydroxycarbonylalkoxy, alkoxycarbonylalkoxy, alkoxyalkoxy, alkylhydroxyimino, alkoxyimino, alkylalkoxyimino, haloalkylalkoxyimino, alkylthio, haloalkylthio, alkoxyalkylthio, alkylthioalkyl, alkylsulfinyl, haloalkylsulfinyl, alkoxyalkylsulfinyl, alkylsulfinylalkyl, alkylsulfonyl, haloalkylsulfonyl, alkoxyalkylsulfonyl, alkylsulfonylalkyl, alkylsulfonyloxy, alkylcarbonyl, haloalkylcarbonyl, carboxyl, alkylcarbonyloxy, alkoxycarbonyl, haloalkoxycarbonyl, alkoxycarbonylalkyl, aminocarbonyl, alkylaminocarbonyl, dialkylaminocarbonyl, alkenylaminocarbonyl, dialkenylaminocarbonyl, cycloalkylaminocarbonyl, alkylsulfonylamino, aminosulfonyl, alkylaminosulfonyl, dialkylaminosulfonyl, alkylsulfoximino, aminothiocarbonyl, alkylaminothiocarbonyl, dialkylaminothiocarbonyl, or represent optionally substituted phenylalkyl, phenoxy, phenylalkyloxy, phenoxyalkyl, phenylthio, phenylthioalkyl, phenylsulfinyl, phenylsulfonyl, hetarylalkyl, hetaryloxy, hetarylalkyloxy, hetarylthio, hetarylsulfinyl, hetarylsulfonyl, or represent optionally substituted saturated or unsaturated cycloalkylalkyl, cycloalkyloxy, cycloalkylalkoxy, cycloalkylthio, cycloalkylalkylthio, cycloalkylsulfinyl, cycloalkylalkylsulfinyl, cycloalkylsulfonyl, cycloalkylalkylsulfonyl, or represent $NR^4R^5$, where $R^4$ and $R^5$ independently of one another represent hydrogen, cyano, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl, alkoxycarbonyl, or $R^4$ and $R^5$ together with the nitrogen atom to which they are attached may form an optionally substituted saturated or unsaturated five-to eight-membered ring which is optionally interrupted by heteroatoms from the group consisting of O, S and N, or represent a 3- to 6-membered saturated, partially saturated or aromatic ring which may optionally contain one to three heteroatoms from the group consisting of O, S and N and which is optionally mono- or polysubstituted by identical or different substituents from the group consisting of halogen, cyano, nitro, hydroxy, amino, carboxy, alkyl, haloalkyl, alkenyl, haloalkenyl, alkynyl, alkoxy, haloalkoxy, alkylthio, alkylsulfinyl, alkylsulfonyl, alkylsulfonyloxy, haloalkylthio, haloalkylsulfinyl, haloalkylsulfonyl, alkylamino, dialkylamino, alkylcarbonylamino, alkoxycarbonyl, alkylcarbonyl, alkylcarbonyloxy, aminocarbonyl, alkylaminocarbonyl, dialkylaminocarbonyl, aminothiocarbonyl, alkylaminothiocarbonyl, dialkylaminothiocarbonyl, cycloalkylamino, alkylsulfonylamino, aminosulfonyl, alkylaminosulfonyl and dialkylaminosulfonyl, or by optionally substituted cycloalkyl, cycloalkoxy, cycloalkylalkyl or cycloalkylalkoxy which are optionally interrupted by heteroatoms from the group consisting of O, S and N, or $X^2$ and $X^3$ or $X^3$ and $X^4$, form, together with the carbon atoms to which they are attached, a 5- or 6-membered ring which is optionally substituted and optionally interrupted by heteroatoms from the group consisting of O, S, N and CO, $R^2$ represents hydrogen, cyano, alkyl, haloalkyl, alkoxy, cyanoalkyl, hydroxyalkyl, alkoxyalkyl, alkylthioalkyl, alkenyl, haloalkenyl, cyanoalkenyl, alkynyl, haloalkynyl, cyanoalkynyl, represent optionally substituted alkylcarbonyl, alkoxycarbonyl, arylcarbonyl, hetarylcarbonyl, aryloxycarbonyl, hetaryloxycarbonyl, alkylsulfinyl, haloalkylsulfinyl, arylsulfinyl, arylalkylsulfinyl, hetarylsulfinyl, hetarylalkylsulfinyl, alkylsulfonyl, haloalkylsulfonyl, arylsulfonyl, arylalkylsulfonyl, hetarylsulfonyl, hetarylalkylsulfonyl, or represents a 3- to 6-membered saturated, partially saturated or aromatic ring which may optionally contain one to three heteroatoms from the group consisting of O, S and N, which may optionally be interrupted once or twice by C=O, SO or $SO_2$ and which is optionally mono- or polysubstituted by identical or different substituents from the group consisting of halogen, cyano, nitro, hydroxy, amino, carboxy, alkyl, haloalkyl, alkenyl, haloalkenyl, alkynyl, alkoxy, haloalkoxy, alkylthio, alkylsulfinyl, alkylsulfonyl, alkylsulfonyloxy, haloalkylthio, haloalkylsulfinyl, haloalkylsulfonyl, alkylamino, dialkylamino, alkylcarbonylamino, alkoxycarbonyl, alkylcarbonyl, alkylcarbonyloxy, aminocarbonyl, alkylaminocarbonyl, dialkylaminocarbonyl, aminothiocarbonyl, alkylaminothiocarbonyl, dialkylaminothiocarbonyl, cycloalkylamino, alkylsulfonylamino, aminosulfonyl, alkylaminosulfonyl and dialkylaminosulfonyl, or by optionally substituted cycloalkyl, cycloalkoxy, cycloalkylalkyl or cycloalkylalkoxy which are optionally interrupted by heteroatoms from the group consisting of O, S and N, or represents —$(CH_2)_m$—$R^6$, —O—$(CH_2)_m$—$R^6$, —$(CH_2)_m$—O—$R^6$, where $R^6$ represents a 3- to 6-membered saturated, partially saturated or aromatic ring which may optionally contain one to three heteroatoms from the group consisting of O, S and N, which may optionally be interrupted once or twice by C=O and which is optionally mono- or polysubstituted by identical or different substituents from the group consisting of halogen, cyano, nitro, hydroxy, amino, carboxy, alkyl, haloalkyl, alkenyl, haloalkenyl, alkynyl, alkoxy, haloalkoxy, alkylthio, alkylsulfinyl, alkylsulfonyl, alkylsulfonyloxy, haloalkylthio, haloalkylsulfinyl, haloalkylsulfonyl, alkylamino, dialkylamino, alkylcarbonylamino, alkoxycarbonyl, alkylcarbonyl, alkylcarbonyloxy, aminocarbonyl, alkylaminocarbonyl, dialkylaminocarbonyl, aminothiocarbonyl, alkylaminothiocarbonyl, dialkylaminothiocarbonyl, cycloalkylamino, alkylsulfonylamino, aminosulfonyl, alkylaminosulfonyl and dialkylaminosulfonyl, or by optionally substituted cycloalkyl, cycloalkoxy, cycloalkylalkyl or cycloalkylalkoxy which are optionally interrupted by heteroatoms from the group consisting of O, S and N, where m represents the number 1, 2, 3 or 4, and/or diastereomers, enantiomers, rotamers, tautomers, and/or salts thereof, wherein (A) anilines of the formula (X)

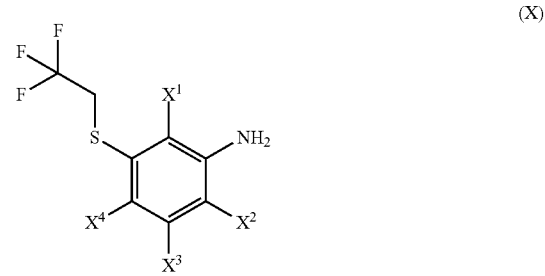

are converted with isocyanates or isothiocyanates, optionally in the presence of a base and optionally in the presence of an organic solvent, into compounds of the formula (XXXVIII),

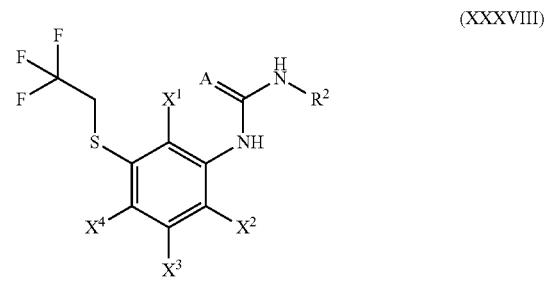

and (B) compounds of the formula (XXXVIII) are converted by cycloacylation into compounds of the formula (Ia-g),

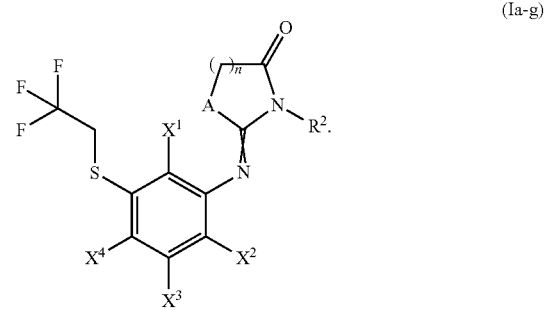

2. The process according to claim 1, further comprising
(C) oxidizing the compound of formula (Ia-g)

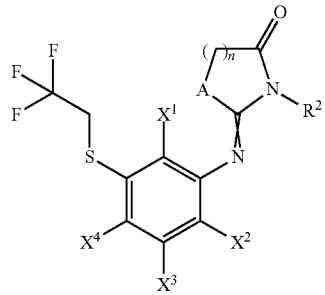
(Ia-g)

to a compound of formula (Ib-g)

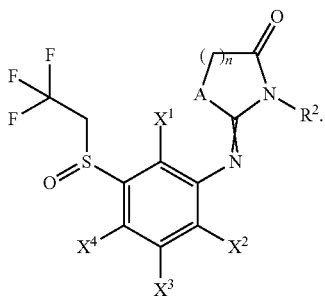
(Ib-g)

3. The process according to claim 2, wherein the compound of formula (Ib-g) is

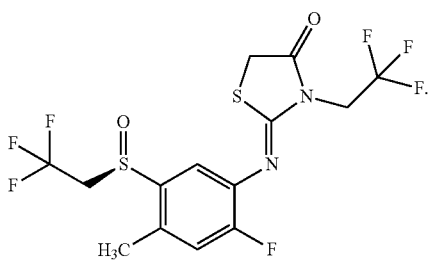

4. The process according to claim 1, wherein A represents oxygen.

5. The process according to claim 1, wherein A represents sulfur.

6. The process according to claim 1, wherein n represents the number 0.

7. The process according to claim 1, wherein n represents the number 1.

8. The process according to claim 1, wherein anilines of the formula (X)

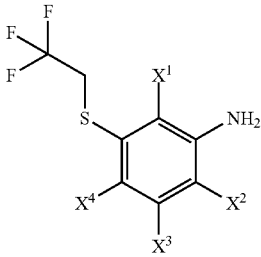
(X)

are converted with isocyanates or isothiocyanates, in the presence of a base, into compounds of the formula (XXXVIII),

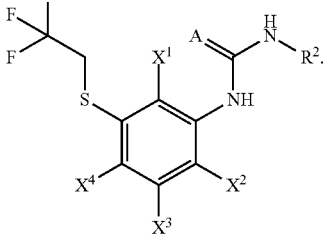
(XXXVIII)

9. The process according to claim 1, wherein anilines of the formula (X)

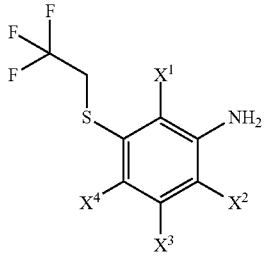
(X)

are converted with isocyanates or isothiocyanates, in the presence of an organic solvent, into compounds of the formula (XXXVIII),

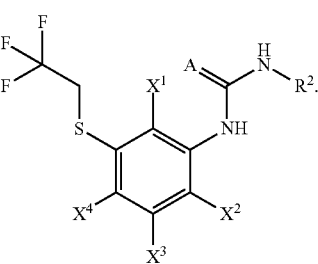
(XXXVIII)

10. The process according to claim 1, wherein anilines of the formula (X)

(X)

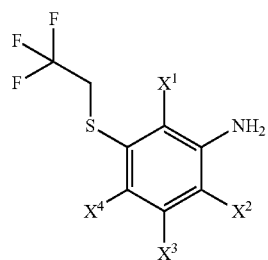

are converted with isocyanates or isothiocyanates, in the presence of pyridine, into compounds of the formula (XXXVIII), (XXXVIII)

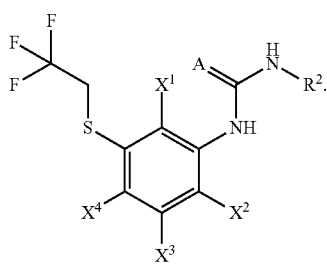

11. The process according to claim 1, wherein $X^1$, $X^2$, $X^3$, $X^4$ independently of one another represent hydrogen, fluorine, chlorine, bromine, iodine, ($C_1$-$C_4$)-alkyl, ($C_1$-$C_4$)-haloalkyl, ($C_2$-$C_4$)-alkenyl, ($C_2$-$C_4$)-alkynyl, ($C_1$-$C_4$)-alkoxy, ($C_1$-$C_4$)-haloalkoxy, or aminothiocarbonyl.

12. The process according to claim 1, wherein $X^1$ and $X^3$ represent hydrogen.

13. The process according to claim 1, wherein $X^2$ and $X^4$ independently of one another represent hydrogen, fluorine, chlorine, bromine, methyl, ethyl, trifluoromethyl, difluoromethyl, difluoromethoxy, trifluoromethoxy, or $OCH_2CF_3$.

14. The process according to claim 1, wherein $X^2$ and $X^4$ represent one of the combinations $X_2/X_4$: fluorine/fluorine, chlorine/chlorine, fluorine/chlorine, chlorine/fluorine, bromine/bromine, bromine/chlorine, chlorine/bromine, bromine/fluorine, fluorine/bromine, methyl/methyl, methyl/fluorine, fluorine/methyl, methyl/chlorine, chlorine/methyl, methyl/bromine, bromine/methyl, ethyl/ethyl, ethyl/fluorine, fluorine/ethyl, ethyl/chlorine, chlorine/ethyl, ethyl/bromine, bromine/ethyl.

15. The process according to claim 2, wherein the compound of formula (Ib-g) is selected from the group consisting of:

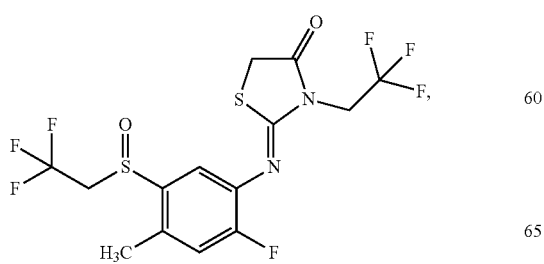

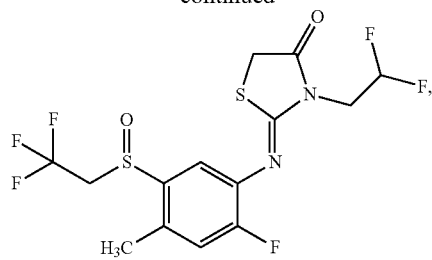

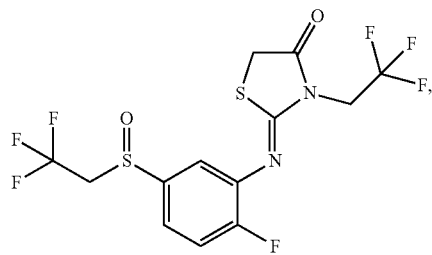

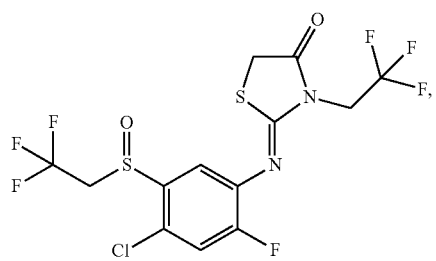

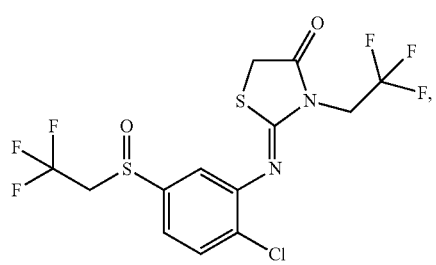

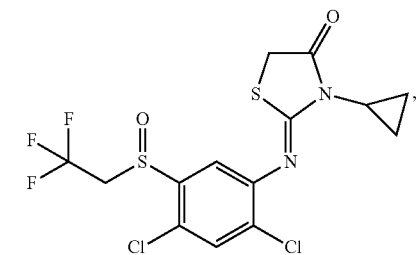

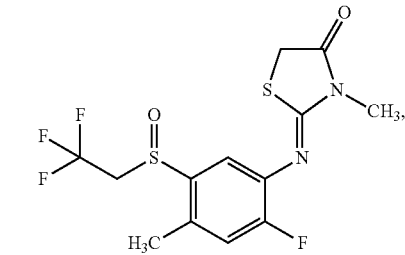

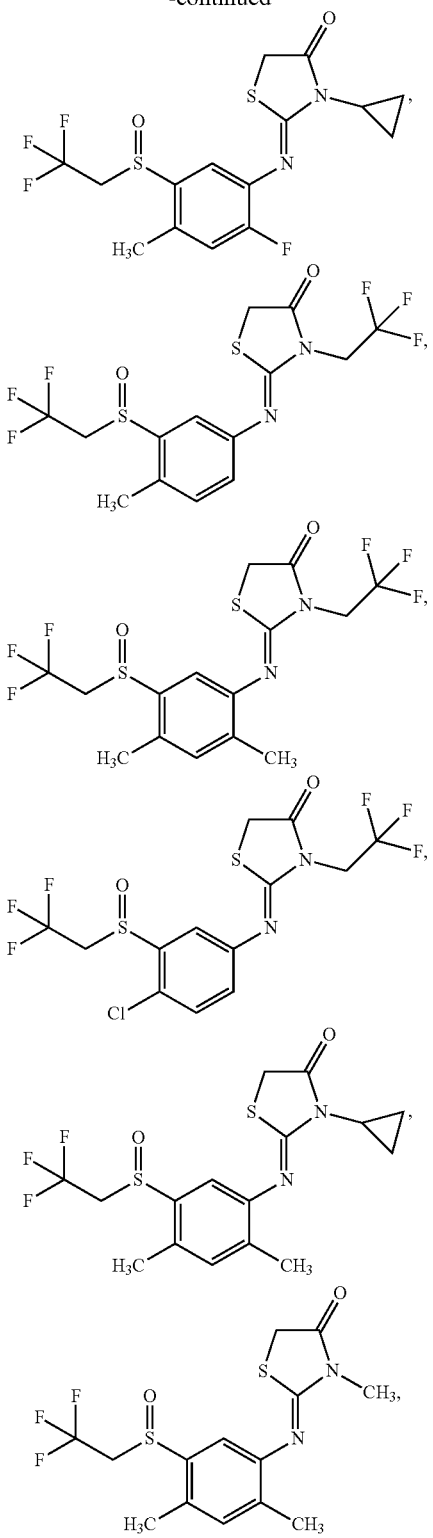
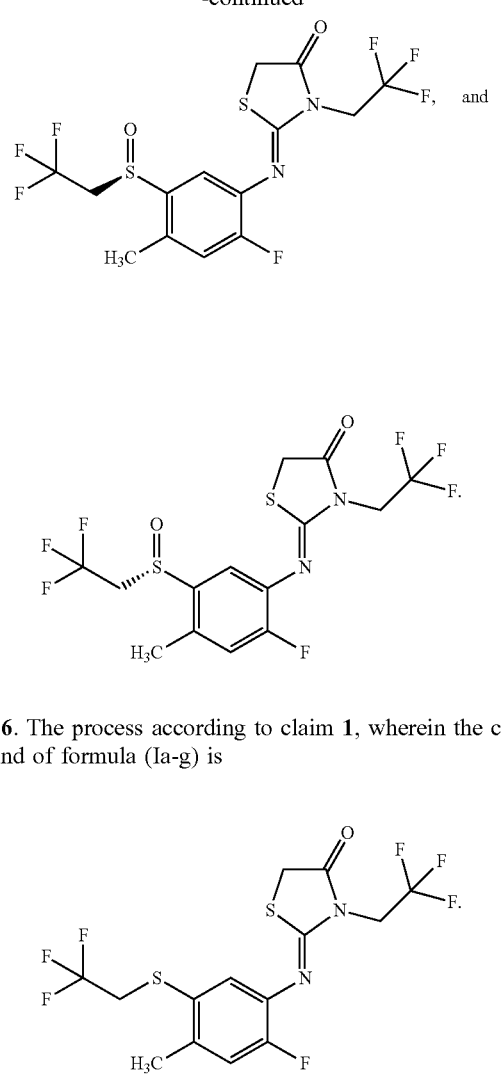
16. The process according to claim 1, wherein the compound of formula (Ia-g) is
17. The process according to claim 2, wherein the compound of formula (Ib-g) is
* * * * *